United States Patent
Zipp et al.

(10) Patent No.: US 11,207,414 B2
(45) Date of Patent: Dec. 28, 2021

(54) CANNABINOID GLYCOSIDE PRODRUGS AND METHODS OF SYNTHESIS

(71) Applicant: Graphium Biosciences, Inc., Cleveland, OH (US)

(72) Inventors: Brandon J. Zipp, Roseville, CA (US); Janee M. Hardman, Fair Oaks, CA (US); Robert T. Brooke, El Segundo, CA (US)

(73) Assignee: Graphium Biosciences, Inc., Cleveland, OH (US)

( * ) Notice: Subject to any disclaimer, the term of this patent is extended or adjusted under 35 U.S.C. 154(b) by 0 days.

(21) Appl. No.: 15/762,180

(22) PCT Filed: Sep. 22, 2016

(86) PCT No.: PCT/US2016/053122
§ 371 (c)(1),
(2) Date: Mar. 22, 2018

(87) PCT Pub. No.: WO2017/053574
PCT Pub. Date: Mar. 30, 2017

(65) Prior Publication Data
US 2018/0264122 A1    Sep. 20, 2018

Related U.S. Application Data

(60) Provisional application No. 62/363,808, filed on Jul. 18, 2016, provisional application No. 62/245,928, filed on Oct. 23, 2015, provisional application No. 62/222,144, filed on Sep. 22, 2015.

(51) Int. Cl.
| | | |
|---|---|---|
| *A61K 31/352* | (2006.01) | |
| *A61K 47/54* | (2017.01) | |
| *A61K 31/7012* | (2006.01) | |
| *A61K 31/7016* | (2006.01) | |
| *A61K 31/7034* | (2006.01) | |
| *C07H 15/203* | (2006.01) | |
| *C07H 15/10* | (2006.01) | |
| *A61P 25/00* | (2006.01) | |
| *A61P 29/00* | (2006.01) | |
| *A61P 1/10* | (2006.01) | |
| *A61K 9/00* | (2006.01) | |

(52) U.S. Cl.
CPC .......... *A61K 47/549* (2017.08); *A61K 31/352* (2013.01); *A61K 31/7012* (2013.01); *A61K 31/7016* (2013.01); *A61K 31/7034* (2013.01); *A61P 1/10* (2018.01); *A61P 25/00* (2018.01); *A61P 29/00* (2018.01); *C07H 15/10* (2013.01); *C07H 15/203* (2013.01); *A61K 9/0014* (2013.01); *A61K 9/0019* (2013.01); *A61K 9/0053* (2013.01)

(58) Field of Classification Search
CPC ... A61K 47/549; A61K 31/352; A61K 9/0019

USPC ........................................................ 536/4.1
See application file for complete search history.

(56) References Cited

U.S. PATENT DOCUMENTS

| | | |
|---|---|---|
| 5,292,899 A | 3/1994 | Tius et al. |
| 5,627,270 A | 5/1997 | Kahne et al. |
| 8,227,627 B2 | 7/2012 | Stinchcomb et al. |
| 8,410,064 B2 | 4/2013 | Radominska-Pandya et al. |
| 8,858,970 B2 | 10/2014 | Supamahitorn et al. |
| 9,168,276 B2 | 10/2015 | Bombardelli et al. |
| 9,497,299 B2 | 11/2016 | Cai |
| 2012/0202281 A1 | 8/2012 | Stinchcomb et al. |
| 2014/0298511 A1 | 10/2014 | Lewis et al. |
| 2015/0258040 A1* | 9/2015 | Lynch ................... A61K 31/05 424/450 |
| 2016/0374958 A1 | 12/2016 | Anastassov et al. |
| 2019/0382814 A1 | 12/2019 | Peet et al. |
| 2020/0046639 A1 | 2/2020 | Sayre et al. |
| 2020/0206185 A1 | 7/2020 | Zipp et al. |

FOREIGN PATENT DOCUMENTS

| | | |
|---|---|---|
| WO | WO 2009/018389 | 2/2009 |
| WO | WO 2009/158499 | 12/2009 |
| WO | WO 2012/011112 | 1/2012 |
| WO | WO 2014/108899 | 7/2014 |
| WO | WO 2014/122227 | 8/2014 |
| WO | WO 2017/053574 | 3/2017 |
| WO | WO 2018/011813 | 1/2018 |
| WO | WO 2018/176055 | 9/2018 |

OTHER PUBLICATIONS

Huestis (Chem Biodivers. Aug. 2007; 4(8): 1770-1804).*
European Search Report for App. No. 16849598.4, dated Apr. 25, 2019.
Hiroyuki Tanaka Et Al: "Cannabis, 21.1 Biotransformation of Cannabinol to its Glycosides by In Vitro Plant Tissue", Journal of Natural Products, Jan. 1, 1993 (Jan. 1, 1993), pp. 2068-2072.
Hiroyuki Tanaka Et Al: "Cannabis 25 1, Biotranformation of Cannabidiol and Cannabidiolic Acid by Pinellia Ternata Tissue Segments", Plant Cell Reports, vol. 15, No. 11, Aug. 1, 1996 (Aug. 1, 1996), pp. 819-823.
Hiroyuki Tanaka Et Al: "Monoclonal Antibody Against Tetrahydrocannabinolic Acid Distinguishes Cannabis Sativa Samples from Different Plant Species", Forensic Science International, vol. 106, No. 3, Dec. 1, 1999 (Dec. 1, 1999), pp. 135-146.
Hiroyuki Tanaka Et Al: "A New Cannabinoid, Delta6—Tetrahydrocannabinol 2'-O-beta-D-Glucopyranoside, Biotransformed by Plant issue", Jan. 1, 1997 (Jan. 1, 1997).

(Continued)

*Primary Examiner* — Shaojia A Jiang
*Assistant Examiner* — Michael C Henry
(74) *Attorney, Agent, or Firm* — Polsinelli PC

(57) ABSTRACT

The present invention relates to cannabinoid glycoside prodrugs suitable for site- and tissue-specific delivery of cannabinoid molecules. The present invention also relates to methods of forming the cannabinoid glycoside prodrugs through glycosyltransferase mediated glycosylation of cannabinoid molecules.

17 Claims, 32 Drawing Sheets

Specification includes a Sequence Listing.

(56) References Cited

OTHER PUBLICATIONS

H. Tanaka: "Immunochemical Approach Using Monoclonal Antibody Against delta9-Tetrahydrocannabinolic Acid (THCA) to Discern Cannabis Plants and to Investigate New Drug Candidates", Current Drug Discovery Technologies, vol. 8, No. 1, Jan. 1, 2011 (Jan. 1, 2011), pp. 3-15.
International Search Report and Written Opinion, PCT/US2018/031727, dated Jul. 12, 2018.
Ali, E.M.M., et al. (2012). "Antimicrobial Activity of *Cannabis sativa* L." Chinese Medicine. 3:61¬64.
Appendino, G., et al. (2008). "Antibacterial Cannabinoids from Cannabis sativa: A Structure-Activity Study." J Nat Prod. 71(8): 1427-1430.
Gigli, S., et al. (2017). "Cannabidiol restores intestinal barrier dysfunction and inhibits the apoptotic process induced by Clostridium difficile toxin A in Caco-2 cells." United European Gastroenterology J. 0(0): 1-8.
Kabelik, J. et al. (1960). "Cannabis as a medicament. UN Office on Drugs and Crime." https://www.unodc.org/unodc/en/data-and-analysis/bulletin/bulletin_1960-01-01_3_page003.html, accessed Aug. 5, 2020.
Van Klingeren, B., Ten Ham, M. (1976). "Antibacterial activity of (delta9)-tetrahydrocannabinol and cannabidiol. Antonie van Leeuwenhoek." 42(1976): 9-12.
CDC, "Antibiotic Resistance Threats in the United States," 2013, 114 pages.
CDC. (2015). "Nearly half a million Americans suffered from Clostridium difficile infections in a single year", https://www.cdc.gov/media/releases/2015/p0225-clostridium-difficile.html, accessed Aug. 5, 2020.
WHO. (2014). Antimicrobial Resistance, Global Report on Surveillance, 256 pages.
WHO. (2017). "Global priority list of antibiotic-resistant bacteria to guide research, discovery, and development of new antibiotics." 7 pages.
Bartzokis G. (2004). Age-related myelin breakdown: a developmental model of cognitive decline and Alzheimer's disease. Neurobiology of Aging. 25:5-18.
Bisogno T, et al. (2001) Molecular targets for cannabidiol and its synthetic analogues: effect on vanilloid VR1 receptors and on the cellular uptake and enzymatic hydrolysis of anandamide. British Journal of Pharmacology. 134, 845-852.
Chen Q, et al. (2009). Synthesis, in vitro and in vivo characterization of glycosyl derivatives of ibuprofen as novel prodrugs for brain drug delivery. J Drug Targeting. 17(4):318-328.
Conchie J., Findlay J., Levvy GA. (1958). Mammalian Glycosidases, Distribution in the body. Biochem J. 71(2):318-325.
De Petrocellis L, et al. (2011) Effects of cannabinoids and cannabinoid-enriched Cannabis extracts on TRP channels and endocannabinoid metabolic enzymes. British Journal of Pharmacology. 163, 1479-1494.
Friend DR., Chang GW. (1984). A Colon-Specific Drug-Delivery System Based on Drug Glycosides and the Glycosidases of the Colonic Bacteria. J Med Chem. 27:261-266.
Friend DR., Chang GW. (1985). Drug Glycosides: Potential Prodrugs for Colon-Specific Drug Delivery. J Med Chem. 28:51-57.
Gomez O., Arevalo-Martin A., Garcia-Ovejero D., Ortega-Gutierrez S., Cisneros JA., Almazan G, Sanchez-Rodriguez MA., Molina-Holgado F., Molina-Holgado E. (2010). The Constitutive Production of the Endocannabinoid 2-Arachidonoylglycerol Participates in Oligodendrocyte Differentiation. Glia. 58:1913-1927.
Iuvone T., Esposito G., De Filippis D., Scuderi C., Steardo L. (2009). Cannabidiol: a promising drug for neurodegenerative disorders? CNS Neurosci Ther. 15(1):65-75.
Jarho, P., Pate DW., Brenneisen R., Jarvinen T. (1998). Hydroxypropyl-beta-cyclodextrin and its combination with hydroxypropyl-methylcellulose increases aqueous solubility of delta9-tetrahydrocannabinol. Life Sci. 63(26):PL381-384.
Jiang R, et al. (2011) Identification of cytochrome P450 enzymes responsible for metabolism of cannabidiol by human liver microsomes. Life Sciences. 89, 165-170.
Kren V, Rezanka T (2008) Sweet antibiotics—the role of glycosidic residues in antibiotic and antitumor activity and their randomization. FEMS Microbiol Rev. 32, 858-889.
Kren V (2008) Glycoside vs. Aglycon: The Role of Glycosidic Residue in Biologic Activity. Glycoscience. pp. 2589-2644.
Li S., Li W., Xiao Q., Xia Y. (2012). Transglycosylation of stevioside to improve the edulcorant quality by lower substitution using cornstarch hydrolyzate and CGTase. J Food Chem. 138(2013):2064-2069.
Mazur A., et al. (2009). Characterization of Human Hepatic and Extrahepatic UDP-Glucuronosyltransferase Enzymes Involved in the Metabolism of Classic Cannabinoids. Drug Metabolism and Disposition. 37(7):1496-1504.
Mecha M., Torrao AS., Mestre L., Carrillo-Salinas FJ., Mechoulam R., Guaza C. (2012). Cannabidiol protects oligodendrocyte progenitor cells from inflammation-induced apoptosis by attenuating endoplasmic reticulum stress. Cell Death and Disease. 3(e331).
Mechoulam R., Parker LA., Gallily R. (2002). Cannabidiol: An Overview of Some Pharmacological Aspects. 42(S1):11S-19S.
Mighdoll MI., Tao R., Kleinman JE., Hyde TM. (2015). Myelin, myelin-related disorders, and psychosis. Schizophr Res. 161(1):85-93.
Molina-Holgado E., Vela JM., Arevalo-Martin A., Almazan G., Molina-Holgado F., Borrell J., Guaza C. (2002). Cannabinoids Promote Oligodendrocyte Progenitor Survival: Involvement of Cannabinoid Receptors and Phosphatidylinositol-3-Kinase/Akt Signaling. J. Neurosci. 22(22):9742-9753.
Noguchi A, et al. (2009). Identification of an inducible glucosyltransferase from *Phytolacca americana* L. cells that are capable of glucosylating capsaicin. Plant Biotechnology. 26, 285-292.
Pacher P, et al. (2006) The endocannabinoid system as an emerging target of pharmacotherapy. Pharmacology Review. 58(3), 389-462.
Richman A., Swanso, A., Humphrey T., Chapman R., McGarvey B., Pocs R., Brandle J. (2005). Functional genomics uncovers three glucosyltransferases involved in the synthesis of the major sweet glucosides of Stevia rebaudiana. Plant J. 41(1):56-67.
Russo E., Guy, GW. (2006) A tale of two cannabinoids: the therapeutic rationale for combining tetrahydrocannabinol and cannabidiol. Medical Hypotheses. 66(2):234-46.
Terao J., Murota K., Kawai Y. (2011). Conjugated quercetin glucuronides as bioactive metabolites and precursors of aglycone in vivo. Food Function. 2:11-17.
Thomas A., et al. (2007) Cannabidiol displays unexpectedly high potency as an antagonist of CB1 and CB2 receptor agonists in vitro. British Journal of Pharmacology. 150, 613-623.
Watanabe K, et al. (1998) Distribution and characterization of anandamide amidohydrolase in mouse brain and liver. Life Sciences. 62(14), 1223-1229.
Yamaori S, et al. (2011) Potent inhibition of human cytochrome P450 3A isoforms by cannabidiol: Role of phenolic hydroxyl groups in the resorcinol moiety. Life Sciences, 88, 730-736.
Zuardi AW, et al. (2012). A Critical Review of the Antipsychotic Effects of Cannabidiol: 30 Years of a Translational Investigation. Current Pharmaceutical Design, 18, 5131-5140.
Bruni et al., Cannabinoid Delivery Systems for Pain and Inflammation Treatment, *Moleulces*, 2018, 23, 2478, 25 pages.
Dewitte et al., "Screening of recombinant glycosyltransferases reveals the broad acceptor specificity of stevia UGT-76G1,"*Journal of Biotechnology*, 233 (2016), pp. 49-55.
McPartland et al., "Affinity and Efficacy Studies of Tetrahydrocannabinolic Acid A at Cannabinoid Receptor Types One and Two," *Cannabis and Cannabinoid Research*, vol. 2.7, 2017,pp. 87-95.
Bowes, J. et al. "Reducing safety-related drug attrition: the use of in vitro pharmacological profiling." *Nature Reviews Drug Discovery*, 11, No. 12 (2012): 909.
Friend, "New oral delivery systems for treatment of inflammatory bowel disease," *Advanced Drug Delivery Reviews*, 57 (2005), 247-265.

(56) References Cited

OTHER PUBLICATIONS

Friend et al., "Colon-specific drug delivery from a glucoside prodrug in the guinea-pig. Efficacy study," Journal of Controlled Release, vol. 15, No. 1, Feb. 1991, pp. 47-54.

* cited by examiner

SEQUENCE LISTING

```
<160> NUMBER OF SEQ ID NOS: 34

<210> SEQ ID NO 1
<211> LENGTH: 458
<212> TYPE: PRT
<213> ORGANISM: Stevia rebaudiana

<400> SEQUENCE: 1

Met Glu Asn Lys Thr Glu Thr Thr Val Arg Arg Arg Arg Ile Ile
1               5                   10                  15

Leu Phe Pro Val Pro Phe Gln Gly His Ile Asn Pro Ile Leu Gln Leu
                20                  25                  30

Ala Asn Val Leu Tyr Ser Lys Gly Phe Ser Ile Thr Ile Phe His Thr
            35                  40                  45

Asn Phe Asn Lys Pro Lys Thr Ser Asn Tyr Pro His Phe Thr Phe Arg
50                      55                      60

Phe Ile Leu Asp Asn Asp Pro Gln Asp Glu Arg Ile Ser Asn Leu Pro
65                  70                  75                  80

Thr His Gly Pro Leu Ala Gly Met Arg Ile Pro Ile Ile Asn Glu His
                85                  90                  95

Gly Ala Asp Glu Leu Arg Arg Glu Leu Glu Leu Leu Met Leu Ala Ser
            100                 105                 110

Glu Glu Asp Glu Glu Val Ser Cys Leu Ile Thr Asp Ala Leu Trp Tyr
        115                 120                 125

Phe Ala Gln Ser Val Ala Asp Ser Leu Asn Leu Arg Arg Leu Val Leu
130                 135                 140

Met Thr Ser Ser Leu Phe Asn Phe His Ala His Val Ser Leu Pro Gln
145                 150                 155                 160

Phe Asp Glu Leu Gly Tyr Leu Asp Pro Asp Asp Lys Thr Arg Leu Glu
                165                 170                 175

Glu Gln Ala Ser Gly Phe Pro Met Leu Lys Val Lys Asp Ile Lys Ser
            180                 185                 190

Ala Tyr Ser Asn Trp Gln Ile Leu Lys Glu Ile Leu Gly Lys Met Ile
        195                 200                 205

Lys Gln Thr Lys Ala Ser Ser Gly Val Ile Trp Asn Ser Phe Lys Glu
    210                 215                 220

Leu Glu Glu Ser Glu Leu Glu Thr Val Ile Arg Glu Ile Pro Ala Pro
225                 230                 235                 240

Ser Phe Leu Ile Pro Leu Pro Lys His Leu Thr Ala Ser Ser Ser Ser
                245                 250                 255

Leu Leu Asp His Asp Arg Thr Val Phe Gln Trp Leu Asp Gln Gln Pro
            260                 265                 270

Pro Ser Ser Val Leu Tyr Val Ser Phe Gly Ser Thr Ser Glu Val Asp
        275                 280                 285

Glu Lys Asp Phe Leu Glu Ile Ala Arg Gly Leu Val Asp Ser Lys Gln
    290                 295                 300

Ser Phe Leu Trp Val Val Arg Pro Gly Phe Val Lys Gly Ser Thr Trp
305                 310                 315                 320

Val Glu Pro Leu Pro Asp Gly Phe Leu Gly Glu Arg Gly Arg Ile Val
                325                 330                 335
```

```
Lys Trp Val Pro Gln Gln Glu Val Leu Ala His Gly Ala Ile Gly Ala
                340                 345                 350

Phe Trp Thr His Ser Gly Trp Asn Ser Thr Leu Glu Ser Val Cys Glu
            355                 360                 365

Gly Val Pro Met Ile Phe Ser Asp Phe Gly Leu Asp Gln Pro Leu Asn
        370                 375                 380

Ala Arg Tyr Met Ser Asp Val Leu Lys Val Gly Val Tyr Leu Glu Asn
385                 390                 395                 400

Gly Trp Glu Arg Gly Glu Ile Ala Asn Ala Ile Arg Arg Val Met Val
                405                 410                 415

Asp Glu Glu Gly Glu Tyr Ile Arg Gln Asn Ala Arg Val Leu Lys Gln
                420                 425                 430

Lys Ala Asp Val Ser Leu Met Lys Gly Gly Ser Ser Tyr Glu Ser Leu
            435                 440                 445

Glu Ser Leu Val Ser Tyr Ile Ser Ser Leu
        450                 455

<210> SEQ ID NO 2
<211> LENGTH: 1377
<212> TYPE: DNA
<213> ORGANISM: Stevia rebaudiana

<400> SEQUENCE: 2
atggaaaata aaacggagac caccgttcgc cggcgccgga gaataatatt attcccggta        60
ccatttcaag gccacattaa cccaattctt cagctagcca atgtgttgta ctctaaagga       120
ttcagtatca ccatctttca caccaacttc aacaaaccca aacatctaa ttaccctcac        180 ttcactttca gattcatcct cgacaacgac ccacaagacg aacgcatttc caatctaccg       240
actcatggtc cgctcgctgg tatgcggatt ccgattatca cgaacacgg agctgacgaa        300 ttacgacgcg aactggaact gttgatgtta gcttctgaag aagatgaaga ggtatcgtgt       360
ttaatcacgg atgctctttg gtacttcgcg caatctgttg ctgacagtct aacctccga        420 cggcttgttt tgatgacaag cagcttgttt aattttcatg cacatgtttc acttcctcag       480
tttgatgagc ttggttacct cgatcctgat gacaaaaccc gtttggaaga caagcgagt        540 gggtttccta tgctaaaagt gaaagacatc aagtctgcgt attcgaactg gcaaatactc       600
aaagagatat tagggaagat gataaaacaa acaagagcat cttcaggagt catctggaac       660
tcatttaagg aactcgaaga gtctgagctc gaaactgtta ccgtgagat cccggctcca        720 agttcttga taccactccc caagcatttg acagcctctt ccagcagctt actagaccac        780
gatcgaaccg ttttcaatg gttagaccaa caaccgccaa gttcggtact gtatgttagt        840
tttggtagta ctagtgaagt ggatgagaaa gatttcttgg aaatagctcg tgggttggtt       900
gatagcaagc agtcgttttt atgggtggtt cgacctgggt ttgtcaaggg ttcgacgtgg       960
gtcgaaccgt tgccagatgg gttcttgggt gaaagaggac gtattgtgaa atgggttcca      1020
cagcaagaag tgctagctca tggagcaata ggcgcattct ggactcatag cggatggaac      1080
tctacgttgg aaagcgtttg tgaaggtgtt cctatgattt tctcggattt tgggctcgat      1140
caaccgttga atgctagata catgagtgat gttttgaagg tagggtgta tttggaaaat       1200 gggtgggaaa gaggagagat agcaaatgca ataagaagag ttatggtgga tgaagaagga      1260
gaatacatta gacagaatgc aagagttttg aacaaaagg cagatgtttc tttgatgaag       1320
ggtggttcgt cttacgaatc attagagtct ctagtttctt acatttcatc gttgtaa         1377
```

<210> SEQ ID NO 3
<211> LENGTH: 467
<212> TYPE: PRT
<213> ORGANISM: Artificial Sequence
<220> FEATURE:
<223> OTHER INFORMATION: UGT76G1 with a 6x Histidine tag at the N-terminus

<400> SEQUENCE: 3

```
Met His His His His His Gly Ser Gly Glu Asn Lys Thr Glu Thr
1               5                   10                  15

Thr Val Arg Arg Arg Arg Ile Ile Leu Phe Pro Val Pro Phe Gln
                20                  25                  30

Gly His Ile Asn Pro Ile Leu Gln Leu Ala Asn Val Leu Tyr Ser Lys
            35                  40                  45

Gly Phe Ser Ile Thr Ile Phe His Thr Asn Phe Asn Lys Pro Lys Thr
    50                  55                  60

Ser Asn Tyr Pro His Phe Thr Phe Arg Phe Ile Leu Asp Asn Asp Pro
65              70                  75                  80

Gln Asp Glu Arg Ile Ser Asn Leu Pro Thr His Gly Pro Leu Ala Gly
                85                  90                  95

Met Arg Ile Pro Ile Ile Asn Glu His Gly Ala Asp Glu Leu Arg Arg
            100                 105                 110

Glu Leu Glu Leu Leu Met Leu Ala Ser Glu Glu Asp Glu Glu Val Ser
        115                 120                 125

Cys Leu Ile Thr Asp Ala Leu Trp Tyr Phe Ala Gln Ser Val Ala Asp
130                 135                 140

Ser Leu Asn Leu Arg Arg Leu Val Leu Met Thr Ser Ser Leu Phe Asn
145                 150                 155                 160

Phe His Ala His Val Ser Leu Pro Gln Phe Asp Glu Leu Gly Tyr Leu
                165                 170                 175

Asp Pro Asp Asp Lys Thr Arg Leu Glu Glu Gln Ala Ser Gly Phe Pro
            180                 185                 190

Met Leu Lys Val Lys Asp Ile Lys Ser Ala Tyr Ser Asn Trp Gln Ile
        195                 200                 205

Leu Lys Glu Ile Leu Gly Lys Met Ile Lys Thr Lys Ala Ser Ser
210                 215                 220

Gly Val Ile Trp Asn Ser Phe Lys Glu Leu Glu Glu Ser Glu Leu Glu
225                 230                 235                 240

Thr Val Ile Arg Glu Ile Pro Ala Pro Ser Phe Leu Ile Pro Leu Pro
                245                 250                 255

Lys His Leu Thr Ala Ser Ser Ser Ser Leu Leu Asp His Asp Arg Thr
            260                 265                 270

Val Phe Gln Trp Leu Asp Gln Gln Pro Pro Ser Ser Val Leu Tyr Val
        275                 280                 285

Ser Phe Gly Ser Thr Ser Glu Val Asp Glu Lys Asp Phe Leu Glu Ile
290                 295                 300

Ala Arg Gly Leu Val Asp Ser Lys Gln Ser Phe Leu Trp Val Val Arg
305                 310                 315                 320

Pro Gly Phe Val Lys Gly Ser Thr Trp Val Glu Pro Leu Pro Asp Gly
                325                 330                 335

Phe Leu Gly Glu Arg Gly Arg Ile Val Lys Trp Val Pro Gln Gln Glu
            340                 345                 350

Val Leu Ala His Gly Ala Ile Gly Ala Phe Trp Thr His Ser Gly Trp
        355                 360                 365
```

```
Asn Ser Thr Leu Glu Ser Val Cys Glu Gly Val Pro Met Ile Phe Ser
    370                 375                 380

Asp Phe Gly Leu Asp Gln Pro Leu Asn Ala Arg Tyr Met Ser Asp Val
385                 390                 395                 400

Leu Lys Val Gly Val Tyr Leu Glu Asn Gly Trp Glu Arg Gly Glu Ile
                405                 410                 415

Ala Asn Ala Ile Arg Arg Val Met Val Asp Glu Glu Gly Glu Tyr Ile
            420                 425                 430

Arg Gln Asn Ala Arg Val Leu Lys Gln Lys Ala Asp Val Ser Leu Met
        435                 440                 445

Lys Gly Gly Ser Ser Tyr Glu Ser Leu Glu Ser Leu Val Ser Tyr Ile
    450                 455                 460

Ser Ser Leu
465

<210> SEQ ID NO 4
<211> LENGTH: 1404
<212> TYPE: DNA
<213> ORGANISM: Artificial Sequence
<220> FEATURE:
<223> OTHER INFORMATION: Sequence encoding SEQ ID NO:3 codon optimized
      for expression in Pichia pastoris

<400> SEQUENCE: 4
atgcaccacc atcaccacca tggttctggt gaaaacaaaa ctgaaactac tgttagaaga      60
agaagaagaa tcatttttgtt tccagtacca tttcaaggcc atatcaatcc aattcttcaa    120
ttggccaatg ttttgtactc caaaggattc tccatcacca tttttcacac caatttcaac    180
aaaccaaaga cttccaacta tcctcacttc actttcagat ttattttgga taatgatcct    240
caagatgaaa gaatttccaa tcttccgact catggtcctt ggctggtat gagaattcca     300 atcatcaatg aacatggtgc tgatgaatta agaagagaat ggaacttttt gatgttggct    360
tctgaagaag atgaagaagt tcatgtttta atcactgatg ctttatggta ttttgctcaa    420
tctgttgctg attctttgaa tttgcgacgg ttggttttga tgacttcttc tttgttcaac    480
tttcatgctc atgtttcttt acctcagttt gatgaacttg atatttggga tccagatgac    540
aaaactagat tggaagaaca agctagtggg tttcctatgt tgaaagtcaa agatatcaaa    600
tctgcttact ccaactggca aattctcaaa gaatttttgg gaaaaatgat caaacaaaca    660
aaagcttctt ctggagtcat ttggaactca ttcaaagaat tggaagaatc tgaattggaa    720
actgttatta gagaaattcc tgctccaagt tttttgattc ctttgccaaa acatttgact    780
gcttcttctt cttctttatt ggatcacgat agaactgttt tcaatggtt agatcaacaa     840 cctccatctt ctgttttgta tgttagttttt ggatctactt ctgaagttga tgaaaaagat    900 ttttttggaaa ttgctagagg tttggttgat tccaaacaaa gttttttatg ggttgttaga   960
ccaggatttg tcaaaggatc tacttgggtc gaacctttgc cagatggatt tttgggagaa   1020
agaggaagaa ttgtcaaatg ggttccacag caagaagttt ggctcatgg tgctattggt    1080 gcttttttgga ctcattctgg atggaactct actttggaat ctgtttgtga aggtgttcca   1140 atgattttt ctgattttgg tttggatcaa ccattgaatg ctagatacat gtctgatgtt   1200
ttgaaagttg gtgtttattt ggaaaatggg tgggaaagag gtgaaattgc caatgctatt   1260
agaagagtca tggttgatga agaaggagaa tacattagac aaaatgctag agttttgaaa  1320
caaaaagctg atgtttcttt gatgaagggt ggatcttctt atgaatcttt ggaatctttg  1380
gtttcttaca tttcttctct ttaa                                          1404
```

<210> SEQ ID NO 5
<211> LENGTH: 468
<212> TYPE: PRT
<213> ORGANISM: Artificial Sequence
<220> FEATURE:
<223> OTHER INFORMATION: UGT76G1 with a 6x Histidine-Glutamine tag at the N-terminus

<400> SEQUENCE: 5

```
Met His Gln His Gln His Gln Ser Gly Ser Met Glu Asn Lys Thr Glu
1               5                   10                  15

Thr Thr Val Arg Arg Arg Arg Ile Ile Leu Phe Pro Val Pro Phe
            20                  25                  30

Gln Gly His Ile Asn Pro Ile Leu Gln Leu Ala Asn Val Leu Tyr Ser
                35                  40                  45

Lys Gly Phe Ser Ile Thr Ile Phe His Thr Asn Phe Asn Lys Pro Lys
    50                  55                  60

Thr Ser Asn Tyr Pro His Phe Thr Phe Arg Phe Ile Leu Asp Asn Asp
65                  70                  75                  80

Pro Gln Asp Glu Arg Ile Ser Asn Leu Pro Thr His Gly Pro Leu Ala
                85                  90                  95

Gly Met Arg Ile Pro Ile Ile Asn Glu His Gly Ala Asp Glu Leu Arg
                100                 105                 110

Arg Glu Leu Glu Leu Leu Met Leu Ala Ser Glu Glu Asp Glu Glu Val
            115                 120                 125

Ser Cys Leu Ile Thr Asp Ala Leu Trp Tyr Phe Ala Gln Ser Val Ala
130                 135                 140

Asp Ser Leu Asn Leu Arg Arg Leu Val Leu Met Thr Ser Ser Leu Phe
145                 150                 155                 160

Asn Phe His Ala His Val Ser Leu Pro Gln Phe Asp Glu Leu Gly Tyr
                165                 170                 175

Leu Asp Pro Asp Asp Lys Thr Arg Leu Glu Glu Gln Ala Ser Gly Phe
            180                 185                 190

Pro Met Leu Lys Val Lys Asp Ile Lys Ser Ala Tyr Ser Asn Trp Gln
        195                 200                 205

Ile Leu Lys Glu Ile Leu Gly Lys Met Ile Lys Gln Thr Lys Ala Ser
    210                 215                 220

Ser Gly Val Ile Trp Asn Ser Phe Lys Glu Leu Glu Ser Glu Leu
225                 230                 235                 240

Glu Thr Val Ile Arg Glu Ile Pro Ala Pro Ser Phe Leu Ile Pro Leu
                245                 250                 255

Pro Lys His Leu Thr Ala Ser Ser Ser Ser Leu Leu Asp His Asp Arg
            260                 265                 270

Thr Val Phe Gln Trp Leu Asp Gln Gln Pro Pro Ser Ser Val Leu Tyr
        275                 280                 285

Val Ser Phe Gly Ser Thr Ser Glu Val Asp Glu Lys Asp Phe Leu Glu
    290                 295                 300

Ile Ala Arg Gly Leu Val Asp Ser Lys Gln Ser Phe Leu Trp Val Val
305                 310                 315                 320

Arg Pro Gly Phe Val Lys Gly Ser Thr Trp Val Glu Pro Leu Pro Asp
                325                 330                 335

Gly Phe Leu Gly Glu Arg Gly Arg Ile Val Lys Trp Val Pro Gln Gln
            340                 345                 350

Glu Val Leu Ala His Gly Ala Ile Gly Ala Phe Trp Thr His Ser Gly
```

```
                  355                 360                 365
Trp Asn Ser Thr Leu Glu Ser Val Cys Glu Gly Val Pro Met Ile Phe
    370                 375                 380

Ser Asp Phe Gly Leu Asp Gln Pro Leu Asn Ala Arg Tyr Met Ser Asp
385                 390                 395                 400

Val Leu Lys Val Gly Val Tyr Leu Glu Asn Gly Trp Glu Arg Gly Glu
                405                 410                 415

Ile Ala Asn Ala Ile Arg Arg Val Met Val Asp Glu Glu Gly Glu Tyr
            420                 425                 430

Ile Arg Gln Asn Ala Arg Val Leu Lys Gln Lys Ala Asp Val Ser Leu
        435                 440                 445

Met Lys Gly Gly Ser Ser Tyr Glu Ser Leu Glu Ser Leu Val Ser Tyr
    450                 455                 460

Ile Ser Ser Leu
465

<210> SEQ ID NO 6
<211> LENGTH: 1407
<212> TYPE: DNA
<213> ORGANISM: Artificial Sequence
<220> FEATURE:
<223> OTHER INFORMATION: Sequence encoding SEQ ID NO:5 codon optimized
      for expression in Pichia pastoris

<400> SEQUENCE: 6
atgcatcaac atcaacacca atctggatct atggagaaca agaccgagac tacagttaga        60
agaagaagaa gaataatcct gtttccagta ccattccaag acacatcaa cccaatcttg        120 cagttagcaa atgtacttta ttctaaaggc tttagtatta cgattttca cactaatttt        180 aataagccaa aacatccaa ttaccctcac ttcacattca gatttatctt ggataacgat        240
cctcaagatg aacgtatctc caacctgcca acacatggac cattggccgg tatgcgtatt        300
cctataatca cgagcatgg tgctgatgag cttagacgtg aactggaact gttgatgctg        360
gcatcggagg aagatgaaga ggttagttgc ttgataacgg atgccctctg gtatttcgca        420
caatcagtcg ctgactcctt gaaccttagg agattggtat tgatgactag ttcgttgttc        480
aacttccatg cccatgtttc tttgcctcaa tttgatgagc tgggttattt ggatcctgac        540
gataagactc gtttagaaga acaggcgtca ggcttcccca tgttaaaggt taagatatt         600 aagtccgcct attctaactg gcaaattctc aaagagattc tagggaaaat gattaaacaa        660
accaaggcct cttcaggagt aatctggaac agtttcaaag aactagaaga tccgagttg         720 gaaactgtta ttcgtgaaat ccctgctcca tctttcctta tcccattacc aaagcacctc        780
actgcctcct ctagttctct tctgaccat gatagaacag tctttcagtg gctcgatcag        840
caacctccat cttctgtctt gtacgttagt tttggttcca cctcggaagt agatgaaaaa        900
gactttctgg aaattgctcg aggactagtt gactccaagc aatccttct gtgggttgtt        960 agacctggat tcgtaaaagg atccacctgg gtagaaccc tcccagatgg attttgggc         1020 gaaaggggaa gaattgttaa atgggtgcct caacaagaag ttttagctca tggggccatt        1080 ggagctttt ggactcatag tggatggaat tctaccttag aatctgtttg tgaaggagtt        1140
ccaatgattt tttctgattt tggattggat cagcctctta atgccagata tatgtccgat        1200
gtcctcaagg tcggagtgta cctggaaaat ggttgggaga gagtgagat tgcaaatgct        1260 atacgtagag tcatggttga tgaagagggc gagtatatta acaaaacgc tagagtgcta        1320 aagcagaagg ccgatgtttc ccttatgaag ggggaagtt catatgagag tttggaatcc        1380
```
ctagtgtcct acatttcttc gctataa                                         1407

<210> SEQ ID NO 7
<211> LENGTH: 466
<212> TYPE: PRT
<213> ORGANISM: Artificial Sequence
<220> FEATURE:
<223> OTHER INFORMATION: UGT76G1 with a 6x Histidine tag at the C-
      terminus

<400> SEQUENCE: 7

Met Glu Asn Lys Thr Glu Thr Thr Val Arg Arg Arg Arg Ile Ile
1               5                   10                  15

Leu Phe Pro Val Pro Phe Gln Gly His Ile Asn Pro Ile Leu Gln Leu
                20                  25                  30

Ala Asn Val Leu Tyr Ser Lys Gly Phe Ser Ile Thr Ile Phe His Thr
            35                  40                  45

Asn Phe Asn Lys Pro Lys Thr Ser Asn Tyr Pro His Phe Thr Phe Arg
        50                  55                  60

Phe Ile Leu Asp Asn Asp Pro Gln Asp Glu Arg Ile Ser Asn Leu Pro
65                  70                  75                  80

Thr His Gly Pro Leu Ala Gly Met Arg Ile Pro Ile Ile Asn Glu His
                85                  90                  95

Gly Ala Asp Glu Leu Arg Arg Glu Leu Glu Leu Leu Met Leu Ala Ser
            100                 105                 110

Glu Glu Asp Glu Glu Val Ser Cys Leu Ile Thr Asp Ala Leu Trp Tyr
        115                 120                 125

Phe Ala Gln Ser Val Ala Asp Ser Leu Asn Leu Arg Arg Leu Val Leu
    130                 135                 140

Met Thr Ser Ser Leu Phe Asn Phe His Ala His Val Ser Leu Pro Gln
145                 150                 155                 160

Phe Asp Glu Leu Gly Tyr Leu Asp Pro Asp Asp Lys Thr Arg Leu Glu
                165                 170                 175

Glu Gln Ala Ser Gly Phe Pro Met Leu Lys Val Lys Asp Ile Lys Ser
            180                 185                 190

Ala Tyr Ser Asn Trp Gln Ile Leu Lys Glu Ile Leu Gly Lys Met Ile
        195                 200                 205

Lys Gln Thr Arg Ala Ser Ser Gly Val Ile Trp Asn Ser Phe Lys Glu
    210                 215                 220

Leu Glu Glu Ser Glu Leu Glu Thr Val Ile Arg Glu Ile Pro Ala Pro
225                 230                 235                 240

Ser Phe Leu Ile Pro Leu Pro Lys His Leu Thr Ala Ser Ser Ser Ser
                245                 250                 255

Leu Leu Asp His Asp Arg Thr Val Phe Gln Trp Leu Asp Gln Gln Pro
            260                 265                 270

Pro Ser Ser Val Leu Tyr Val Ser Phe Gly Ser Thr Ser Glu Val Asp
        275                 280                 285

Glu Lys Asp Phe Leu Glu Ile Ala Arg Gly Leu Val Asp Ser Lys Gln
    290                 295                 300

Ser Phe Leu Trp Val Val Arg Pro Gly Phe Val Lys Gly Ser Thr Trp
305                 310                 315                 320

Val Glu Pro Leu Pro Asp Gly Phe Leu Gly Glu Arg Gly Arg Ile Val
                325                 330                 335

Lys Trp Val Pro Gln Gln Glu Val Leu Ala His Gly Ala Ile Gly Ala
            340                 345                 350

Phe Trp Thr His Ser Gly Trp Asn Ser Thr Leu Glu Ser Val Cys Glu
        355                 360                 365

Gly Val Pro Met Ile Phe Ser Asp Phe Gly Leu Asp Gln Pro Leu Asn
    370                 375                 380

Ala Arg Tyr Met Ser Asp Val Leu Lys Val Gly Val Tyr Leu Glu Asn
385                 390                 395                 400

Gly Trp Glu Arg Gly Glu Ile Ala Asn Ala Ile Arg Arg Val Met Val
                405                 410                 415

Asp Glu Glu Gly Glu Tyr Ile Arg Gln Asn Ala Arg Val Leu Lys Gln
            420                 425                 430

Lys Ala Asp Val Ser Leu Met Lys Gly Gly Ser Ser Tyr Glu Ser Leu
                435                 440                 445

Glu Ser Leu Val Ser Tyr Ile Ser Ser Leu Gly Ser His His His His
    450                 455                 460

His His
465

<210> SEQ ID NO 8
<211> LENGTH: 1401
<212> TYPE: DNA
<213> ORGANISM: Artificial Sequence
<220> FEATURE:
<223> OTHER INFORMATION: Sequence encoding SEQ ID NO:7 codon optimized
      for expression in Escherichia coli

<400> SEQUENCE: 8
atggaaaata aaaccgaaac caccgtccgt cgccgtcgtc gtatcattct gttcccggtc      60
ccgttccaag gtcacatcaa cccgattctg cagctggcca acgtgctgta tagcaaaggt     120
ttctctatca ccatcttcca tacgaacttc aacaaaccga aacctctaa ctacccgcac     180 tttacgttcc gttttattct ggataacgac ccgcaggatg aacgcatcag taatctgccg     240
acccatggtc cgctggcggg tatgcgtatt ccgattatca cgaacacgg cgcagatgaa     300 ctgcgtcgcg aactggaact gctgatgctg gcctctgaag aagatgaaga agttagttgc     360
ctgatcaccg acgcactgtg gtattttgcc cagagtgttg cagattccct gaacctgcgt     420
cgcctggtcc tgatgacgag ctctctgttc aattttcatg cccacgtttc cctgccgcag     480
ttcgatgaac tgggttatct ggacccggat gacaaaaccc gcctggaaga caagcttca     540 ggctttccga tgctgaaagt caaagatatt aaaagtgcgt actccaactg gcagattctg     600
aaagaaatcc tgggtaaaat gatcaaacaa cccgtgcaa gttccggcgt catcctggaat    660 tccttcaaag aactggaaga atcagaactg gaaacggtga ttcgcgaaat cccggctccg    720
tcttttctga ttccgctgcc gaaacatctg accgcgtcat cgagctctct gctggatcac    780
gaccgtacgg tgtttcagtg gctggatcag caaccgccga gttccgtgct gtacgttagc    840
ttcggtagca cctctgaagt ggatgaaaaa gactttctgg aaatcgctcg tggcctggtt    900
gattcaaaac aatcgttcct gtgggtggtt cgcccgggtt ttgtgaaagg cagcacgtgg    960
gttgaaccgc tgccggatgg cttcctgggt aacgtggtc gcattgtcaa atgggtgccg   1020
cagcaagaag tgctggcaca tggtgctatc ggcgcgtttt ggacccactc aggttggaac   1080
tcgacgctgg aaagcgtttg tgaaggtgtc ccgatgattt tctcggattt tggcctggac   1140
cagccgctga atgcacgtta tatgagcgat gttctgaaag tcggtgtgta cctggaaaac   1200
ggttgggaac gcggcgaaat tgcgaatgcc atccgtcgcg ttatggtcga tgaagaaggc   1260
gaatatatcc gtcagaatgc tcgcgtcctg aaacaaaaag cggacgttag tctgatgaaa   1320

```
ggcggttcat cgtacgaatc cctggaatca ctggtctcct acatttcttc tctgggctcg    1380
catcatcatc atcatcatta a                                              1401
```

<210> SEQ ID NO 9
<211> LENGTH: 472
<212> TYPE: PRT
<213> ORGANISM: Oryza sativa

<400> SEQUENCE: 9

```
Met His Gln His Gln His Gln Ser Gly Ser Met Asp Ser Gly Tyr Ser
1               5                   10                  15

Ser Ser Tyr Ala Ala Ala Ala Gly Met His Val Val Ile Cys Pro Trp
            20                  25                  30

Leu Ala Phe Gly His Leu Leu Pro Cys Leu Asp Leu Ala Gln Arg Leu
        35                  40                  45

Ala Ser Arg Gly His Arg Val Ser Phe Val Ser Thr Pro Arg Asn Ile
    50                  55                  60

Ser Arg Leu Pro Pro Val Arg Pro Ala Leu Ala Pro Leu Val Ala Phe
65                  70                  75                  80

Val Ala Leu Pro Leu Pro Arg Val Glu Gly Leu Pro Asp Gly Ala Glu
                85                  90                  95

Ser Thr Asn Asp Val Pro His Asp Arg Pro Asp Met Val Glu Leu His
            100                 105                 110

Arg Arg Ala Phe Asp Gly Leu Ala Ala Pro Phe Ser Glu Phe Leu Gly
        115                 120                 125

Thr Ala Cys Ala Asp Trp Val Ile Val Asp Val Phe His His Trp Ala
    130                 135                 140

Ala Ala Ala Ala Leu Glu His Lys Val Pro Cys Ala Met Met Leu Leu
145                 150                 155                 160

Gly Ser Ala His Met Ile Ala Ser Ile Ala Asp Arg Arg Leu Glu Arg
                165                 170                 175

Ala Glu Thr Glu Ser Pro Ala Ala Gly Gln Gly Arg Pro Ala Ala
            180                 185                 190

Ala Pro Thr Phe Glu Val Ala Arg Met Lys Leu Ile Arg Thr Lys Gly
        195                 200                 205

Ser Ser Gly Met Ser Leu Ala Glu Arg Phe Ser Leu Thr Leu Ser Arg
    210                 215                 220

Ser Ser Leu Val Val Gly Arg Ser Cys Val Glu Phe Glu Pro Glu Thr
225                 230                 235                 240

Val Pro Leu Leu Ser Thr Leu Arg Gly Lys Pro Ile Thr Phe Leu Gly
                245                 250                 255

Leu Met Pro Pro Leu His Glu Gly Arg Arg Glu Asp Gly Glu Asp Ala
            260                 265                 270

Thr Val Arg Trp Leu Asp Ala Gln Pro Ala Lys Ser Val Val Tyr Val
        275                 280                 285

Ala Leu Gly Ser Glu Val Pro Leu Gly Val Glu Lys Val His Glu Leu
    290                 295                 300

Ala Leu Gly Leu Glu Leu Ala Gly Thr Arg Phe Leu Trp Ala Leu Arg
305                 310                 315                 320

Lys Pro Thr Gly Val Ser Asp Ala Asp Leu Leu Pro Ala Gly Phe Glu
                325                 330                 335

Glu Arg Thr Arg Gly Arg Gly Val Val Ala Thr Arg Trp Val Pro Gln
            340                 345                 350
```

```
Met Ser Ile Leu Ala His Ala Ala Val Gly Ala Phe Leu Thr His Cys
            355                 360                 365

Gly Trp Asn Ser Thr Ile Glu Gly Leu Met Phe Gly His Pro Leu Ile
370                 375                 380

Met Leu Pro Ile Phe Gly Asp Gln Gly Pro Asn Ala Arg Leu Ile Glu
385                 390                 395                 400

Ala Lys Asn Ala Gly Leu Gln Val Ala Arg Asn Asp Gly Asp Gly Ser
                405                 410                 415

Phe Asp Arg Glu Gly Val Ala Ala Ile Arg Ala Val Ala Val Glu
                420                 425                 430

Glu Glu Ser Ser Lys Val Phe Gln Ala Lys Ala Lys Lys Leu Gln Glu
            435                 440                 445

Ile Val Ala Asp Met Ala Cys His Glu Arg Tyr Ile Asp Gly Phe Ile
450                 455                 460

Gln Gln Leu Arg Ser Tyr Lys Asp
465                 470

<210> SEQ ID NO 10
<211> LENGTH: 1419
<212> TYPE: DNA
<213> ORGANISM: Oryza sativa

<400> SEQUENCE: 10
```

| | | | | | |
|---|---|---|---|---|---|
| atgcatcagc | accaacatca | gagcggttct | atggactccg | gctactcctc | ctcctacgcc | 60 |
| gccgccgccg | ggatgcacgt | cgtgatctgc | ccgtggctcg | ccttcggcca | cctgctcccg | 120 |
| tgcctcgacc | tcgcccagcg | cctcgcgtcg | cggggccacc | gcgtgtcgtt | cgtctccacg | 180 |
| ccgcggaaca | tatcccgcct | cccgccggtg | cgcccgcgc | tcgcgccgct | cgtcgccttc | 240 |
| gtggcgctgc | cgctcccgcg | cgtcgagggg | ctccccgacg | cgccgagtc | caccaacgac | 300 |
| gtcccccacg | acaggccgga | catggtcgag | ctccaccgga | gggccttcga | cgggctcgcc | 360 |
| gcgcccttct | cggagttctt | gggcaccgcg | tgcgccgact | gggtcatcgt | cgacgtcttc | 420 |
| caccactggg | ccgcagccgc | cgctctcgag | cacaaggtgc | catgtgcaat | gatgttgttg | 480 |
| ggctctgcac | atatgatcgc | ttccatagca | gacagacggc | tcgagcgcgc | ggagacagag | 540 |
| tcgcctgcgg | ctgccgggca | gggacgccca | gcggcggcgc | caacgttcga | ggtggcgagg | 600 |
| atgaagttga | tacgaaccaa | aggctcatcg | gaatgtccc | tcgccgagcg | cttctccttg | 660 |
| acgctctcga | ggagcagcct | cgtcgtcggg | cggagctgcg | tggagttcga | gccggagacc | 720 |
| gtcccgctcc | tgtcgacgct | ccgcggtaag | cctattacct | tccttggcct | tatgccgccg | 780 |
| ttgcatgaag | gccgccgcga | ggacggcgag | gatgccaccg | tccgctggct | cgacgcgcag | 840 |
| ccggccaagt | ccgtcgtgta | cgtcgcgcta | ggcagcgagg | tgccactggg | agtgagaag | 900 |
| gtccacgagc | tcgcgctcgg | gctggagctc | gccgggacgc | gcttcctctg | ggctcttagg | 960 |
| aagcccactg | gcgtctccga | cgccgacctc | ctccccgccg | gcttcgagga | gcgcacgcgc | 1020 |
| ggccgcggcg | tcgtggcgac | gagatgggtt | cctcagatga | gcatactggc | gcacgccgcc | 1080 |
| gtgggcgcgt | tcctgaccca | ctgcggctgg | aactcgacca | tcgagggct | catgttcggc | 1140 |
| cacccgctta | tcatgctgcc | gatcttcggc | gaccagggac | cgaacgcgcg | gctaatcgag | 1200 |
| gcgaagaacg | ccggattgca | ggtggcaaga | acgacggcg | atggatcgtt | cgaccgagaa | 1260 |
| ggcgtcgcgg | cggcgattcg | tgcagtcgcg | gtggaggaag | aaagcagcaa | agtgtttcaa | 1320 |
| gccaaagcca | gaagctgca | ggagatcgtc | gcggacatgg | cctgccatga | gaggtacatc | 1380 |
| gacggattca | ttcagcaatt | gagatcttac | aaggattga | | | 1419 |

<210> SEQ ID NO 11

<400> SEQUENCE: 11

000

<210> SEQ ID NO 12

<400> SEQUENCE: 12

000

<210> SEQ ID NO 13
<211> LENGTH: 460
<212> TYPE: PRT
<213> ORGANISM: Stevia rebaudiana

<400> SEQUENCE: 13

```
Met Ala Glu Gln Gln Lys Ile Lys Lys Ser Pro His Val Leu Leu Ile
 1               5                  10                  15

Pro Phe Pro Leu Gln Gly His Ile Asn Pro Phe Ile Gln Phe Gly Lys
                20                  25                  30

Arg Leu Ile Ser Lys Gly Val Lys Thr Thr Leu Val Thr Thr Ile His
            35                  40                  45

Thr Leu Asn Ser Thr Leu Asn His Ser Asn Thr Thr Thr Thr Ser Ile
        50                  55                  60

Glu Ile Gln Ala Ile Ser Asp Gly Cys Asp Glu Gly Phe Met Ser
 65                  70                  75                  80

Ala Gly Glu Ser Tyr Leu Glu Thr Phe Lys Gln Val Gly Ser Lys Ser
                85                  90                  95

Leu Ala Asp Leu Ile Lys Lys Leu Gln Ser Gly Thr Thr Ile Asp
                100                 105                 110

Ala Ile Ile Tyr Asp Ser Met Thr Glu Trp Val Leu Asp Val Ala Ile
            115                 120                 125

Glu Phe Gly Ile Asp Gly Gly Ser Phe Phe Thr Gln Ala Cys Val Val
        130                 135                 140

Asn Ser Leu Tyr Tyr His Val His Lys Gly Leu Ile Ser Leu Pro Leu
145                 150                 155                 160

Gly Glu Thr Val Ser Val Pro Gly Phe Pro Val Leu Gln Arg Trp Glu
                165                 170                 175

Thr Pro Leu Ile Leu Gln Asn His Glu Gln Ile Gln Ser Pro Trp Ser
            180                 185                 190

Gln Met Leu Phe Gly Gln Phe Ala Asn Ile Asp Gln Ala Arg Trp Val
        195                 200                 205

Phe Thr Asn Ser Phe Tyr Lys Leu Glu Glu Val Ile Glu Trp Thr
        210                 215                 220

Arg Lys Ile Trp Asn Leu Lys Val Ile Gly Pro Thr Leu Pro Ser Met
225                 230                 235                 240

Tyr Leu Asp Lys Arg Leu Asp Asp Asp Lys Asp Asn Gly Phe Asn Leu
                245                 250                 255

Tyr Lys Ala Asn His His Glu Cys Met Asn Trp Leu Asp Asp Lys Pro
            260                 265                 270

Lys Glu Ser Val Val Tyr Val Ala Phe Gly Ser Leu Val Lys His Gly
        275                 280                 285

Pro Glu Gln Val Glu Glu Ile Thr Arg Ala Leu Ile Asp Ser Asp Val
        290                 295                 300
```

```
Asn Phe Leu Trp Val Ile Lys His Lys Glu Glu Gly Lys Leu Pro Glu
305                 310                 315                 320

Asn Leu Ser Glu Val Ile Lys Thr Gly Lys Gly Leu Ile Val Ala Trp
            325                 330                 335

Cys Lys Gln Leu Asp Val Leu Ala His Glu Ser Val Gly Cys Phe Val
        340                 345                 350

Thr His Cys Gly Phe Asn Ser Thr Leu Glu Ala Ile Ser Leu Gly Val
    355                 360                 365

Pro Val Val Ala Met Pro Gln Phe Ser Asp Gln Thr Thr Asn Ala Lys
370                 375                 380

Leu Leu Asp Glu Ile Leu Gly Val Gly Val Arg Val Lys Ala Asp Glu
385                 390                 395                 400

Asn Gly Ile Val Arg Arg Gly Asn Leu Ala Ser Cys Ile Lys Met Ile
                405                 410                 415

Met Glu Glu Glu Arg Gly Val Ile Ile Arg Lys Asn Ala Val Lys Trp
            420                 425                 430

Lys Asp Leu Ala Lys Val Ala Val His Glu Gly Gly Ser Ser Asp Asn
        435                 440                 445

Asp Ile Val Glu Phe Val Ser Glu Leu Ile Lys Ala
    450                 455                 460

<210> SEQ ID NO 14
<211> LENGTH: 1383
<212> TYPE: DNA
<213> ORGANISM: Stevia rebaudiana

<400> SEQUENCE: 14
atggcggaac aacaaaagat caagaaatca ccacacgttc tactcatccc attccctta       60
caaggccata taaaccctt catccagttt ggcaaacgat taatctccaa aggtgtcaaa      120
acaacacttg ttaccaccat ccacacctta aactcaaccc taaaccacag taacaccacc      180
accacctcca tcgaaatcca agcaatttcc gatggttgtg atgaaggcgg ttttatgagt      240
gcaggagaat catatttgga acattcaaa caagttgggt ctaaatcact agctgactta      300
atcaagaagc ttcaaagtga aggaaccaca attgatgcaa tcatttatga ttctatgact      360
gaatgggttt tagatgttgc aattgagttt ggaatcgatg tggttcgtt tttcactcaa      420
gcttgtgttg taaacagctt atattatcat gttcataagg gtttgatttc tttgccattg      480
ggtgaaactg tttcggttcc tggatttcca gtgcttcaac ggtgggagac accgttaatt      540
ttgcagaatc atgagcaaat acagagccct tggtctcaga tgttgtttgg tcagtttgct      600
aatattgatc aagcacgttg ggtcttcaca aatagttttt acaagctcga ggaagaggta      660
atagagtgga cgagaaagat atggaacttg aaggtaatcg ggccaacact tccatccatg      720
taccttgaca aacgacttga tgatgataaa gataacggat taatctctca caaagcaaac      780
catcatgagt gcatgaactg gttagacgat aagccaaagg aatcagttgt tacgtagca       840
tttggtagcc tggtgaaaca tggacccgaa caagtggaag aaatcacacg ggctttaata      900
gatagtgatg tcaacttctt gtgggttatc aaacataaag aagagggaaa gctcccagaa      960
aatctttcgg aagtaataaa aaccggaaag ggtttgattg tagcatggtg caaacaattg     1020
gatgtgttag cacacgaatc agtaggatgc tttgttacac attgtgggtt caactcaact     1080
cttgaagcaa taagtcttgg agtccccgtt gttgcaatgc ctcaattttc ggatcaaact     1140
acaaatgcca agcttctaga tgaaattttg ggtgttggag ttagagttaa ggctgatgag     1200
```

```
aatgggatag tgagaagagg aaatcttgcg tcatgtatta agatgattat ggaggaggaa    1260
agaggagtaa taatccgaaa gaatgcggta aaatggaagg atttggctaa agtagccgtt    1320
catgaaggtg gtagctcaga caatgatatt gtcgaatttg taagtgagct aattaaggct    1380
taa                                                                 1383
```

<210> SEQ ID NO 15
<211> LENGTH: 806
<212> TYPE: PRT
<213> ORGANISM: Stevia rebaudiana

<400> SEQUENCE: 15

```
Met Ala Glu Arg Val Leu Thr Arg Val His Ser Leu Arg Glu Arg Leu
1               5                   10                  15

Asp Ser Thr Leu Ala Thr His Arg Asn Glu Ile Leu Leu Phe Leu Ser
            20                  25                  30

Arg Ile Glu Ser His Gly Lys Gly Ile Leu Lys Pro His Gln Val Met
        35                  40                  45

Thr Glu Phe Glu Ala Ile Cys Lys Glu Asp Gln Ser Lys Leu Ser Asp
    50                  55                  60

Gly Ala Phe Tyr Glu Val Leu Lys Cys Thr Gln Glu Ala Ile Val Gln
65                  70                  75                  80

Pro Pro Trp Val Ala Leu Ala Ile Arg Leu Arg Pro Gly Val Trp Glu
                85                  90                  95

Tyr Val Arg Val Asn Val Asn Val Leu Val Val Glu Glu Leu Ser Val
            100                 105                 110

Pro Glu Tyr Leu His Phe Lys Glu Glu Leu Val Asn Gly Thr Ser Asn
        115                 120                 125

Gly Asn Phe Val Leu Glu Leu Asp Phe Glu Pro Phe Thr Ala Ser Phe
    130                 135                 140

Pro Arg Pro Thr Leu Thr Lys Ser Ile Gly Asn Gly Val Glu Phe Leu
145                 150                 155                 160

Asn Arg His Leu Ser Ala Lys Met Phe His Asp Lys Asp Ser Met His
                165                 170                 175

Pro Leu Leu Asp Phe Leu Arg Thr His His Tyr Lys Gly Lys Thr Met
            180                 185                 190

Met Leu Asn Asp Arg Ile Gln Asn Leu Asn Ala Leu Gln Ser Val Leu
        195                 200                 205

Arg Lys Ala Ser Glu Tyr Leu Ser Thr Leu Asp Ala Ala Thr Pro Tyr
    210                 215                 220

Ser Glu Phe Glu His Lys Phe Gln Glu Ile Gly Leu Glu Arg Gly Trp
225                 230                 235                 240

Gly Asp Lys Ala Glu Val Val Met Glu Met Ile His Met Leu Leu Asp
                245                 250                 255

Leu Leu Glu Ala Pro Asp Ala Cys Thr Leu Glu Lys Phe Leu Gly Arg
            260                 265                 270

Ile Pro Met Val Phe Asn Val Val Ile Leu Ser Pro His Gly Tyr Phe
        275                 280                 285

Ala Gln Glu Asn Val Leu Gly Tyr Pro Asp Thr Gly Gly Gln Val Val
    290                 295                 300

Tyr Ile Leu Asp Gln Val Pro Ala Leu Glu Arg Glu Met Leu Lys Arg
305                 310                 315                 320

Ile Lys Glu Gln Gly Leu Asp Ile Ile Pro Arg Ile Leu Ile Val Thr
                325                 330                 335
```

```
Arg Leu Leu Pro Asp Ala Val Gly Thr Thr Cys Gly Gln Arg Leu Glu
            340                 345                 350
Lys Val Phe Gly Ala Glu His Ser His Ile Leu Arg Val Pro Phe Arg
        355                 360                 365
Thr Glu Lys Gly Ile Leu Arg Lys Trp Ile Ser Arg Phe Glu Val Trp
    370                 375                 380
Pro Tyr Ile Glu Thr Phe Thr Glu Asp Val Ala Lys Glu Val Thr Ala
385                 390                 395                 400
Glu Leu Gln Ala Lys Pro Asp Leu Ile Ile Gly Asn Tyr Ser Glu Gly
                405                 410                 415
Asn Leu Val Ala Ser Leu Leu Ala His Lys Leu Gly Val Thr Gln Cys
            420                 425                 430
Thr Ile Ala His Ala Leu Glu Lys Thr Lys Tyr Pro Asp Ser Asp Ile
        435                 440                 445
Tyr Trp Lys Asn Phe Glu Glu Lys Tyr His Phe Ser Ser Gln Phe Thr
    450                 455                 460
Ala Asp Leu Ile Ala Met Asn His Thr Asp Phe Ile Ile Thr Ser Thr
465                 470                 475                 480
Phe Gln Glu Ile Ala Gly Ser Lys Asp Thr Val Gly Gln Tyr Glu Ser
                485                 490                 495
His Thr Ala Phe Thr Met Pro Gly Leu Tyr Arg Val Val His Gly Ile
            500                 505                 510
Asp Val Phe Asp Pro Lys Phe Asn Ile Val Ser Pro Gly Ala Asp Met
        515                 520                 525
Gly Ile Tyr Tyr Ser Tyr Thr Glu Lys Glu Lys Arg Leu Thr Ala Leu
    530                 535                 540
His Pro Glu Ile Asp Glu Leu Leu Phe Ser Ser Val Glu Asn Glu Glu
545                 550                 555                 560
His Leu Cys Val Leu Lys Asp Lys Ser Lys Pro Ile Leu Phe Thr Met
                565                 570                 575
Ala Arg Leu Asp Asn Val Lys Asn Leu Thr Gly Leu Val Glu Trp Tyr
            580                 585                 590
Ala Lys Asn Asp Arg Leu Arg Glu Leu Val Asn Leu Val Val Val Gly
        595                 600                 605
Gly Asp Arg Arg Lys Glu Ser Lys Asp Leu Glu Glu Gln Ala Gln Met
    610                 615                 620
Gln Lys Met His Glu Leu Ile Glu Thr Tyr Lys Leu Asn Gly Gln Phe
625                 630                 635                 640
Arg Trp Ile Ser Ser Gln Met Asn Arg Val Arg Asn Gly Glu Leu Tyr
                645                 650                 655
Arg Val Ile Ala Asp Thr Arg Gly Ala Phe Ile Gln Pro Ala Phe Tyr
            660                 665                 670
Glu Ala Phe Gly Leu Thr Val Val Glu Ala Met Thr Cys Gly Leu Pro
        675                 680                 685
Thr Phe Ala Thr Leu His Gly Gly Pro Ala Glu Ile Ile Val His Gly
    690                 695                 700
Lys Ser Gly Phe His Ile Asp Pro Tyr His Gly Asp Gln Val Thr Glu
705                 710                 715                 720
Leu Leu Val Asn Phe Phe Glu Lys Thr Lys Gln Asp Pro Gly His Trp
                725                 730                 735
Glu Ala Ile Ser Lys Gly Gly Leu Gln Arg Ile Gln Glu Lys Tyr Thr
            740                 745                 750
Trp Gln Ile Tyr Ser Asp Arg Leu Leu Thr Leu Ala Gly Val Tyr Gly
```

```
            755                 760                 765
Phe Trp Lys His Val Ser Lys Leu Asp Arg Leu Glu Ile Arg Arg Tyr
    770                 775                 780

Leu Glu Met Phe Tyr Ala Leu Lys Tyr Arg Lys Leu Ala Glu Ser Val
785                 790                 795                 800

Pro Leu Ala Val Asp Glu
            805

<210> SEQ ID NO 16
<211> LENGTH: 2421
<212> TYPE: DNA
<213> ORGANISM: Stevia rebaudiana

<400> SEQUENCE: 16
atggcggaac gtgtactcac tcgtgttcac agtcttcgtg agcgtctcga ttcaactctc      60
gcaactcatc gtaatgaaat cctcttgttt ctttcaagga ttgaaagcca tggaaaagga     120
atattgaagc tcatcaagt tatgactgaa tttgaagcta tctgcaaaga agatcagagc      180
aaactctctg atggtgcttt ttatgaagtt cttaaatgca cacaggaagc aatagtgcaa     240
cctccatggg ttgcactcgc gatccgtctt cgacccggtg tttgggaata tgttagagtc     300
aatgttaatg ttttggtggt tgaagaatta agtgttcctg aatatcttca cttcaaagaa     360
gaattggtta tgaacatc gaatggcaac ttcgtgttgg aactggatt tgaaccttt        420 accgcatcgt ttcctcgacc aactttaacc aagtctattg gtaatggtgt tgagtttcta     480
aacagacatt tatctgctaa atgtttcat gataaggata gcatgcaccc tcttcttgat      540
ttcctacgga ctcaccacta agggaaag acaatgatgt tgaatgatag aatccaaaac      600
ctcaatgctc tacaatcggt gttgcgaaag gcgtcagagt acttatcaac actcgacgca    660
gcaacaccgt actctgagtt tgaacataag tttcaagaaa tcgggttgga gagaggttgg     720
ggtgataaag cggaggtcgt aatggagatg atccacatgc ttctagacct tctagaagca     780
cccgacgcat gcacactcga aagtttctc ggaagaatcc caatggtttt caatgttgtc      840
attctttcgc ctcacggcta cttcgcccaa gaaaatgtgt gggatatacc cgacactggc     900
ggtcaggttg tttacatctt ggatcaagtt cccgctctgg aacgcgagat gctcaaaagg     960
attaaggagc aaggactcga tatcattcct cgtatattga ttgttacgag gcttcttccc    1020
gacgcggttg gaccacatg cgggcaacgt ttagagaaag tgtttggagc cgaacactcg     1080
catattcttc gggtcccgtt tagaaccgaa aagggtattc ttcgtaaatg gatctctcgt     1140
tttgaggtgt ggccttacat cgagactttc accgaggatg ttgctaaaga agttacagca     1200
gagttgcaag caaaaccaga tttgatcatt ggaaactata gtgaaggaaa tttggttgca     1260
tctttgctag ctcacaagtt gggtgtcact cagtgtacca ttgctcatgc tttggagaaa    1320
actaaatacc cggattctga tatctactgg aagaactttg aggagaaata tcatttctct    1380
tcgcagttta ccgctgatct tatcgctatg aaccataccg acttcatcat caccagtact    1440
ttccaagaaa ttgctggaag taggacacg gttggacagt acgagagtca taccgcgttc     1500
acaatgccgg gattgtatcg ggtggttcac gggatcgatg ttttgaccc caaattcaat     1560 attgtttcac ccggggccga tatgggaatt tactactcgt ataccgagaa agaaaagagg    1620
ctcactgcgc ttcaccctga aatcgatgaa cttctcttta gttccgtcga aaacgaagaa    1680
cacttatgtg tgttgaagga taagagtaaa ccaatcttgt tcacaatggc gcgattggat    1740
aatgtgaaga atttaaccgg actggttgaa tggtacgcta aaaacgaccg ccttcgtgag    1800
```

```
ctcgtgaacc tcgtggtcgt cggtggtgac cgaaggaaag agtcgaaaga tcttgaagaa   1860
caagctcaga tgcagaagat gcatgaactt atcgaaacct acaaactcaa cggtcagttc   1920
aggtggatat cctcacaaat gaaccgcgtg aggaacggtg agttgtatcg cgttattgct   1980
gacacacgag gtgcgtttat ccagcctgcg ttttacgagg cgtttgggtt gacggttgtg   2040
gaggccatga cttgtggcct gccgacattc gcgacacttc atggtgggcc cgctgagatt   2100
attgttcacg ggaaatccgg gttccatatt gacccgtatc acggtgacca ggtcaccgag   2160
ttgctggtca atttctttga gaaaactaaa caagacccgg gtcattggga ggccatttcc   2220
aagggtggtc tgcaacgtat tcaggagaaa tacacgtggc agatttattc agataggttg   2280
ttgacgcttg ccggagttta tggattctgg aagcatgtgt cgaagcttga caggctcgag   2340
atccgtcgtt atcttgaaat gttttacgcg ctcaagtatc gcaaactggc tgaatctgtt   2400
ccattggctg ttgatgagtg a                                             2421

<210> SEQ ID NO 17
<211> LENGTH: 810
<212> TYPE: PRT
<213> ORGANISM: Stevia rebaudiana

<400> SEQUENCE: 17

Met Ala Thr Ser Lys Leu Ser Arg Thr His Ser Met Arg Glu Arg Val
1               5                   10                  15

Glu Glu Thr Leu Ser Ala His Arg Asn Glu Ile Val Ser Leu Leu Ser
            20                  25                  30

Arg Tyr Val Ala Gln Gly Lys Ala Ile Leu Gln Pro His Gln Ile Leu
        35                  40                  45

His Glu Leu Glu Asn Ile Ile Gly Asp Val Thr Ser Arg Gln Lys Leu
    50                  55                  60

Thr Asp Gly Pro Phe Gly Asp Ala Leu Lys Thr Ala Gln Glu Cys Ile
65                  70                  75                  80

Val Leu Pro Pro Phe Val Ala Leu Ala Val Arg Pro Arg Pro Gly Val
                85                  90                  95

Trp Glu Tyr Val Arg Val Asp Ala Tyr Gln Leu Ser Val Glu Gln Leu
            100                 105                 110

Thr Val Ser Glu Tyr Leu Thr Phe Lys Glu Glu Leu Val Gly Glu Ser
        115                 120                 125

Asn Ser Ser Leu Met Leu Glu Leu Asp Phe Glu Pro Phe Asn Ala Ser
    130                 135                 140

Phe Pro Arg Pro Thr Arg Ser Ser Ser Ile Gly Asn Gly Val Gln Phe
145                 150                 155                 160

Leu Asn Arg His Leu Ser Ser Ser Met Phe Arg Ser Lys Asp Cys Leu
                165                 170                 175

Glu Pro Leu Leu Asp Phe Leu Arg Thr His Arg His Asn Gly His Val
            180                 185                 190

Met Met Leu Asn Asp Arg Ile Thr Ser Met Thr Arg Leu Gln Ser Ser
        195                 200                 205

Leu Val Lys Ala Glu Glu Tyr Leu Ser Lys Leu Pro Ser Asp Thr Asp
    210                 215                 220

Tyr Ser Glu Phe Gln Tyr Glu Leu Gln Gly Met Gly Phe Glu Arg Gly
225                 230                 235                 240

Trp Gly Asn Asn Ala Glu Arg Ile Ile Glu Met Met His Leu Leu Ser
                245                 250                 255

Asp Ile Leu Gln Ala Pro Asp Pro Ser Ile Leu Glu Ser Phe Leu Ala
```

```
              260                 265                 270
Arg Ile Pro Met Val Phe Asn Val Ile Leu Ser Ile His Gly Tyr
            275                 280                 285
Phe Gly Gln Ala Asn Val Leu Gly Leu Pro Asp Thr Gly Gln Ile
            290                 295                 300
Val Tyr Ile Leu Asp Gln Val Arg Ala Leu Glu Asn Glu Met Leu Leu
305                 310                 315                 320
Lys Leu Lys His Gln Gly Leu Asp Ile Lys Pro Arg Ile Leu Ile Val
            325                 330                 335
Thr Arg Leu Ile Pro Asp Ala Lys Gly Thr Ser Cys Asn Gln Arg Leu
            340                 345                 350
Glu Arg Val Ser Gly Thr Glu His Thr His Ile Leu Arg Val Pro Phe
            355                 360                 365
Arg Thr Glu Lys Gly Ile Leu Arg Lys Trp Ile Ser Arg Phe Asp Val
            370                 375                 380
Trp Pro Phe Leu Glu Lys Phe Thr Gln Asp Ala Ala Ser Glu Ile Ser
385                 390                 395                 400
Ala Glu Leu His Gly Thr Pro Asp Leu Ile Ile Gly Asn Tyr Ser Asp
            405                 410                 415
Gly Asn Leu Val Ala Ser Leu Leu Ser Tyr Lys Met Gly Val Thr Gln
            420                 425                 430
Cys Asn Ile Ala His Ala Leu Glu Lys Thr Lys Tyr Pro Asp Ser Asp
            435                 440                 445
Leu Tyr Trp Lys Lys Phe Asp Glu Lys Tyr His Phe Ser Cys Gln Phe
            450                 455                 460
Thr Ala Asp Leu Leu Ala Met Asn Asn Ala Asp Phe Ile Ile Thr Ser
465                 470                 475                 480
Thr Tyr Gln Glu Ile Ala Gly Thr Lys Asn Thr Val Gly Gln Tyr Glu
            485                 490                 495
Ser His Ser Ser Phe Thr Leu Pro Gly Leu Tyr Arg Val Val His Gly
            500                 505                 510
Ile Asp Val Phe Asp Pro Lys Phe Asn Ile Val Ser Pro Gly Ala Asp
            515                 520                 525
Met Ser Ile Tyr Phe Ser Tyr Thr Glu Lys Glu Lys Arg Leu Thr Ser
            530                 535                 540
Leu His Thr Thr Ile Glu Lys Leu Leu Phe Asp Pro Thr Gln Thr Glu
545                 550                 555                 560
Asp Tyr Ile Gly Asn Leu Ser Asp Lys Ser Lys Pro Ile Ile Phe Ser
            565                 570                 575
Met Ala Arg Leu Asp His Val Lys Asn Ile Thr Gly Leu Val Glu Trp
            580                 585                 590
Tyr Ala Lys Asn Glu Lys Leu Arg Gly Leu Ala Asn Leu Val Val Val
            595                 600                 605
Ala Gly Tyr Asn Asn Val Lys Arg Ser Ser Asp Arg Glu Glu Ile Ala
            610                 615                 620
Glu Ile Glu Lys Met His Gln Leu Ile Lys Lys Tyr Lys Leu Asp Gly
625                 630                 635                 640
Gln Met Arg Trp Ile Ser Ala Gln Thr Asn Arg Ala Gln Asn Gly Glu
            645                 650                 655
Leu Tyr Arg Tyr Ile Ala Asp Gly Arg Gly Ile Phe Val Gln Pro Ala
            660                 665                 670
Ile Tyr Glu Ala Phe Gly Leu Thr Val Val Glu Ala Met Thr Cys Gly
            675                 680                 685
```

```
Leu Pro Thr Phe Ala Thr Cys His Gly Gly Pro Gly Glu Ile Ile Glu
        690                 695                 700

Asn Gly Val Ser Gly Phe His Ile Asp Pro Tyr His Pro Asp Thr Ala
705                 710                 715                 720

Ser Ala Thr Met Ala Asp Phe Phe Gln Lys Cys Lys Glu Asp Pro Ser
                725                 730                 735

Tyr Trp Phe Lys Ile Ser Glu Ala Gly Leu Lys Arg Ile Tyr Glu Arg
                740                 745                 750

Tyr Thr Trp Lys Ile Tyr Ser Glu Arg Leu Met Thr Leu Ala Gly Val
            755                 760                 765

Tyr Ser Phe Trp Lys Tyr Val Ser Lys Leu Glu Arg Arg Glu Thr Arg
        770                 775                 780

Arg Tyr Leu Glu Met Phe Tyr Ile Leu Lys Phe Arg Asp Leu Val Lys
785                 790                 795                 800

Ser Val Pro Val Ala Thr Asp Asp Glu Ala
                805                 810

<210> SEQ ID NO 18
<211> LENGTH: 2433
<212> TYPE: DNA
<213> ORGANISM: Stevia rebaudiana

<400> SEQUENCE: 18
atggcgacaa gtaagttgag cagaacgcat agtatgcgtg agcgtgttga agaaactctt      60
tccgctcatc gcaacgaaat cgtttctctt ctttctaggt atgtggctca ggggaaggcg     120
atattgcagc cgcatcagat actccatgaa cttgagaata tcatcggtga tgttacttcg     180
cgccaaaagc ttacagatgg tccgtttgga gatgcgttga agacagcaca ggaatgtata     240
gttctacctc catttgtagc tttagcagtt cgtccaagac ctggtgtttg gaatacgtg      300 cgcgtggatg catatcaact aagtgtggaa caactaactg tttcagagta tcttaccttc     360
aaagaagaac ttgttggaga gtctaatagt tctttaatgc tcgagttgga ttttgagcca     420
tttaatgctt cgtttcctag accaacccgt tcttcatcca ttggcaatgg agttcagttc     480
ctgaatcgcc acctgtcgtc aagcatgttt cgcagcaaag attgtttaga accgcttctg     540
gatttcctac gcacacacag acataatgga catgtaatga tgttaaatga ccgcataaca     600
agcatgacta gacttcaatc ttctttggtc aaagcagagg aatatctttc taaactacca     660
tctgatacag actactctga gtttcaatat gaattgcaag gaatgggttt tgaaagagga     720
tggggaaaca atgctgaaag aatcattgag atgatgcatc ttctctcaga cattctacaa     780
gctccagatc cttccatttt ggaatctttt cttgctagaa taccatggt gtttaatgtt      840 gttatattat caatacatgg ctactttggg caagcaaatg ttttgggttt gccagatact     900
ggtggccaga ttgtatatat attggatcaa gtccgtgcat ggaaaatga dgatgcttctt    960 aaattaaagc accaaggact ggatatcaaa cctaggattc tgattgtgac tcggttaata    1020
cctgatgcaa aaggtacttc atgtaaccaa cgactggaaa gagtcagtgg aactgaacac    1080
acacatatac ttcgtgttcc ttttagaacc gagaaaggaa ttcttcgtaa atggatctca    1140
aggtttgatg tatggccttt tttggagaaa tttacacagg atgcagcaag tgaaatttct    1200
gctgagttgc atggtactcc agatcttata attggaaatt atagtgatgg caatcttgtt    1260
gcctctttat tatcttacaa aatgggagta acccagtgta acattgctca tgctttagag    1320
aaaacaaagt atccagattc tgatttatat tggaagaaat ttgatgagaa atatcacttt    1380
```

-continued

```
tcttgtcaat ttactgctga tcttttagcc atgaacaatg cagattttat catcaccagc    1440
acataccaag aaatcgcggg aacgaaaaat actgtcggac aatacgagag tcattcgtct    1500
ttcactctcc cggggctcta cagggttgtt catggtattg acgtttttga ccctaagttc    1560
aacattgtgt ctccaggggc agatatgtct atatacttct catacaccga aaggaaaaa     1620
agacttacat ctcttcatac tacaattgag aagttattgt ttgaccctac acaaactgaa    1680
gattacattg gaaatctgag tgataaatca aaaccgataa ttttttcaat ggcaagactt    1740
gatcatgtga agaacattac gggtctggtt gagtggtacg ctaagaatga aagcttaga     1800
ggactagcaa accttgttgt ggttgctggt tataataatg tgaagaggtc tagtgacaga    1860
gaagaaattg cagaaattga aaaatgcat caacttatta agaaatacaa attagatggt     1920
cagatgagat ggatttcagc acaaacaaac cgcgcacaaa atggtgaact ttatcgctat    1980
attgctgatg aagggggaat ctttgtacag cccgctattt atgaagcttt tgggctgaca    2040
gtggtggagg ccatgacttg tgggcttcca acatttgcaa cttgccatgg tgggccagga    2100
gagataattg aaaatggtgt tcgggcttc catatcgacc cgtatcatcc ggatactgca     2160
tcagccacaa tggctgattt ttttcagaaa tgcaaggagg acccgagtta ttggttcaag    2220
atatctgaag cagggcttaa aagaatatat gaaaggtaca catggaaat ttactctgaa     2280
cggttgatga cattagctgg agtttatagc ttctggaagt atgtctcgaa acttgagaga    2340
cgtgaaacaa gacgatatct tgagatgttt tatattctta agttccgtga tctggtaaaa    2400
tctgttccag tggctactga tgatgaggct tag                                 2433
```

<210> SEQ ID NO 19
<211> LENGTH: 811
<212> TYPE: PRT
<213> ORGANISM: Stevia rebaudiana

<400> SEQUENCE: 19

```
Met Ala Thr Pro Lys Leu Thr Arg Thr Pro Ser Met Arg Glu Arg Leu
1               5                   10                  15

Glu Glu Thr Leu Ser Ala His Arg Asn Asp Ile Val Ser Leu Leu Ser
            20                  25                  30

Arg Tyr Val Asp Gln Gly Lys Ala Ile Leu Gln Pro His Leu Leu
        35                  40                  45

Asp Glu Ile Asp Asn Phe Ile Gly Asp Gln Asn Cys Arg Gln Lys Leu
    50                  55                  60

Ala Asp Ser Leu Phe Gly Glu Ile Leu Lys Ser Ala Gln Glu Gly Ile
65                  70                  75                  80

Ile Leu Pro Pro Tyr Val Thr Leu Ala Val Arg Pro Arg Pro Gly Val
                85                  90                  95

Trp Asp Phe Leu Arg Val Asn Val Asp Glu Leu Ser Val Glu Gln Leu
            100                 105                 110

Thr Val Ser Glu Tyr Leu Ser Phe Lys Glu Glu Leu Val Asp Gly Gln
        115                 120                 125

Ser Arg Asn Pro Phe Val Leu Glu Leu Asp Leu Glu Pro Phe Asn Ala
    130                 135                 140

Thr Phe Pro Arg Met Ser Arg Ser Ser Ile Gly Asn Gly Val Gln
145                 150                 155                 160

Phe Leu Asn Arg His Leu Ser Ser Ile Met Phe Arg Asn Lys Asp Cys
                165                 170                 175

Met Asp Pro Phe Leu Asp Phe Leu Arg Ala His Lys His Lys Gly Tyr
            180                 185                 190
```

```
Ala Met Met Leu Asn Asp Arg Ile Gln Thr Met Ser Arg Leu Glu Ser
        195                 200                 205

Ser Leu Ala Lys Ala Glu Asp His Leu Ser Lys Leu Pro Pro Glu Thr
    210                 215                 220

Pro Tyr Ser Glu Phe Glu Tyr Val Leu Gln Gly Met Gly Phe Glu Arg
225                 230                 235                 240

Gly Trp Gly Asp Asn Cys Glu Arg Val Leu Gly Met Met His Leu Leu
                245                 250                 255

Ser Asp Ile Leu Gln Ala Pro Asp Pro Ser Ile Leu Glu Lys Phe Leu
            260                 265                 270

Gly Lys Met Pro Met Ile Phe Asn Val Val Leu Ser Ile His Gly
        275                 280                 285

Tyr Phe Gly Gln Ala Asn Val Leu Gly Leu Pro Asp Thr Gly Gly Gln
    290                 295                 300

Val Val Tyr Ile Leu Asp Gln Val Arg Ser Leu Glu Asn Glu Met Leu
305                 310                 315                 320

Leu Lys Leu Arg His Gln Gly Leu Asp Ile Lys Pro Lys Ile Leu Ile
                325                 330                 335

Val Thr Arg Leu Ile Pro Asn Ala Lys Gly Thr Ser Cys Asn Gln Arg
            340                 345                 350

Leu Glu Lys Val Ser Gly Thr Glu Tyr Thr Tyr Ile Leu Arg Val Pro
        355                 360                 365

Phe Arg Thr Glu Lys Gly Ile Leu Gly Lys Trp Leu Ser Arg Phe Asp
    370                 375                 380

Ile Trp Pro Tyr Leu Glu Ala Phe Thr Thr Asp Ala Ala Ser Glu Ile
385                 390                 395                 400

Ala Ala Glu Leu His Gly Val Pro Asp Leu Leu Ile Gly Asn Tyr Ser
                405                 410                 415

Asp Gly Asn Leu Val Ala Ser Leu Leu Ser Asn Lys Leu Gly Val Thr
            420                 425                 430

Gln Cys Asn Ile Ala His Ala Leu Glu Lys Thr Lys Tyr Pro Asp Ser
        435                 440                 445

Asp Leu Tyr Trp Lys Lys Phe Glu Asp Lys Tyr His Phe Ser Cys Gln
    450                 455                 460

Phe Thr Ala Asp Leu Leu Ala Met Asn Asn Ala Asp Phe Ile Ile Thr
465                 470                 475                 480

Ser Thr Tyr Gln Glu Ile Ala Gly Thr Lys Asn Thr Val Gly Gln Tyr
                485                 490                 495

Glu Asn His Ser Ser Phe Thr Leu Pro Gly Leu Tyr Arg Val Val His
            500                 505                 510

Gly Ile Asp Val Phe Asp Pro Lys Phe Asn Ile Val Ser Pro Gly Ala
        515                 520                 525

Asp Met Ala Ile Tyr Phe Ser Tyr Ala Asp Lys Glu Arg Arg Leu Thr
    530                 535                 540

Ser Leu His Pro Thr Ile Glu Lys Leu Leu Phe Asp Thr Glu Gln Asn
545                 550                 555                 560

Asp Val His Ile Gly Asn Ile Asn Asp Pro Ser Lys Pro Met Ile Phe
                565                 570                 575

Thr Met Ala Arg Leu Asp His Val Lys Asn Ile Thr Gly Phe Val Glu
            580                 585                 590

Cys Tyr Ala Lys Asn Asn Lys Leu Arg Glu His Ala Asn Leu Val Val
        595                 600                 605
```

```
Ile Ala Gly Tyr Asn Asp Ala Lys Lys Ser Ser Asp Arg Glu Ile
    610                 615                 620
Ala Glu Ile Glu Lys Met His Asn Leu Ile Lys Gln Tyr Lys Leu Asp
625                 630                 635                 640
Gly Gln Met Arg Trp Ile Ser Ala Gln Thr Asn Arg Ala Arg Asn Gly
            645                 650                 655
Glu Phe Tyr Arg Tyr Ile Ala Asp Gly Arg Gly Val Phe Val Gln Pro
        660                 665                 670
Ala Phe Tyr Glu Ala Phe Gly Leu Thr Val Val Glu Ala Met Thr Cys
    675                 680                 685
Gly Leu Pro Thr Phe Ala Thr Cys His Gly Gly Pro Ala Glu Ile Ile
690                 695                 700
Glu Asp Gly Val Ser Gly Phe His Ile Asp Pro Tyr His Pro Asp Lys
705                 710                 715                 720
Met Ser Thr Thr Leu Ala Asp Phe Phe Gln Lys Cys Lys Glu Glu Pro
            725                 730                 735
Ser Tyr Trp Gly Lys Ile Ser Asp Gly Gly Leu Lys Arg Ile Ser Glu
        740                 745                 750
Arg Tyr Thr Trp Lys Ile Tyr Ser Glu Arg Leu Met Thr Leu Ala Gly
    755                 760                 765
Val Tyr Ser Phe Trp Lys Tyr Val Ser Lys Leu Glu Arg Arg Glu Thr
770                 775                 780
Arg Arg Tyr Leu Glu Met Phe Tyr Ile Leu Lys Phe Arg Gln Leu Val
785                 790                 795                 800
Lys Ser Val Pro Leu Ala Val Asp Glu Glu Pro
            805                 810
```

<210> SEQ ID NO 20
<211> LENGTH: 2436
<212> TYPE: DNA
<213> ORGANISM: Stevia rebaudiana

<400> SEQUENCE: 20

```
atggcgacac ctaagcttac gcgaacacca agcatgcgag agcgtcttga agaaacttta      60
tcagctcatc gcaacgatat cgtctctctt ctttccaggt atgtagatca aggtaaggcc     120
atattgcagc cccaccacct acttgacgaa atcgataact tcatcggaga tcaaaattgc     180
cgccaaaagc ttgctgatag tctattcggt gaaatcctca gtccgcaca ggaaggtata      240
attcttcctc catatgtaac gcttgctgtt cgtccaagac ctggtgtttg gacttttttg     300
cgtgtgaatg tcgatgaatt gagtgtcgag caacttactg tttctgagta tttaagcttc     360
aaggaggagc ttgtagatgg ccagagtagg aacccgtttg tgttggaact ggatctggaa     420
ccgtttaatg caacatttcc ccggatgtca cgatcttcat ccatcggcaa tggagttcag     480
tttctcaacc gtcatctctc gtcaattatg tttcgcaaca aagattgtat ggatccgttt     540
cttgatttcc ttcgtgctca taaacataaa ggatacgcga tgatgttgaa tgatcggata     600
caaacaatgt ctagacttga atcttcttta gcaaaagcgg aggatcatct ctctaaacta     660
ccacccgaaa caccgtactc cgaattcgaa tacgtattgc aaggaatggg gtttgaaaga     720
ggttgggggg ataattgtga aagagttctt ggtatgatgg atcttctttc tgacattctt     780
caagctccag atccttcgat tcttgaaaag tttcttggaa agatgccgat gatcttcaat     840
gttgttgtgt tatcgattca tggttacttt ggtcaggcta atgtttttgg tttgccggat     900
accggtggtc aggttgtata tatattggat caagtacgtt ctttggagaa tgaaatgtta     960
```

-continued

```
cttaaattaa ggcatcaagg acttgatatc aaacccaaga ttctaattgt aactcgattg    1020
ataccaaatg ccaaaggtac ttcatgcaac caacgattgg agaaagtaag tggaaccgaa    1080
tacacgtata tattacgtgt cccttttagg acagagaaag ggattcttgg taaatggtta    1140
tcaaggtttg atatatggcc ttatttggag gcgtttacaa cggatgcagc aagtgaaatt    1200
gctgctgagt tacacggtgt tccggatctt ttaataggaa actacagtga tgggaatctc    1260
gttgcctcct tgctatctaa caaattgggc gtaacccagt gcaacattgc acacgcgtta    1320
gagaaaacaa agtatccaga ttccgactta tattggaaga atttgaggac caaatatcac    1380
ttttcatgtc aatttaccgc cgaccttcta gcaatgaaca atgcagattt tatcatcact    1440
agcacatacc aagagattgc aggaacgaaa acaccgttg acaatacga gaatcattca     1500
tcgttcactc ttccgggtct atacaggggtt gttcacggta tcgatgtctt tgacccgaag    1560
ttcaacatcg tgtcaccagg ggcagatatg gcaatttact tctcatatgc cgataaagag    1620
agacgactta catctctaca tcccacaatt gagaagctat tgttcgacac tgagcagaac    1680
gatgtacaca ttggaaatat aaatgacccg tctaaaccca tgattttcac aatggcgagg    1740
cttgatcatg tgaagaatat aactggattc gtcgagtgtt atgctaaaaa taataagttg    1800
agggaacacg caaatcttgt ggttattgct ggttataatg acgcgaagaa atcaagtgat    1860
cgagaagaaa ttgcggaaat tgaaaagatg cataatctta tcaagcaata caaacttgat    1920
ggtcagatga gatggatatc agcccaaaca aaccgggccc gaaatgggga atttttatcgg   1980
tatatcgctg atggtagggg cgttttcgtc cagcccgctt tctatgaagc atttgggctt    2040
acggttgtgg aggcgatgac atgtgggctc ccaacatttg ccacgtgtca tggtgggcct    2100
gctgagatca ttgaggatgg tgtgtcgggg ttccatattg atccatatca tcctgataag    2160
atgtcgacta cgttagctga ttttttttcaa aagtgcaaag aggaacctag ttactggggt    2220
aaaatatccg atggcgggct gaaaagaata agtgaaaggt acacatggaa gatatattcg    2280
gaacggttga tgacgttggc gggcgtatat agcttttgga aatatgtgtc aaaactcgag    2340
aggcgtgaaa cccgtcgata ccttgagatg ttctacattt taaagtttcg tcaactggtg    2400
aagtcggttc cgctagctgt tgatgaggag ccgtaa                              2436
```

<210> SEQ ID NO 21
<211> LENGTH: 842
<212> TYPE: PRT
<213> ORGANISM: Stevia rebaudiana

<400> SEQUENCE: 21

```
Met Ala Ser Ala Ser Ser Ser Ile Met Lys Arg Ser Glu Ser Ile Val
  1               5                  10                  15

Asp Thr Met Pro Glu Ala Leu Lys Gln Ser Arg Tyr His Met Lys Lys
             20                  25                  30

Cys Phe Leu Lys Tyr Val Glu Lys Gly Ile Arg Met Met Lys Arg His
         35                  40                  45

His Leu Ile Gln Glu Met Glu Thr Ala Ile Glu Asp Lys Asp Glu Lys
     50                  55                  60

Ala Gln Leu Leu Asp Gly Leu Leu Gly Tyr Ile Leu Cys Thr Thr Gln
 65                  70                  75                  80

Glu Ala Ala Val Val Pro Cys Val Ala Phe Ala Ile Arg Pro Asn
                 85                  90                  95

Pro Gly Phe Trp Glu Phe Val Lys Val Asn Ser Asn Asp Leu Ser Val
            100                 105                 110
```

-continued

```
Asp Gly Ile Thr Ala Thr Asp Tyr Leu Lys Phe Lys Glu Met Ile Val
            115                 120                 125

Asp Glu Thr Trp Ala Lys Asp Glu Asn Ala Leu Glu Ile Asp Phe Gly
        130                 135                 140

Ser Met Asp Phe Asn Leu Pro Asn Met Ser Leu Ser Cys Ser Ile Gly
145                 150                 155                 160

Asn Gly Val Asn Phe Thr Ser Lys Phe Ile Thr Cys Lys Leu Tyr Ala
                165                 170                 175

Gln Ser Ser Cys Gln Gln Leu Leu Val Asp Tyr Leu Leu Ser Leu Asn
            180                 185                 190

His Gln Gly Glu Asn Leu Met Ile Asn Asp Ala Leu Asn Ser Val Ser
        195                 200                 205

Lys Leu Arg Ala Ala Leu Ile Val Ala His Ala Ser Leu Ser Ser Leu
    210                 215                 220

Pro Asn Asp Thr Pro Tyr Gln Ser Phe Glu Leu Arg Phe Lys Glu Trp
225                 230                 235                 240

Gly Phe Glu Lys Gly Trp Gly Asp Asn Ala Glu Arg Ala Arg Glu Thr
                245                 250                 255

Ile Arg Phe Leu Leu Glu Val Leu Gln Ala Pro Asp Pro Ile Asn Leu
            260                 265                 270

Glu Ala Leu Phe Ser Arg Ile Pro Asn Ile Phe Asn Val Val Leu Phe
        275                 280                 285

Ser Ile His Gly Tyr Phe Gly Gln Ser Asn Val Leu Gly Leu Pro Asp
    290                 295                 300

Thr Gly Gly Gln Val Val Tyr Val Leu Asp Gln Val Val Ala Met Glu
305                 310                 315                 320

Glu Glu Leu Leu Met Arg Ile Lys Gln Gln Gly Leu Asn Phe Lys Pro
                325                 330                 335

Gln Ile Leu Val Val Thr Arg Leu Leu Pro Asp Ala Lys Gly Thr Lys
            340                 345                 350

Cys Asn Gln Val Leu Glu Pro Val Leu Asn Thr Lys His Ser His Ile
        355                 360                 365

Leu Arg Val Pro Phe Arg Thr Asp Lys Gly Val Leu Arg Lys Trp Val
    370                 375                 380

Ser Arg Phe Asp Ile Tyr Pro Tyr Leu Glu Asn Phe Thr Gln Asp Ala
385                 390                 395                 400

Ser Ala Lys Ile Ile Glu Met Met Glu Gly Lys Pro Asp Leu Ile Ile
                405                 410                 415

Gly Asn Tyr Thr Asp Gly Asn Leu Val Ala Ser Leu Met Ala Asn Lys
            420                 425                 430

Leu Gly Thr Thr Leu Gly Thr Ile Ala His Ala Leu Glu Lys Thr Lys
        435                 440                 445

Tyr Glu Asp Ser Asp Met Asn Trp Lys Gln Phe Asp Pro Lys Tyr His
    450                 455                 460

Phe Ser Cys Gln Phe Thr Ala Asp Met Ile Ala Met Asn Ser Ala Asp
465                 470                 475                 480

Phe Ile Ile Thr Ser Thr Phe Gln Glu Ile Ala Gly Ser Lys Asp Arg
                485                 490                 495

Pro Gly Gln Tyr Glu Ser His Glu Ala Phe Thr Leu Pro Gly Leu Tyr
            500                 505                 510

Arg Val Val Ser Gly Ile Asn Val Phe Asp Pro Lys Phe Asn Ile Ala
        515                 520                 525

Ser Pro Gly Ala Asp Gln Thr Val Tyr Phe Pro Tyr Thr Glu Thr Lys
```

```
            530                 535                 540
Lys Arg Phe Thr Ala Phe Gln Pro Ala Ile Glu Glu Leu Leu Phe Ser
545                 550                 555                 560

Lys Val Glu Asn Glu Glu His Ile Gly Tyr Leu Glu Asp Lys Thr Lys
                565                 570                 575

Pro Ile Ile Phe Ser Met Ala Arg Leu Asp Thr Val Lys Asn Ile Thr
            580                 585                 590

Gly Leu Thr Glu Trp Phe Gly Glu Asn Lys Arg Leu Arg Ser Leu Val
            595                 600                 605

Asn Leu Val Ile Val Ala Gly Phe Phe Asp Pro Ser Lys Ser Lys Asp
610                 615                 620

Arg Glu Glu Met Ala Glu Ile Lys Lys Met His Leu Leu Ile Glu Lys
625                 630                 635                 640

Tyr Gln Leu Lys Gly Gln Ile Arg Trp Ile Ala Ala Gln Thr Asp Lys
                645                 650                 655

Asn Arg Asn Ser Glu Leu Tyr Arg Phe Ile Ala Asp Ser Lys Gly Ala
            660                 665                 670

Phe Val Gln Pro Ala Leu Tyr Glu Ala Phe Gly Leu Thr Val Ile Glu
            675                 680                 685

Ala Met Asn Cys Gly Leu Pro Thr Phe Ala Thr Asn Gln Gly Gly Pro
690                 695                 700

Ala Glu Ile Ile Val Asp Gly Val Ser Gly Phe Gln Ile Asp Pro Asn
705                 710                 715                 720

Phe Gly Asp Gln Ser Ser Asn Lys Ile Ala Asp Phe Phe Gln Lys Cys
                725                 730                 735

Lys Glu Asp Pro Gly Tyr Trp Asn Asn Ile Ser Glu Gly Gly Leu Lys
            740                 745                 750

Arg Ile Tyr Glu Cys Tyr Thr Trp Lys Ile Tyr Ala Asn Lys Val Leu
            755                 760                 765

Asn Met Gly Asn Ile Tyr Ser Phe Trp Lys Arg Leu Asn Lys Glu Gln
770                 775                 780

Lys Glu Ala Lys Gln Arg Tyr Ile Glu Leu Phe Tyr Asn Leu His Tyr
785                 790                 795                 800

Lys Asn Leu Val Arg Thr Val Pro Ile Ala Ser Asp Glu Ala Gln Pro
                805                 810                 815

Ala Pro Val Ser Arg Ala Lys Leu Ala Thr Gln Pro Thr Arg Arg Thr
            820                 825                 830

Gln Ser Arg Leu Gln Arg Leu Phe Gly Ala
            835                 840

<210> SEQ ID NO 22
<211> LENGTH: 2529
<212> TYPE: DNA
<213> ORGANISM: Stevia rebaudiana

<400> SEQUENCE: 22
atggcatctg cttcaagttc tatcatgaaa cggtctgaat caatagttga caccatgcca     60
gaagccttaa agcagagccg ctatcatatg aaaaaatgtt ttctaaaata tgtagaaaaa    120
ggaattcgca tgatgaaaag acatcatttg atacaagaaa tggagaccgc aattgaagac    180
aaggatgaaa aggctcagct tctagatggc ttacttggct acatcttgtg cacaactcag    240
gaagcagccg ttgttcctcc ttgtgttgca tttgctataa gaccgaatcc tggattctgg    300
gagtttgtta aagtcaactc taatgatcta tcggttgatg ggataactgc cacagattac    360
```

```
ttgaagttca aggaaatgat cgtagatgag acatgggcta agatgaaaaa tgcattggag    420
attgactttg gatcgatgga ctttaaccta ccaaacatga gtttatcttg ttcgattgga    480
aatggtgtta acttcacatc aaaattcatt acttgtaaac tttacgcaca atctagttgc    540
caacaactgc ttgttgatta cttgctctca ttgaatcatc aaggagaaaa tcttatgatc    600
aatgatgcat taaactcagt ctcaaaactt cgagcggctt taattgtagc tcatgcgtcg    660
ctatcttcgt tgcccaacga tactccatat caaagcttcg agcttagatt caaagaatgg    720
ggatttgaga agggatgggg agataacgcg gaacgcgcga gggaaacaat tcggtttctt    780
ttggaggttc ttcaagcacc cgatccgata aacctcgagg ctttattcag caggattcca    840
aacatattca acgttgtttt attctcgatt catgggtatt ttggtcaatc caatgttctt    900
ggattgcccg atactggtgg ccaagtggtt tatgttttgg atcaagtggt agctatggaa    960
gaagaactac tcatgaggat caaacaacaa ggactcaact tcaagcctca aattcttgtg   1020
gtgacccgac ttcttcctga tgctaaaggg accaagtgta atcaggtgtt ggaaccagtt   1080
ctgaacacga acattcgca tattcttagg gttccattca ggactgataa aggtgttctt   1140
cgtaaatggg tatctcgatt tgatatctat ccatatctcg aaaacttcac tcaggatgca   1200
agtgcgaaaa tcattgaaat gatggaaggg aaaccggatc ttatcatcgg aaactatacc   1260
gatgaaaacc ttgttgcatc actcatggct aacaaactcg gaacgacatt gggaacaatt   1320
gcacatgctt tggagaaaac caaatacgaa gattcagaca tgaattggaa gcaattcgac   1380
ccaaaatatc acttctcctg ccaatttaca gccgatatga ttgcaatgaa ctcagctgat   1440
ttcatcatca caagtacttt ccaagaaatc gctggaagta agatagacc cggacaatat   1500 gaaagccatg aagcatttac acttccagga ttatacagag ttgtttcagg catcaacgtg   1560
ttcgatccca aattcaatat cgcgtctcca ggagccgatc aaaccgttta tttcccgtac   1620
accgaaacaa agaaacgatt cactgcattt caacccgcca tagaggaatt actcttcagt   1680
aaagttgaaa acgaagaaca cattggatac ttagaagaca aaaccaaacc gatcatattc   1740
tcaatggcgc gtctcgacac agttaagaac ataacaggac taaccgaatg gtttggagag   1800
aacaaacggc tccgaagctt ggttaatctt gtaatcgtgg cgggtttctt tgacccgtca   1860
aagtcaaaag acagagaaga aatggcggaa ataagaaaaa tgcatttatt gattgaaaaa   1920
tatcagctta aaggtcaaat aagatggatt gctgcacaaa ctgataagaa ccgaaacagt   1980
gagctttacc ggtttattgc tgactcaaaa ggcgcgtttg tgcagcccgc tttgtatgag   2040
gcgtttgggc tcacggttat tgaggcgatg aactgtggtt taccgacttt tgcaactaat   2100
caaggtggtc cagctgagat tatcgttgat ggtgtttctg ggttccagat tgatcctaat   2160
tttggtgatc agtctagtaa taagattgct gatttcttcc agaagtgtaa ggaagatcct   2220
ggttattgga ataatatttc agaaggcggt ttgaagcgta tatacgaatg ttatacttgg   2280
aagatttatg cgaataaagt gttgaatatg gggaacatat actcgttttg gaagcggtta   2340
aacaaggaac aaaagaagc aaaacaaaga tacattgaac tattctacaa tctacactac   2400
aagaacttgg ttaggactgt accaattgct agtgatgaag ctcaacctgc accagtgtca   2460
agggcaaaac ttgcaacaca acccacaaga cgtacgcaat ccaggttgca aaggctgttt   2520
ggagcttaa                                                          2529
```

<210> SEQ ID NO 23
<211> LENGTH: 842
<212> TYPE: PRT
<213> ORGANISM: Stevia rebaudiana

<400> SEQUENCE: 23

```
Met Ala Ala Ser Ser Pro Ile Met Lys Arg Ser Glu Ser Val Leu
1               5                   10                  15

Asp Thr Met Pro Glu Ala Leu Arg Gln Ser Arg Tyr His Met Lys Lys
            20                  25                  30

Cys Phe Leu Lys Tyr Val Gly Lys Gly Lys Arg Met Val Lys Leu His
        35                  40                  45

His Leu Met Gln Glu Met Glu Thr Val Ile Glu Asp Lys Asp Glu Lys
    50                  55                  60

Ala Gln Leu Leu Glu Gly Leu Leu Gly Tyr Ile Leu Cys Thr Thr Gln
65                  70                  75                  80

Glu Ala Ala Val Val Pro Pro Tyr Val Ala Phe Ala Ile Arg Pro Asn
                85                  90                  95

Pro Gly Phe Trp Glu Phe Val Lys Val Asn Ser Asn Asp Leu Ser Val
            100                 105                 110

Lys Gly Ile Thr Ser Thr Asp Tyr Leu Lys Phe Lys Glu Met Ile Val
        115                 120                 125

Asp Glu Thr Trp Ala Asn Asp Glu Asn Ala Leu Glu Ile Asp Phe Gly
    130                 135                 140

Ala Met Asp Phe Asn Leu Pro Thr Met Ser Leu Ser Ser Ser Ile Gly
145                 150                 155                 160

Asn Gly Val Asn Phe Thr Ser Lys Phe Ile Ile Ser Lys Leu Tyr Ala
                165                 170                 175

His Ser Gly Ser Gln Leu Gln Ser Leu Val Asp Tyr Leu Leu Ser Leu
            180                 185                 190

Asn His Gln Gly Glu Lys Leu Met Ile Asn Asp Lys Leu Asn Thr Val
        195                 200                 205

Ser Lys Leu Gln Ala Ala Leu Ile Val Ala His Ser Phe Leu Ser Ser
    210                 215                 220

Leu Pro Asn Asp Thr Pro Tyr Gln Ser Phe Glu Leu Arg Phe Lys Glu
225                 230                 235                 240

Trp Gly Phe Glu Lys Gly Trp Gly Asp Tyr Ala Glu Arg Val Gln Glu
                245                 250                 255

Thr Ile Arg Phe Leu Leu Glu Val Leu Gln Ala Pro Asp Pro Val Asn
            260                 265                 270

Leu Glu Ala Phe Phe Ser Arg Val Pro Asn Ile Phe Asn Ile Val Leu
        275                 280                 285

Phe Ser Ile His Gly Tyr Phe Gly Gln Ser Asn Val Leu Gly Leu Pro
    290                 295                 300

Asp Thr Gly Gly Gln Val Val Tyr Val Leu Asp Gln Val Val Ala Met
305                 310                 315                 320

Glu Glu Glu Leu Leu Leu Arg Ile Lys Gln Gln Gly Leu Ser Phe Lys
                325                 330                 335

Pro His Ile Leu Val Val Thr Arg Leu Leu Pro Asp Ala Lys Gly Thr
            340                 345                 350

Glu Cys Ser Gln Val Leu Glu Pro Val Leu Asn Thr Lys His Ser His
        355                 360                 365

Ile Leu Arg Val Pro Phe Arg Thr Glu Lys Gly Val Leu Arg Lys Trp
    370                 375                 380

Val Ser Arg Phe Asp Ile Tyr Pro Tyr Leu Glu Lys Phe Thr Gln Asp
385                 390                 395                 400

Ala Ser Ala Lys Ile Thr Glu Met Met Glu Gly Lys Pro Asp Leu Ile
```

```
            405                 410                 415
Ile Gly Asn Tyr Thr Asp Gly Asn Leu Val Ala Ser Leu Met Ala Asn
            420                 425                 430

Lys Leu Gly Ser Thr Leu Gly Thr Ile Ala His Ala Leu Glu Lys Thr
            435                 440                 445

Lys Tyr Glu Asp Ser Asp Met Lys Trp Lys His Leu Asp Thr Lys Tyr
            450                 455                 460

His Phe Ser Cys Gln Phe Thr Ala Asp Met Ile Ala Met Asn Ser Ala
465                 470                 475                 480

Asp Phe Ile Ile Thr Ser Thr Phe Gln Glu Ile Ala Gly Ser Lys Asp
            485                 490                 495

Arg Pro Gly Gln Tyr Glu Ser His Glu Ala Phe Thr Leu Pro Gly Leu
            500                 505                 510

Tyr Arg Val Val Ser Gly Ile Asn Val Phe Asp Pro Lys Phe Asn Ile
            515                 520                 525

Ala Ser Pro Gly Ala Asp Gln Thr Val Tyr Phe Pro Tyr Thr Glu Thr
            530                 535                 540

Pro Lys Arg Phe Thr Thr Phe Gln Pro Ala Ile Gln Glu Leu Leu Phe
545                 550                 555                 560

Ser Lys Val Glu Asn Asp Glu His Ile Gly Tyr Leu Glu Asp Lys Asn
            565                 570                 575

Lys Pro Ile Ile Phe Ser Met Ala Arg Leu Asp Met Val Lys Asn Ile
            580                 585                 590

Thr Gly Leu Thr Glu Trp Phe Gly Glu Asn Lys Arg Leu Arg Ser Leu
            595                 600                 605

Val Asn Leu Val Ile Val Ala Gly Phe Phe Asp Pro Ser Lys Ser Lys
            610                 615                 620

Asp Arg Glu Glu Met Glu Glu Ile Lys Lys Met His Leu Leu Ile Glu
625                 630                 635                 640

Lys Tyr Glu Leu Lys Gly Gln Ile Arg Trp Ile Val Ala Gln Thr Asp
            645                 650                 655

Lys Asn Arg Asn Ser Glu Leu Tyr Arg Cys Ile Ala Asp Ser Lys Gly
            660                 665                 670

Ala Phe Val Gln Pro Ala Leu Tyr Glu Ala Phe Gly Leu Thr Val Ile
            675                 680                 685

Glu Ala Met Asn Cys Gly Leu Pro Thr Phe Ala Thr Asn Gln Gly Gly
            690                 695                 700

Pro Ala Glu Ile Ile Val Asp Gly Val Ser Gly Phe Gln Ile Asp Pro
705                 710                 715                 720

Asn Tyr Gly Asp Glu Ser Ser Asn Lys Ile Ala Asp Phe Phe Gln Lys
            725                 730                 735

Cys Lys Gln Asp Pro Gly Tyr Trp Asn Arg Ile Ser Asp Gly Gly Leu
            740                 745                 750

Met Arg Ile Tyr Glu Cys Tyr Thr Trp Lys Ile Tyr Ala Asn Lys Val
            755                 760                 765

Leu Asn Met Gly Asn Ile Tyr Thr Phe Trp Lys Gln Leu Asn Lys Glu
            770                 775                 780

Gln Lys Asp Ala Lys Gln Arg Tyr Ile Glu Leu Phe Tyr Asn Gln His
785                 790                 795                 800

Tyr Lys Asn Leu Val Arg Thr Val Pro Ile Val Ser Asp Glu Asp Asp
            805                 810                 815

Gln Val Thr Arg Ala Lys Pro Ala Thr Gln Pro Ser Thr Arg Arg Thr
            820                 825                 830
```

Gln Ser Ala Leu Gln Arg Leu Leu Gly Ala
        835                 840

<210> SEQ ID NO 24
<211> LENGTH: 2529
<212> TYPE: DNA
<213> ORGANISM: Stevia rebaudiana

<400> SEQUENCE: 24

| | | | | |
|---|---|---|---|---|
| atggcagctt cttcaagtcc cattatgaaa cggtctgagt cagtactcga caccatgcca | | | | 60 |
| gaagctttga ggcaaagtcg gtatcatatg aaaaaatgct ttctaaaata tgtagggaaa | | | | 120 |
| ggaaagcgga tggtgaaact ccaccatttg atgcaagaaa tggagaccgt cattgaggac | | | | 180 |
| aaggacgaaa aggctcagct cttggaaggc ttacttggtt acatcttgtg caccactcag | | | | 240 |
| gaagcagcag ttgttcctcc ttatgtcgcc tttgcaataa ggccaaaccc tggattttgg | | | | 300 |
| gagtttgtta agtcaactc taatgatctc tcggttaaag ggatcacttc caccgattac | | | | 360 |
| ttgaagttca aggaaatgat cgttgacgaa acatgggcta atgatgaaaa tgcattggag | | | | 420 |
| atcgactttg gagcaatgga cttta acttg ccaacaatga gcttatcttc ttcaattgga | | | | 480 |
| aatggagtta acttcacatc aaagtttatt atttctaaac tttatgctca ttctggcagc | | | | 540 |
| caattacaat ctctagttga ttacttactt tcattaaatc atcaaggaga aaaacttatg | | | | 600 |
| ataaatgaca aactaaacac agtttcaaaa cttcaagccg ctctaatagt agctcattct | | | | 660 |
| ttcctttctt cattgcccaa cgacacaccg tatcaaagct ttgaacttag atttaaagag | | | | 720 |
| tggggttttg aaaaaggatg gggagattat gcagaaaggg tgcaagaaac aattcggttt | | | | 780 |
| ttgttggagg ttcttcaagc acccgacccc gtaaacctag aggccttttt tagcagggtt | | | | 840 |
| ccaaacatat tcaatattgt tttattctcg attcatgggt attttggtca atccaatgtt | | | | 900 |
| cttggcttgc ccgataccgg aggtcaggta gtttatgttt tggatcaagt tgtggcaatg | | | | 960 |
| gaagaagaat tgctacttag gattaagcaa caaggactca gcttcaagcc tcatattctt | | | | 1020 |
| gtggtgactc gacttcttcc cgatgccaaa gggaccgagt gtagccaagt tttggaacca | | | | 1080 |
| gttctcaaca cgaaacactc acacattctt agagtcccat ttaggacaga aaaaggtgtt | | | | 1140 |
| cttcgtaaat gggtgtctcg atttgatatc tatccatacc tcgaaaagtt tactcaggat | | | | 1200 |
| gcaagtgcaa aaataactga atgatggaa ggaaaacctg atcttatcat tggaaactac | | | | 1260 |
| actgacggaa acttggttgc atctctcatg gctaacaaac tcggaagcac attgggaacg | | | | 1320 |
| attgcacacg cgttagagaa gactaaatac gaagattcag acatgaaatg gaaacatttg | | | | 1380 |
| gacacaaaat atcactttc ttgtcaattt acagctgata tgatagcaat gaattcagca | | | | 1440 |
| gatttcatca tcactagtac tttccaagaa attgctggaa gtaaagatag acccggtcag | | | | 1500 |
| tatgaaagcc atgaagcatt tacactcccg ggtttatata gagttgtttc gggcatcaac | | | | 1560 |
| gtgtttgatc ccaaattcaa cattgcatct ccgggagctg atcaaaccgt ttatttccct | | | | 1620 |
| tacacggaaa caccaaaacg attcactact tttcaacccg ctatacaaga attactcttt | | | | 1680 |
| agtaaagttg aaaacgacga acacattgga tatttagaag ataagaataa accaatcatc | | | | 1740 |
| ttctcaatgg caagactcga catggttaag aacataacgg gctaaccga atggtttggg | | | | 1800 |
| gaaaacaagc ggttaagaag tttggttaat cttgtaattg tggcggggtt ttttgatccg | | | | 1860 |
| tcaaaatcaa aagatagaga agaaatggaa gaaataaaga aatgcatttt gttgattgag | | | | 1920 |
| aaatatgaac ttaaaggtca aataagatgg ataagtagcac aaactgataa aaacagaaat | | | | 1980 |
| agtgaacttt atcgttgtat cgctgactca aaggggggcgt ttgtgcaacc ggctttatat | | | | 2040 |

```
gaagcgtttg ggttaaccgt tattgaggct atgaattgtg ggttaccaac ttttgcaact    2100
aaccaaggtg gtccggctga gattattgtt gatggtgttt ctgggttcca aatcgatcct    2160
aattatggcg acgagtctag caacaagatc gctgatttt ttcaaaaatg caaacaggat    2220
ccaggatact ggaataggat ttcagacggt ggtttgatgc gtatatacga atgctacaca    2280
tggaagattt atgcaaataa agtgttgaat atggggaaca tttacacatt ttggaagcag    2340
ttaaacaagg aacagaaaga tgcgaaacaa agatacattg agctattcta caatcaacat    2400
tacaagaatt tggttaggac tgtgccgatt gtaagtgatg aagatgacca agttacaagg    2460
gcaaaaccgg caacacaacc ttcaacaagg cgcacacaat ctgccttgca aaggctgctt    2520
ggagcttaa                                                            2529
```

<210> SEQ ID NO 25
<211> LENGTH: 881
<212> TYPE: PRT
<213> ORGANISM: Stevia rebaudiana

<400> SEQUENCE: 25

```
Met Asp Phe Gly Ile Ala Glu Thr Leu Ala Glu Ala Leu Lys Gln Asn
1               5                   10                  15

Arg Tyr His Ala Arg Arg Cys Phe Glu Arg Phe Thr Ser Arg Gly Lys
            20                  25                  30

Arg Met Val Lys Pro Gln Glu Leu Leu His Met Ile Glu Lys Thr Ile
        35                  40                  45

Asp Asp Lys Leu Glu Arg Thr Lys Val Leu Gly Ser Met Gly Gln
    50                  55                  60

Ile Leu Ser Ser Thr Gln Glu Ala Ile Val Ile Pro Pro Tyr Val Ile
65                  70                  75                  80

Leu Gly Leu Arg Ala Asn Pro Gly Gln Trp Ala Tyr Val Lys Ile Asn
                85                  90                  95

Ala Asp Asp Val Thr Val Glu Ser Leu Thr Pro Ser Gln Tyr Leu Lys
            100                 105                 110

Phe Lys Glu Ser Ile Tyr Asp Gln Glu Trp Ala Lys Asp Glu Asn Ala
        115                 120                 125

Leu Glu Leu Asp Phe Gly Ala Phe Asp Phe Asp Thr Pro Arg Leu Ile
    130                 135                 140

Leu Pro Ser Ser Ile Gly Asn Gly Leu Gly Tyr Ile Ser Lys Phe Met
145                 150                 155                 160

Thr Ser Arg Ile Gly Gly Asp Leu Glu Asn Ala Lys Pro Leu Leu Asp
                165                 170                 175

His Leu Leu Ala Leu Lys Tyr His Gly Glu Lys Leu Met Ile Asn Glu
            180                 185                 190

Thr Ile Asp Thr Val Ser Lys Leu Gln Lys Ala Leu Ile Val Ala Asp
        195                 200                 205

Val Tyr Leu Ser Ala His Pro Lys Asp Glu Gln Tyr Gln Thr Leu Glu
    210                 215                 220

Pro Lys Leu Lys Glu Trp Gly Phe Glu Lys Gly Trp Gly Asp Thr Ala
225                 230                 235                 240

Glu Arg Val Arg Glu Thr Met Lys Met Leu Ser Glu Ile Leu Gln Ala
                245                 250                 255

Pro Asp Pro Ile Asn Met Gln Ser Phe Phe Ser Arg Leu Pro Val Val
            260                 265                 270

Phe Asn Ile Val Ile Phe Ser Ile His Gly Tyr Phe Gly Gln Ser Asp
```

```
            275                 280                 285
Val Leu Gly Leu Pro Asp Thr Gly Gln Val Val Tyr Ile Leu Asp
    290                 295                 300
Gln Val Lys Ala Leu Glu Glu Ile Leu Leu Arg Ile Lys Met Gln
305                 310                 315                 320
Gly Leu Asn Ala Lys Pro Arg Ile Leu Val Ser Arg Leu Ile Pro
                325                 330                 335
Asp Ala Gln Gly Thr Lys Cys Asn Glu Met Glu Pro Ile Leu Asn
                340                 345                 350
Thr Met His Ser His Ile Leu Arg Val Pro Phe Arg Thr Ser Lys Gly
                355                 360                 365
Val Val Pro Gln Trp Val Ser Arg Phe Asp Ile Tyr Pro Tyr Leu Glu
    370                 375                 380
Arg Phe Ser Gln Asp Ala Ala Ser Lys Ile Leu Glu Val Met Glu Cys
385                 390                 395                 400
Lys Pro Asp Leu Ile Leu Gly Asn Tyr Thr Asp Gly Asn Ile Val Ala
                405                 410                 415
Ser Leu Ile Ala Lys Lys Phe Gly Val Thr Gln Gly Thr Ile Ala His
                420                 425                 430
Ala Leu Glu Lys Thr Lys Tyr Glu Asp Ser Asp Val Asn Trp Lys Asn
                435                 440                 445
Phe Glu Lys Lys Tyr His Phe Ser Cys Gln Phe Thr Ala Asp Leu Ile
                450                 455                 460
Ser Met Asn Ala Ala Asp Phe Ile Ile Thr Ser Thr Tyr Gln Glu Ile
465                 470                 475                 480
Val Gly Ser Lys Gln Arg Pro Gly Gln Tyr Glu Thr His Gly Ala Phe
                485                 490                 495
Ser Met Pro Gly Leu Cys Arg Val Val Ser Gly Ile Asn Val Phe Asp
                500                 505                 510
Pro Lys Phe Asn Ile Ala Ser Pro Gly Ala Glu Gln Ser Val Tyr Phe
                515                 520                 525
Pro Tyr Thr Glu Lys Glu Lys Arg Leu Thr Asp Phe His Pro Ala Ile
                530                 535                 540
Lys Glu Leu Leu Phe Asn Glu Gln Asp Asn Asp Glu His Met Gly Tyr
545                 550                 555                 560
Leu Ala Asp Val Thr Lys Pro Ile Ile Phe Ser Met Ala Arg Leu Asp
                565                 570                 575
Thr Val Lys Asn Ile Thr Gly Leu Thr Glu Trp Phe Gly Lys Asn Lys
                580                 585                 590
Arg Leu Arg Ser Leu Val Asn Leu Val Val Val Ala Gly Phe Phe Asp
                595                 600                 605
Pro Ser Lys Ser Lys Asp Arg Glu Glu Met Glu Ile Lys Lys Met
                610                 615                 620
His Glu Leu Ile Glu Lys Tyr Lys Leu Lys Gly Gln Met Arg Trp Ile
625                 630                 635                 640
Ala Ala Gln Asn Asp Arg Thr Arg Asn Gly Glu Leu Tyr Arg Cys Ile
                645                 650                 655
Ser Asp Thr Lys Gly Ala Phe Val Gln Pro Ala Leu Tyr Glu Ala Phe
                660                 665                 670
Gly Leu Thr Val Ile Glu Ala Met Asn Cys Gly Leu Pro Thr Phe Ala
                675                 680                 685
Thr Asn Gln Gly Gly Pro Ala Glu Ile Ile Val Asp Gly Val Ser Gly
                690                 695                 700
```

```
Phe His Ile Asp Pro Val Asn Gly Asp Glu Ser Ser Asn Lys Ile Ala
705                 710                 715                 720

Asp Phe Phe Thr Lys Cys Lys Val Asp Gly Glu Tyr Trp Asp Arg Val
            725                 730                 735

Ser Gln Ala Gly Leu Gln Arg Ile Tyr Glu Cys Tyr Thr Trp Lys Met
        740                 745                 750

Tyr Ala Asn Lys Ala Leu Asn Met Gly Ser Met Tyr Gly Phe Trp Arg
    755                 760                 765

Gln Leu Asn Lys Glu Thr Lys Gln Ala Lys Gln Arg Tyr Ile Asp Ile
770                 775                 780

Leu Tyr Asn Leu Gln Phe Lys Asn Leu Ala Lys Thr Ile Glu Ile Pro
785                 790                 795                 800

Asp Phe Val Thr Pro Lys Leu Gln Glu Pro Val Lys Thr Glu Pro Thr
                805                 810                 815

Lys Pro Leu Gln Glu Ala Arg Pro Arg Glu Pro Val Gln Lys Leu Val
            820                 825                 830

Pro Glu Glu Thr Arg Leu Pro Lys Leu Glu Leu Thr Lys Leu Gly Gln
        835                 840                 845

Pro Asn Leu Met Ser Asn Ala Arg Lys Pro Leu Ile Val Leu Val Ser
    850                 855                 860

Val Leu Ile Val Ala Tyr Ala Ser Lys Asn Leu Tyr Arg Arg Tyr Phe
865                 870                 875                 880

Lys
```

```
<210> SEQ ID NO 26
<211> LENGTH: 2646
<212> TYPE: DNA
<213> ORGANISM: Stevia rebaudiana

<400> SEQUENCE: 26
atggatttcg gtatagcaga gactttggcc gaggcattga agcaaaaccg gtaccatgca      60
aggagatgct ttgagcgttt tacatcacgt ggaaaaagga tggtgaagcc tcaagagtta     120
ttacacatga ttgaaaaaac cattgacgac aagcttgaaa gaacgaaggt cttggagggc     180
tcaatgggac aaatcttgag ttccacacag gaggcaatcg ttattccacc atatgttatt     240
ttaggattga gagcgaatcc aggacaatgg catacgtta agatcaatgc tgatgacgtc      300
actgttgagt cactcacacc ttcacaatat ctaaagttca agaatccat ctacgatcaa      360 gaatgggcaa aggacgaaaa tgcccttgaa ctagatttcg gagcgttcga ctttgatacg     420
cctcgattaa tcctcccgtc atctatcggc aacggactcg gttacatttc aaagttcatg     480
acttcaagaa ttggtggtga tctagaaaac gcgaagccgt tgcttgacca cttgcttgct     540
ctaaaatatc atggagagaa gcttatgatc aatgagacaa tagatacagt ttcaaagctc     600
cagaaagcat taattgttgc tgatgtctac ttatctgcac acccgaaaga cgaacaatat     660
caaaccttag agcccaagct taagaatgg ggatttgaga aaggatgggg agatactgct      720
gaaagagtta gagagacaat gaaaatgctt tcggagattc ttcaagcacc cgacccgatt     780
aacatgcaat cgttctttag caggcttccg gtggtcttca atattgtcat attttctatt     840
catgggtatt ttggtcaatc agatgttctt ggattacctg ataccggagg gcaggttgtt     900
tacattcttg atcaagttaa agcattagag gaagagatat tgctaagaat aaaaatgcaa     960
ggattgaatg caaagcctcg gattcttgtg gtgagtcgac tcattcccga cgcacaagga    1020
acaaagtgta acgaggaaat ggaaccgatc ttgaacacaa tgcattcaca catccttcgg    1080
```

```
gttcctttca gaacctcaaa aggcgttgtt cctcaatggg tatcgcggtt tgacatctac   1140
ccgtatcttg aagattctc acaggacgct gcctctaaaa tacttgaagt aatggaatgt    1200
aaaccagatc tcatacttgg aaactacaca gatggaaaca ttgttgcatc acttatagcc   1260 aaaagtttg gagtaacaca ggggacgatt gcacacgcgt tagagaagac aaagtacgaa    1320
gattcggatg ttaactggaa aaactttgaa aaaagtatc atttctcatg tcaatttacc    1380
gcggatttga tctcaatgaa cgctgcagat ttcataatca caagcactta tcaagaaatt   1440
gtgggaagca acaaagacc cggacagtat gagacccacg gggcgtttag tatgcccgga    1500
ctttgtagag tcgtgtcggg catcaacgtg tttgatccta agttcaacat tgcttcaccc   1560
ggtgcggaac aatcggttta ttttccgtac accgagaagg agaaacggtt aacggatttt   1620
catcccgcaa ttaaagaact acttttcaac gaacaagaca atgacgagca tatgggatac   1680
ctcgcggatg taaccaaacc gataatattc tcaatggcga ggctcgatac ggtgaagaac   1740
ataacagggt taaccgagtg gttcggtaag aacaaacgac ttagaagtct tgtaaacttg   1800
gttgttgtcg cggggttctt cgatccatca aaatctaaag accgtgaaga gatggaggaa   1860
atcaagaaaa tgcatgaact aatagagaaa tacaaactca agggtcagat gagatggatc   1920
gcggctcaaa acgataggac ccgcaatggt gaattgtatc ggtgtatttc cgatacgaag   1980
ggagcgtttg tgcagcccgc gttgtatgag gcttttgggc tcacggttat cgaggcaatg   2040
aactgcggtc tcccgacttt tgcaaccaat caaggcgggc ccgcggagat catagttgac   2100
ggagtttcgg gatttcatat tgatcccgtt aacggagatg aatcaagcaa caagattgct   2160
gatttcttca cgaaatgcaa agtcgatggc gagtattggg accgcgtgtc gcaagcggga   2220
cttcaacgta tttacgagtg ctacacatgg aagatgtatg ctaacaaagc attgaacatg   2280
ggttcgatgt atggttttg gaggcaatta acaaagaaa ctaagcaagc gaagcaacga    2340
tacatcgata tcttgtataa cttacaattc aagaatttgg caaaaaccat tgaaatccct   2400
gattttgtga ctcctaaact tcaagaaccg gtcaaaaccg aaccaacaaa accattacaa   2460
gaagcaagac tcgagaacc ggtgcaaaaa ctggtaccgg aagaaacccg actgccaaaa    2520
ctagagttga ccaagcttgg tcaaccgaat ttgatgagca atgcaagaaa accattgatt   2580
gttcttgttt ctgtgttgat agttgcatat gcatccaaga acttgtatag gaggtatttc   2640
aaatag                                                             2646
```

<210> SEQ ID NO 27
<211> LENGTH: 458
<212> TYPE: PRT
<213> ORGANISM: Stevia rebaudiana

<400> SEQUENCE: 27

Met Glu Asn Lys Thr Glu Thr Thr Val Arg Arg Arg Arg Ile Ile
1               5                   10                  15

Leu Phe Pro Val Pro Val Gln Gly His Ile Asn Pro Ile Leu Gln Leu
            20                  25                  30

Ala Asn Val Leu Tyr Ser Lys Gly Phe Ser Ile Thr Ile Phe His Thr
        35                  40                  45

Asn Phe Asn Lys Pro Lys Thr Ser Asn Tyr Pro His Phe Thr Phe Arg
    50                  55                  60

Phe Ile Leu Asp Asn Asp Pro Gln Asp Val Arg Ile Ser Asn Leu Pro
65                  70                  75                  80

Thr His Gly Pro Leu Thr Val Met Arg Ile Leu Ile Ile Asn Glu His

```
            85                  90                  95
Gly Ala Asp Glu Leu Gln Arg Glu Leu Glu Leu Leu Met Leu Ala Ser
            100                 105                 110
Glu Glu Asp Gly Glu Val Ser Cys Leu Ile Thr Asp Gln Ile Trp Tyr
            115                 120                 125
Phe Thr Gln Ser Val Ala Asp Ser Leu Asn Leu Arg Arg Leu Val Leu
        130                 135                 140
Met Thr Ser Ser Leu Phe Asn Phe His Ala His Val Ser Leu Pro Gln
145                 150                 155                 160
Phe Asp Glu Leu Gly Tyr Leu Asp Pro Asp Lys Thr Arg Leu Glu
                165                 170                 175
Glu Gln Ala Ser Gly Phe Pro Met Leu Lys Val Lys Asp Ile Lys Cys
            180                 185                 190
Gly Phe Ser Met Trp Lys Gln Gly Lys Glu Ile Phe Glu Asn Ile Thr
            195                 200                 205
Lys Gln Thr Lys Ala Ser Ser Gly Val Ile Trp Asn Ser Phe Lys Glu
        210                 215                 220
Leu Glu Glu Ser Glu Leu Glu Thr Val Ile Arg Glu Ile Pro Ala Pro
225                 230                 235                 240
Ser Phe Leu Ile Pro Leu Pro Lys His Leu Thr Ala Ser Ser Ser Ser
                245                 250                 255
Leu Leu Asp His Asp Arg Thr Val Phe Pro Trp Leu Asp Gln Gln Pro
            260                 265                 270
Ser Arg Ser Val Leu Tyr Val Ser Phe Gly Ser Ala Thr Glu Val Asp
            275                 280                 285
Ala Lys Asp Phe Leu Glu Ile Ala Arg Gly Leu Val Asp Ser Lys Gln
        290                 295                 300
Ser Phe Leu Trp Val Val Arg Pro Gly Phe Val Lys Gly Ser Thr Trp
305                 310                 315                 320
Val Glu Pro Leu Pro Asp Gly Phe Leu Gly Glu Arg Gly Arg Ile Val
                325                 330                 335
Lys Trp Val Pro Gln Gln Glu Val Leu Ala His Gly Ala Ile Gly Ala
            340                 345                 350
Phe Trp Thr His Ser Gly Trp Asn Ser Thr Leu Glu Ser Val Cys Glu
            355                 360                 365
Gly Val Pro Met Ile Phe Ser Ala Phe Ala Phe Asp Gln Pro Leu Asn
        370                 375                 380
Ala Arg Tyr Met Ser Asp Val Leu Lys Val Gly Val Tyr Leu Glu Asn
385                 390                 395                 400
Gly Trp Glu Arg Gly Glu Ile Ala Asn Ala Ile Arg Arg Val Met Val
                405                 410                 415
Asp Glu Gly Gly Tyr Ile Arg Gln Asn Ala Ser Val Leu Lys Gln
            420                 425                 430
Lys Ala Asp Val Ser Leu Met Lys Gly Gly Ser Ser Tyr Glu Ser Leu
            435                 440                 445
Glu Ser Leu Val Ala Tyr Ile Ser Ser Leu
450                 455

<210> SEQ ID NO 28
<211> LENGTH: 1377
<212> TYPE: DNA
<213> ORGANISM: Stevia rebaudiana

<400> SEQUENCE: 28
```

| | |
|---|---|
| atggaaaata aaacggagac caccgttcgc cggcgccgga gaataatatt attcccggta | 60 |
| ccagttcaag gccacattaa cccaattctt cagctagcca atgtgttgta ctccaaagga | 120 |
| ttcagtatca ccatctttca caccaacttc aacaaaccca aacatctaa ttaccctcac | 180 |
| ttcactttca gattcatcct cgacaacgac ccacaagacg tacgcatttc aatctaccg | 240 |
| actcatggtc cgctcactgt tatgcggatt ctgattatca acgaacacgg agctgacgaa | 300 |
| ttacaacgcg aactggaact gttgatgtta gcttctgaag aagatggaga ggtatcgtgt | 360 |
| ttaatcaccg atcagatttg gtacttcacg caatctgttg ctgacagtct taacctccga | 420 |
| cggcttgttt tgatgacaag cagcttgttt aattttcatg cacatgtttc acttcctcag | 480 |
| tttgatgagc ttggttacct cgatcctgat gacaaaaccc gtttggaaga caagcgagt | 540 |
| gggtttccta tgctgaaagt gaaagatatc aagtgtggtt tttcgatgtg aaacaaggc | 600 |
| aaagagatat tcgagaacat tacgaaacaa acaaaagcat cttcaggagt catctggaac | 660 |
| tcatttaagg aactcgaaga gtctgagctc gaaactgtta tccgtgagat cccggctcca | 720 |
| agtttcttga taccactccc caagcatttg acagcctctt ccagcagctt actagaccac | 780 |
| gatcgaaccg tttttccatg gttagaccaa caaccgtcac gttcggtact gtatgttagt | 840 |
| tttggtagtc tactgaagt ggatgcgaaa gatttcttgg aaatagctcg tgggttggtt | 900 |
| gatagcaagc agtcgttttt atgggtggtt cgacctggtt ttgtcaaggg ttcgacgtgg | 960 |
| gtcgaaccgt tgccagatgg gttcttgggt gaaagaggac gtattgtgaa atgggttccg | 1020 |
| cagcaagaag tgctagctca tggagcaata ggcgcattct ggactcatag cggatggaac | 1080 |
| tctacgttgg aaagcgtttg tgaaggtgtt cctatgattt tctcggcttt tgcgttcgat | 1140 |
| caaccgttga atgctagata catgagtgat gttttgaagg tagggtgta tttggaaaat | 1200 |
| gggtgggaaa gaggagagat agcaaatgca ataagaagag ttatggtgga tgaagaagga | 1260 |
| ggatacatta gacagaatgc aagtgttttg aaacaaaagg cagatgtttc tttgatgaag | 1320 |
| ggtggttcgt cttacgaatc attagagtct ctagttgctt acatttcatc gttgtaa | 1377 |

<210> SEQ ID NO 29
<211> LENGTH: 424
<212> TYPE: PRT
<213> ORGANISM: Stevia rebaudiana

<400> SEQUENCE: 29

```
Met Leu Gln Leu Ala Thr Tyr Leu His Ser Gln Gly Ile Ser Ile Thr
1               5                   10                  15

Ile Ala Gln Tyr Pro Asn Phe Asn Ser Pro Asp Ser Ser Asn His Pro
            20                  25                  30

Glu Leu Thr Phe Leu Pro Leu Ser Ser Gly Asn Leu Ser Val Ala Asp
        35                  40                  45

Ile Ser Gly Gly Phe Phe Lys Phe Ile Gln Thr Leu Asn His Asn Cys
    50                  55                  60

Lys Pro His Phe Arg Glu Tyr Leu Val Gln Asn Met Ser Ser Asp Asp
65                  70                  75                  80

Lys Glu Ser Ile Val Ile Ile Arg Asp Asn Leu Met Phe Phe Ala Gly
                85                  90                  95

Glu Ile Ala Gly Glu Leu Gly Leu Pro Ser Ile Ile Leu Arg Gly Ser
            100                 105                 110

Asn Ala Val Met Leu Thr Ala Ser Asp Ile Ile Pro Gln Leu His Gln
        115                 120                 125

Glu Gly Arg Phe Pro Pro Pro Asp Ser Leu Leu Gln Glu Thr Ile Pro
```

```
        130                 135                 140
Glu Leu Val Pro Phe Arg Tyr Lys Asp Leu Pro Phe Ile Gly Tyr Pro
145                 150                 155                 160

Ile His Gln Thr Leu Glu Phe Ser Ile Thr Met Met Thr Pro Lys Ser
                165                 170                 175

Pro Ala Ser Ala Ile Leu Ile Asn Thr Leu Glu Phe Leu Glu Gln Ser
            180                 185                 190

Ala Leu Thr Gln Ile Arg Asp His Tyr Lys Val Pro Val Phe Thr Ile
        195                 200                 205

Gly Pro Leu His Lys Ile Val Thr Thr Arg Ser Thr Ser Ile Leu Glu
    210                 215                 220

Glu Asp Thr Ser Cys Ile Asn Trp Leu Asp Lys Gln Ser Pro Lys Ser
225                 230                 235                 240

Val Val Tyr Val Ser Leu Gly Ser Leu Ala Lys Leu Asp Glu Lys Val
                245                 250                 255

Ala Ser Glu Met Ala Cys Gly Leu Ala Met Ser Asn His Lys Phe Leu
            260                 265                 270

Trp Val Val Arg Pro Gly Met Val His Gly Phe Glu Trp Val Glu Phe
        275                 280                 285

Leu Pro Asp Ser Leu Val Gly Glu Met Lys Ala Arg Gly Leu Ile Val
    290                 295                 300

Lys Trp Ala Pro Gln Thr Thr Val Leu Ala His Asn Ala Val Gly Gly
305                 310                 315                 320

Phe Trp Ser His Cys Gly Trp Asn Ser Thr Ile Glu Cys Leu Ala Glu
                325                 330                 335

Gly Val Pro Met Met Cys Gln Pro Phe Phe Ala Asp Gln Leu Leu Asn
            340                 345                 350

Ala Arg Tyr Val Ser Asp Val Trp Lys Thr Gly Phe Glu Ile Val Ile
        355                 360                 365

Glu Lys Gly Glu Ile Ala Cys Ala Ile Lys Arg Val Leu Val Asp Glu
    370                 375                 380

Glu Gly Glu Glu Met Arg Gln Arg Ala Met Glu Ile Lys Glu Lys Val
385                 390                 395                 400

Lys Ile Ala Ile Asn Asp Gly Gly Ser Ser Tyr Asp Ser Phe Lys Asp
                405                 410                 415

Leu Val Ala Phe Ile Ser Ser Leu
            420

<210> SEQ ID NO 30
<211> LENGTH: 1275
<212> TYPE: DNA
<213> ORGANISM: Stevia rebaudiana

<400> SEQUENCE: 30
atgcttcagc ttgcaactta cctccattct caagggattt caataaccat cgctcagtac      60
cccaacttca actcgccgga ttcttccaac catccagaac taaccttcct cccactatcc     120
tccggcaact atccgtcgc cgacatctcc ggcggctttt tcaagttcat ccaaactctt     180
aaccataact gcaaacccca tttccgggaa taccttgttc agaacatgag ttctgatgat     240
aaggaatcaa tcgttatcat ccgtgataat ctcatgtttt cgccggaga atcgccggc     300 gagctgggtc tgccttcgat cattttacgt ggcagcaatg ctgtcatgtt gactgctagc     360
gacatcatcc ctcaacttca tcaagaaggt cgttttccgc caccagattc tttgttgcag     420
gaaacaattc cagaactggt tccattcaga tacaaagatc taccatttat tggctatcca     480
```

```
atacatcaaa ccccttgaatt tagtatcacc atgatgaccc ccaaatcacc tgcttccgcc      540
attcttatca acaccctcga atttcttgaa caatcggcat taacccagat ccgtgatcat      600
tacaaagttc cagttttttac aatcggacca ttgcacaaaa tagtcacaac tcgttccact      660
agcattcttg aagaagatac aagttgcatc aattggttag ataaacaatc acccaaatca      720
gtggtttatg tgagtttagg aagcttagca aagttggatg aaaaggttgc atctgaaatg      780
gcatgtggtt tagccatgag taaccataag ttcctatggg tggttcgacc cggtatggtt      840
catgggtttg aatgggtcga gttttttgccg gatagtttgg tgggtgaaat gaaggctaga      900
ggtttgattg tgaaatgggc accccagacg acggttttgg cgcataacgc ggttggtgga      960
ttttggagtc attgcggttg gaactcgacc atagaatgct tagctgaagg ggtcccgatg     1020
atgtgtcaac cgttttttgc tgatcagttg ttgaatgcta ggtatgtgag tgatgtttgg     1080
aagacgggtt ttgagattgt tatcgagaaa ggtgagattg cgtgcgcgat taaacgagtt     1140
ttggtggatg aagaaggcga agaaatgagg cagagagcta tggagattaa agaaaaggtt     1200
aaaattgcaa tcaacgatgg tggttcttct tatgactcgt tcaaggactt ggtggcgttt     1260
atttcatcac tctaa                                                      1275
```

<210> SEQ ID NO 31
<211> LENGTH: 485
<212> TYPE: PRT
<213> ORGANISM: Stevia rebaudiana

<400> SEQUENCE: 31

```
Met Tyr Asn Val Thr Tyr His Gln Asn Ser Lys Ala Met Ala Thr Ser
1               5                   10                  15

Asp Ser Ile Val Asp Asp Arg Lys Gln Leu His Val Ala Thr Phe Pro
            20                  25                  30

Trp Leu Ala Phe Gly His Ile Leu Pro Phe Leu Gln Leu Ser Lys Leu
        35                  40                  45

Ile Ala Glu Lys Gly His Lys Val Ser Phe Leu Ser Thr Thr Arg Asn
    50                  55                  60

Ile Gln Arg Leu Ser Ser His Ile Ser Pro Leu Ile Asn Val Val Gln
65                  70                  75                  80

Leu Thr Leu Pro Arg Val Gln Glu Leu Pro Glu Asp Ala Glu Ala Thr
                85                  90                  95

Thr Asp Val His Pro Glu Asp Ile Gln Tyr Leu Lys Lys Ala Val Asp
            100                 105                 110

Gly Leu Gln Pro Glu Val Thr Arg Phe Leu Glu Gln His Ser Pro Asp
        115                 120                 125

Trp Ile Ile Tyr Asp Phe Thr His Tyr Trp Leu Pro Ser Ile Ala Ala
    130                 135                 140

Ser Leu Gly Ile Ser Arg Ala Tyr Phe Cys Val Ile Thr Pro Trp Thr
145                 150                 155                 160

Ile Ala Tyr Leu Ala Pro Ser Ser Asp Ala Met Ile Asn Asp Ser Asp
                165                 170                 175

Gly Arg Thr Thr Val Glu Asp Leu Thr Thr Pro Pro Lys Trp Phe Pro
            180                 185                 190

Phe Pro Thr Lys Val Cys Trp Arg Lys His Asp Leu Ala Arg Met Glu
        195                 200                 205

Pro Tyr Glu Ala Pro Gly Ile Ser Asp Gly Tyr Arg Met Gly Met Val
    210                 215                 220
```

```
Phe Lys Gly Ser Asp Cys Leu Leu Phe Lys Cys Tyr His Glu Phe Gly
225                 230                 235                 240

Thr Gln Trp Leu Pro Leu Leu Glu Thr Leu His Gln Val Pro Val Val
            245                 250                 255

Pro Val Gly Leu Leu Pro Pro Glu Ile Pro Gly Asp Glu Lys Asp Glu
        260                 265                 270

Thr Trp Val Ser Ile Lys Lys Trp Leu Asp Gly Lys Gln Lys Gly Ser
    275                 280                 285

Val Val Tyr Val Ala Leu Gly Ser Glu Ala Leu Val Ser Gln Thr Glu
290                 295                 300

Val Val Glu Leu Ala Leu Gly Leu Glu Leu Ser Gly Leu Pro Phe Val
305                 310                 315                 320

Trp Ala Tyr Arg Lys Pro Lys Gly Pro Ala Lys Ser Asp Ser Val Glu
            325                 330                 335

Leu Pro Asp Gly Phe Val Glu Arg Thr Arg Asp Arg Gly Leu Val Trp
                340                 345                 350

Thr Ser Trp Ala Pro Gln Leu Arg Ile Leu Ser His Glu Ser Val Cys
        355                 360                 365

Gly Phe Leu Thr His Cys Gly Ser Gly Ser Ile Val Glu Gly Leu Met
370                 375                 380

Phe Gly His Pro Leu Ile Met Leu Pro Ile Phe Cys Asp Gln Pro Leu
385                 390                 395                 400

Asn Ala Arg Leu Leu Glu Asp Lys Gln Val Gly Ile Glu Ile Pro Arg
                405                 410                 415

Asn Glu Glu Asp Gly Cys Leu Thr Lys Glu Ser Val Ala Arg Ser Leu
            420                 425                 430

Arg Ser Val Val Glu Asn Glu Gly Glu Ile Tyr Lys Ala Asn Ala
        435                 440                 445

Arg Ala Leu Ser Lys Ile Tyr Asn Asp Thr Lys Val Glu Lys Glu Tyr
    450                 455                 460

Val Ser Gln Phe Val Asp Tyr Leu Glu Lys Asn Ala Arg Ala Val Ala
465                 470                 475                 480

Ile Asp His Glu Ser
            485

<210> SEQ ID NO 32
<211> LENGTH: 1458
<212> TYPE: DNA
<213> ORGANISM: Stevia rebaudiana
<220> FEATURE:

<400> SEQUENCE: 32
atgtacaacg ttacttatca tcaaaattca aaagcaatgg ctaccagtga ctccatagtt      60
gacgaccgta agcagcttca tgttgcgacg ttcccatggc ttgctttcgg tcacatcctc     120
cctttccttc agctttcgaa attgatagct gaaaagggtc acaaagtctc gtttctttct     180
accaccagaa acattcaacg tctctcttct catatctcgc cactcataaa tgttgttcaa     240
ctcacacttc cacgtgtcca agagctgccg gaggatgcag aggcgaccac tgacgtccac     300
cctgaagata ttcaatatct caagaaggct gttgatggtc ttcaaccgga ggtcacccgg     360
tttctagaac aacactctcc ggactggatt atttatgatt ttactcacta ctggttgcca     420
tccatcgcgg ctagcctcgg tatctcacga gcctacttct gcgtcatcac tccatggacc     480
attgcttatt tggcacccct catctgacgc atgataaatg attcagatgg tcgaaccacg     540
gttgaggatc tcacgacacc gcccaagtgg tttcccttc cgaccaaagt atgctggcgg     600
```

```
aagcatgatc ttgcccgaat ggagccttac gaagctccgg ggatatctga tggataccgt    660
atggggatgg ttttaaggg atctgattgt ttgcttttca atgttacca tgagtttgga    720 actcaatggc tacctctttt ggagacacta caccaagtac cggtggttcc ggtgggatta    780
ctgccgccgg aaatacccgg agacgagaaa gatgaaacat gggtgtcaat caagaaatgg    840
ctcgatggta aacaaaaagg cagtgtggtg tacgttgcat taggaagcga ggctttggtg    900
agccaaaccg aggttgttga gttagcattg ggtctcgagc tttctgggtt gccatttgtt    960
tgggcttata gaaaaccaaa aggtcccgcg aagtcagact cggtggagtt gccagacggg   1020
ttcgtggaac gaactcgtga ccgtgggttg gtctggacga gttgggcacc tcagttacga   1080
atactgagcc acgagtcagt ttgtggtttc ttgactcatt gtggttctgg atcaattgtg   1140
gaagggctaa tgtttggtca ccctctaatc atgctaccga tttttgtga ccaacctctg   1200 aatgctcgat tactggagga caaacaggtg ggaatcgaga taccaagaaa tgaggaagat   1260
ggttgcttga ccaaggagtc ggttgctaga tcactgaggt ccgttgttgt ggaaaacgaa   1320
ggggagatct acaaggcgaa cgcgagggcg ctgagtaaaa tctataacga cactaaggtg   1380
gaaaaagaat atgtaagcca attcgtagac tatttggaaa agaatgcgcg tgcggttgcc   1440
atcgatcatg agagttaa                                                 1458

<210> SEQ ID NO 33
<211> LENGTH: 473
<212> TYPE: PRT
<213> ORGANISM: Stevia rebaudiana

<400> SEQUENCE: 33

Met Ala Thr Ser Asp Ser Ile Val Asp Asp Arg Lys Gln Leu His Val
1               5                   10                  15

Ala Thr Phe Pro Trp Leu Ala Phe Gly His Ile Leu Pro Tyr Leu Gln
            20                  25                  30

Leu Ser Lys Leu Ile Ala Glu Lys Gly His Lys Val Ser Phe Leu Ser
        35                  40                  45

Thr Thr Arg Asn Ile Gln Arg Leu Ser Ser His Ile Ser Pro Leu Ile
    50                  55                  60

Asn Val Val Gln Leu Thr Leu Pro Arg Val Gln Glu Leu Pro Glu Asp
65                  70                  75                  80

Ala Glu Ala Thr Thr Asp Val His Pro Glu Asp Ile Pro Tyr Leu Lys
                85                  90                  95

Lys Ala Ser Asp Gly Leu Gln Pro Glu Val Thr Arg Phe Leu Glu Gln
            100                 105                 110

His Ser Pro Asp Trp Ile Ile Tyr Asp Tyr Thr His Tyr Trp Leu Pro
        115                 120                 125

Ser Ile Ala Ala Ser Leu Gly Ile Ser Arg Ala His Phe Ser Val Thr
    130                 135                 140

Thr Pro Trp Ala Ile Ala Tyr Met Gly Pro Ser Ala Asp Ala Met Ile
145                 150                 155                 160

Asn Gly Ser Asp Gly Arg Thr Thr Val Glu Asp Leu Thr Thr Pro Pro
                165                 170                 175

Lys Trp Phe Pro Phe Pro Thr Lys Val Cys Trp Arg Lys His Asp Leu
            180                 185                 190

Ala Arg Leu Val Pro Tyr Lys Ala Pro Gly Ile Ser Asp Gly Tyr Arg
        195                 200                 205

Met Gly Leu Val Leu Lys Gly Ser Asp Cys Leu Leu Ser Lys Cys Tyr
```

```
His Glu Phe Gly Thr Gln Trp Leu Pro Leu Leu Glu Thr Leu His Gln
225                 230                 235                 240

Val Pro Val Val Pro Val Gly Leu Leu Pro Pro Glu Ile Pro Gly Asp
                245                 250                 255

Glu Lys Asp Glu Thr Trp Val Ser Ile Lys Lys Trp Leu Asp Gly Lys
            260                 265                 270

Gln Lys Gly Ser Val Val Tyr Val Ala Leu Gly Ser Glu Val Leu Val
        275                 280                 285

Ser Gln Thr Glu Val Val Glu Leu Ala Leu Gly Leu Glu Leu Ser Gly
    290                 295                 300

Leu Pro Phe Val Trp Ala Tyr Arg Lys Pro Lys Gly Pro Ala Lys Ser
305                 310                 315                 320

Asp Ser Val Glu Leu Pro Asp Gly Phe Val Glu Arg Thr Arg Asp Arg
                325                 330                 335

Gly Leu Val Trp Thr Ser Trp Ala Pro Gln Leu Arg Ile Leu Ser His
            340                 345                 350

Glu Ser Val Cys Gly Phe Leu Thr His Cys Gly Ser Gly Ser Ile Val
        355                 360                 365

Glu Gly Leu Met Phe Gly His Pro Leu Ile Met Leu Pro Ile Phe Gly
    370                 375                 380

Asp Gln Pro Leu Asn Ala Arg Leu Leu Glu Asp Lys Gln Val Gly Ile
385                 390                 395                 400

Glu Ile Pro Arg Asn Glu Glu Asp Gly Cys Leu Thr Lys Glu Ser Val
                405                 410                 415

Ala Arg Ser Leu Arg Ser Val Val Glu Lys Glu Gly Glu Ile Tyr
            420                 425                 430

Lys Ala Asn Ala Arg Glu Leu Ser Lys Ile Tyr Asn Asp Thr Lys Val
        435                 440                 445

Glu Lys Glu Tyr Val Ser Gln Phe Val Asp Tyr Leu Glu Lys Asn Ala
    450                 455                 460

Arg Ala Val Ala Ile Asp His Glu Ser
465                 470
```

<210> SEQ ID NO 34
<211> LENGTH: 1422
<212> TYPE: DNA
<213> ORGANISM: Stevia rebaudiana

<400> SEQUENCE: 34

```
atggccacat ctgactctat cgttgatgac agaaaacaat tgcatgttgc tactttccca      60
tggttggcct ttggacacat tctgccctac ttgcaattgt caaagctgat tgcagaaaaa     120
ggtcataagg tgtccttttt gtctaccaca agaaacatcc agagactaag ttctcatatt     180
tctccattga ttaatgtggt tcagttgacc ttgcctagag tccaagaact tcccgaagac     240
gcagaagcta ctactgatgt tcaccctgaa gatatcccat atctaaagaa ggcatctgat     300
ggacttcaac agaagtaac caggtttttg gagcagcaca gtcctgactg gattatctat     360
gattatactc attactggct tccatccatc gcagctagtc taggcatttc cagagctcat     420
ttctctgtca ctaccccatg ggcaattgca tatatgggtc cttctgctga tgcaatgatc     480
aacggttctg atggtaggac cactgttgaa gatttaacta cacctccaaa gtggttccca     540
tttcctacta agtttgttg gcgaaaacac gatctggcac gtttggtccc atataaggct     600
ccaggtatct ccgatggata tcgaatgggt ctggtgctaa agggttctga ttgtctgtta     660
```

```
tctaagtgtt accacgaatt tggaactcaa tggcttcctc tattagagac tctgcatcaa    720
gttccagttg ttcctgtcgg tctgctacca cctgaaattc ccggtgacga aaaggacgaa    780
acttgggttt ccataaaaaa atggctggat ggtaagcaga agggtagtgt tgtatatgtc    840
gctttaggct ccgaggtttt ggtatcccag actgaagttg tggaacttgc cttaggattg    900
gagttgtccg gtttgccatt cgtctgggca tatagaaagc caagggacc agctaagtca     960
gactcagttg aattgccaga tggtttcgta gaaaggacaa gagacagagg attggtttgg   1020
acatcatggg ccccacaatt gagaattctg agtcatgaaa gtgtgtgtgg attcttgact   1080
cactgtggct ctggcagtat tgttgaagga ctgatgtttg gacacccact gataatgttg   1140
ccaatcttcg gtgaccaacc tctgaatgca agattgctgg aggataaaca agttggtatc   1200
gaaatcccaa gaaacgagga agacggctgc ctgactaagg aatcagttgc acgtagttta   1260
agatctgtag ttgttgaaaa agaaggtgaa atatataagg ctaacgctag agaactttca   1320
aagatataca atgataccaa ggtggagaaa gaatatgttt cacagtttgt ggactatttg   1380
gagaaaaacg ctagagccgt tgctatcgat cacgaatcat ag                       1422
```

CANNABINOID GLYCOSIDE PRODRUGS AND METHODS OF SYNTHESIS

FIELD OF THE INVENTION

The present invention pertains to the field of drug development and in particular to novel cannabinoid glycoside prodrugs and methods for their production by enzyme-mediated carbohydrate transfer.

BACKGROUND

Phytocannabinoids from *Cannabis sativa* have long been used for altering mental states, but recent findings have illuminated the potential of specific cannabinoid compounds for treatment and maintenance of various diseases and conditions. Of particular importance is the non-psychotropic molecule cannabidiol (CBD) which has potential therapeutic application as an anti-psychotic, a neuroprotectant, and has potential for treatment of numerous other maladies (Zuardi 2012, Iuvone 2009, for review Mechoulam 2002, respectively). One shortcoming of CBD is that it is easily oxidized to THC and CBN derivatives by light, heat, and acidic or basic conditions, and another detrimental attribute to CBD is that its extremely hydrophobic nature makes it difficult for formulation and delivery. Additionally, current pharmaceutical compositions of CBD and THC have unpleasant organoleptic properties, and their hydrophobic nature results in a lingering on the palate.

Cannabinoids are extremely hydrophobic in nature, complicating their use in drug formulations. Non-covalent methods have been found to improve the solubility of cannabinoids by utilizing carrier carbohydrates such as cyclized maltodextrins (Jarho 1998). Covalent chemical manipulations have produced novel CBD prodrugs with improved solubility (WO2009018389, WO 2012011112). Even fluorine substituted CBD compounds have been created through synthetic chemical manipulations in an effort to functionalize CBD (WO2014108899). The aforementioned strategies were somewhat successful in improving the solubility of CBD, but they create unnatural compositions which alter the composition and will release the unnatural prodrug moieties upon hydrolysis.

A growing body of evidence shows that glycosides are capable of acting as prodrugs and also to have direct therapeutic effects. Glycoside prodrugs may enable improved drug bioavailability or improved drug pharmacokinetics including more site-specific or tissue-specific drug delivery, more consistent levels of drug in the plasma, and sustained or delayed release of the drug. Site-specific delivery of steroid glycosides to the colon has previously been demonstrated (Friend 1985, Friend 1984), and could enable treatment of local disorders such as inflammatory bowel disease. Glycosylation of steroids enabled survival of stable bioactive molecules in the acidic stomach environment and delivery into the large intestine, where the aglycones were liberated by glycosidases produced by colonic bacteria, and then absorbed into the systemic circulation. Glycosidases are also present universally in different tissues (Conchie 1959), so delivery of glycosides by methods that bypass the digestive tract and colon, such as intravenous delivery, will enable targeted delivery to other cells and tissues that have increased expression of glycosidases. In addition, the distribution of alpha-glycosidase and beta-glycosidase enzymes differ throughout the intestinal tract and other tissues, and different forms of glycosides may therefore provide unique pharmacokinetic profiles, including formulations that target delivery of specific diseased areas, or targeted release at locations that can promote or restrict systemic absorption of the cannabinoids and other compounds described herein. Many biologically active compounds are glycosides, including members of classes of compounds such as hormones, antibiotics, sweeteners, alkaloids, and flavonoids. While it is generally accepted that glycosides will be more water-soluble than the aglycones, literature reviews have analyzed structure-activity relationships and determined that it is nearly impossible to define a general pattern for the biological activities of glycosides across different classes of compounds (Kren 2008).

As with synthetic chemistry, in vivo detoxification strategies serve as another model for improving the solubility of cannabinoids. CBD is glucuronidated in humans by the liver glucosyltransferases, but to date only minor activity has been demonstrated with UGT1A9 and UGT2B7 in in vitro assays (U.S. Pat. No. 8,410,064). In vitro assays showed that cannabinol (CBN) is efficiently glucuronidated by the Human UGT1A10 (U.S. Pat. No. 8,410,064). The glucuronidation of CBD is one mechanism to increase CBD solubility and facilitate removal and excretion through the kidneys. Searching for glucosyltransferase activity towards cannabinoids, cannabinol was found to be glycosylated when incubated with in vitro cell culture of *Pinellia ternata* (Tanaka 1993). Similarly, cannabidiol was shown to be glycosylated when incubated with tissue cultures from *Pinellia ternata* and *Datura inoxia*, yielding CBD-6'-O-β-D-glucopyranoside and CBD-(2',6')-O-β-D-diglucopyranoside (Tanaka 1996). These biotransformation studies demonstrate the potential for limited glycosylation of these two compounds to occur by unknown plant glucosyltransferases, and for them to be produced in minute quantities, but to date, no specific plant glucosyltransferase proteins capable of glycosylation of cannabinoids have been identified, no cannabinoid glycosides been produced in large, purified quantities, and the biological activity or pharmaceutical properties of cannabinoid glycosides have never been characterized.

Cannabinoids contain a hydroxylated hydrophobic backbone, similar to the steviol backbone of steviol glycosides found in the *Stevia rebaudiana* plant. UGT76G1 is a glucosyltransferase from *Stevia* that is capable of transferring a secondary glucose to the 3C-hydroxyl of the primary glycosylation on both O13-OH and C19-COOH position of the steviol glycoside, and thus its substrates include steviolmonoside, stevioside, rubusoside, RebA, RebD, RebG, RebE, etc. (Richman et al. 2005, Stevia First Corp unpublished work). The substrate recognition site of UGT76G1 is capable of binding and glycosylating multiple steviol glycosides, but it was previously not known to have glycosylation activity towards any other glycosides, and there previously was no established activity of UGT76G1 towards any aglycone compounds at all. As UGT76G1 is capable of glycosylating steviol glycosides on the primary sugar located on both C13 hydroxyl group and the C19 carboxyl group it demonstrates bi-functional glycosylation. Cyclodextrin glucanotransferase (CGTase, Toruzyme 3.0L, Novozymes Inc.) is a member of the amylase family of enzymes and is best known for its ability to cyclize maltodextrin chains. A lesser known activity of CGTase is disproportionation of linear maltodextrin chains and transfer to an acceptor sugar molecule (Li 2012).

There are no known cannabinoid glycosides available as cannabinoid prodrugs. Nor is there a known method for the efficient regioselective production of cannabinoid glycosides, which is necessary in order to produce large, purified quantities of individual glycosides and to assess their pharmaceutical properties, including evaluation of in vivo drug pharmacokinetics and pharmacodynamics. To solve the aforementioned problem, screening of glucosyltransferase enzymes from various organisms has been conducted to identify candidates for the glycosylation of cannabinoids, and to identify cannabinoid glycosides as potential prodrugs of cannabinoids, and as novel cannabinoid compositions with novel properties and functions.

This background information is provided to reveal information believed by the applicant to be of possible relevance to the present invention. No admission is necessarily intended, nor should be construed, that any of the preceding information constitutes prior art against the present invention.

SUMMARY OF THE INVENTION

The present invention relates to novel cannabinoid glycoside prodrugs and methods for their production by enzyme-mediated carbohydrate transfer.

An object of the present invention is to provide a cannabinoid glycoside prodrug. In accordance with an aspect of the present invention, there is provided a cannabinoid glycoside prodrug compound having formula (I):

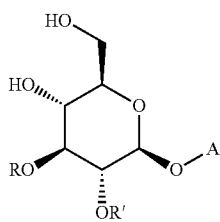

(I)

wherein R is H, β-D-glucopyranosyl, or 3-O-β-D-glucopyranosyl-β-D-glucopyranosyl; R' is H or β-D-glucopyranosyl, or 3-O-β-D-glucopyranosyl-β-D-glucopyranosyl; and A is an aglycone moiety formed through reaction of a hydroxyl group on a cannabinoid compound, an endocannabinoid compound, or a vanilloid compound, or a pharmaceutically compatible salt thereof.

In accordance with another aspect of the present invention, there is provided a method for the site-specific delivery of a cannabinoid drug to a subject, comprising the step of administering a cannabinoid glycoside prodrug in accordance with the present invention to a subject in need thereof.

In accordance with another aspect of the present invention, there is provided a method of producing a cannabinoid glycoside, comprising incubating a cannabinoid aglycone with one or more sugar donors in the presence of one or more glycosyltransferases.

Further aspects of the technology described herein will be brought out in the following portions of the specification, wherein the detailed description is for the purpose of fully disclosing preferred embodiments of the technology without placing limitations thereon.

DETAILED DESCRIPTION OF THE INVENTION

Figure 1A:
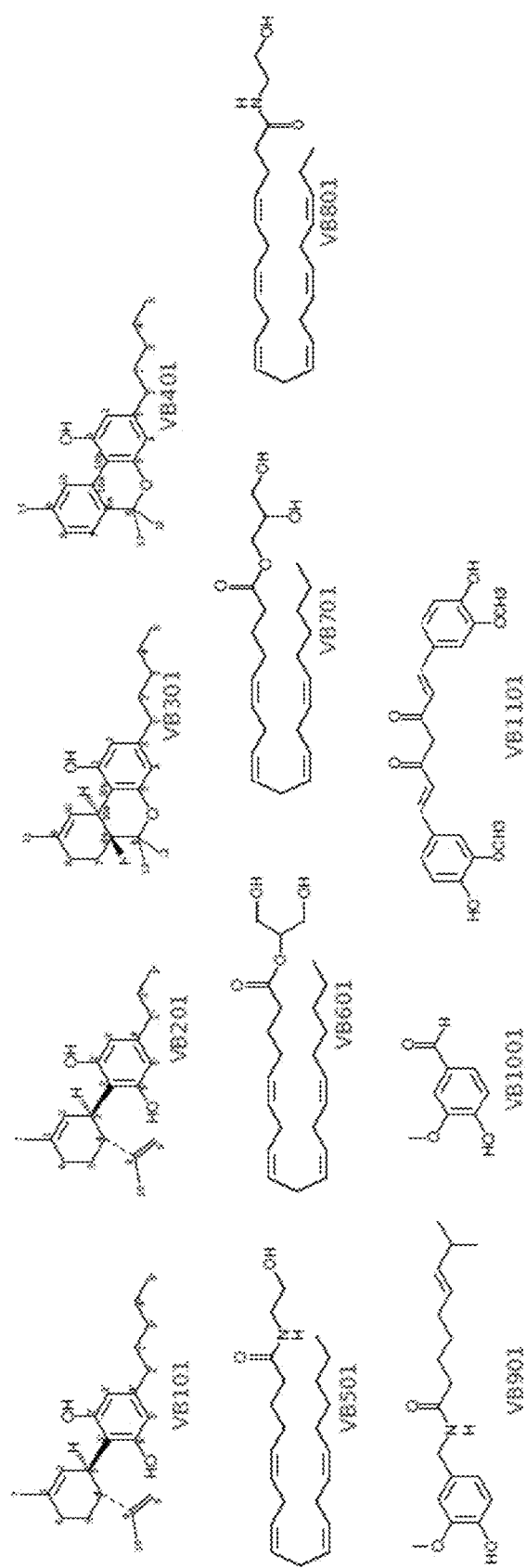
FIG. 1A illustrates aglycones employed in the glycosylation methods of the present invention.

The following abbreviations are used throughout:
CB Cannabinoid
CBD Cannabidiol.
CBDV Cannabidivarin
CBG Cannabigerol
Δ9-THC or THC Tetrahydrocannabinol
CBN Cannabinol
CBNV Cannabinavarin
CBDA Cannabidiolic acid
THCV Tetrahydrocannabivarin
UGT UDPG-dependent glucosyltransferase
UDPG Uridine diphosphoglucose
UDP Uridine diphosphate
AEA Arachidonoyl ethanolamide (aka, anandamide)
2-AG 2-Arachidonoyl ethanolamide.
1-AG 1-Arachidonoyl ethanolamide.
DHEA N-Docosahexaenoylethanolamine (aka, synaptamide)
SUS Sucrose synthase.

The term "glucopyranoside" is used for naming molecules and is shorthand for a β-D-glucose attached through the hydroxyl at the 1-position (the anomeric carbon) of the glucose to the aglycone.

The term "aglycone" is used in the present application to refer to the non-glycosidic portion of a glycoside compound.

The term "prodrug" refers to a compound that, upon administration, must undergo a chemical conversion by metabolic processes before becoming an active pharmacological agent.

The term "cannabinoid glycoside prodrug" refers generally to the glycosides of cannabinoid compounds, endocannabinoid compounds and vanilloid compounds. The cannabinoid glycoside prodrug undergoes hydrolysis of the glycosidic bond, typically by action of a glycosidase, to release the active cannabinoid, endocannabinoid or vanilloid compounds to a desired site in the body of the subject. The cannabinoid glycoside prodrug of the present invention may also be referred to using the term "cannaboside".

The term "cannabinoid" is used in the present application to refer generally to compounds found in *cannabis* and which act on cannabinoid receptors. "Cannabinoid" compounds include, but are not limited to, cannabidiol (CBD), cannabidivarin (CBDV), cannabigerol (CBG), tetrahydrocannabinol (Δ9-THC or THC), cannabinol (CBN), cannabidiolic acid (CBDA), and tetrahydrocannabivarin (THCV). Particularly preferred cannabinoids compounds are CBD, CBDV, THC and CBN.

The term "endocannabinoid" is used in the present application to refer to compounds including arachidonoyl ethanolamide (anandamide, AEA), 2-arachidonoyl ethanolamide (2-AG), 1-arachidonoyl ethanolamide (1-AG), and docosahexaenoyl ethanolamide (DHEA, synaptamide), oleoyl ethanolamide (OEA), eicsapentaenoyl ethanolamide, prostaglandin ethanolamide, docosahexaenoyl ethanolamide, linolenoyl ethanolamide, 5(Z),8(Z),11(Z)-eicosatrienoic acid ethanolamide (mead acid ethanolamide), heptadecanoul ethanolamide, stearoyl ethanolamide, docosaenoyl ethanolamide, nervonoyl ethanolamide, tricosanoyl ethanolamide, lignoceroyl ethanolamide, myristoyl ethanolamide, pentadecanoyl ethanolamide, palmitoleoyl ethanolamide, docosahexaenoic acid (DHA). Particularly preferred endocannabinoids are AEA, 2-AG, 1-AG, and DHEA.

The term "vanilloid" is used in the present application to refer to compounds comprising a vanillyl group and which act on vanilloid receptors like TRPV1. "Vanilloid" compounds include, but are not limited to, vanillin, capsaicin and curcumin.

As used herein, the term "about" refers to a +/−10% variation from the nominal value. It is to be understood that such a variation is always included in a given value provided herein, whether or not it is specifically referred to.

The term "subject" or "patient" as used herein refers to an animal in need of treatment. In one embodiment, the animal is a human.

Unless defined otherwise, all technical and scientific terms used herein have the same meaning as commonly understood by one of ordinary skill in the art to which this invention belongs.

In accordance with the present invention, cannabinoids, endocannabinoids and vanilloids are employed as substrates for glucosyltransferases to which one or more sugar molecules are attached to create novel cannabinoid glycoside prodrugs. The resulting cannabinoid glycoside prodrugs demonstrate site-specific or tissue-specific delivery, improved aqueous solubility for improved pharmacological delivery, and/or sustained or delayed release of the cannabinoid, endocannabinoid and vanilloid drug molecules.

Also in accordance with the present invention, the cannabinoid glycoside prodrugs are converted upon hydrolysis of the glycosidic bond to provide the active cannabinoid, endocannabinoid and vanilloid drug. Accordingly, the present invention has demonstrated that glycosides with a hydrophobic aglycone moiety undergo glucose hydrolysis in the gastrointestinal tract or in tissues having increased expression of glycosidases, yielding the hydrophobic cannabinoid compound in the targeted tissue or organ.

The glucose residues of glycosides are commonly acid-hydrolyzed in the stomach or cleaved by glycosidase enzymes in the intestinal tract, including by alpha-glycosidases and beta-glycosidases, which are expressed by intestinal microflora across different regions of the intestine. Accordingly, glycosides are hydrolyzed upon ingestion to release the desired compound into the intestines or target tissues.

In one embodiment, glycosylation of cannabinoid drugs provides cannabinoid glycoside prodrugs capable of persisting in the acidic stomach environment upon oral administration, thereby allowing delivery of the prodrug into the large intestine, where the cannabinoid aglycones can be liberated by glycosidases produced by colonic bacteria.

In one embodiment, glycosylation of cannabinoid drugs provides cannabinoid glycoside prodrugs suitable for targeted delivery to tissues having increased expression of glycosidases. Upon parenteral administration of the cannabinoid glycoside prodrug formulation to the subject, the cannabinoid aglycones are liberated by the glycosidases in the target tissues.

It is also within the scope of the present invention that the cannabinoid glycoside prodrug are also useful as pharmaceutical agents without glucose cleavage, where they exhibit novel pharmacodynamic properties compared to the parent compound alone. The increased aqueous solubility of the cannabinoid glycoside prodrugs of the present invention also enables new formulations for delivery in transdermal or aqueous formulations that would not have been achievable if formulating hydrophobic cannabinoid, endocannabinoid and vanilloid molecules.

In one embodiment of the present invention, there are provided cannabinoid glycoside prodrug compounds having formula (I):

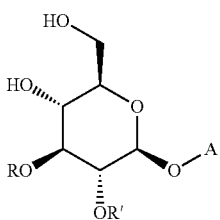

(I)

or a pharmaceutically compatible salt thereof, wherein R is H, β-D-glucopyranosyl, or 3-O-β-D-glucopyranosyl-β-D-glucopyranosyl; R' is H or β-D-glucopyranosyl, or 3-O-β-D-glucopyranosyl-β-D-glucopyranosyl; and A is an aglycone moiety formed through reaction of a hydroxyl group on a cannabinoid compound, an endocannabinoid compound, or a vanilloid compound.

In accordance with one embodiment of the present invention, A is A', A" or A'";

wherein A' is:

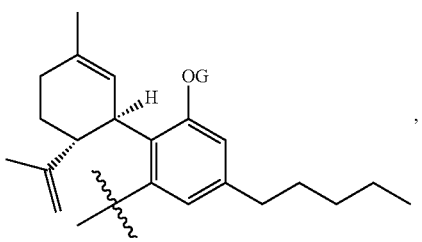

,

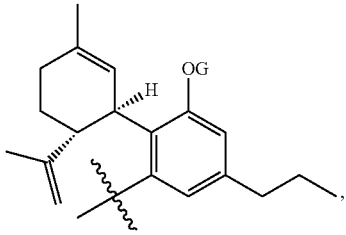

,

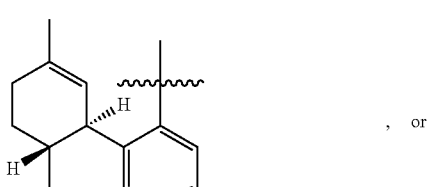

, or

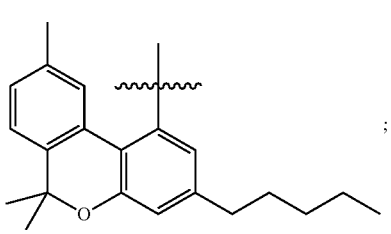

;

wherein A" is:

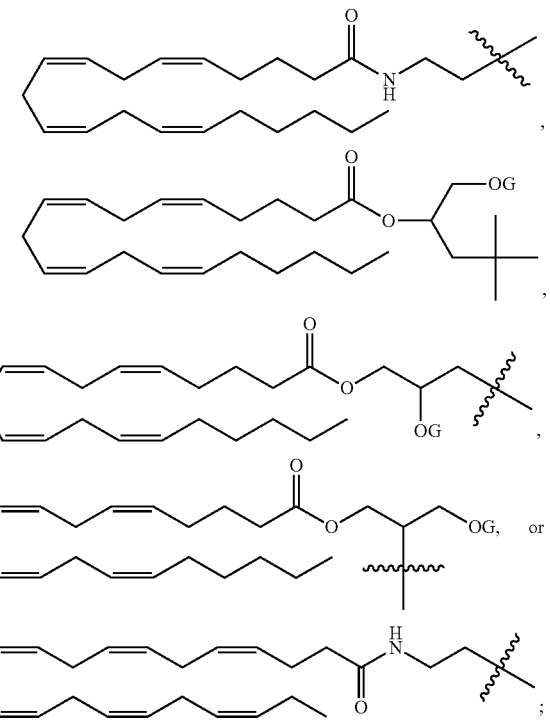

and wherein A'" is:

wherein G is H, β-D-glucopyranosyl, 3-O-β-D-glucopyranosyl-β-D-glucopyranosyl, or β-D-glucopyranosyl-(1→3)-β-D-glucopyranosyl-(1→3)-D-glucopyranosyl; or a pharmaceutically compatible salt thereof.

In accordance with one embodiment of the present invention, the cannabinoid glycoside prodrug is a glycoside of a cannabinoid, wherein the prodrug has the formula (I'):

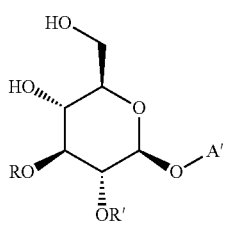
(I')

wherein R is H, β-D-glucopyranosyl, or 3-O-β-D-glucopyranosyl-β-D-glucopyranosyl; R' is H, β-D-glucopyranosyl, or 3-O-β-D-glucopyranosyl-β-D-glucopyranosyl; and wherein A' is:

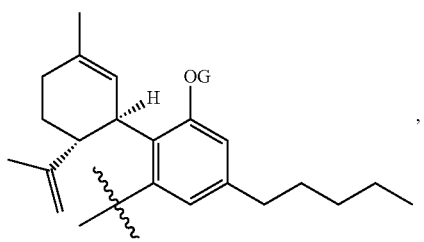,

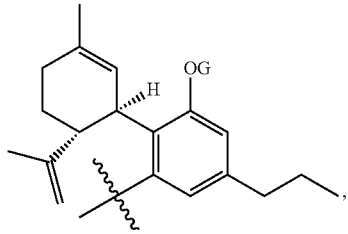,

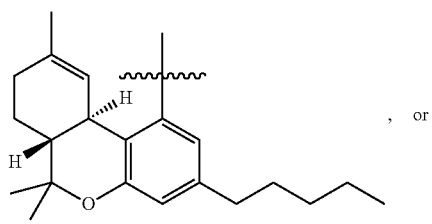, or

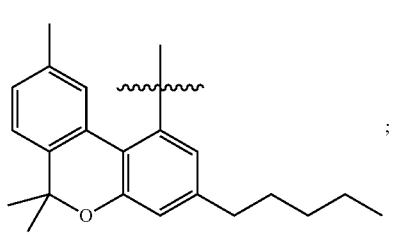;

wherein G is β-D-glucopyranosyl, 3-O-β-D-glucopyranosyl-β-D-glucopyranosyl, or β-D-glucopyranosyl-(1-3)-β-D-glucopyranosyl-(1-3)-D-glucopyranosyl.

Compounds of Formula (I') include the compounds listed in Tables 1 to 4.

Exemplary cannabidiol (CBD)-glycosides falling within the scope of Formula (I'), produced by the glycosylation of CBD (VB101) in accordance with the present invention, include:

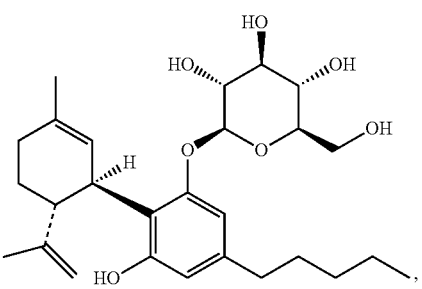
VB102

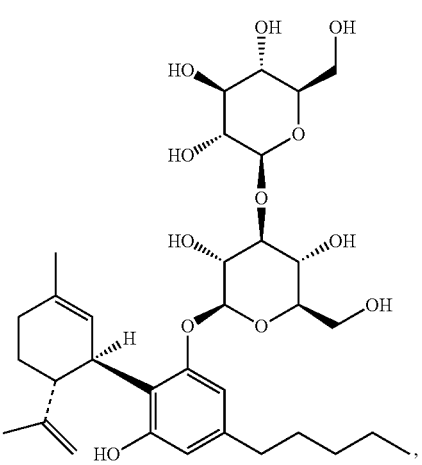
VB104

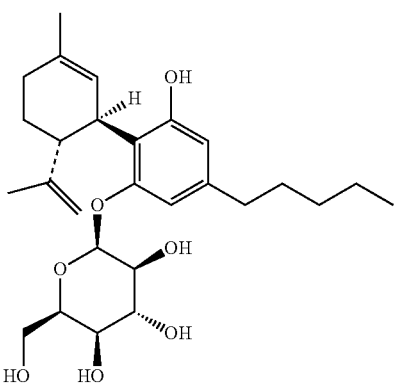
VB106

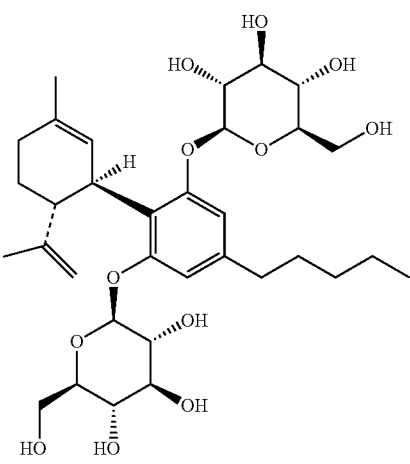
VB110

VB108
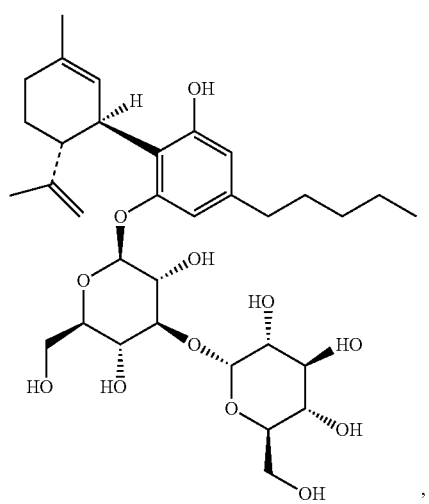
VB118
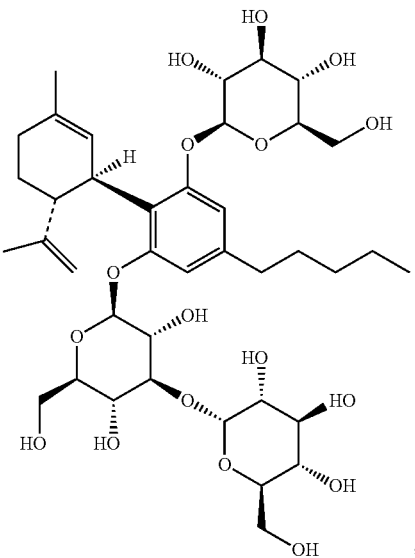
, and
VB112
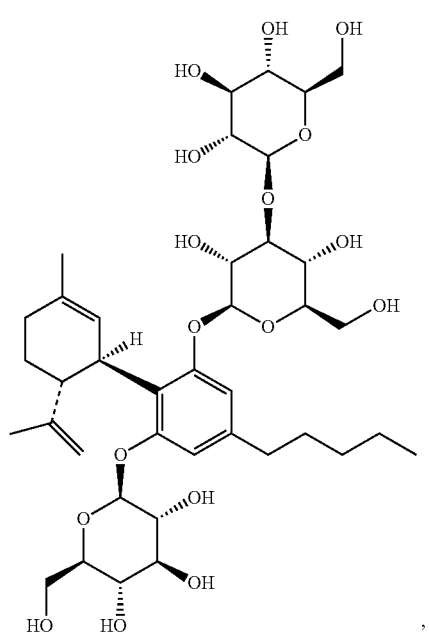
VB119
Exemplary cannabidivarin (CBDV)-glycosides falling within the scope of Formula (I'), produced by the glycosylation of CBDV (VB201) in accordance with the present invention, include:

VB202
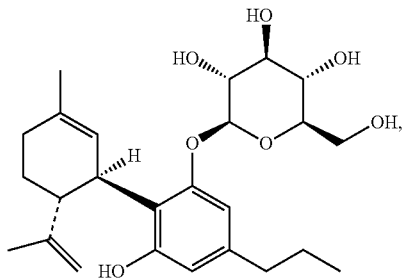
VB204
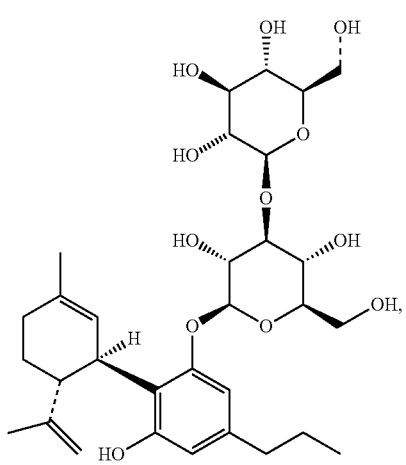
VB206
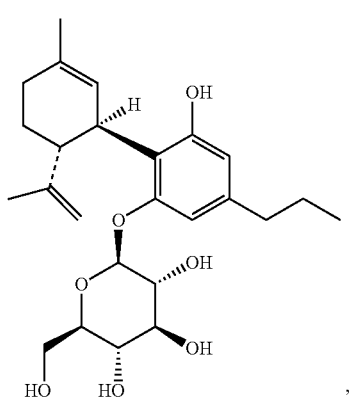
VB210
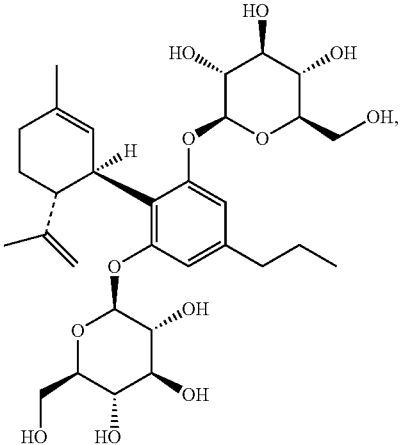
VB208
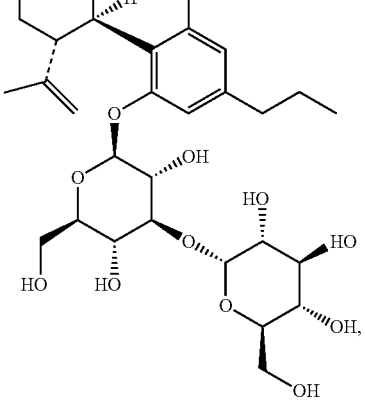
VB212
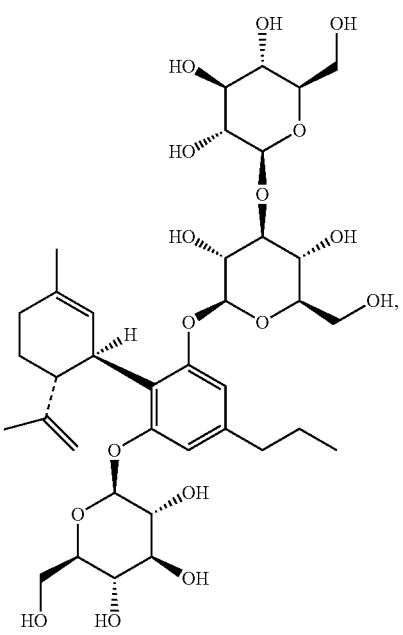

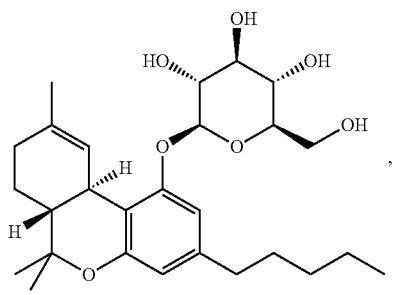
VB302
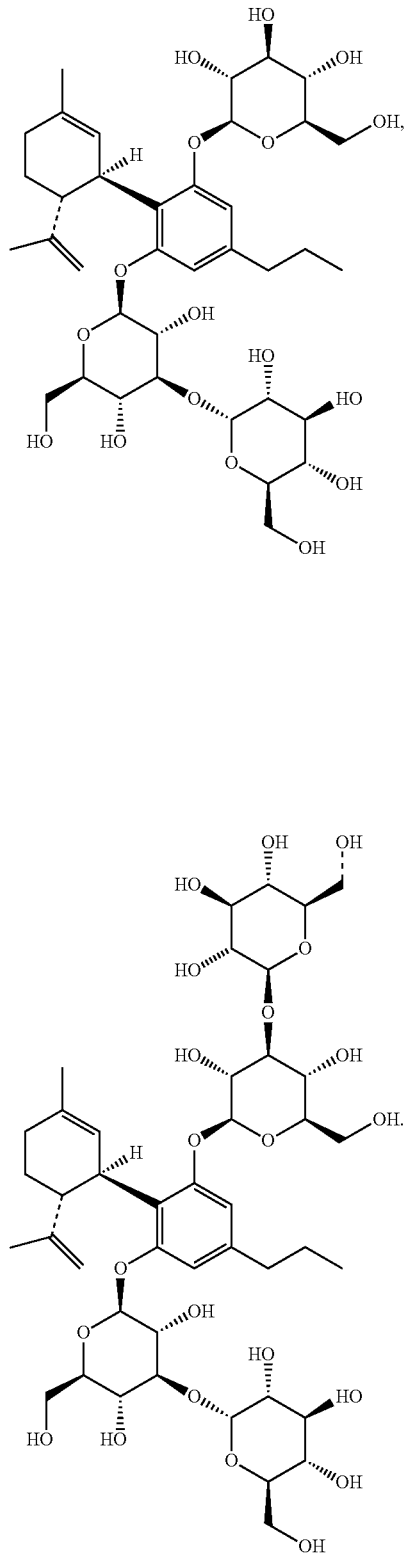
VB218
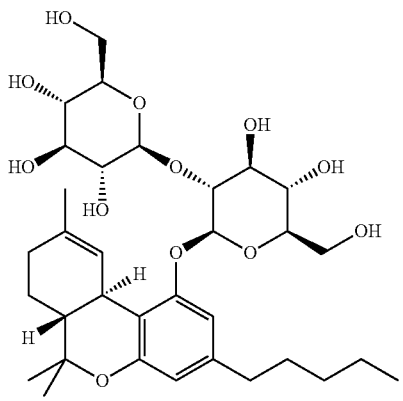
VB303
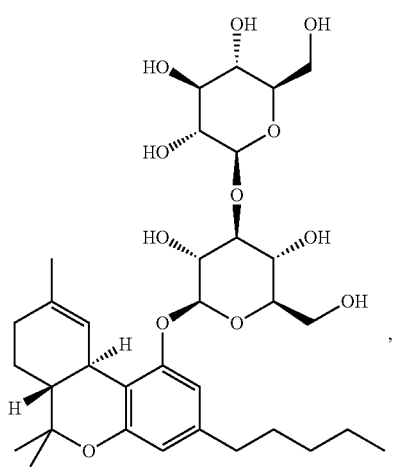
VB304
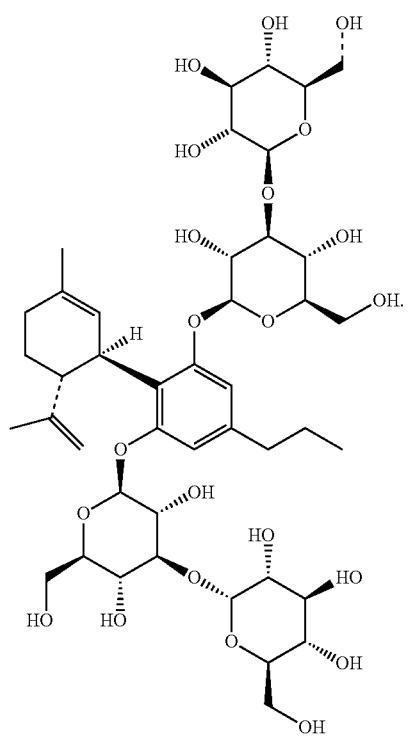
VB219
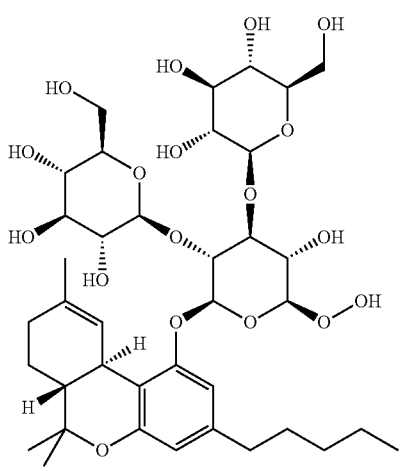
VB305 and
Exemplary tetrahydrocannabinol (Δ9-THC)-glycosides falling within the scope of Formula (I'), produced by the glycosylation of Δ9-THC (VB301) in accordance with the present invention, include:

VB308
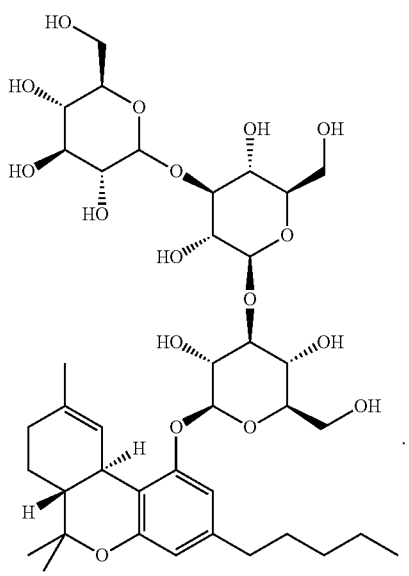
Exemplary cannabinol (CBN)-glycosides falling within the scope of Formula (I'), produced by the glycosylation of CBN (VB401) in accordance with the present invention, include:
VB402
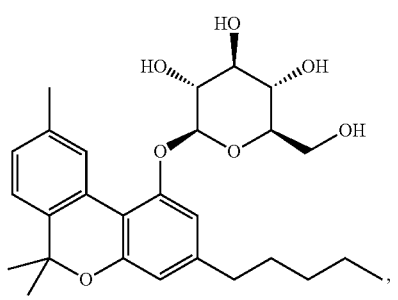
VB403
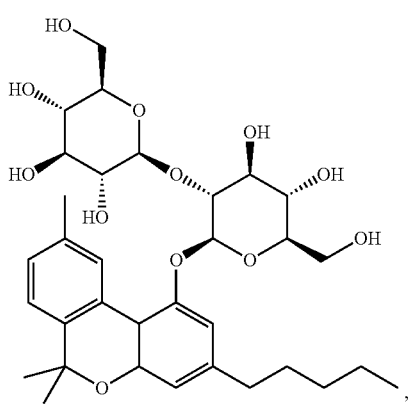
VB404
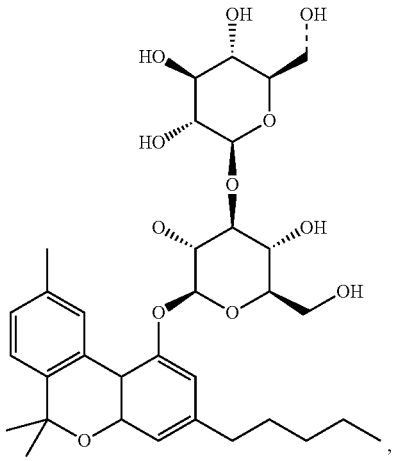
VB405
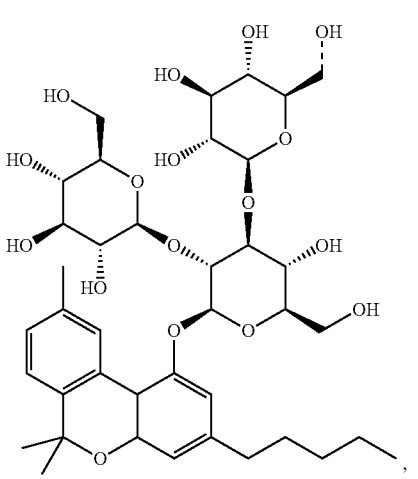
, and
VB408
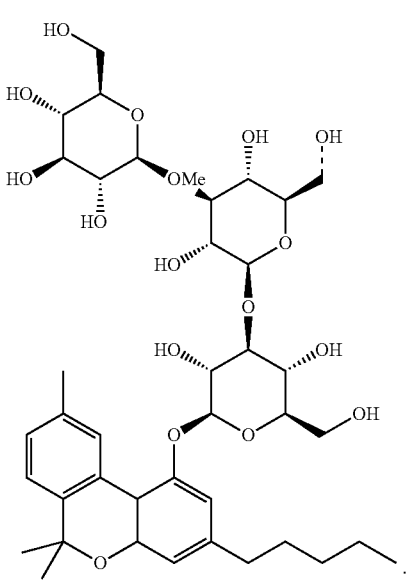
.
In accordance with one embodiment of the present invention, the cannabinoid glycoside prodrug is a glycoside of an endocannabinoid, the prodrug having the formula (I"):

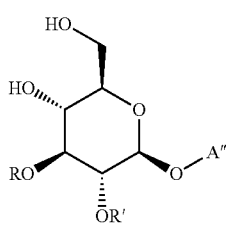

(I″)

wherein

R is H, β-D-glucopyranosyl, or 3-O-β-D-glucopyranosyl-β-D-glucopyranosyl;

R' is H, β-D-glucopyranosyl, or 3-O-β-D-glucopyranosyl-β-D-glucopyranosyl; and wherein A″ is:

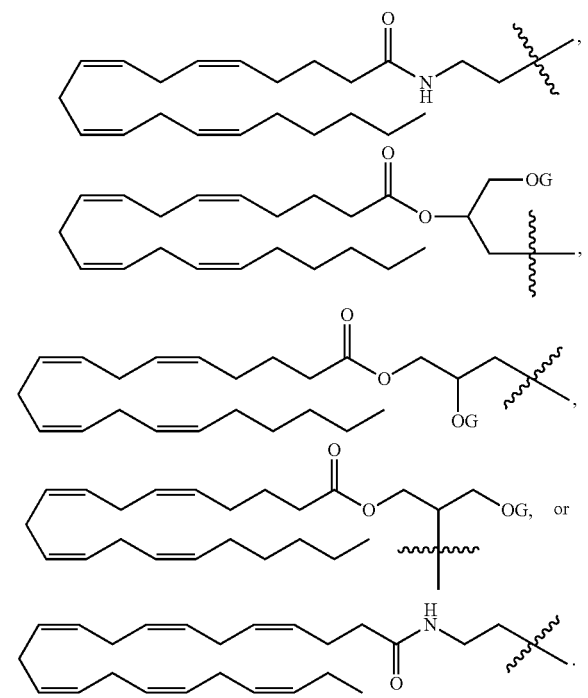

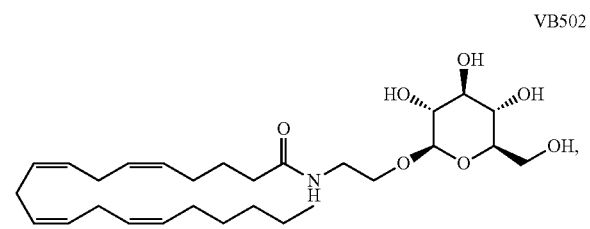

Compounds of Formula (I″) include the compounds listed in Tables 5 to 8.

Exemplary arachidonoyl ethanolamide (AEA)-glycosides falling within the scope of Formula (I″), produced by the glycosylation of AEA (VB501) in accordance with the present invention, include:

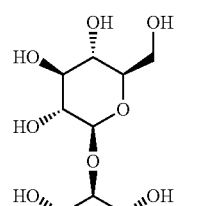
VB502

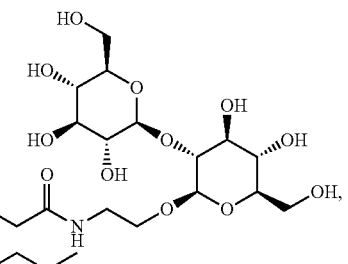
VB503

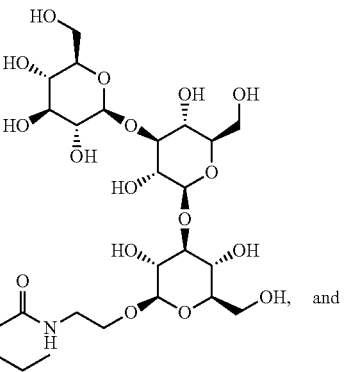
VB504

VB505

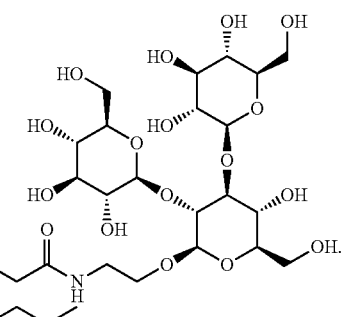
VB506

Exemplary 2-arachidonoyl ethanolamide (2-AG)-glycosides falling within the scope of Formula (I″), produced by the glycosylation of 2-AG (VB601) in accordance with the present invention, include:

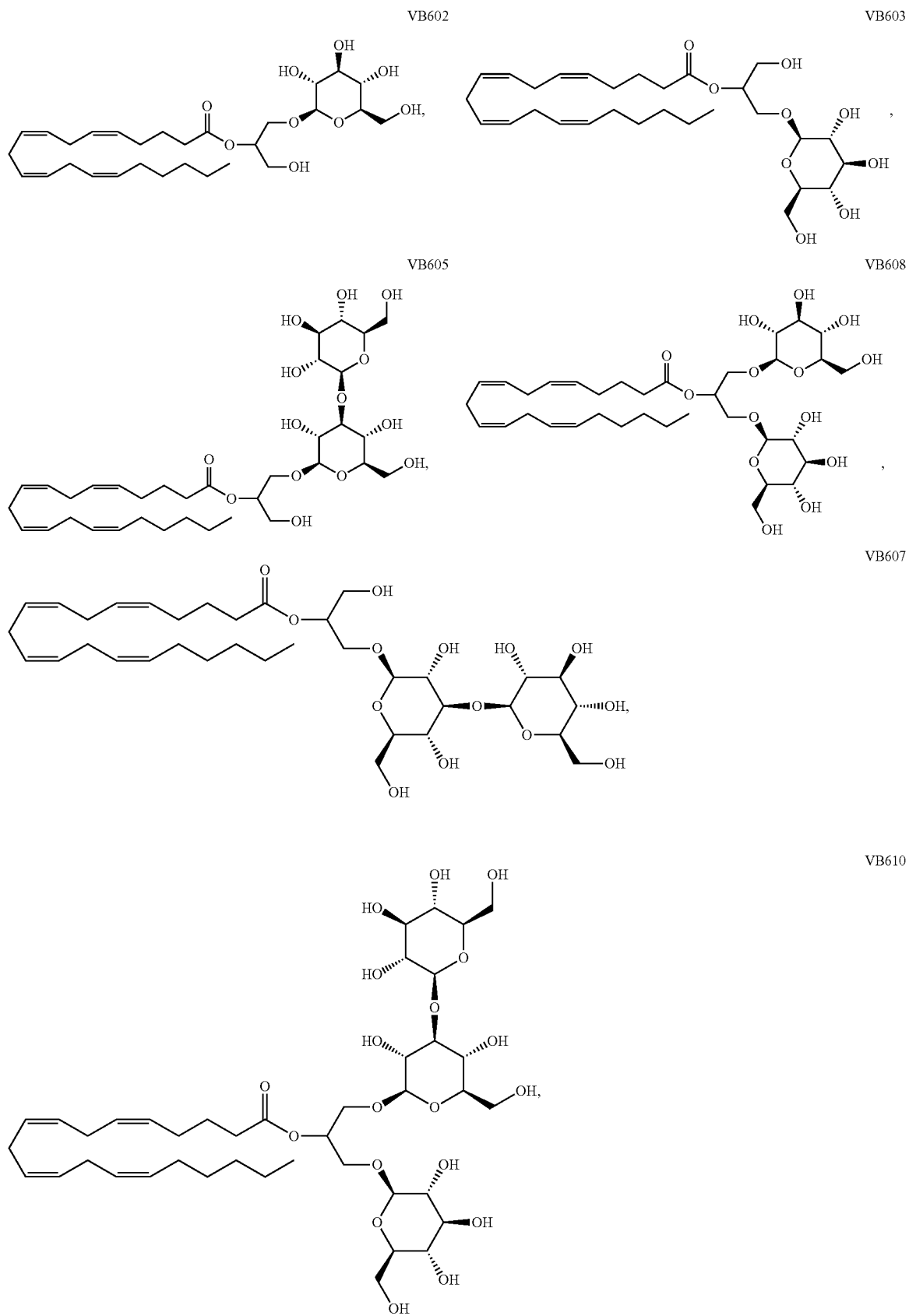

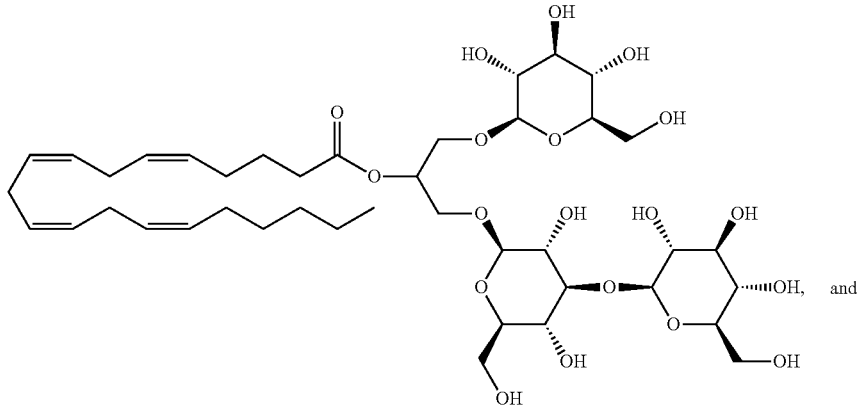
VB609
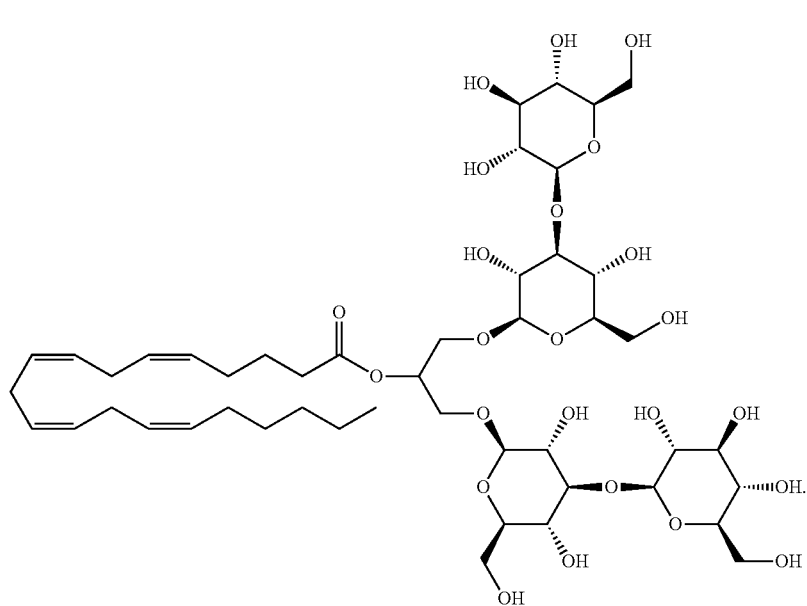
VB615
Exemplary 1-arachidonoyl ethanolamide (1-AG)-glycosides falling within the scope of Formula (I''), produced by the glycosylation of 1-AG (VB701) in accordance with the present invention, include:
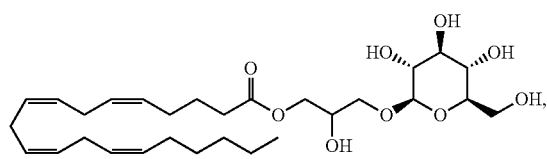
VB702
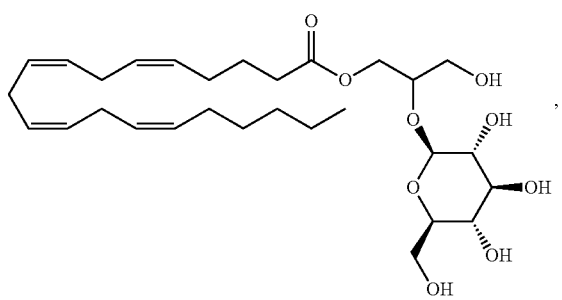
VB703

-continued
VB705
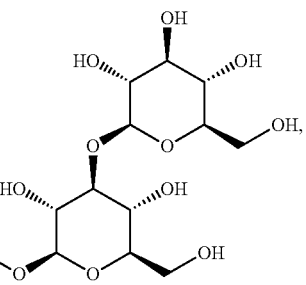
VB708
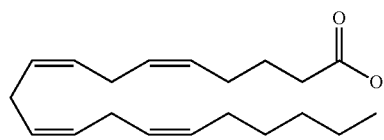
VB707
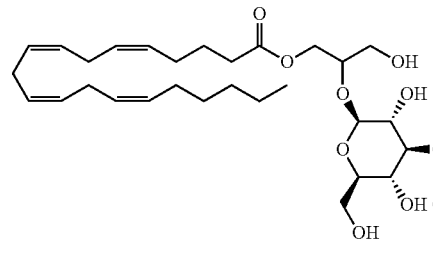
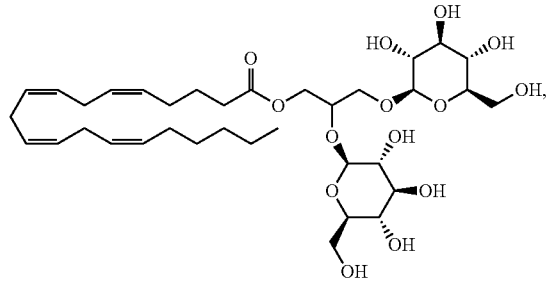
VB710
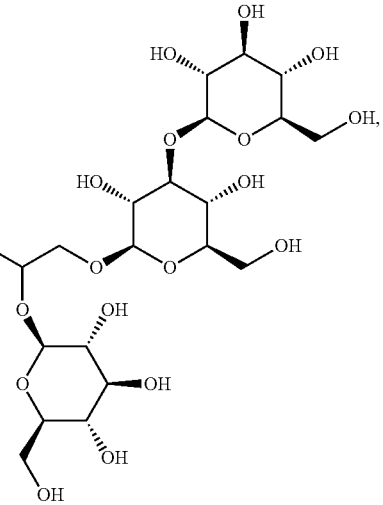
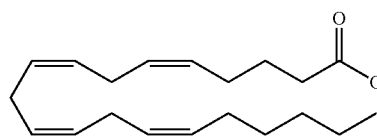
VB709
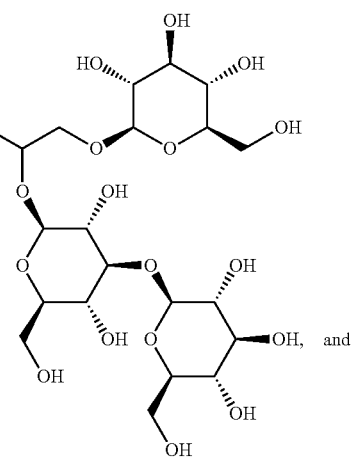
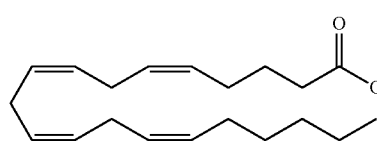
, and

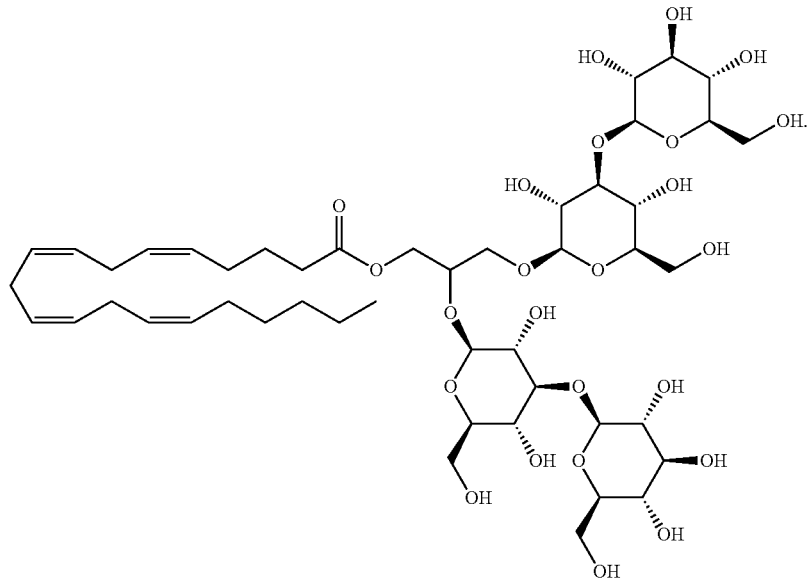
VB715
Exemplary N-docosahexaenoylethanolamine (DHEA)-glycosides falling within the scope of Formula (I"), produced by the glycosylation of DHEA (VB801) in accordance with the present invention, include:
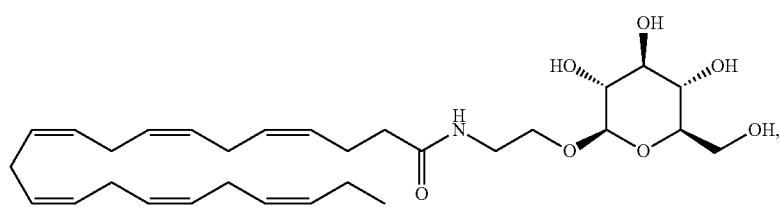
VB802
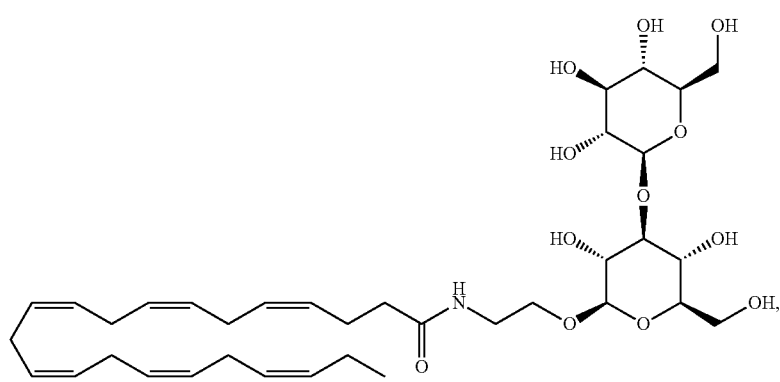
VB803
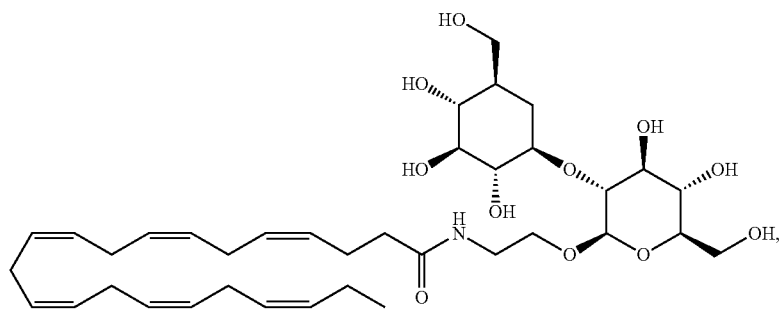
VB804

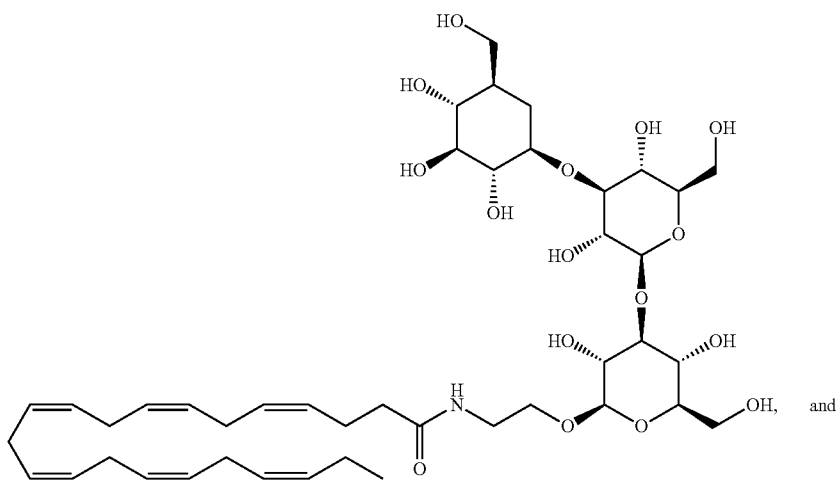

VB805

VB806

In accordance with one embodiment of the present invention, the cannabinoid glycoside prodrug is a glycoside of a vanilloid, the prodrug having the formula (I″):

(I‴)

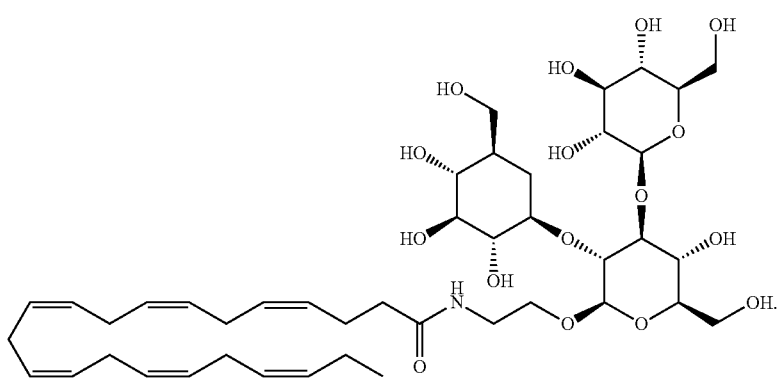

wherein
R is H, β-D-glucopyranosyl, or 3-O-β-D-glucopyranosyl-β-D-glucopyranosyl;
R' is H or β-D-glucopyranosyl, or 3-O-β-D-glucopyranosyl-β-D-glucopyranosyl; and,
wherein A‴ is:

Compounds of Formula (I‴) include the compounds listed in Tables 9 to 11.

Exemplary capsaicin-glycosides falling within the scope of Formula (I″), produced by the glycosylation of capsaicin (VB901) in accordance with the present invention, include:

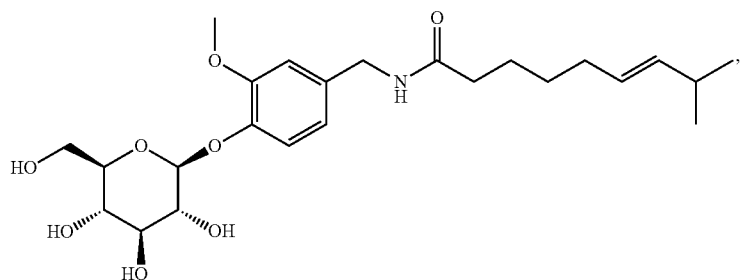
VB902
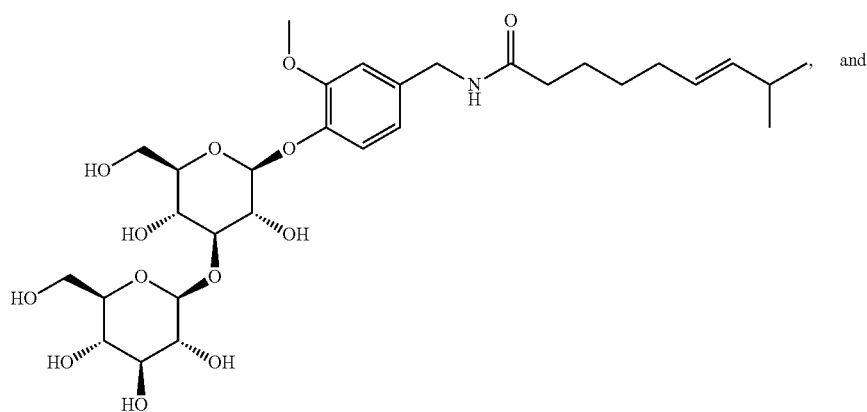
VB903, and
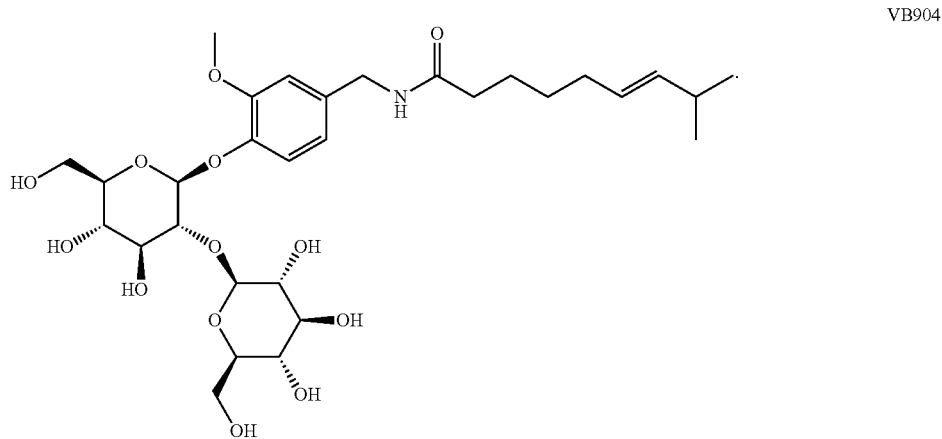
VB904
Exemplary vanillin-glycosides falling within the scope of Formula (I'''), produced by the glycosylation of vanillin (VB1001) in accordance with the present invention, include:
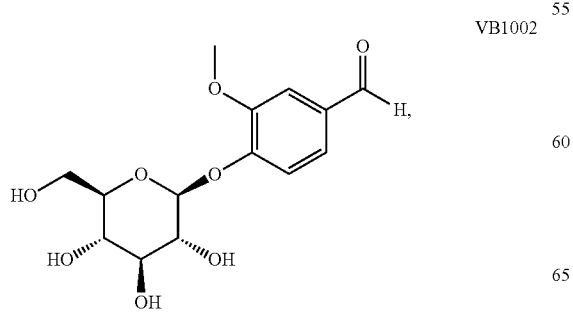
VB1002
-continued
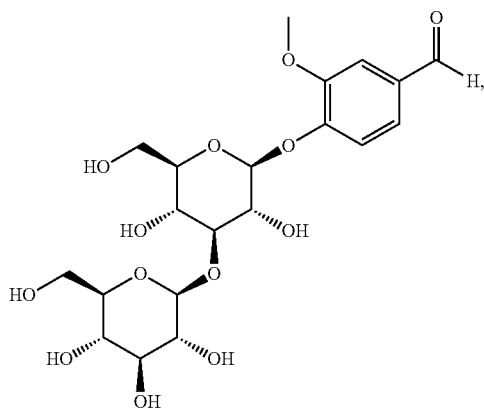
VB1003

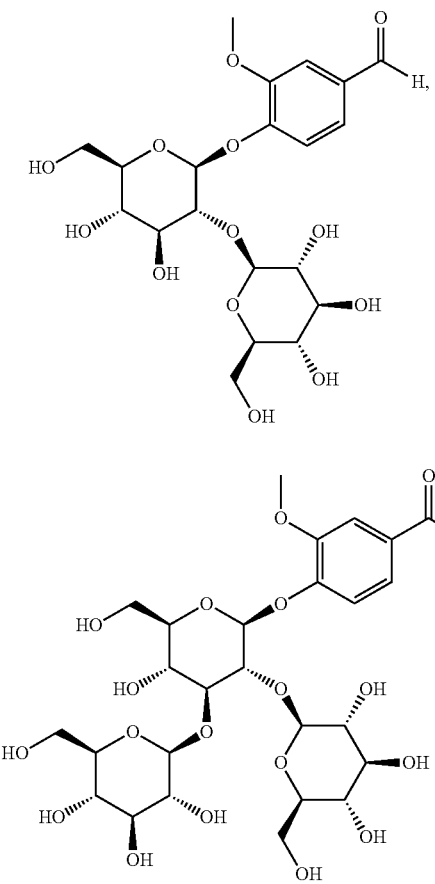
VB1004
VB1005
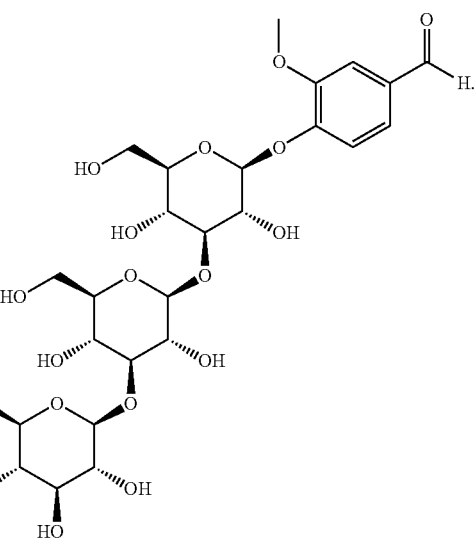
VB1006
Exemplary curcumin-glycosides falling within the scope of Formula (I'''), produced by the glycosylation of curcumin (VB1101) in accordance with the present invention, include:
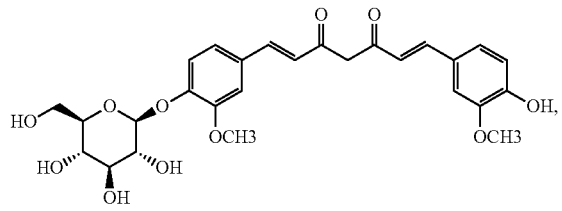
VB1102
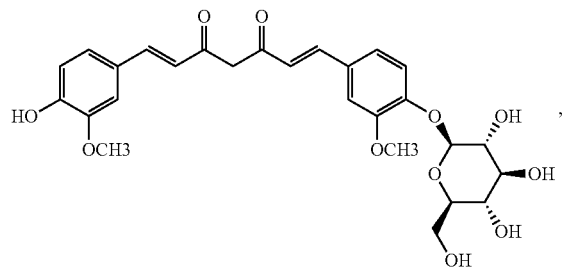
VB1103
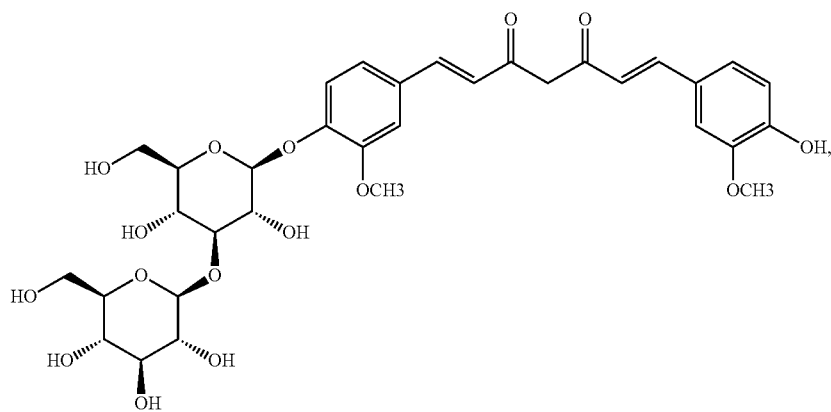
VB1104

-continued
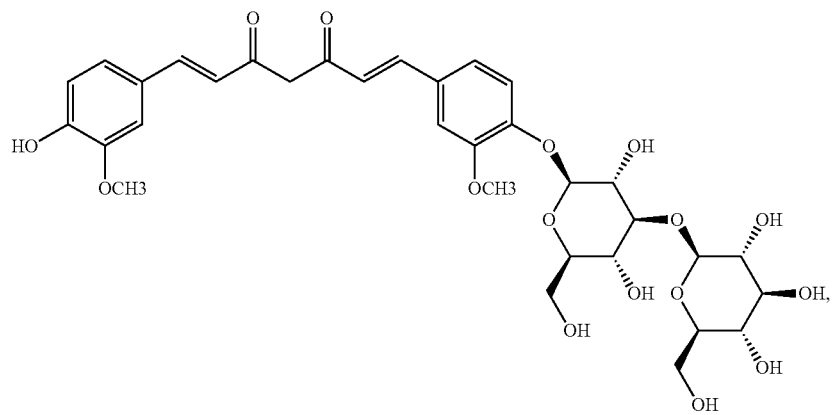
VB1106
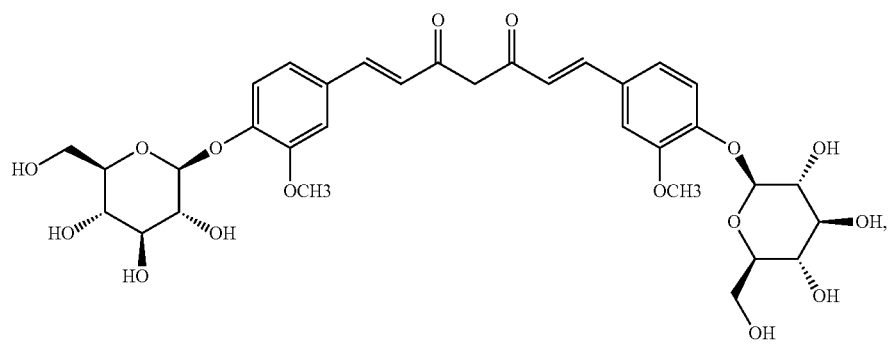
VB1108
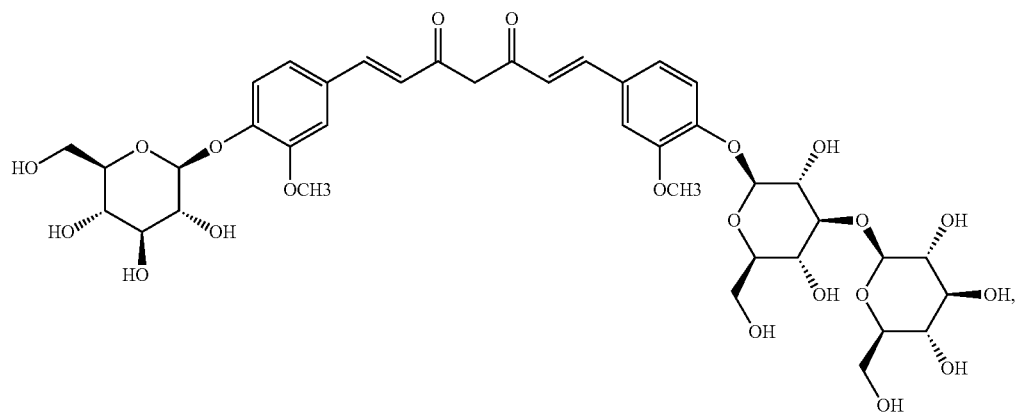
VB1109
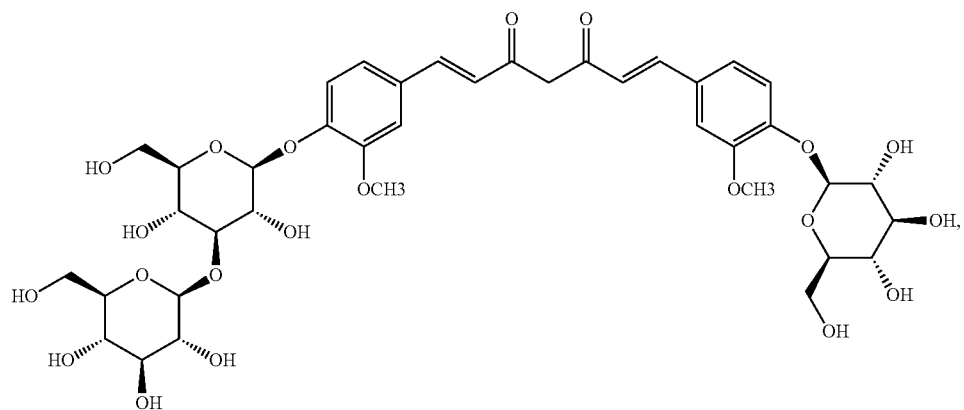
VB1110

-continued
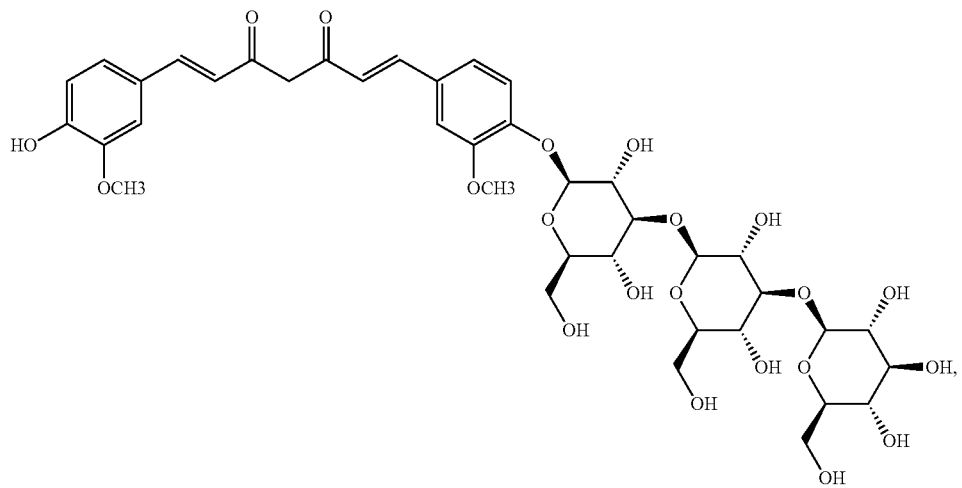
VB1115
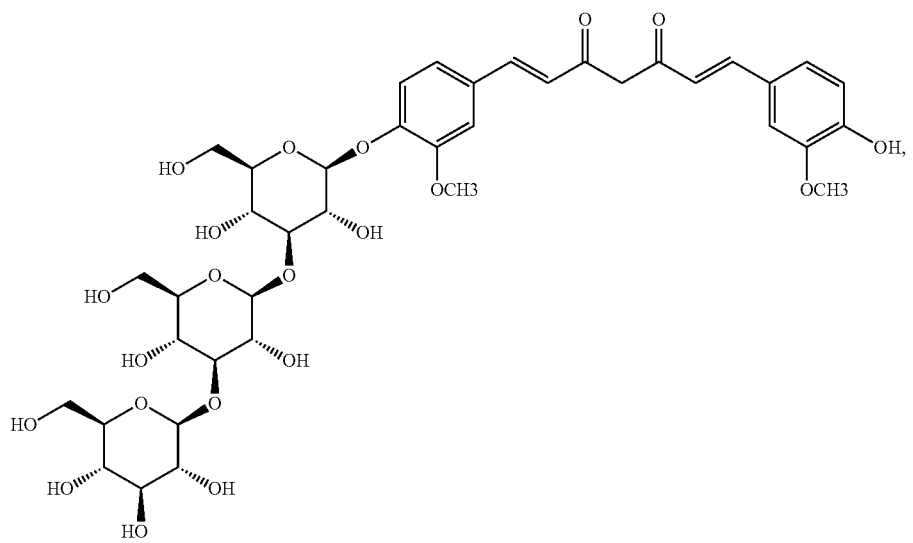
VB1116
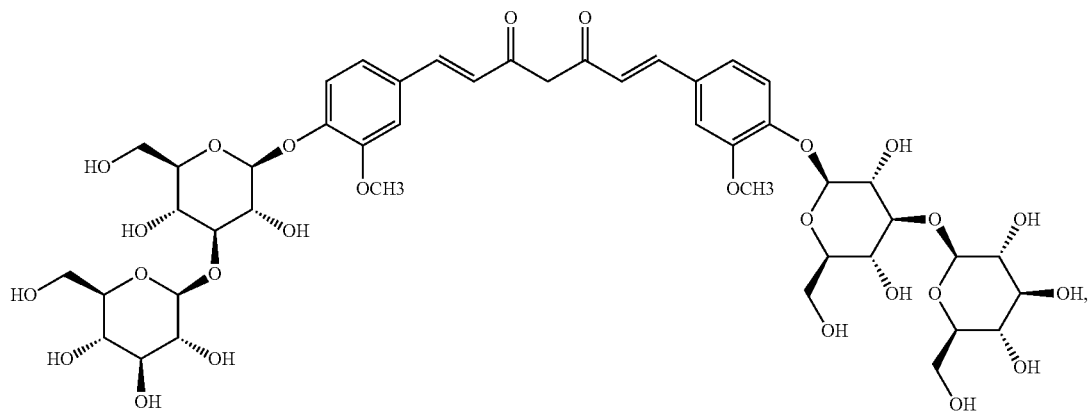
VB1117

-continued
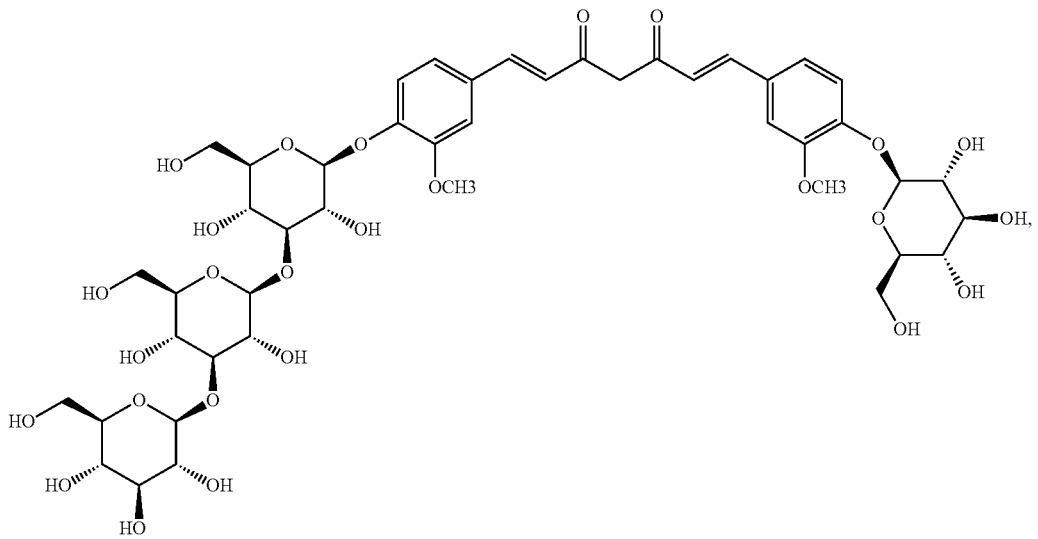
VB1121
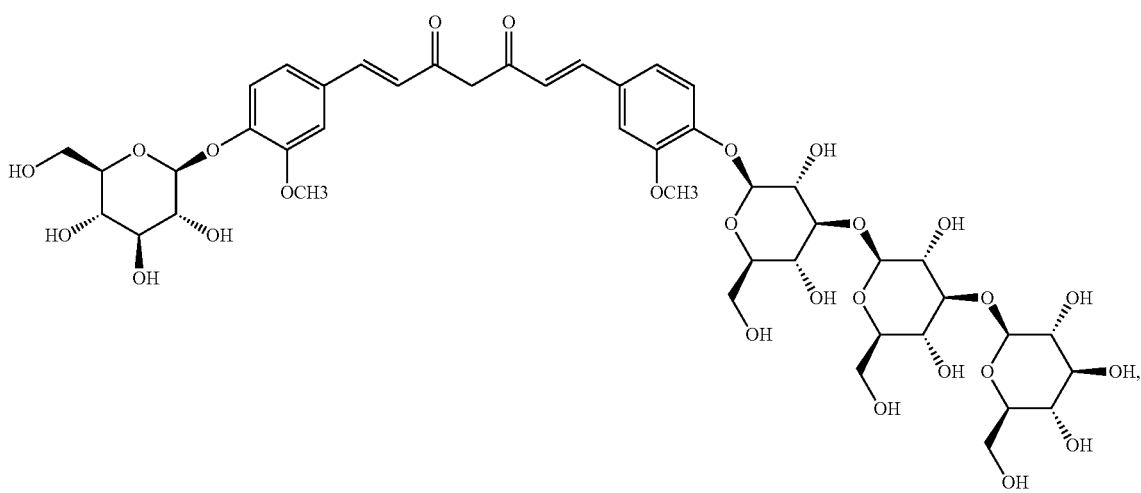
VB1123
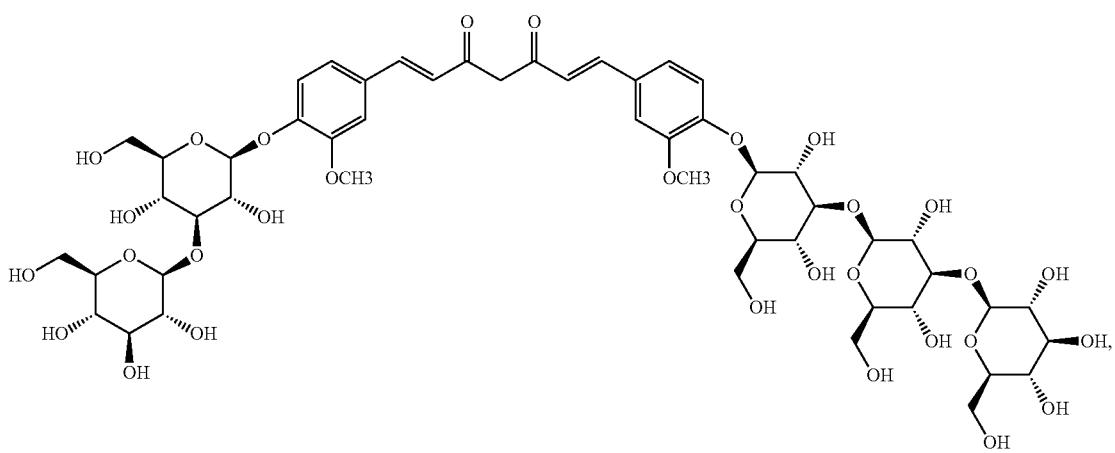
VB1126

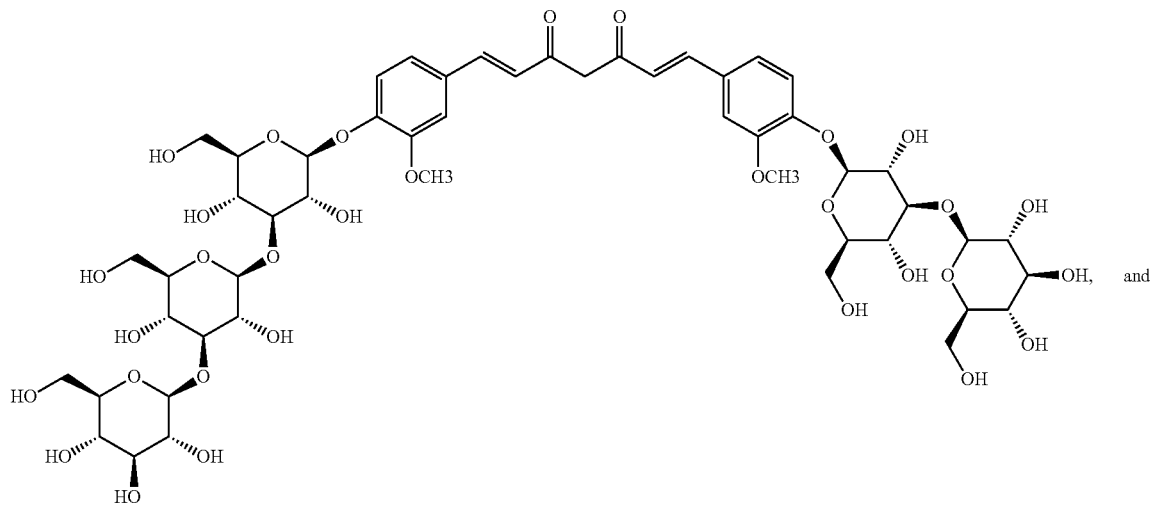

VB1127

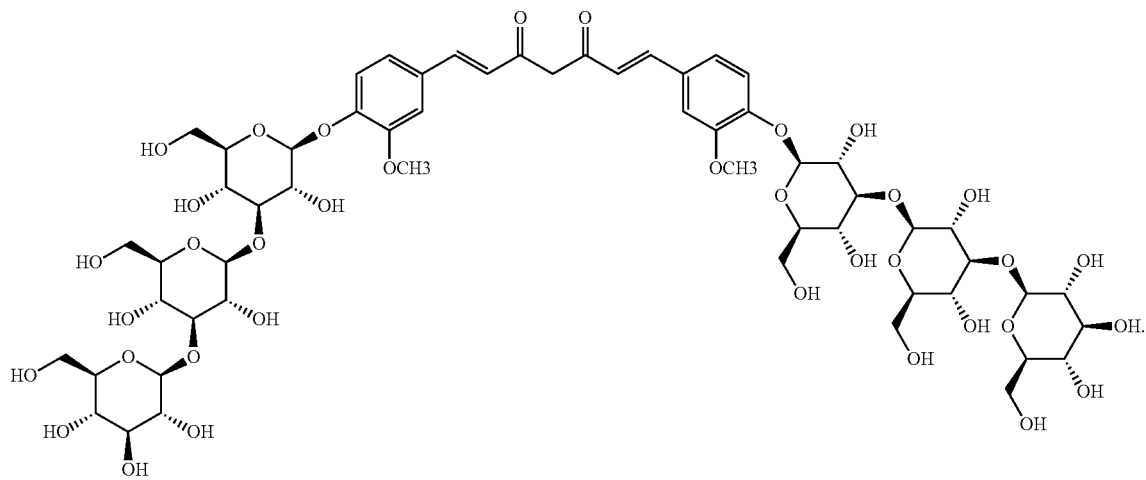

VB1129

In one embodiment, there is provided a method for the site-specific delivery of a cannabinoid drug to a subject, comprising the step of administering to a subject in need thereof one or more cannabinoid glycoside prodrugs in accordance with the present invention. In one embodiment, the site of delivery is the large intestine. In one embodiment, the site of delivery is the rectum. In one embodiment, the site of delivery is the liver. In one embodiment, the site of delivery is the skin.

In one embodiment, there is provided a method for facilitating the transport of a cannabinoid drug to the brain through intranasal, stereotactic, or intrathecal delivery, or delivery across the blood brain barrier of a subject comprising administering a cannabinoid glycoside prodrug in accordance with the present invention to a subject in need thereof.

In accordance with the present invention, the cannabinoid glycoside prodrugs are useful in the treatment of conditions that benefit from or can be ameliorated with the administration of a cannabinoid drug. Conditions that can be treated or ameliorated through the administration of cannabinoid glycoside prodrugs of the present invention, include but are not limited to, inflammatory bowel disease including induction of remission from Crohn's disease, and colitis and induction of remission from ulcerative colitis. Among the benefits that can be achieved through the administration of cannabinoid glycoside prodrugs of the present invention are decreased inflammation of the intestines and rectum, decreased pain in the intestines, rectum, as well as decrease in neuropathic pain and abdominal pain, and inhibition of proliferation or cytotoxicity against colorectal cancer. Additional treatment indications, effects, or applications for cannabinoids or cannabinoid glycosides may include but are not limited to anorexia, nausea, emesis, pain, wasting syndrome, HIV-wasting, chemotherapy induced nausea and vomiting, epilepsy, schizophrenia, irritable bowel syndrome, cramping, spasticity, seizure disorders, alcohol use disorders, substance abuse disorders, addiction, cancer, amyotrophic lateral sclerosis, glioblastoma multiforme, glioma, increased intraocular pressure, glaucoma, *cannabis* use disorders, Tourette's syndrome, dystonia, multiple sclerosis, white matter disorders, demyelinating disorders, chronic traumatic encephalopathy, leukoencephalopathies, Guillain-Barre syndrome, inflammatory bowel disorders, gastrointestinal disorders, bacterial infections, MRSA, sepsis, septic shock, viral infections, arthritis, dermatitis, Rheumatoid arthritis, systemic lupus erythematosus, anti-inflammatory, anti-convulsant, anti-psychotic, anti-oxidant, neuroprotective, anti-cancer, immunomodulatory effects, neuropathic pain, neuropathic pain associated with post-herpetic neuralgia, diabetic neuropathy, shingles, burns, actinic keratosis, oral cavity sores and ulcers, post-episiotomy pain, psoriasis, pruritis, gout, chondrocalcinosis, joint pain, fibromyalgia, musculoskeletal pain, neuropathic-postoperative complications.

In one embodiment, the cannabinoid glycoside prodrug is administered in a pharmaceutical composition further comprising a pharmaceutically acceptable carrier, diluent, excipient, or adjuvant. In one embodiment, the pharmaceutical compositions comprise one or more cannabinoid glycoside prodrugs and one or more pharmaceutically acceptable carriers, diluents, excipients and/or adjuvants. For administration to a subject, the pharmaceutical compositions can be formulated for administration by a variety of routes including but not limited to oral, topical, rectal, parenteral, and intranasal administration.

The pharmaceutical compositions may comprise from about 1% to about 95% of a cannabinoid glycoside prodrug of the invention. Compositions formulated for administration in a single dose form may comprise, for example, about 20% to about 90% of the cannabinoid glycoside prodrug of the invention, whereas compositions that are not in a single dose form may comprise, for example, from about 5% to about 20% of the cannabinoid glycoside prodrug of the invention. Non-limiting examples of unit dose forms include tablets, ampoules, dragees, suppositories, and capsules.

In a preferred embodiment, the pharmaceutical compositions are formulated for oral administration. Pharmaceutical compositions for oral administration can be formulated, for example, as tablets, troches, lozenges, aqueous or oily suspensions, dispersible powders or granules, emulsion hard or soft capsules, or syrups or elixirs. Such compositions can be prepared according to standard methods known in the art for the manufacture of pharmaceutical compositions and may contain one or more agents selected from the group of sweetening agents, flavouring agents, colouring agents and preserving agents in order to provide pharmaceutically elegant and palatable preparations. Tablets contain the active ingredient in admixture with suitable non-toxic pharmaceutically acceptable excipients including, for example, inert diluents, such as calcium carbonate, sodium carbonate, lactose, calcium phosphate or sodium phosphate; granulating and disintegrating agents, such as corn starch, or alginic acid; binding agents, such as starch, gelatine or acacia, and lubricating agents, such as magnesium stearate, stearic acid or talc. The tablets can be uncoated, or they may be coated by known techniques in order to delay disintegration and absorption in the gastrointestinal tract and thereby provide a sustained action over a longer period. For example, a time delay material such as glyceryl monosterate or glyceryl distearate may be employed to further facilitate delivery of the drug compound to the desired location in the digestive tract.

Pharmaceutical compositions for oral use can also be presented as hard gelatine capsules wherein the active ingredient is mixed with an inert solid diluent, for example, calcium carbonate, calcium phosphate or kaolin, or as soft gelatine capsules wherein the active ingredient is mixed with water or an oil medium such as peanut oil, liquid paraffin or olive oil.

Pharmaceutical compositions formulated as aqueous suspensions contain the active compound(s) in admixture with one or more suitable excipients, for example, with suspending agents, such as sodium carboxymethylcellulose, methyl cellulose, hydropropylmethylcellulose, sodium alginate, polyvinylpyrrolidone, hydroxypropyl-β-cyclodextrin, gum tragacanth and gum acacia; dispersing or wetting agents such as a naturally-occurring phosphatide, for example, lecithin, or condensation products of an alkylene oxide with fatty acids, for example, polyoxyethyene stearate, or condensation products of ethylene oxide with long chain aliphatic alcohols, for example, hepta-decaethyleneoxycetanol, or condensation products of ethylene oxide with partial esters derived from fatty acids and a hexitol for example, polyoxyethylene sorbitol monooleate, or condensation products of ethylene oxide with partial esters derived from fatty acids and hexitol anhydrides, for example, polyethylene sorbitan monooleate. The aqueous suspensions may also contain one or more preservatives, for example ethyl, or n-propyl p-hydroxy-benzoate, one or more colouring agents, one or more flavouring agents or one or more sweetening agents, such as sucrose, *stevia*, or saccharin.

Pharmaceutical compositions can be formulated as oily suspensions by suspending the active compound(s) in a vegetable oil, for example, arachis oil, olive oil, sesame oil or coconut oil, or in a mineral oil such as liquid paraffin. The oily suspensions may contain a thickening agent, for example, beeswax, hard paraffin or cetyl alcohol. Sweetening agents such as those set forth above, and/or flavouring agents may be added to provide palatable oral preparations. These compositions can be preserved by the addition of an anti-oxidant such as ascorbic acid.

The pharmaceutical compositions can be formulated as a dispersible powder or granules, which can subsequently be used to prepare an aqueous suspension by the addition of water. Such dispersible powders or granules provide the active ingredient in admixture with one or more dispersing or wetting agents, suspending agents and/or preservatives. Suitable dispersing or wetting agents and suspending agents are exemplified by those already mentioned above. Additional excipients, for example, sweetening, flavouring and colouring agents, can also be included in these compositions.

Pharmaceutical compositions of the invention can also be formulated as oil-in-water emulsions. The oil phase can be a vegetable oil, for example, olive oil or arachis oil, or a mineral oil, for example, liquid paraffin, or it may be a mixture of these oils. Suitable emulsifying agents for inclusion in these compositions include naturally-occurring gums, for example, gum acacia or gum tragacanth; naturally-occurring phosphatides, for example, soy bean, lecithin; or esters or partial esters derived from fatty acids and hexitol, anhydrides, for example, sorbitan monoleate, and condensation products of the said partial esters with ethylene oxide, for example, polyoxyethylene sorbitan monoleate. The emulsions can also optionally contain sweetening and flavouring agents.

Pharmaceutical compositions can be formulated as a syrup or elixir by combining the active ingredient(s) with one or more sweetening agents, for example glycerol, propylene glycol, sorbitol or sucrose. Such formulations can also optionally contain one or more demulcents, preservatives, flavouring agents and/or colouring agents.

If desired, other active ingredients may be included in the compositions. In one embodiment, the glycoside prodrugs may be combined with other ingredients or substances that have glycosidase activity, or that may in other ways alter drug metabolism and pharmacokinetic profile of various compounds in vivo, including ones in purified form as well as such compounds found within food, beverages, and other products. In one embodiment, the cannabinoid glycoside prodrug is administered in combination with, or formulated together with, substances that have direct glycosidase activity, or that contribute to modifications to the gut microflora that will alter the glycosidase activity in one or more regions of the intestines. Examples of such compositions include, but are not limited to, yogurt, prebiotics, probiotics, or fecal transplants.

In a further preferred embodiment, the pharmaceutical compositions are formulated for parenteral administration. The term "parenteral" as used herein includes subcutaneous injections, intravenous, intramuscular, intrathecal, intrasternal injection or infusion techniques.

Parenteral pharmaceutical compositions can be formulated as a sterile injectable aqueous or oleaginous suspension according to methods known in the art and using one or more suitable dispersing or wetting agents and/or suspending agents, such as those mentioned above. The sterile injectable preparation can be a sterile injectable solution or suspension in a non-toxic parentally acceptable diluent or solvent, for example, as a solution in 1,3-butanediol. Acceptable vehicles and solvents that can be employed include, but are not limited to, water, Ringer's solution, lactated Ringer's solution and isotonic sodium chloride solution. Other examples include, sterile, fixed oils, which are conventionally employed as a solvent or suspending medium, and a variety of bland fixed oils including, for example, synthetic mono- or diglycerides. Fatty acids such as oleic acid can also be used in the preparation of injectables.

Due to the highly lipophilic nature of cannabinoids, these molecules are typically poorly absorbed through membranes such as the skin of mammals, including humans, and the success of transdermally administering therapeutically effective quantities of cannabinoid to a subject in need thereof within a reasonable time frame and over a suitable surface area has been substantially limited. It is therefore proposed that the cannabinoid glycoside prodrugs of the present invention, through conjugation of the hydrophobic cannabinoid aglycone to the hydrophilic glycosidic moieties, provide a molecule having an amphiphilic character favourable for passive diffusion which should be more readily absorbed through the skin.

Accordingly, in one embodiment, the pharmaceutical compositions are formulated for topical administration. Such topical formulations may be presented as, for example, aerosol sprays, powders, sticks, granules, creams, liquid creams, pastes, gels, lotions, ointments, on sponges or cotton applicators, or as a solution or a suspension in an aqueous liquid, a non-aqueous liquid, an oil-in-water emulsion, or a water-in-oil liquid emulsion.

Topical pharmaceutical compositions can be formulated with thickening (gelling) agents. The thickening agent used herein may include anionic polymers such as polyacrylic acid (CARBOPOL® by Noveon, Inc., Cleveland, Ohio), carboxypolymethylene, carboxymethylcellulose and the like, including derivatives of Carbopol® polymers, such as Carbopol® Ultrez 10, Carbopol® 940, Carbopol® 941, Carbopol® 954, Carbopol® 980, Carbopol® 981, Carbopol® ETD 2001, Carbopol® EZ-2 and Carbopol® EZ-3, and other polymers such as Pemulen® polymeric emulsifiers, and Noveon® polycarbophils. Thickening agents or gelling agents are present in an amount sufficient to provide the desired rheological properties of the composition.

Topical pharmaceutical compositions can be formulated with a penetration enhancer. Non-limiting examples of penetration enhancing agents include C8-C22 fatty acids such as isostearic acid, octanoic acid, and oleic acid; C8-C22 fatty alcohols such as oleyl alcohol and lauryl alcohol; lower alkyl esters of C8-C22 fatty acids such as ethyl oleate, isopropyl myristate, butyl stearate, and methyl laurate; di(lower)alkyl esters of C6-C22 diacids such as diisopropyl adipate; monoglycerides of C8-C22 fatty acids such as glyceryl monolaurate; tetrahydrofurfuryl alcohol polyethylene glycol ether; polyethylene glycol, propylene glycol; 2-(2-ethoxyethoxyl)ethanol; diethylene glycol monomethyl ether; alkylaryl ethers of polyethylene oxide; polyethylene oxide monomethyl ethers; polyethylene oxide dimethyl ethers; dimethyl sulfoxide; glycerol; ethyl acetate; acetoacetic ester; N-alkylpyrrolidone; and terpenes.

The topical pharmaceutical compositions can further comprise wetting agents (surfactants), lubricants, emollients, antimicrobial preservatives, and emulsifying agents as are known in the art of pharmaceutical formations.

Transdermal delivery of the cannabinoid glycoside prodrug can be further facilitated through the use of a microneedle array drug delivery system.

Other pharmaceutical compositions and methods of preparing pharmaceutical compositions are known in the art and are described, for example, in "*Remington: The Science and Practice of Pharmacy*" (formerly "*Remingtons Pharmaceutical Sciences*"); Gennaro, A., Lippincott, Williams & Wilkins, Philadelphia, Pa. (2000).

The pharmaceutical compositions of the present invention described above include one or more cannabinoid glycoside prodrugs of the invention in an amount effective to achieve the intended purpose. Thus the term "therapeutically effective dose" refers to the amount of the cannabinoid glycoside prodrug that improves the status of the subject to be treated, for example, by ameliorating the symptoms of the disease or disorder to be treated, preventing the disease or disorder, or altering the pathology of the disease. Determination of a therapeutically effective dose of a compound is well within the capability of those skilled in the art. In one embodiment, cannabinoid glycosides can be combined to enable simultaneous delivery of multiple cannabinoids in a site-specific manner, including THC and CBD, whose effects in some ways may be synergistic (Russo 2006). Accordingly, in one embodiment, the pharmaceutical composition comprises one or more CBD-glycosides and one or more THC-glycosides formulated together in a single dosage form.

The exact dosage to be administered to a subject can be determined by the practitioner, in light of factors related to the subject requiring treatment. Dosage and administration are adjusted to provide desired levels of the cannabinoid glycoside prodrug and/or the cannabinoid drug compound obtained upon hydrolysis of the prodrug. Factors which may be taken into account when determining an appropriate dosage include the severity of the disease state, general health of the subject, age, weight, and gender of the subject, diet, time and frequency of administration, drug combination(s), reaction sensitivities, and tolerance/response to therapy. Dosing regimens can be designed by the practitioner depending on the above factors as well as factors such as the half-life and clearance rate of the particular formulation.

In accordance with the present invention, there is provided a method of producing a cannabinoid glycoside, comprising incubating a cannabinoid aglycone with one or more sugar donors in the presence of one or more glycosyltransferases.

In one embodiment, the one or more glycosyltransferases is a UGT76G1 or UGT76G1-like glucosyltransferase. In one embodiment, the one or more glycosyltransferases comprise a UGT76G1 or UGT76G1-like glucosyltransferase and a Os03g0702000 or Os03g0702000-like glucosyltransferase.

In one embodiment, the one or more sugar donors are selected from the group consisting of UDP-glucose, UDP-glucuronic acid, UDP-mannose, UDP-fructose, UDP-xylose, UDP-rhamnose, UDP-fluoro-deoxyglucose, and combinations thereof. In a preferred embodiment, the sugar donor is UDP-glucose.

In accordance with the present invention, the cannabinoid aglycone is a cannabinoid, an endocannabinoid, or a vanilloid. In a preferred embodiment, the cannabinoid glycoside prodrug produced by the methods of the present invention is a compound of the Formula (I).

In one embodiment, the method of producing a cannabinoid glycoside comprises incubating a cannabinoid aglycone with UDP-glucose, in the presence of a UGT76G1 or UGT76G1-like glucosyltransferase under conditions that allow for glycosylation.

In one embodiment, the method of producing a cannabinoid glycoside comprises incubating a cannabinoid aglycone with one or more sugar donors in the presence of a first glycosyltransferase and a second glycosyltransferase under conditions which allow for glycosylation. In one embodiment, sugar donor is UDP-glucose, the first glycosyltransferase is a UGT76G1 or UGT76G1-like glucosyltransferase, and the second glycosyltransferase is a Os03g0702000 or Os03g0702000-like glucosyltransferase.

In one embodiment, the method of producing a cannabinoid glycoside comprises incubating a cannabinoid aglycone with UDP-glucose in the presence of a UGT76G1 or UGT76G1-like glucosyltransferase and Os03g0702000 or Os03g0702000-like glucosyltransferase under conditions which allow for glycosylation.

In one embodiment, the method of producing a cannabinoid glycoside comprises incubating a cannabinoid aglycone with maltodextrin, in the presence of a cyclodextrin glucanotransferase under conditions that allow for glycosylation.

In one embodiment, the method of producing a cannabinoid glycoside comprises incubating a cannabinoid aglycone with UDP-glucose and maltodextrin in the presence of a UGT76G1 or UGT76G1-like glucosyltransferase and cyclodextrin glucanotransferase under conditions which allow for glycosylation.

In a preferred embodiment, the glycosyltransferase employed in the methods of producing the cannabinoid glycoside is UGT76G1 or UGT76G1-like glucosyltransferase. In one embodiment, the UGT76G1 or UGT76G1-like glucosyltransferase comprises the sequence as set forth in SEQ ID NO:1, 3, 5 or 7.

In one embodiment, the glycosyltransferase employed in the methods of producing the cannabinoid glycoside is Os03g0702000 or Os03g0702000-like glucosyltransferase. In one embodiment, the Os03g0702000 or Os03g0702000-like glucosyltransferase comprises the sequence as set forth in SEQ ID NO:9.

In one embodiment, the method of producing the cannabinoid glycoside further comprises incubating with sucrose synthase. In one embodiment, the sucrose synthase comprises the sequence as set forth in SEQ ID NO: 15, 17, 19, 21, 23 or 25.

In one embodiment, the method for the production of a cannabinoid glycoside prodrug comprises expressing one or more of the glycosyltransferases in a cell or plant which produces the cannabinoid aglycone and isolating the cannabinoid glycoside prodrug.

Glycosylation of cannabinoids improves solubility in aqueous solutions, as demonstrated by accelerated elution from an C18 analytical HPLC column, indicating that the new cannabinoid-glycosides require far less organic solvent for elution from the hydrophobic chromatography column. This improved solubility was further demonstrated by testing the aqueous solubility of purified solid cannabosides, where solutions were successfully prepared up to 500 mg/ml (50% mass/volume) with a mixture of higher glycoside forms of cannabosides. Given the markedly improved solubility and novel secondary and tertiary glycosylation on cannabinoids, glycosylated cannabinoids can act as efficient prodrugs for selective delivery of cannabinoids to desired tissues where the glucose molecules can be hydrolyzed to release the aglycone cannabinoids. Additionally the glycosylations promote stability of CBD and CBDV by protecting them from oxidation and ring-closure of the C6'-hydroxyl group, which prevents degradation into $\Delta 9$-THC or $\Delta 9$-THCV, respectively, and subsequently into cannabinol (CBN) or cannabinavarin (CBNV), respectively Increasing the diversity and complexity of sugar attachments to cannabinoids, and administration of a mixture of glycosides will provide altered prodrug delivery kinetics, thus providing an extended release formulation of the drug. The primary detoxification mechanism for cannabinoids in humans is CYP450 mediated hydroxylation of the C7 methyl group of CBD and CBDV, or the C11 methyl group of THC and CBN, glycosylation of the acceptor hydroxyl groups of the cannabinoid resorcinol ring may afford protection from C7/C11 hydroxylation and subsequent elimination from the body due to steric hindrance preventing the cannabinoid-glycoside from binding in the CYP450 active site. In fact, the hydroxyl groups of CBD are thought to facilitate the binding to the detoxification cytochrome P450 CYP3A4 in the epithelium of the small intestine (Yamaori 2011). Reduced degradation or metabolism in the stomach and small intestine due to these effects could also lead to higher total bioavailability of any glycosylated product upon oral delivery.

Figure 2:
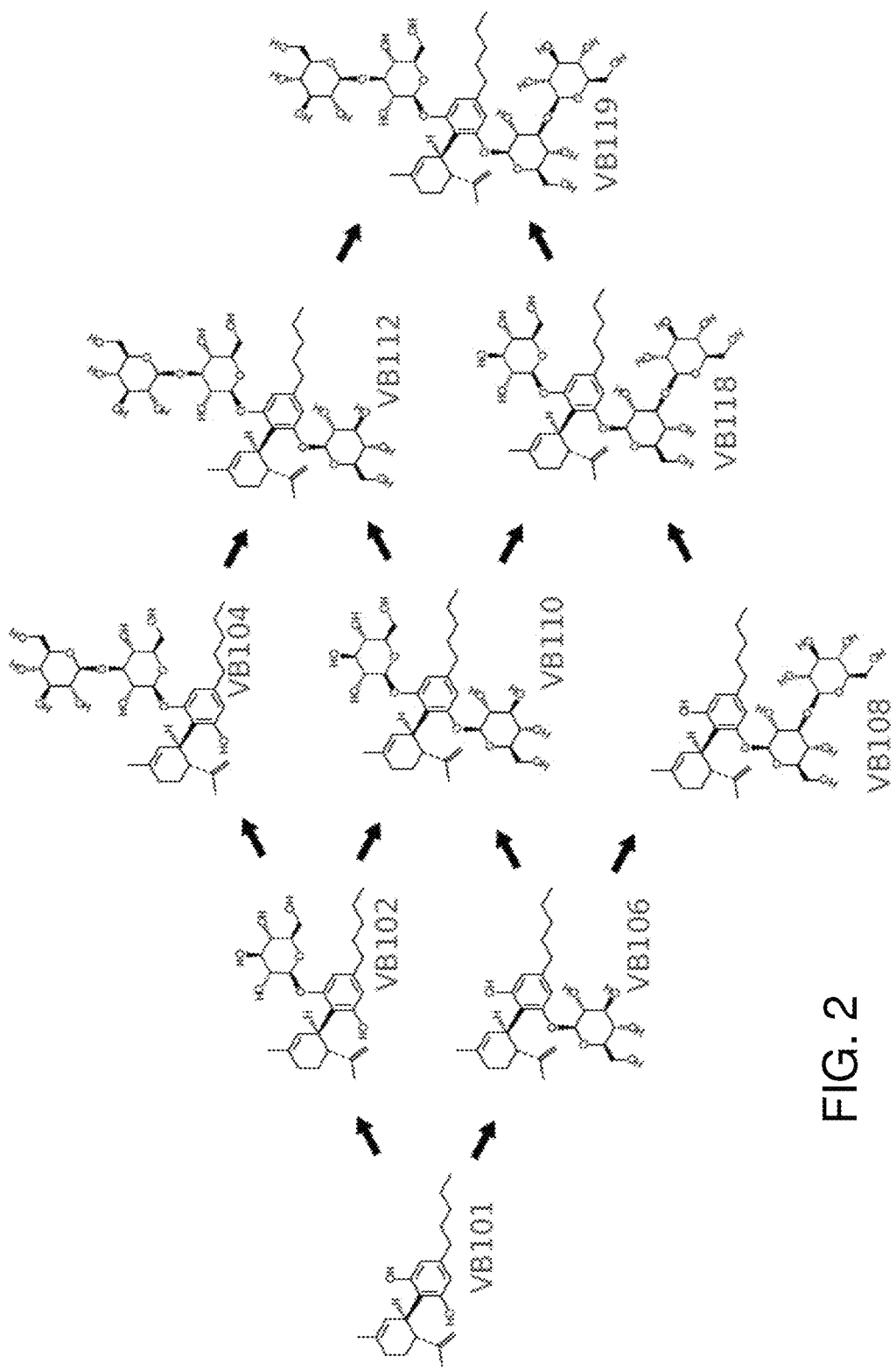
FIG. 2 illustrates possible products of the glycosylation of cannabidiol (CBD).
Figure 3:
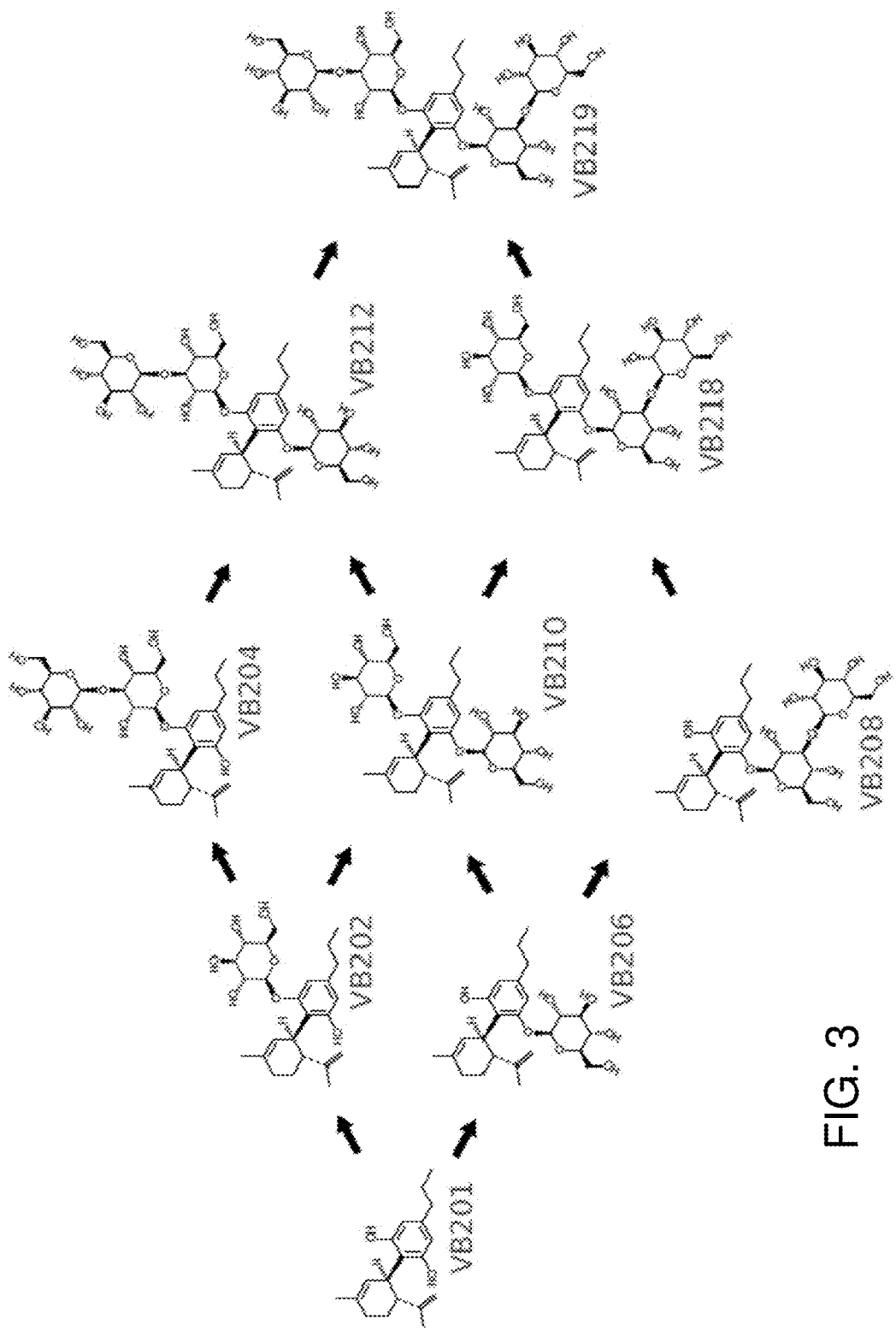
FIG. 3 illustrates possible products of the glycosylation of cannabidivarin (CBDV).
Figure 4:
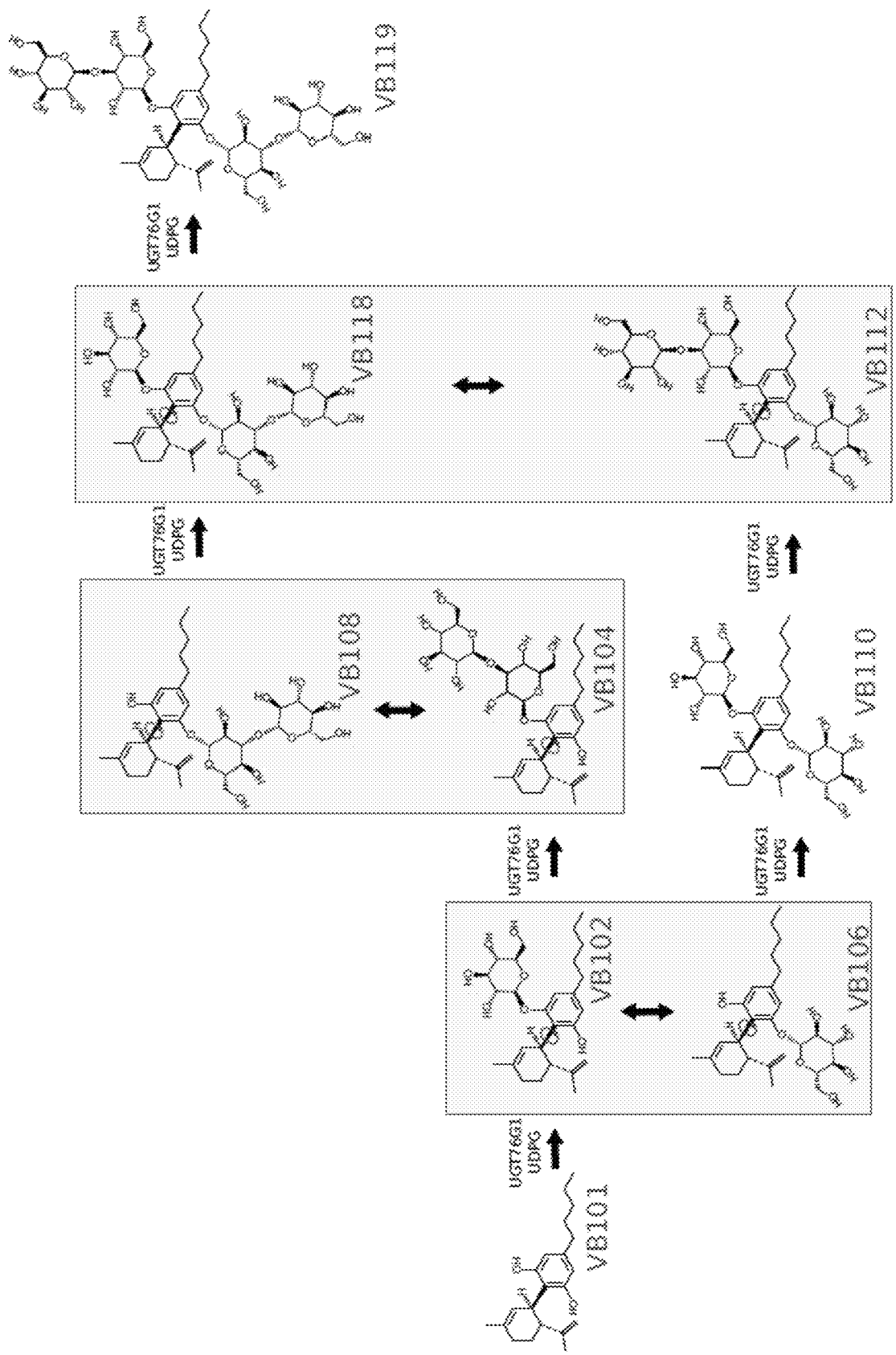
FIG. 4 illustrates possible rotational products of the glycosylation of cannabidiol (CBD).
Figure 5:
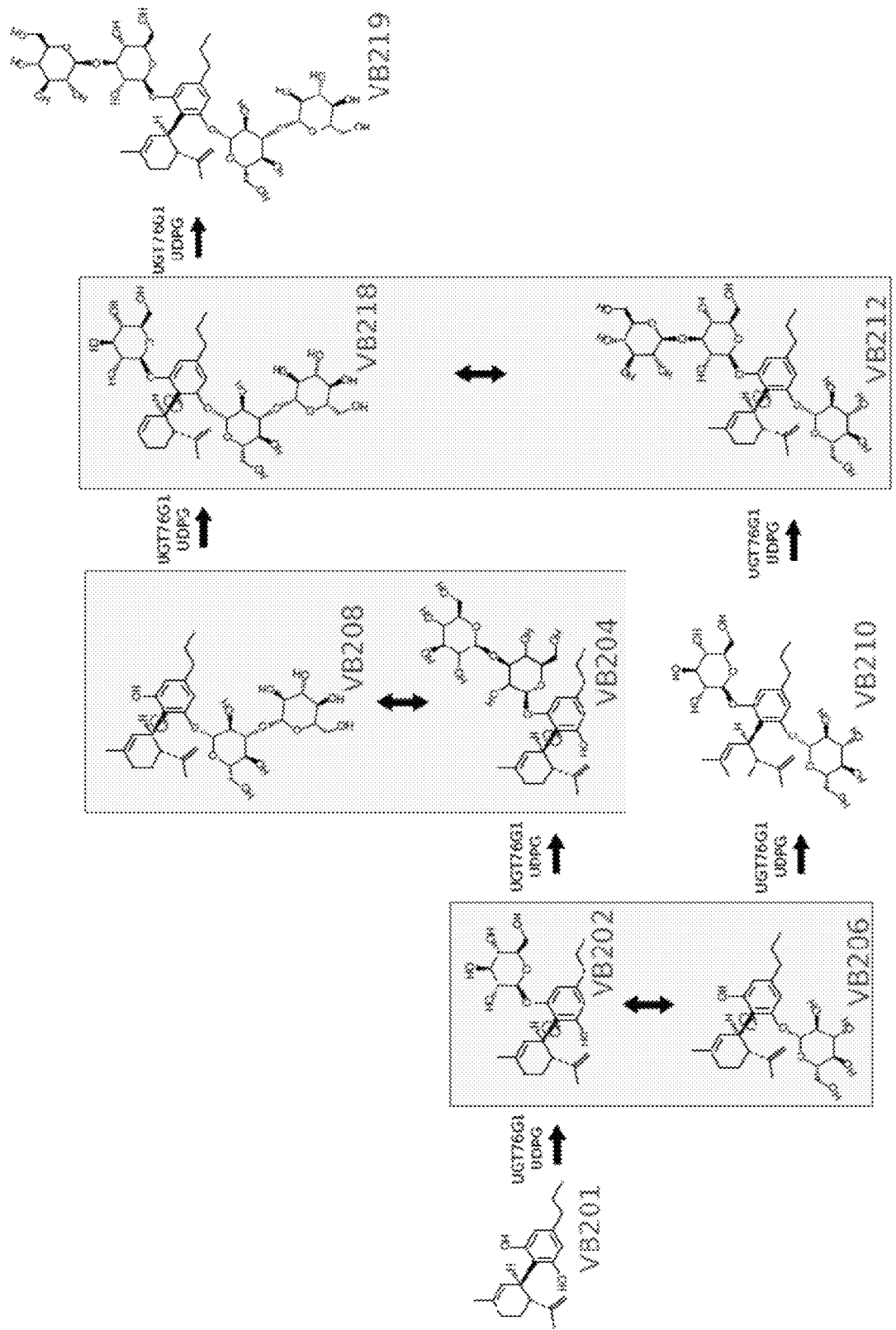
FIG. 5 illustrates possible rotational products of the glycosylation of cannabidivarin (CBDV).
Figure 6:
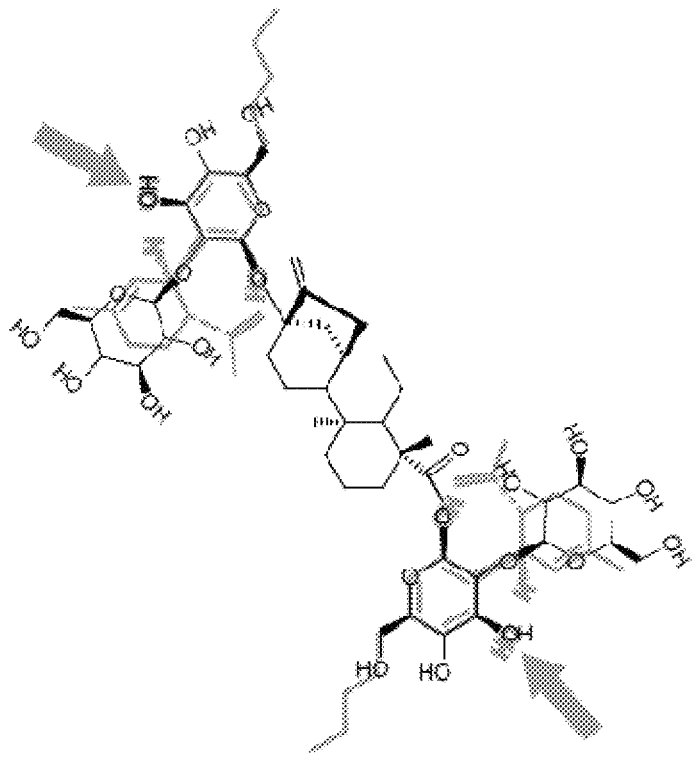
FIG. 6 illustrates the proposed superpositioning of the substrate cannabidiol (CBD) in the catalytic site of UGT76G1.
Figure 6:
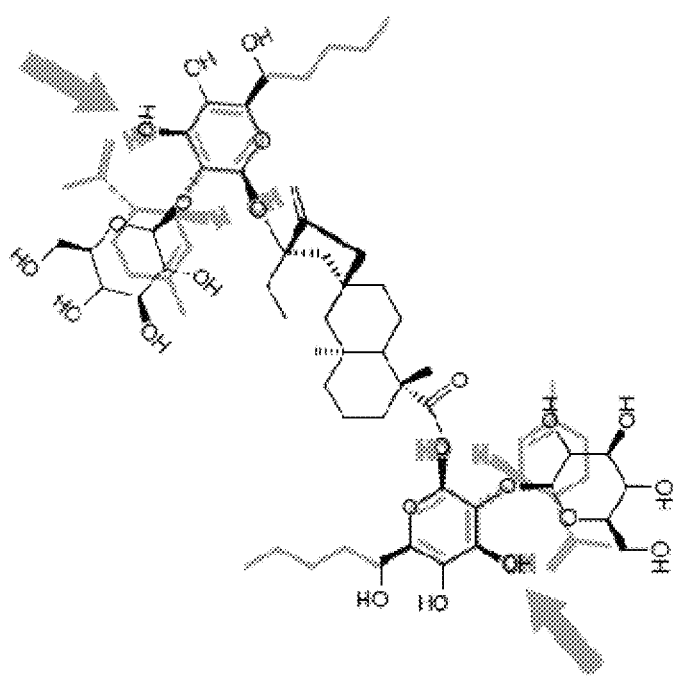

In some cases, removal of the sugar from glycosides in the body may be required in order for the compounds to exert their primary biological activity. Therefore, glycoside prodrugs may enable stable drug formulations that are resistant to abuse, due to the potential for their primary biological effects to only occur after oral ingestion. As most abuse-deterrent compounds are simply mixing or formulation based deterrents, they can still be compromised by simple physical and chemical methods. As one example, the beta-glycosides described herein will only release the aglycone upon the action of beta-glycosidase enzymes. Beta-glycosidases are known to be secreted by microbes that occupy the large intestines of mammals, therefore upon oral ingestion the glycoside prodrugs will remain glycosylated until they reach the large intestine. A similar approach may be used for abuse-resistant, abuse-deterrent, and site-specific delivery of other compounds through glycosylation. It has been found that the UGT76G1 enzyme (SEQ ID NO.1) from Stevia rebaudiana transfers a glucose molecule from the sugar donor UDP-glucose (UDPG) to the hydroxyl groups of CBD to create novel CBD-O-glycosides (Table 1, FIGS. 2 & 4). The UDPG is inverted by UGT76G1 to produce β-D-glucose residues covalently linked through the to the hydroxyl acceptor sites on CBD. To improve the catalytic efficiency UGT76G1 open reading frame (ORF) codon optimization was performed (SEQ ID NOs. 4 and 6) for expression in Pichia pastoris. Similar to its activity towards steviol glycosides, UGT76G1 is highly productive and has an equilibrium constant (Keq) for CBD of ~24. Through experimentation and analysis it was determined that UGT76G1 has the unique ability to apply multiple glucose moieties to the CBD molecule. Upon prolonged incubation of CBD with UGT76G1 and UDPG, HPLC analysis of the reaction mixture yielded 8 glycoside product mobility groups, suggesting that UGT76G1 is able to glycosylate both the C2' and C6' hydroxyl groups on CBD, as well as glycosylating the primary glucose residues with a secondary and tertiary glucose moieties. The secondary and tertiary glycosylations by UGT76G1 occurs at the C3 hydroxyl group of the recipient sugar (3→1 connectivity), as would be suggested by its activity in *Stevia*, creating O-(3-1)-glycosides, and the subsequent products. The CBD-glycoside product mobility groups also suggest that CBD can dock in the UGT76G1 active site both forwards and backwards creating a cis-like-conformation for the glycosylations relative to the cannabinoid backbone (mechanism depicted in FIG. 3), or possibly the rotational freedom about the bond at C1' (C6 described by Mazur 2009) allows the hydroxyl group to rotate after glycosylation, placing the other hydroxyl group adjacent to the UDPG in the active site and creating a trans-like-conformation for the glycosylations on the cannabinoid backbone (mechanism depicted in FIG. 4). Potential CBD molecular docking in the active site of UGT76G1 is depicted in FIG. 6 where CBD is superpositioned over the bi-functional substrate for UGT76G1, Rebaudioside E (RebE) (FIG. 6)

As CBD was successfully glycosylated by UGT76G1, CBDV was incubated with UGT76G1 and UDPG to test for glycosylation activity. CBDV depletion was observed upon HPLC analysis, in addition to the appearance of four additional product peak mobility groups, which were dependent on addition of both UGT76G1 and UDPG. The four new products formed displayed the same absorbance characteristics as CDBV and were determined to be the primary glycosides CBDV-2'-O-glucopyranosides, CBDV-6'-O-glucopyranosides, and the secondary glycosides CBDV-2'-O-(3-1)-diglucopyranoside, and CBDV-6'-O-(3-1)-diglucopyranoside (compounds VB202, VB206, VB204 and VB208, respectively, Table 2). With additional reaction time it was determined that higher order glycoside products were also formed. CBDV-glycoside production was similar to CBD-glycosides from UGT76G1 (Table 2), and proceeded to completion with a $K_{eq}$~24. Given the number of CBDV-glycoside products, UGT76G1 transfers multiple glucose molecules onto CBDV on both C2' and C6' hydroxyl groups, as well as onto the primary and secondary glycosylations.

Figure 7:
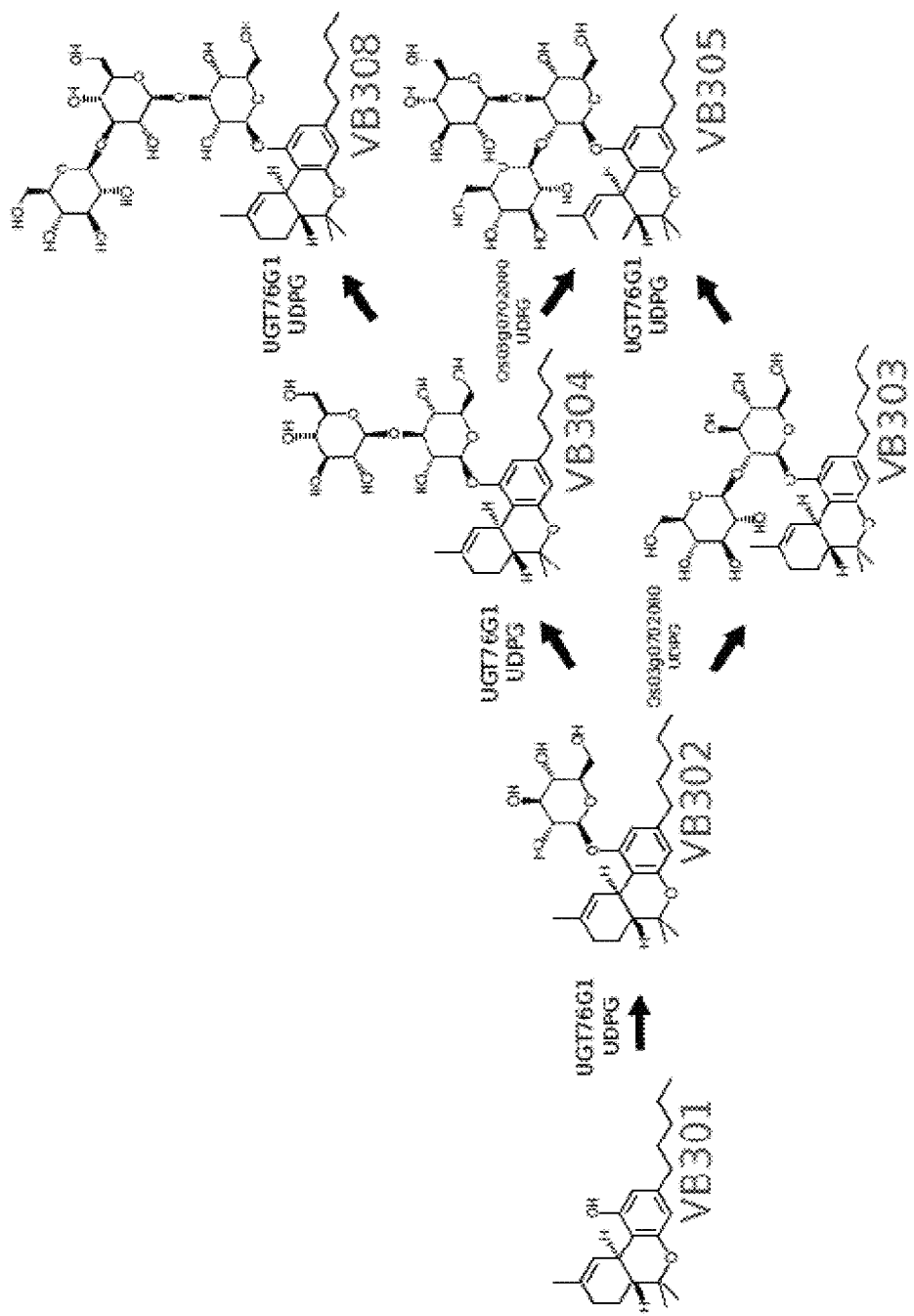
FIG. 7 illustrates possible products of the glycosylation of tetrahydrocannabinol (49-THC).
Figure 8:
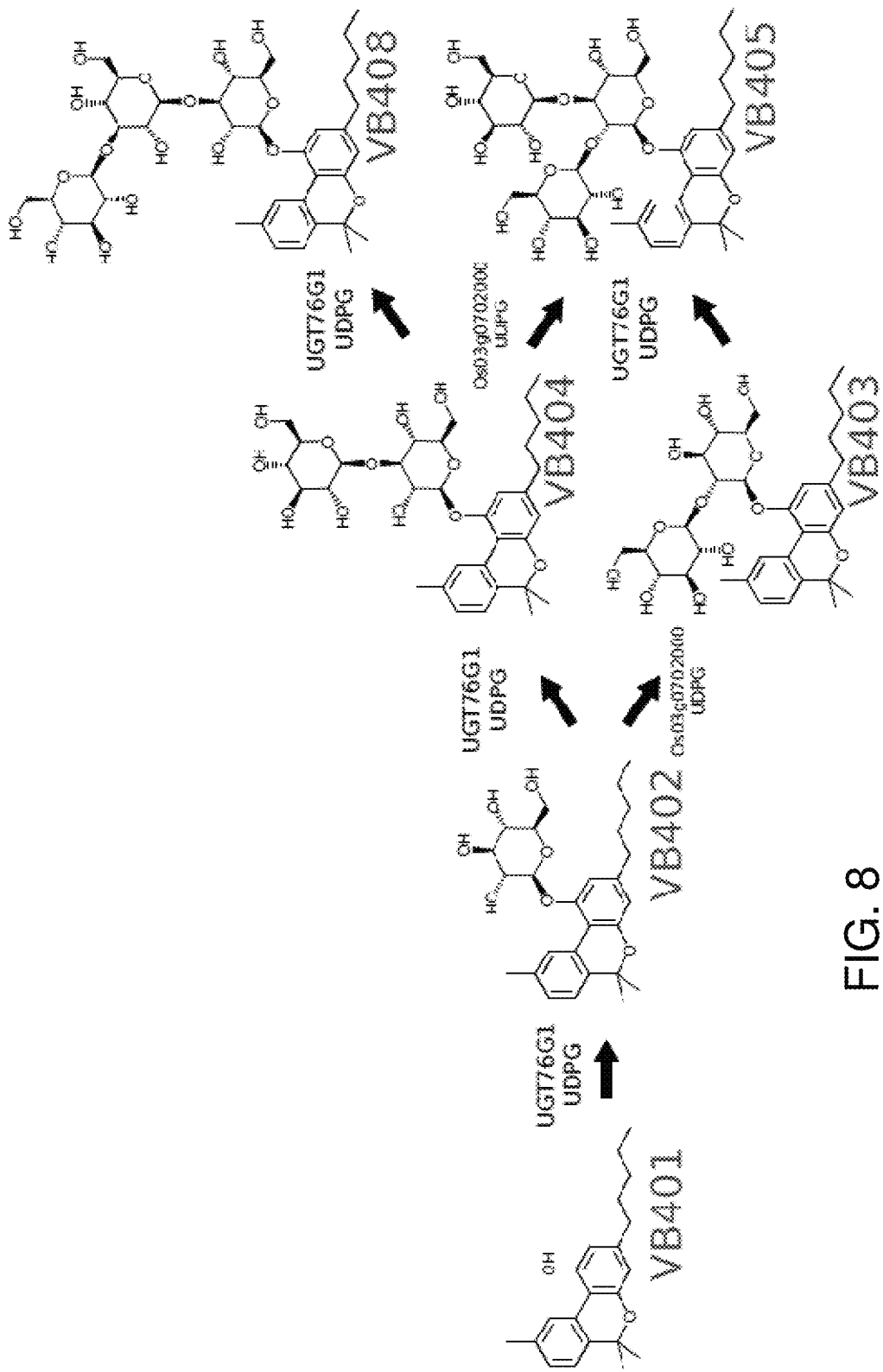
FIG. 8 illustrates possible products of the glycosylation of cannabinol (CBN).
Figure 9:
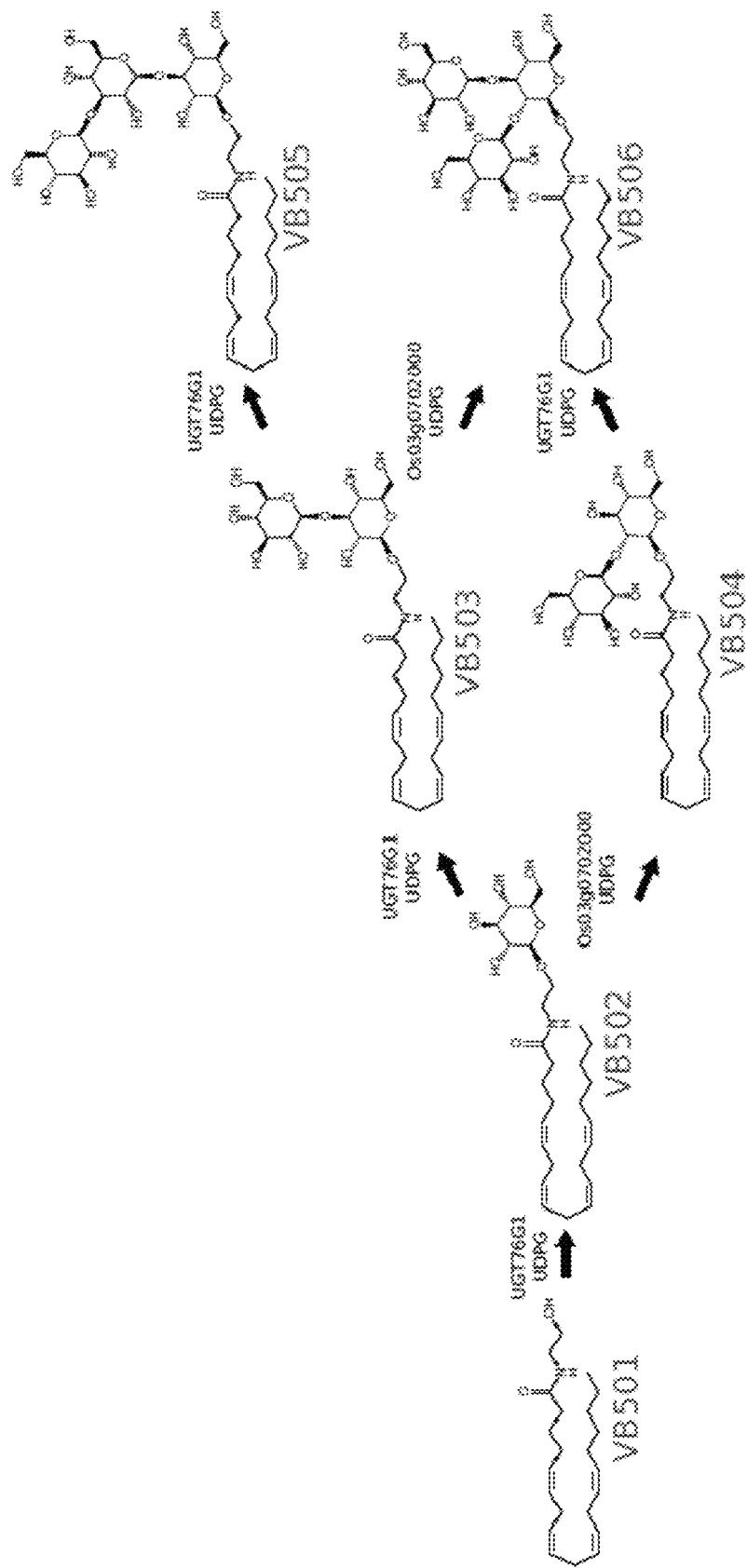
FIG. 9 illustrates possible products of the glycosylation of arachidonoyl ethanolamide (AEA).
Figure 10:
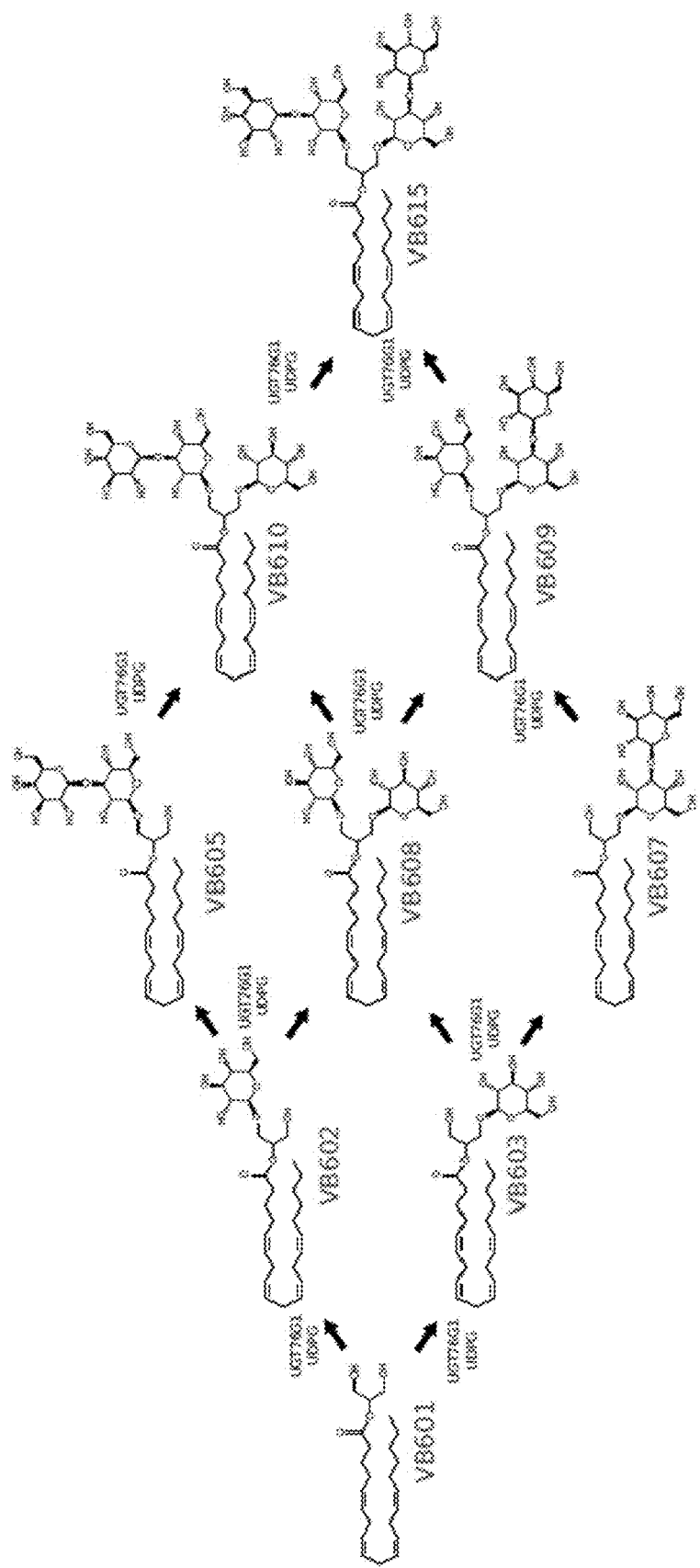
FIG. 10 illustrates possible products of the glycosylation of 2-arachidonoyl ethanolamide (2-AG).
Figure 11:
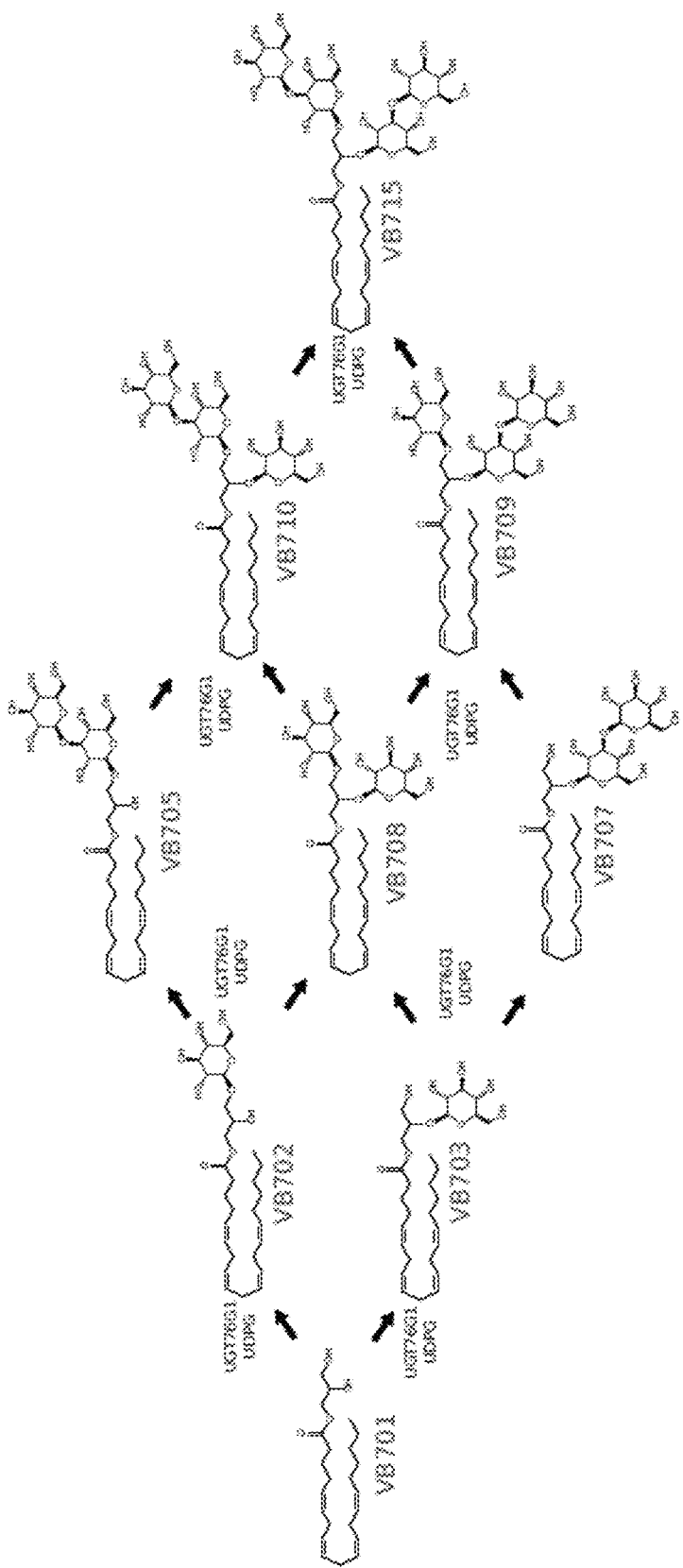
FIG. 11 illustrates possible products of the glycosylation of 1-arachidonoyl ethanolamide (1-AG).
Figure 12:
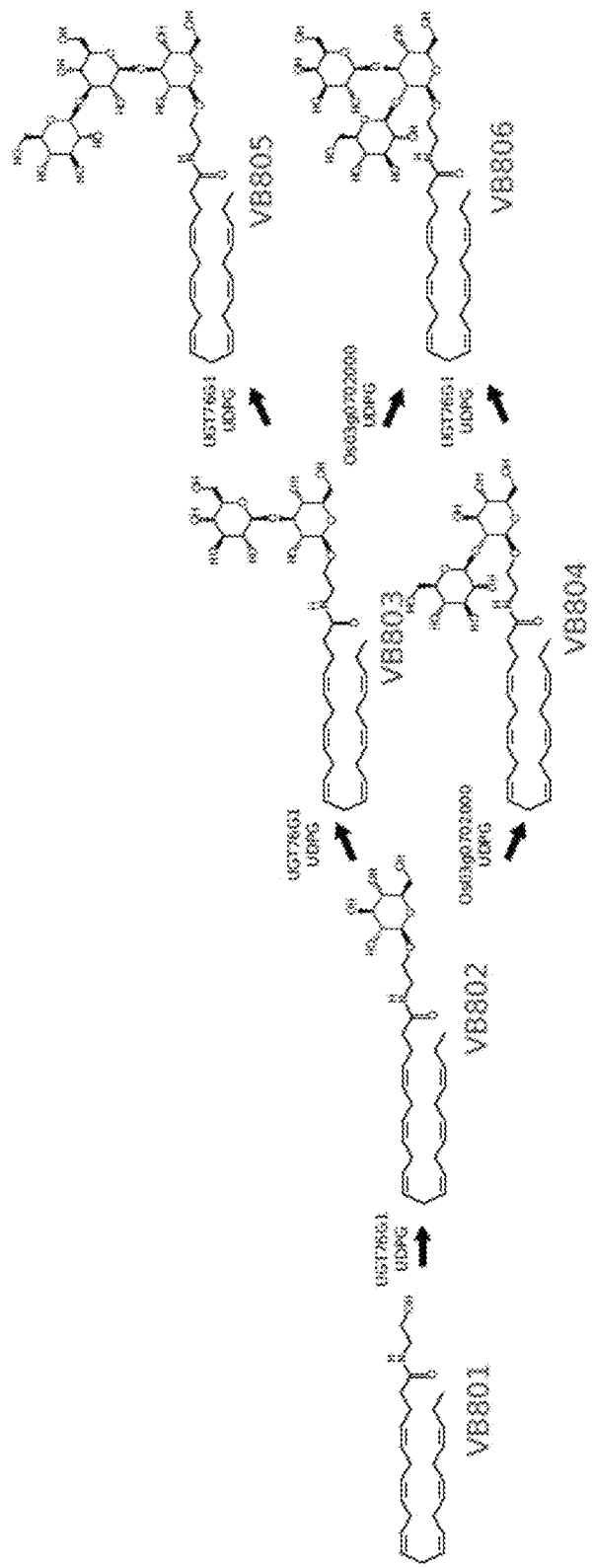
FIG. 12 illustrates possible products of the glycosylation of N-docosahexaenoylethanolamine (DHEA).
Figure 13:
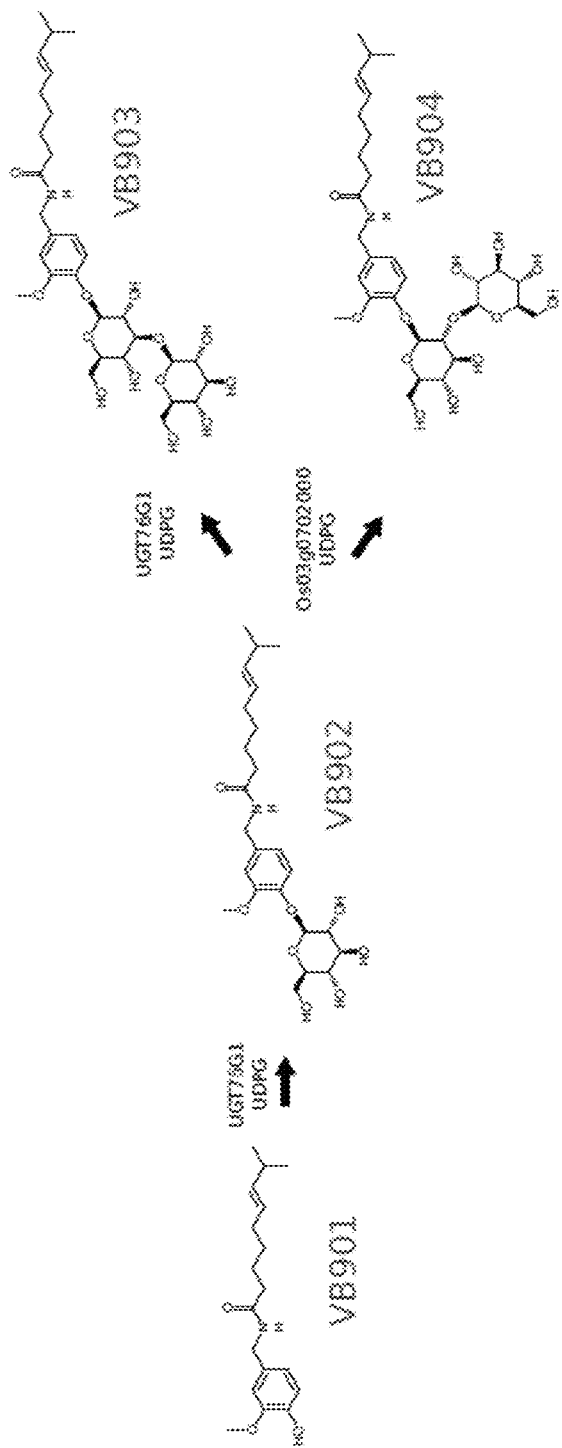
FIG. 13 illustrates possible products of the glycosylation of capsaicin.

When the cannabinoid Δ9-THC was incubated with UGT76G1 and UDPG, HPLC analysis of the reaction mixture showed three main product peak mobility groups. The three products were identified as Δ9-THC-1-O-glucopyranoside, Δ9-THC-1-O-(3-1)-diglucopyranoside, and Δ9-THC-1-O-(3-1,3-1)-triglucopyranoside (formal pyran numbering, Table 3, FIG. 7). Given that the rigid structure of Δ9-THC does not have the same rotational freedom as CBD around the C1' resorcinol ring attachment, the cannabinoid backbone is recognized in the active site of UGT76G1 with the Δ9-THC C1 hydroxyl group situated towards the UDPG sugar donor (pyran numbering, FIG. 1B).

As UGT76G1 demonstrated glycosylation activity for all other phytocannabinoids analyzed, it was also tested for glycosylation activity against cannabinol (CBN). Effective glycosylation of CBN by UGT76G1 was observed, in a similar pattern to Δ9-THC, as both share a single hydroxyl recipient group at the C1 position of the resorcinol ring. The activity seen with UGT76G1 is consistent with a broad recognition of cannabinoids by the enzyme active site.

Alternative cannabinoid substrates may be inserted into this UGT76G1 glycosylation reaction infrastructure to generate novel cannabinoid-glycosides, given they possess hydroxyl groups in similar positions on the cannabinoid backbone. Ideal candidates are cannabigerol (CBG), cannabichromene (CBC), cannabidiol hydroxyquinone (CBDHQ), HU-331, other isomers of Δ9-THC such as Δ8-THC, etc., and synthetic analogues of Δ9-THC such as HU-210.

Similar to the secondary 3→1 glycosylation activity of UGT76G1, it was determined that following a primary glycosylation by UGT76G1, the UGT enzyme Os03g0702000 (SEQ ID NO.9) from *Oryza sativa* is also capable of transferring an additional glucose moiety from UDP-glucose onto the C2-hydroxyl of the primary sugar (Tables 1-11, FIGS. 7-9 & 12-14). This glycosylation activity is consistent with the activity of UGT Os03g0702000 towards steviol glycosides in establishing C2-hydroxyl secondary glycosylations (2→1 connectivity) on existing primary glucose residues. This secondary glycosylation was observed with CBDV (Table 2, FIG. 3), and THC (Table 2, FIG. 7), generating novel CBDV and Δ9THC-1-O-(2-1)-diglucopyranoside species, respectively. Consistent with broad substrate recognition and reactivity, this activity of Os03g0702000 was further demonstrated for the remainder of the substrates identified in FIG. 1.

In addition to the UDPG-dependent glucosyltransferase activity, cyclodextrin-glucanotransferase (CGTase, Toruzyme 3.0L, trademark of Novozymes Inc.) is capable of transferring a short α-(1-4)-maltodextrin chain onto the hydroxyl groups of cannabinoids. The CGTase is also capable of glycosylating primary and secondary glycosylations established by UGT76G1 and Os03g0702000, resulting in carbohydrate attachments that start with β-D-glucose molecules, but terminating in α-D-glucose molecules termed β-primed-α-glucosyl (Tables 1-11). α-glycosylation by cyclodextrin glucanotransferase mediated maltodextrin transfer can occur on any of the hydroxyl groups of the primary or secondary sugars covalently linked to the cannabinoid. One skilled in the art will appreciate that this makes possible any number of conformations of α-glycosyl chains linked to the glycosides listed in Tables 1-11.

Alternative enzymes with homology to UGT76G1 and Os03g0702000 may be used to produce the same glycosylation of cannabinoids. Suitable enzymes for establishing the primary glycosylation similar to UGT76G1 are additional members of the UGT76 clade such as UGT76G2 or UGT76H1. BLAST results with the UGT76G1 protein sequence yield a maximum homology of 49% identity, as much as 66% positives (similar identity). Ideal candidates may have low overall peptide identity or similarity, but will likely have conserved amino acids at the opening adjacent to the UDPG catalytic site. This sequence is exemplified by a leucine at position 379, and a broader peptide sequence of SDFGLDQ (AA's 375 to 381 of UGT76G1). Suitable enzymes for producing the secondary glycosylation of Os03g0702000 are members of the UGT91 clade, including UGT91 D1 and UGT91 D2.

The glycosylation reactions performed herein included UDP-glucose as the nucleotide sugar donor, however there is some cross-reactivity amongst UGTs that allows for use of alternative nucleotide sugars such as UDP-glucuronic acid, etc. Glucuronic acid is the predominant nucleotide sugar utilized by phase-II detoxification UGTs in the liver, and cannabinoid-glucuronides are a common detoxification product. Additional nucleotide sugars which could be used to donate carbohydrate moieties to create novel glycosides with similar properties include UDP-glucuronic acid, UDP-mannose, UDP-fructose, UDP-xylose, UDP-rhamnose, UDP-fluorodeoxyglucose, etc. In addition, nucleotide sugars can also be used in combination to create glycosides that contain multiple types of residues on the same aglycone backbone. Alternative strategies to further improve the solubility and delivery of cannabinoids and other compounds described herein include their glycosylation and then functionalizing the sugar moieties with additional ligands or modifications. Examples of this include sulfation, myristoylation, phosphorylation, acetylation, etc.

The endocannabinoid system has recently been the subject of intense research efforts due to its demonstrated role in and impact on a broad range of clinical pathologies. As UGT76G1 has been determined to recognize a broad class of phytocannabinoids, it was hypothesized that the same enzyme would also recognize and glycosylate endocannabinoids, which are the endogenous signaling molecules recognized by the cannabinoid receptors in Humans. Upon testing a sample of four prototypic endocannabinoids including arachidonoylethanolamide (anandamide, AEA), 2-arachidonoylethanolamide (2-AG), 1-arachidonoylethanolamide (1-AG), and docosahexaenoyl ethanolamide (DHEA, synaptamide), it was found that UGT76G1 effectively glycosylated each endocannabinoid (Tables 5-8, FIGS. 9-12). Glycosylation of endocannabinoids enables the creation of endocannabinoid-glycosides and other fatty acid neurotransmitter-glycosides, representing a new method of targeted delivery of endocannabinoids.

As endocannabinoids such as AEA, 2-AG, 1-AG, and synaptamide are glycosylated by UGT76G1, it is hypothesized that similar endocannabinoids will also be suitable substrates for glycosylation by UGT76G1. Other endocannabinoid candidates that are likely to be glycosylated by UGT76G1 include oleoyl ethanolamide (OEA), eicsapentaenoyl ethanolamide, prostaglandin ethanolamide, docosahexaenoyl ethanolamide, linolenoyl ethanolamide, 5(Z),8(Z),11(Z)-eicosatrienoic acid ethanolamide (mead acid ethanolamide), heptadecanoul ethanolamide, stearoyl ethanolamide, docosaenoyl ethanolamide, nervonoyl ethanolamide, tricosanoyl ethanolamide, lignoceroyl ethanolamide, myristoyl ethanolamide, pentadecanoyl ethanolamide, palmitoleoyl ethanolamide, docosahexaenoic acid (DHA), and similar compounds. These glycolipids may have a wide range of commercial uses, ranging from pharmaceutical use as a novel endocannabinoid drug with improved solubility and pharmacokinetic properties, to use as an antibacterial agent, to use as a detergent similar to other glycolipids, etc.

Figure 14:
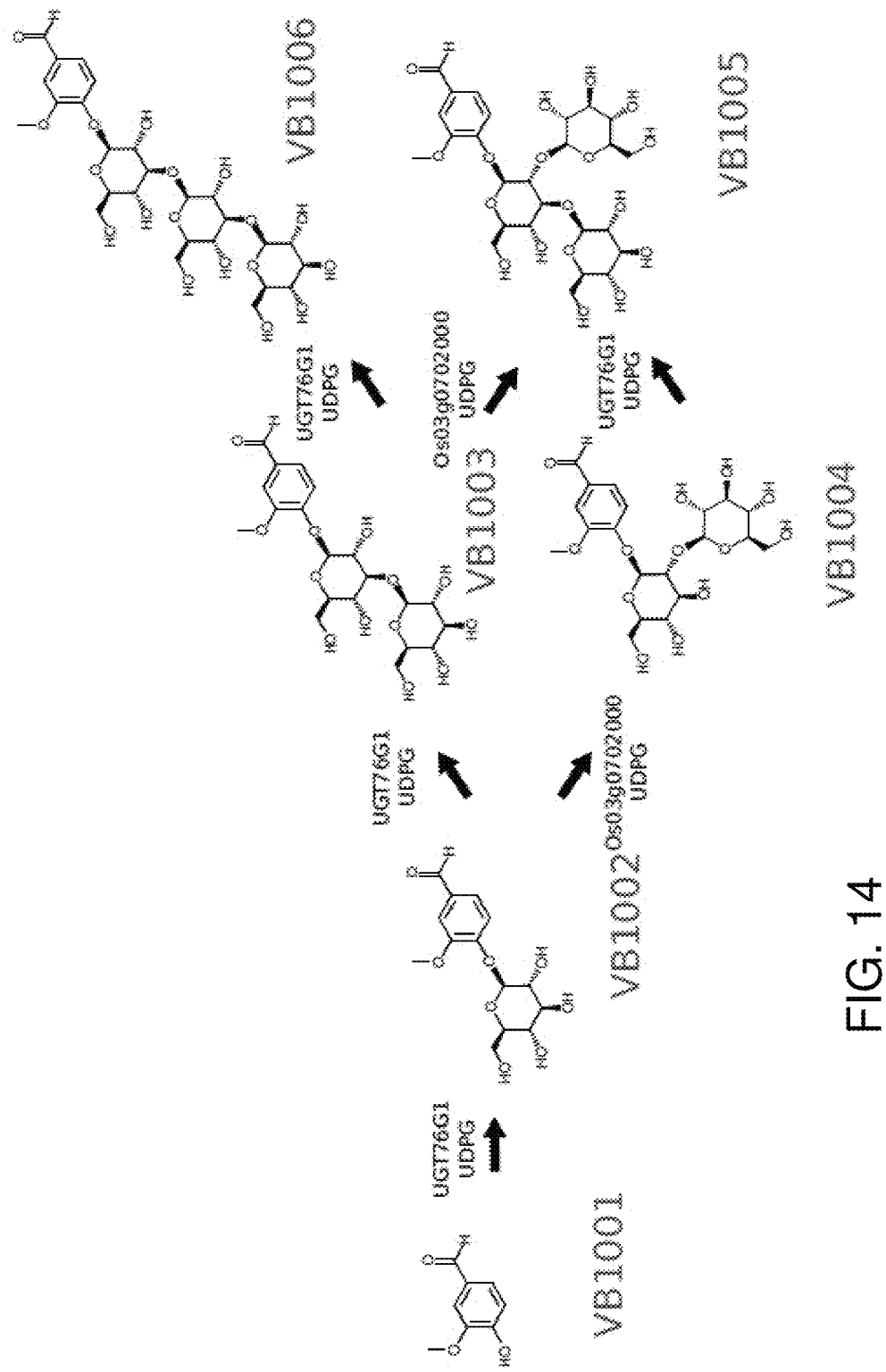
FIG. 14 illustrates possible products of the glycosylation of vanillin.
Figure 15A:
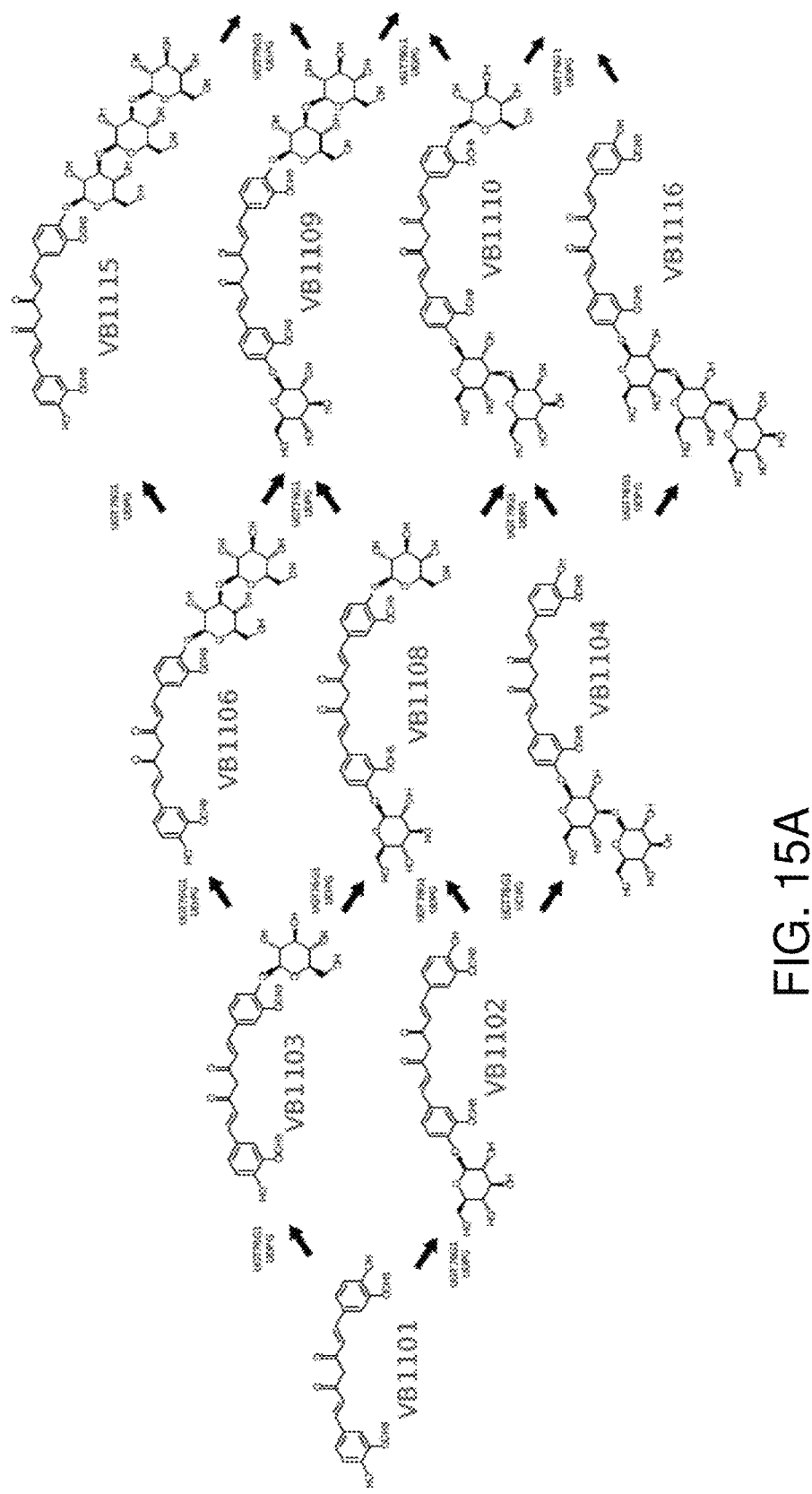
FIGS. 15A and 15B illustrate possible products of the glycosylation of curcumin.
Figure 15B:
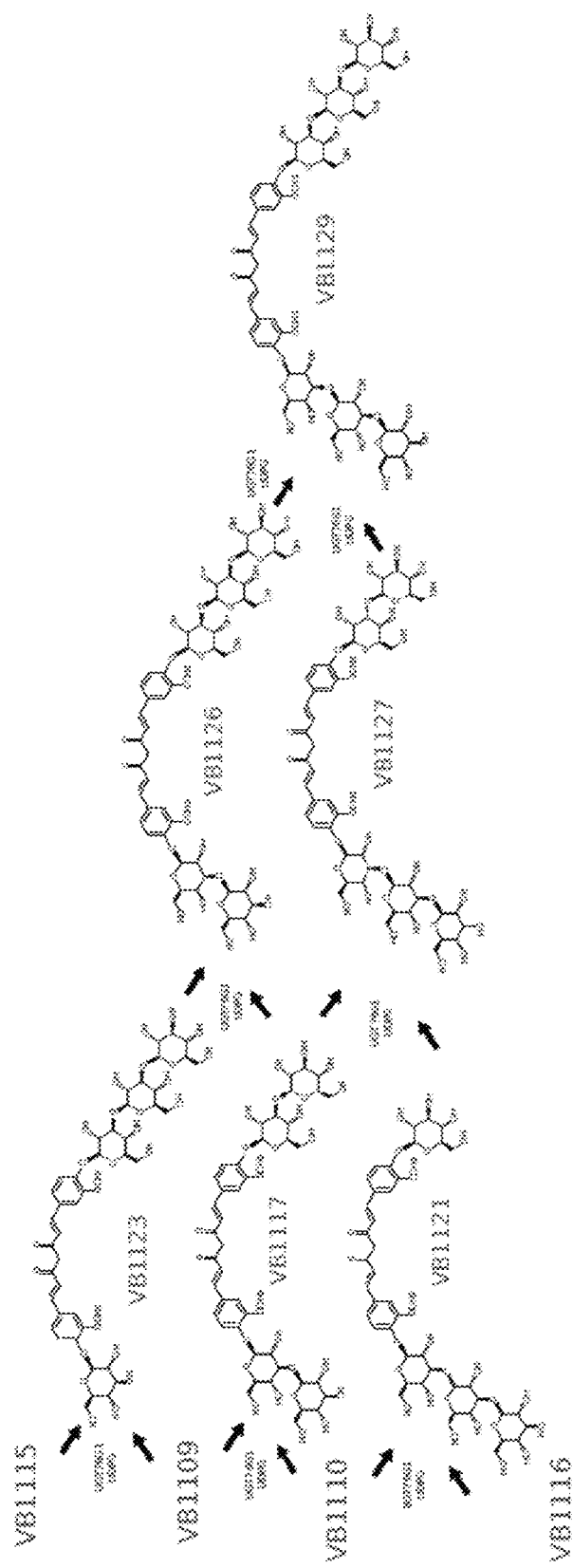

It has been characterized that AEA and CBD are full agonists of the toll-like vanilloid receptor type 1 (TRPV1), which is the receptor for capsaicin. In addition, other cannabinoids and botanical extracts, including but not limited to CBD, CBN, cannabigerol (CBG), and various propyl homologues of CBD, THC, and CBG have been demonstrated to bind and have activity towards transient receptor potential channels (TRPs) (De Petrocellis 2011). This includes stimulating and desensitizing TRPV1, as well as TRPA1, TRPV2, and also antagonism of TRPM8. Although stimulation of TRPV1 leads to vasodilation and inflammation, capsaicin and its analogues act to desensitize the receptors to stimulants, and provide potent anti-inflammatory effects (Bisogno 2001). Analogous effects may occur with TRPA1 in addition to other TRPs. For CBD, this may occur at concentrations that are lower than what is required for binding of cannabinoid receptors, and at concentrations that are within the range of those typically attained in human clinical testing and use. In addition to acting as a direct agonist of the TRPV1 receptor, CBD has been shown to inhibit fatty acid amide hydroxylase (FAAH), the enzyme responsible for facilitating the metabolism of the endocannabinoid anandamide (Watanabe, 1998; DE e Petrocellis 2010). Given that these phytocannabinoids act as ligands of diverse TRPs, it was postulated that UGT76G1 would be capable of glycosylating many different ligands of the same TRPs, including TRPM8, TRPV2, TRPA1, and TRPV1. Capsaicin is capable of contorting into a CBD-like structure (Bisogno 2001), therefore it was postulated that capsaicin was likely to be a suitable substrate for glycosylation by UGT76G1. To this end, it was shown that UGT76G1 is capable of glycosylating the vanilloid moiety of capsaicin in a structurally identical way to PaGT3 from *Phytolacca americana* (Noguchi 2009). As the glycosylated structure of capsaicin is the vanilloid head, it was further hypothesized that UGT76G1 would be capable of glycosylation of the minimal vanilloid, i.e., vanillin, as well as many analogues. Consistent with this hypothesis, through HPLC analysis it was determined that UGT76G1 created multiple glycoside products of vanillin (FIG. 14, Table 10). Seeking to test the ability of UGT76G1 to glycosylate vanilloids more broadly, curcumin, the well characterized vanilloid found in turmeric spice, isolated from the ginger *Curcuma longa* was applied as a substrate in the glycosylation reaction. Consistent with the glycosylation of vanillin, UGT76G1 effectively glycosylated curcumin, creating multiple glycoside product peaks, suggesting a bifunctional recognition and glycosylation by UGT76G1 similar to that seen with CBD and steviol glycosides (FIGS. 15A & 15B, Table 11).

Cannabinoid glycosides may also have direct bioactive and therapeutic effects, beyond their utility a prodrug for their aglycone form. Quercetin is an antioxidant flavonoid that is ubiquitous in vegetables and often present both in its aglyone and glycosylated forms. It has been demonstrated through in vitro studies that quercetin glucuronides act as a bioactive agent as well as a precursor molecule to aglycone quercetin (Terao 2011). In many cases, including with glycosides that exert antibacterial and antitumor effects, the glycosidic residues are crucial to activity (Kren & Rezanka 2008).

Glycosides have also been demonstrated to receive facilitated transport across the blood brain barrier (BBB) by the glucose transporter GLUT1. A prime example is the glycoside of ibuprofen achieving a significant increase of ibuprofen aglycone concentration in the brain (Chen 2009). Similar to these glycosides, glycosides of cannabinoids and other compounds described herein may benefit from enhanced facilitated transport across the BBB or other barriers. Glucose transporters are a wide group of membrane proteins encoded by the human genome and that are found not only in the BBB but across many different cells and tissues, including brain, erythrocytes, fat, muscle, kidney, liver, intestine, and pancreas, so glycosylation will be tailored to provide site-specific delivery to any of these tissues. Accordingly, in one embodiment, there is provided a method for facilitating the transport of a cannabinoid drug across the blood brain barrier of a subject comprising administering to the subject a cannabinoid glycoside prodrug in accordance with the present invention.

Delivery of cannabinoids and cannabidiol to the brain may be especially useful because of oligodendrocyte protective (oligoprotective) and general neuroprotective effects. It has been demonstrated that cannabinoid signaling is involved with both oligodendrocyte differentiation (Gomez 2010) and that cannabinoids promote oligodendrocyte progenitor survival (Molina-Holgado 2002). Drug formulations that include cannabidiol as a major ingredient have been approved to treat muscle spasticity and pain from multiple sclerosis, a neurodegenerative disorder that causes loss of myelin and oligodendrocyte progenitor cells. The effects of cannabidiol have been demonstrated to mediate oligoprotective effects through attenuation of endoplasmic reticulum stress pathways (Mecha 2012). Cannabidiol has also been studied extensively for its antipsychotic effects, however the exact role in protection of oligodendroctyes and promotion of remyelination has not yet been described (Zuardi 2012). Despite the correlation between the clinical symptoms of psychosis with neuropathological analysis that indicates dysmyelination is involved, the role of dysmyelination as a driver or cause of schizophrenia and other psychoses remains controversial (Mighdoll 2015). Remyelination has also been described as potentially useful for treatment of Alzheimer's disease and other forms of dementia (Bartzokis 2004). Therefore, delivery of cannabinoids to the brain may be especially useful for its established neuroprotective and oligoprotective effects. Cannabinoid glycoside drug formulations co-administered in combination with other agents that influence other aspects of repair or regeneration, such as oligodendrocyte progenitor differentiation or remyelination, may also prove to be beneficial. This includes compounds such as anti-LINGO-1 monoclonal antibodies, guanabenz, sephin1, benzatropine, clemastine, polyunsaturated fatty acids, etc.

In the course of the present work, it was discovered that UGT76G1, 0503g0702000 and cyclodextrin glucanotransferase (CGTase) were capable of primary, secondary and tertiary glycosylations of steviol glycosides and aglycone products of diverse chemical structure, including cannabinoids, endocannabinoids, vanillin, curcumin, and capsaicin.

In the screening and analysis methods described by Dewitte 2016, a 50 mm HPLC separation column combined with a high solvent flow rate was used limiting the separation and overall detection of glycoside products. Thus, the interpretation of the glycosylation reaction products for many compounds is speculative, yet still reinforces the significance of the present finding that UGT76G1 has broad substrate specificity. Clearly, the work described herein demonstrate that UGT76G1 can glycosylate not only steviol glycosides, but other forms of glycosides, and novel aglycone compounds such as cannabidiol as well. Internal studies that used an improved separation methodology involving a 150 mm length C18 column coupled with a low solvent flowrate also enabled the clear detection of secondary and tertiary glycosides. These compounds were unable to be detected by the methods described in Dewitte 2016, and provide additional verification of the ability of UGT76G1 to not only glycosylate compounds with diverse chemical structures, but also to perform multiple higher order glycosylations on glycosides of these same compounds.

The reactions described herein take place in vitro using recombinant enzymes and all necessary cofactors, and the expression of UGT76G1 enzyme within the cells of a *Cannabis* plant is possible for the in vivo biotransformation of cannabinoids prior to extraction of cannabinoids from plant tissue. As UGT76G1 is an enzyme from the plant *Stevia rebaudiana*, it will be compatible with expression in the genus *Cannabis*. The ideal strategy for expression of UGT76G1 within the *Cannabis* plant is to genetically engineer the UGT76G1 open reading frame under a promoter element that is specific for the same tissue that cannabinoids are produced in, namely the secretory trichomes of the plant. Suitable promoter elements include the promoter for the cytosolic O-acetylserine(thiol)lyase (OASA1) enzyme from *Arabidopsis thaliana* (Gutierrez-Alcala 2005). Candidates for transformation with UGT76G1 include *Cannabis sativa*, *Cannabis indica*, and *Cannabis ruderalis*. A similar approach may be used with UGT76G1 and similar enzymes for in planta production of glycosylated secondary metabolites within many other different plant species, and may be especially useful when plant species already produce large quantities of the desired aglycone product or known enzyme substrate.

In the course of performing phytocannabinoid glycosylation reactions CBD and THC displayed noticeable antimicrobial activity, even preventing large-scale reaction mixtures from becoming contaminated after failure of the sterile filter apparatus. Prior pilot-scale glycosylation reaction utilizing steviol glycosides as substrates during enzymatic processing were quite susceptible to infection in the absence of strict sanitation techniques. CBD and THC pilot-scale reactions remained aseptic for over a week in the same reaction vessels with very limited ongoing maintenance or care. To this end, the use of the aglycone cannabinoids and their respective glycosides is proposed as efficient antimicrobial agents. Accordingly, in one embodiment, there is provided an antimicrobial agent comprising an effective amount of a cannabinoid glycoside prodrug in accordance with the present invention.

Similarly, upon the production of large quantities of cannabinoid-glycosides and formulation in aqueous solutions, it was observed that multiple cannabinoid-glycosides in water had foaming properties similar to detergents. This is consistent with other glycoside detergents like 8-octylglycoside, 8-octylthioglycoside, and similar, and establishes a potential use for cannabinoid-glycosides as a detergent. Accordingly, in one embodiment, there is provided a detersive agent comprising an effective amount of a cannabinoid glycoside prodrug in accordance with the present invention.

Nucleic Acids

The present invention provides for nucleic acids comprising nucleotide sequences encoding a glycosyltransferase. The glycosyltransferases of the present invention are capable of primary, secondary, tertiary glycosylations or a combination thereof. In certain embodiments, the glycosyltransferases are capable of primary, secondary and tertiary glycosylations. In other embodiments, the glycosyltransferases are capable of secondary and tertiary glycosylations. In certain embodiments, the nucleic acids encode a glucosyltransferase, including but not limited to a UDP-glucosyltransferase. The glucosyltransferases include but are not limited to a *Stevia rebaudiana* UDP-glucosyltransferase, such as UGT76G1 or UGT74G1 or an *Oryza sativa* glucosyltrasferase, such as Os03g0702000. In other embodiments, the invention provides for nucleic acids comprising nucleotide sequences encoding a cyclodextrin glucanotransferase. Also provided are nucleic acids comprising nucleotide sequences that encode a sucrose synthase.

Nucleic acids include, but are not limited to, genomic DNA, cDNA, RNA, fragments and modified versions, including but not limited to codon optimized versions thereof. For example, the nucleotide sequences may be codon optimized for expression in *Pichia pastoris* or *E. coli*. The nucleic acids may include the coding sequence of the glycosyltransferase or sucrose synthase, in isolation, in combination with additional coding sequences (e.g., including but not limited to a purification tag).

In certain embodiments, the nucleic acid comprises a sequence encoding UGT76G1 or UGT76G1-like glucosyltransferase. UGT76G1-like glucosyltransferase include for example, other members of the UGT76G1 clade such as UGT76G2 or UGT76H1. In certain embodiments, the nucleic acid comprises a sequence encoding an UGT76G1 glucosyltransferase having the amino acid sequence as set forth in any one of SEQ ID NOs:1, 3, 5 and 7 and listed below or fragments and variants thereof.

(UGT76G1 (native protein sequence))
SEQ ID NO: 1
MENKTETTVRRRRRIILFPVPFQGHINPILQLANVLYSKGFSITIFHTNF
NKPKTSNYPHFTFRFILDNDPQDERISNLPTHGPLAGMRIPIINEHGADE
LRRELELLMLASEEDEEVSCLITDALWYFAQSVADSLNLRRLVLMTSSLF
NFHAHVSLPQFDELGYLDPDDKTRLEEQASGFPMLKVKDIKSAYSNWQIL
KEILGKMIKQTKASSGVIWNSFKELEESELETVIREIPAPSFLIPLPKHL
TASSSSLLDHDRTVFQWLDQQPPSSVLYVSFGSTSEVDEKDFLEIARGLV
DSKQSFLWVVRPGFVKGSTWVEPLPDGFLGERGRIVKWVPQQEVLAHGAI
GAFWTHSGWNSTLESVCEGVPMIFSDFGLDQPLNARYMSDVLKVGVYLEN
GWERGEIANAIRRVMVDEEGEYIRQNARVLKQKADVSLMKGGSSYESLES
LVSYISSL (UGT76G1 with a 6x Histidine tag at the N-terminus)
SEQ ID NO: 3
MHHHHHHGSGENKTETTVRRRRRIILFPVPFQGHINPILQLANVLYSKGF
SITIFHTNFNKPKTSNYPHFTFRFILDNDPQDERISNLPTHGPLAGMRIP
IINEHGADELRRELELLMLASEEDEEVSCLITDALWYFAQSVADSLNLRR
LVLMTSSLFNFHAHVSLPQFDELGYLDPDDKTRLEEQASGFPMLKVKDIK
SAYSNWQILKEILGKMIKQTKASSGVIWNSFKELEESELETVIREIPAPS
FLIPLPKHLTASSSSLLDHDRTVFQWLDQQPPSSVLYVSFGSTSEVDEKD
FLEIARGLVDSKQSFLWVVRPGFVKGSTWVEPLPDGFLGERGRIVKWVPQ
QEVLAHGAIGAFWTHSGWNSTLESVCEGVPMIFSDFGLDQPLNARYMSDV
LKVGVYLENGWERGEIANAIRRVMVDEEGEYIRQNARVLKQKADVSLMKG
GSSYESLESLVSYISSL (UGT76G1 with a 6x Histidine-Glutamine tag at the N-terminus)
SEQ ID NO: 5
MHQHQHQSGSMENKTETTVRRRRRIILFPVPFQGHINPILQLANVLYSKG
FSITIFHTNFNKPKTSNYPHFTFRFILDNDPQDERISNLPTHGPLAGMRI
PIINEHGADELRRELELLMLASEEDEEVSCLITDALWYFAQSVADSLNLR
RLVLMTSSLFNFHAHVSLPQFDELGYLDPDDKTRLEEQASGFPMLKVKDI
KSAYSNWQILKEILGKMIKQTKASSGVIWNSFKELEESELETVIREIPAP
SFLIPLPKHLTASSSSLLDHDRTVFQWLDQQPPSSVLYVSFGSTSEVDEK
DFLEIARGLVDSKQSFLWVVRPGFVKGSTWVEPLPDGFLGERGRIVKWVP
QQEVLAHGAIGAFWTHSGWNSTLESVCEGVPMIFSDFGLDQPLNARYMSD
VLKVGVYLENGWERGEIANAIRRVMVDEEGEYIRQNARVLKQKADVSLMK
GGSSYESLESLVSYISSL SEQ ID NO: 7
MENKTETTVRRRRRIILFPVPFQGHINPILQLANVLYSKGFSITIFHTNF
NKPKTSNYPHFTFRFILDNDPQDERISNLPTHGPLAGMRIPIINEHGADE
LRRELELLMLASEEDEEVSCLITDALWYFAQSVADSLNLRRLVLMTSSLF
NFHAHVSLPQFDELGYLDPDDKTRLEEQASGFPMLKVKDIKSAYSNWQIL
KEILGKMIKQTRASSGVIWNSFKELEESELETVIREIPAPSFLIPLPKHL
TASSSSLLDHDRTVFQWLDQQPPSSVLYVSFGSTSEVDEKDFLEIARGLV
DSKQSFLWVVRPGFVKGSTWVEPLPDGFLGERGRIVKWVPQQEVLAHGAI
GAFWTHSGWNSTLESVCEGVPMIFSDFGLDQPLNARYMSDVLKVGVYLEN
GWERGEIANAIRRVMVDEEGEYIRQNARVLKQKADVSLMKGGSSYESLES
LVSYISSLGSHHHHHH In certain embodiments, the nucleic acid comprises a sequence encoding UGT76G1 having the amino acid sequence as set forth in AAR06912.1. In certain embodiments, the nucleic acid molecule comprises a sequence encoding UGT76G1 glucosyltransferase and comprising the nucleotide sequence as set forth in any one of SEQ ID NOs: 2, 4, 6 and 8 and listed below, or fragments and variants thereof.

(UGT76G1 native nucleic acid sequence)
SEQ ID NO: 2
ATGGAAAATAAAACGGAGACCACCGTTCGCCGGCGCCGGAGAATAATATT
ATTCCCGGTACCATTTCAAGGCCACATTAACCCAATTCTTCAGCTAGCCA
ATGTGTTGTACTCTAAAGGATTCAGTATCACCATCTTTCACACCAACTTC
AACAAACCCAAAACATCTAATTACCCTCACTTCACTTTCAGATTCATCCT
CGACAACGACCCACAAGACGAACGCATTTCCAATCTACCGACTCATGGTC
CGCTCGCTGGTATGCGGATTCCGATTATCAACGAACACGGAGCTGACGAA
TTACGACGCGAACTGGAACTGTTGATGTTAGCTTCTGAAGAAGATGAAGA
GGTATCGTGTTTAATCACGGATGCTCTTTGGTACTTCGCGCAATCTGTTG
CTGACAGTCTTAACCTCCGACGGCTTGTTTTGATGACAAGCAGCTTGTTT
AATTTTCATGCACATGTTTCACTTCCTCAGTTTGATGAGCTTGGTTACCT
CGATCCTGATGACAAAACCCGTTTGGAAGAACAAGCGAGTGGGTTTCCTA
TGCTAAAAGTGAAAGACATCAAGTCTGCGTATTCGAACTGGCAAATACTC
AAAGAGATATTAGGGAAGATGATAAAACAAACAAGAGCATCTTCAGGAGT
CATCTGGAACTCATTTAAGGAACTCGAAGAGTCTGAGCTCGAAACTGTTA
TCCGTGAGATCCCGGCTCCAAGTTTCTTGATACCACTCCCCAAGCATTTG
ACAGCCTCTTCCAGCAGCTTACTAGACCACGATCGAACCGTTTTTCAATG
GTTAGACCAACAACCGCCAAGTTCGGTACTGTATGTTAGTTTTGGTAGTA
CTAGTGAAGTGGATGAGAAAGATTTCTTGGAAATAGCTCGTGGGTTGGTT
GATAGCAAGCAGTCGTTTTTATGGGTGGTTCGACCTGGGTTTGTCAAGGG
TTCGACGTGGGTCGAACCGTTGCCAGATGGGTTCTTGGGTGAAAGAGGAC
GTATTGTGAAATGGGTTCCACAGCAAGAAGTGCTAGCTCATGGAGCAATA
GGCGCATTCTGGACTCATAGCGGATGGAACTCTACGTTGGAAAGCGTTTG
TGAAGGTGTTCCTATGATTTTCTCGGATTTTGGGCTCGATCAACCGTTGA
ATGCTAGATACATGAGTGATGTTTTGAAGGTAGGGGTGTATTTGGAAAAT
GGGTGGGAAAGAGGAGAGATAGCAAATGCAATAAGAAGAGTTATGGTGGA
TGAAGAAGGAGAATACATTAGACAGAATGCAAGAGTTTTGAAACAAAAGG
CAGATGTTTCTTTGATGAAGGGTGGTTCGTCTTACGAATCATTAGAGTCT
CTAGTTTCTTACATTTCATCGTTGTAA (Sequence encoding SEQ ID NO: 3 codon optimized
for expression in Pichia pastoris)
SEQ ID NO: 4
ATGCACCACCATCACCACCATGGTTCTGGTGAAAACAAAACTGAAACTAC

TGTTAGAAGAAGAAGAAGAATCATTTTGTTTCCAGTACCATTTCAAGGCC

ATATCAATCCAATTCTTCAATTGGCCAATGTTTTGTACTCCAAAGGATTC

TCCATCACCATTTTTCACACCAATTTCAACAAACCAAAGACTTCCAACTA

TCCTCACTTCACTTTCAGATTTATTTTGGATAATGATCCTCAAGATGAAA

GAATTTCCAATCTTCCGACTCATGGTCCTTTGGCTGGTATGAGAATTCCA

ATCATCAATGAACATGGTGCTGATGAATTAAGAAGAGAATTGGAACTTTT

GATGTTGGCTTCTGAAGAAGATGAAGAAGTTTCATGTTTAATCACTGATG

CTTTATGGTATTTTGCTCAATCTGTTGCTGATTCTTTGAATTTGCGACGG

TTGGTTTTGATGACTTCTTCTTTGTTCAACTTTCATGCTCATGTTTCTTT

ACCTCAGTTTGATGAACTTGGATATTTGGATCCAGATGACAAAACTAGAT

TGGAAGAACAAGCTAGTGGGTTTCCTATGTTGAAAGTCAAAGATATCAAA

TCTGCTTACTCCAACTGGCAAATTCTCAAAGAATTTTGGGAAAAATGAT

CAAACAAACAAAAGCTTCTTCTGGAGTCATTTGGAACTCATTCAAAGAAT

TGGAAGAATCTGAATTGGAAACTGTTATTAGAGAAATTCCTGCTCCAAGT

TTTTTGATTCCTTTGCCAAAACATTTGACTGCTTCTTCTTCTTCTTTATT

GGATCACGATAGAACTGTTTTTCAATGGTTAGATCAACAACCTCCATCTT

CTGTTTTGTATGTTAGTTTTGGATCTACTTCTGAAGTTGATGAAAAAGAT

TTTTTGGAAATTGCTAGAGGTTTGGTTGATTCCAAACAAAGTTTTTTATG

GGTTGTTAGACCAGGATTTGTCAAAGGATCTACTTGGGTCGAACCTTTGC

CAGATGGATTTTTGGGAGAAAGAGGAAGAATTGTCAAATGGGTTCCACAG

CAAGAAGTTTTGGCTCATGGTGCTATTGGTGCTTTTTGGACTCATTCTGG

ATGGAACTCTACTTTGGAATCTGTTTGTGAAGGTGTTCCAATGATTTTTT

CTGATTTTGGTTTGGATCAACCATTGAATGCTAGATACATGTCTGATGTT

TTGAAAGTTGGTGTTTATTTGGAAAATGGGTGGGAAAGAGGTGAAATTGC

CAATGCTATTAGAAGAGTCATGGTTGATGAAGAAGGAGAATACATTAGAC

AAAATGCTAGAGTTTTGAAACAAAAGCTGATGTTTCTTTGATGAAGGGT

GGATCTTCTTATGAATCTTTGGAATCTTTGGTTTCTTACATTTCTTCTCT

TTAA (Sequence encoding SEQ ID NO: 5 codon optimized
for expression in Pichia pastoris)
SEQ ID NO: 6
ATGCATCAACATCAACACCAATCTGGATCTATGGAGAACAAGACCGAGAC

TACAGTTAGAAGAAGAAGAATAATCCTGTTTCCAGTACCATTCCAAG

GACACATCAACCCAATCTTGCAGTTAGCAAATGTACTTTATTCTAAAGGC

TTTAGTATTACGATTTTCACACTAATTTTAATAAGCCAAAAACATCCAA

TTACCCTCACTTCACATTCAGATTTATCTTGGATAACGATCCTCAAGATG

AACGTATCTCCAACCTGCCAACACATGGACCATTGGCCGGTATGCGTATT

CCTATAATCAACGAGCATGGTGCTGATGAGCTTAGACGTGAACTGGAACT

GTTGATGCTGGCATCGGAGGAAGATGAAGAGGTTAGTTGCTTGATAACGG

ATGCCCTCTGGTATTTCGCACAATCAGTCGCTGACTCCTTGAACCTTAGG

AGATTGGTATTGATGACTAGTTCGTTGTTCAACTTCCATGCCCATGTTTC

TTTGCCTCAATTTGATGAGCTGGGTTATTTGGATCCTGACGATAAGACTC

GTTTAGAAGAACAGGCGTCAGGCTTCCCCATGTTAAAGGTTAAAGATATT

AAGTCCGCCTATTCTAACTGGCAAATTCTCAAAGAGATTCTAGGGAAAAT

GATTAAACAAACCAAGGCCTCTTCAGGAGTAATCTGGAACAGTTTCAAAG

AACTAGAAGAATCCGAGTTGGAAACTGTTATTCGTGAAATCCCTGCTCCA

TCTTTCCTTATCCCATTACCAAAGCACCTCACTGCCTCCTCTAGTTCTCT

TCTGGACCATGATAGAACAGTCTTTCAGTGGCTCGATCAGCAACCTCCAT

CTTCTGTCTTGTACGTTAGTTTTGGTTCCACCTCGGAAGTAGATGAAAAA

GACTTTCTGGAAATTGCTCGAGGACTAGTTGACTCCAAGCAATCCTTTCT

GTGGGTTGTTAGACCTGGATTCGTAAAAGGATCCACCTGGGTAGAACCCC

TCCCAGATGGATTTTTGGGCGAAAGGGGAAGAATTGTTAAATGGGTGCCT

CAACAAGAAGTTTTAGCTCATGGGGCCATTGGAGCTTTTTGGACTCATAG

TGGATGGAATTCTACCTTAGAATCTGTTTGTGAAGGAGTTCCAATGATTT

TTTCTGATTTTGGATTGGATCAGCCTCTTAATGCCAGATATATGTCCGAT

GTCCTCAAGGTCGGAGTGTACCTGGAAAATGGTTGGGAGAGAGGTGAGAT

TGCAAATGCTATACGTAGAGTCATGGTTGATGAAGAGGGCGAGTATATTA

GACAAAACGCTAGAGTGCTAAAGCAGAAGGCCGATGTTTCCCTTATGAAG

GGGGGAAGTTCATATGAGAGTTTGGAATCCCTAGTGTCCTACATTTCTTC

GCTATAA (Sequence encoding SEQ ID NO: 7 codon optimized
for expression in Escherichia coli)
SEQ ID NO: 8
ATGGAAATAAAACCGAAACCACCGTCCGTCGCCGTCGTCGTATCATTCT

GTTCCCGGTCCCGTTCCAAGGTCACATCAACCCGATTCTGCAGCTGGCCA

ACGTGCTGTATAGCAAAGGTTTCTCTATCACCATCTTCCATACGAACTTC

AACAAACCGAAAACCTCTAACTACCGCACTTTACGTTCCGTTTTATTCT

GGATAACGACCCGCAGGATGAACGCATCAGTAATCTGCCGACCCATGGTC

CGCTGGCGGGTATGCGTATTCCGATTATCAACGAACACGGCGCAGATGAA

CTGCGTCGCGAACTGGAACTGCTGATGCTGGCCTCTGAAGAAGATGAAGA

AGTTAGTTGCCTGATCACCGACGCACTGTGGTATTTTGCCCAGAGTGTTG

CAGATTCCCTGAACCTGCGTCGCCTGGTCCTGATGACGAGCTCTCTGTTC

AATTTTCATGCCCACGTTTCCCTGCCGCAGTTCGATGAACTGGGTTATCT

GGACCCGGATGACAAAACCCGCCTGGAAGAACAAGCTTCAGGCTTTCCGA

TGCTGAAAGTCAAAGATATTAAAAGTGCGTACTCCAACTGGCAGATTCTG

AAAGAAATCCTGGGTAAAATGATCAAACAAACCCGTGCAAGTTCCGGCGT

CATCTGGAATTCCTTCAAAGAACTGGAAGAATCAGAACTGGAAACGGTGA

TTCGCGAAATCCCGGCTCCGTCTTTTCTGATTCCGCTGCCGAAACATCTG

ACCGCGTCATCGAGCTCTCTGCTGGATCACGACCGTACGGTGTTCAGTG

GCTGGATCAGCAACCGCCGAGTTCCGTGCTGTACGTTAGCTTCGGTAGCA

CCTCTGAAGTGGATGAAAAAGACTTTCTGGAAATCGCTCGTGGCCTGGTT

```
GATTCAAAACAATCGTTCCTGTGGGTGGTTCGCCCGGGTTTTGTGAAGG

CAGCACGTGGGTTGAACCGCTGCCGGATGGCTTCCTGGGTGAACGTGGTC

GCATTGTCAAATGGGTGCCGCAGCAAGAAGTGCTGGCACATGGTGCTATC

GGCGCGTTTTGGACCCACTCAGGTTGGAACTCGACGCTGGAAAGCGTTTG

TGAAGGTGTCCCGATGATTTTCTCGGATTTTGGCCTGGACCAGCCGCTGA

ATGCACGTTATATGAGCGATGTTCTGAAAGTCGGTGTGTACCTGGAAAAC

GGTTGGGAACGCGGCGAAATTGCGAATGCCATCCGTCGCGTTATGGTCGA

TGAAGAAGGCGAATATATCCGTCAGAATGCTCGCGTCCTGAAACAAAAAG

CGGACGTTAGTCTGATGAAAGGCGGTTCATCGTACGAATCCCTGGAATCA

CTGGTCTCCTACATTTCTTCTCTGGGCTCGCATCATCATCATCATCATTA

A
```

In certain embodiments, the nucleic acid molecule encodes an UGT76G1 glucosyltransferase and comprises the nucleotide sequence as set forth in Gen Bank Accession number AY345974.1 or a variant or fragment thereof.

In certain embodiments, the nucleic acid comprises a sequence encoding UGT76G2 glucosyltransferase. In specific embodiments, the nucleic acid comprises a sequence encoding UGT76G2 glucosyltransferase having the amino acid sequence as set forth in SEQ ID NO:27 and listed below or variants and fragments thereof.

```
                                         SEQ ID NO: 27
MENKTETTVRRRRRIILFPVPVQGHINPILQLANVLYSKGFSITIFHTNF

NKPKTSNYPHFTFRFILDNDPQDVRISNLPTHGPLTVMRILIINEHGADE

LQRELELLMLASEEDGEVSCLITDQIWYFTQSVADSLNLRRLVLMTSSLF

NFHAHVSLPQFDELGYLDPDDKTRLEEQASGFPMLKVKDIKCGFSMWKQG

KEIFENITKQTKASSGVIWNSFKELEESELETVIREIPAPSFLIPLPKHL

TASSSSLLDHDRTVFPWLDQQPSRSVLYVSFGSATEVDAKDFLEIARGLV

DSKQSFLWVVRPGFVKGSTWVEPLPDGFLGERGRIVKWVPQQEVLAHGAI

GAFWTHSGWNSTLESVCEGVPMIFSAFAFDQPLNARYMSDVLKVGVYLEN

GWERGEIANAIRRVMVDEEGGYIRQNASVLKQKADVSLMKGGSSYESLES

LVAYISSL
```

In specific embodiments, the nucleic acid comprises a sequence encoding UGT76G2 glucosyltransferase and having the nucleic acid sequence as set forth in SEQ ID NO:28 and listed below or variants and fragments thereof.

```
                                         SEQ ID NO: 28
ATGGAAAATAAAACGGAGACCACCGTTCGCCGGCGCCGGAGAATAATATT

ATTCCCGGTACCAGTTCAAGGCCACATTAACCCAATTCTTCAGCTAGCCA

ATGTGTTGTACTCCAAAGGATTCAGTATCACCATCTTTCACACCAACTTC

AACAAACCCAAAACATCTAATTACCCTCACTTCACTTTCAGATTCATCCT

CGACAACGACCCACAAGACGTACGCATTTCCAATCTACCGACTCATGGTC

CGCTCACTGTTATGCGGATTCTGATTATCAACGAACACGGAGCTGACGAA

TTACAACGCGAACTGGAACTGTTGATGTTAGCTTCTGAAGAAGATGGAGA

GGTATCGTGTTTAATCACCGATCAGATTTGGTACTTCACGCAATCTGTTG

CTGACAGTCTTAACCTCCGACGGCTTGTTTTGATGACAAGCAGCTTGTTT

AATTTTCATGCACATGTTTCACTTCCTCAGTTTGATGAGCTTGGTTACCT

CGATCCTGATGACAAAACCCGTTTGGAAGAACAAGCGAGTGGGTTTCCTA

TGCTGAAAGTGAAAGATATCAAGTGTGGTTTTTCGATGTGGAAACAAGGC

AAAGAGATATTCGAGAACATTACGAAACAAACAAAAGCATCTTCAGGAGT

CATCTGGAACTCATTTAAGGAACTCGAAGAGTCTGAGCTCGAAACTGTTA

TCCGTGAGATCCCGGCTCCAAGTTTCTTGATACCACTCCCCAAGCATTTG

ACAGCCTCTTCCAGCAGCTTACTAGACCACGATCGAACCGTTTTTCCATG

GTTAGACCAACAACCGTCACGTTCGGTACTGTATGTTAGTTTTGGTAGTG

CTACTGAAGTGGATGCGAAAGATTTCTTGGAAATAGCTCGTGGGTTGGTT

GATAGCAAGCAGTCGTTTTTATGGGTGGTTCGACCTGGTTTTGTCAAGGG

TTCGACGTGGGTCGAACCGTTGCCAGATGGGTTCTTGGGTGAAAGAGGAC

GTATTGTGAAATGGGTTCCGCAGCAAGAAGTGCTAGCTCATGGAGCAATA

GGCGCATTCTGGACTCATAGCGGATGGAACTCTACGTTGGAAAGCGTTTG

TGAAGGTGTTCCTATGATTTTCTCGGCTTTTGCGTTCGATCAACCGTTGA

ATGCTAGATACATGAGTGATGTTTTGAAGGTAGGGGTGTATTTGGAAAAT

GGGTGGGAAAGAGGAGAGATAGCAAATGCAATAAGAAGAGTTATGGTGGA

TGAAGAAGGAGGATACATTAGACAGAATGCAAGTGTTTTGAAACAAAAGG

CAGATGTTTCTTTGATGAAGGGTGGTTCGTCTTACGAATCATTAGAGTCT

CTAGTTGCTTACATTTCATCGTTGTAA
```

In certain embodiments, the nucleic acid comprises a sequence encoding UGT76H1 glucosyltransferase. In specific embodiments, the nucleic acid comprises a sequence encoding UGT76H1 glucosyltransferase having the amino acid sequence as set forth in SEQ ID NO:29 and listed below or variants and fragments thereof.

```
                                         SEQ ID NO: 29
MLQLATYLHSQGISITIAQYPNFNSPDSSNHPELTFLPLSSGNLSVADIS

GGFFKFIQTLNHNCKPHFREYLVQNMSSDDKESIVIIRDNLMFFAGEIAG

ELGLPSIILRGSNAVMLTASDIIPQLHQEGRFPPPDSLLQETIPELVPFR

YKDLPFIGYPIHQTLEFSITMMTPKSPASAILINTLEFLEQSALTQIRDH

YKVPVFTIGPLHKIVTTRSTSILEEDTSCINWLDKQSPKSVVYVSLGSLA

KLDEKVASEMACGLAMSNHKFLWVVRPGMVHGFEWVEFLPDSLVGEMKAR

GLIVKWAPQTTVLAHNAVGGFWSHCGWNSTIECLAEGVPMMCQPFFADQL

LNARYVSDVWKTGFEIVIEKGEIACAIKRVLVDEEGEEMRQRAMEIKEKV

KIAINDGGSSYDSFKDLVAFISSL
```

In specific embodiments, the nucleic acid comprises a sequence encoding UGT76H1 glucosyltransferase and having the nucleic acid sequence as set forth in SEQ ID NO:30 and listed below or variants and fragments thereof.

```
ATGCTTCAGCTTGCAACTTACCTCCATTCTCAAGGGATTTCAATAACCAT

CGCTCAGTACCCCAACTTCAACTCGCCGGATTCTTCCAACCATCCAGAAC
```

-continued
TAACCTTCCTCCCACTATCCTCCGGCAACTTATCCGTCGCCGACATCTCC
GGCGGCTTTTTCAAGTTCATCCAAACTCTTAACCATAACTGCAAACCCCA
TTTCCGGGAATACCTTGTTCAGAACATGAGTTCTGATGATAAGGAATCAA
TCGTTATCATCCGTGATAATCTCATGTTTTTCGCCGGAGAAATCGCCGGC
GAGCTGGGTCTGCCTTCGATCATTTTACGTGGCAGCAATGCTGTCATGTT
GACTGCTAGCGACATCATCCCTCAACTTCATCAAGAAGGTCGTTTTCCGC
CACCAGATTCTTTGTTGCAGGAAACAATTCCAGAACTGGTTCCATTCAGA
TACAAAGATCTACCATTTATTGGCTATCCAATACATCAAACCCTTGAATT
TAGTATCACCATGATGACCCCCAAATCACCTGCTTCCGCCATTCTTATCA
ACACCCTCGAATTTCTTGAACAATCGGCATTAACCCAGATCCGTGATCAT
TACAAAGTTCCAGTTTTTACAATCGGACCATTGCACAAAATAGTCACAAC
TCGTTCCACTAGCATTCTTGAAGAAGATACAAGTTGCATCAATTGGTTAG
ATAAACAATCACCCAAATCAGTGGTTTATGTGAGTTTAGGAAGCTTAGCA
AAGTTGGATGAAAAGGTTGCATCTGAAATGGCATGTGGTTTAGCCATGAG
TAACCATAAGTTCCTATGGGTGGTTCGACCCGGTATGGTTCATGGGTTTG
AATGGGTCGAGTTTTTGCCGGATAGTTTGGTGGGTGAAATGAAGGCTAGA
GGTTTGATTGTGAAATGGGCACCCCAGACGACGGTTTTGGCGCATAACGC
GGTTGGTGGATTTTGGAGTCATTGCGGTTGGAACTCGACCATAGAATGCT
TAGCTGAAGGGGTCCCGATGATGTGTCAACCGTTTTTTGCTGATCAGTTG
TTGAATGCTAGGTATGTGAGTGATGTTTGGAAGACGGGTTTTGAGATTGT
TATCGAGAAAGGTGAGATTGCGTGCGCGATTAAACGAGTTTTGGTGGATG
AAGAAGGCGAAGAAATGAGGCAGAGAGCTATGGAGATTAAAGAAAAGGTT
AAAATTGCAATCAACGATGGTGGTTCTTCTTATGACTCGTTCAAGGACTT
GGTGGCGTTTATTTCATCACTCTAA In certain embodiments, the nucleic acid comprises a sequence encoding *Oryza sativa* Os03g0702000 or Os03g0702000-like glucosyltransferase. Os03g0702000-like glucosyltransferase include for example, other members of the UGT91clade such as UGT91D1 or UGT91D2. In certain embodiments, the nucleic acid comprises a sequence encoding Os03g0702000 glucosyltransferase having the amino acid sequence as set forth in SEQ ID NO: 9 and listed below or a variant or fragment thereof.

SEQ ID NO: 9
MHQHQHQSGSMDSGYSSSYAAAAGMHVVICPWLAFGHLLPCLDLAQRLAS
RGHRVSFVSTPRNISRLPPVRPALAPLVAFVALPLPRVEGLPDGAESTND
VPHDRPDMVELHRRAFDGLAAPFSEFLGTACADWVIVDVFHHWAAAAALE
HKVPCAMMLLGSAHMIASIADRRLERAETESPAAAGQGRPAAAPTFEVAR
MKLIRTKGSSGMSLAERFSLTLSRSSLVVGRSCVEFEPETVPLLSTLRGK
PITFLGLMPPLHEGRREDGEDATVRWLDAQPAKSVVYVALGSEVPLGVEK
VHELALGLELAGTRFLWALRKPTGVSDADLLPAGFEERTRGRGVVATRWV
PQMSILAHAAVGAFLTHCGWNSTIEGLMFGHPLIMLPIFGDQGPNARLIE
AKNAGLQVARNDGDGSFDREGVAAAIRAVAVEEESSKVFQAKAKKLQEIV
ADMACHERYIDGFIQQLRSYKD

In certain embodiments, the nucleic acid molecule encodes Os03g0702000 glucosyltransferase and comprises a nucleotide sequence as set forth in SEQ ID NO: 10 and as detailed below or a variant or fragment thereof.

SEQ ID NO: 10
ATGCATCAGCACCAACATCAGAGCGGTTCTATGGACTCCGGCTACTCCTC
CTCCTACGCCGCCGCCGCCGGGATGCACGTCGTGATCTGCCCGTGGCTCG
CCTTCGGCCACCTGCTCCCGTGCCTCGACCTCGCCCAGCGCCTCGCGTCG
CGGGGCCACCGCGTGTCGTTCGTCTCCACGCCGCGGAACATATCCCGCCT
CCCGCCGGTGCGCCCCGCGCTCGCGCCGCTCGTCGCCTTCGTGGCGCTGC
CGCTCCCGCGCGTCGAGGGGCTCCCCGACGGCGCCGAGTCCACCAACGAC
GTCCCCCACGACAGGCCGGACATGGTCGAGCTCCACCGGAGGGCCTTCGA
CGGGCTCGCCGCGCCCTTCTCGGAGTTCTTGGGCACCGCGTGCGCCGACT
GGGTCATCGTCGACGTCTTCCACCACTGGGCCGCAGCCGCCGCTCTCGAG
CACAAGGTGCCATGTGCAATGATGTTGTTGGGCTCTGCACATATGATCGC
TTCCATAGCAGACAGACGGCTCGAGCGCGCGGAGACAGAGTCGCCTGCGG
CTGCCGGGCAGGGACGCCCAGCGGCGGCGCCAACGTTCGAGGTGGCGAGG
ATGAAGTTGATACGAACCAAAGGCTCATCGGGAATGTCCCTCGCCGAGCG
CTTCTCCTTGACGCTCTCGAGGAGCAGCCTCGTCGTCGGGCGGAGCTGCG
TGGAGTTCGAGCCGGAGACCGTCCCGCTCCTGTCGACGCTCCGCGGTAAG
CCTATTACCTTCCTTGGCCTTATGCCGCCGTTGCATGAAGGCCGCCGCGA
GGACGGCGAGGATGCCACCGTCCGCTGGCTCGACGCGCAGCCGGCCAAGT
CCGTCGTGTACGTCGCGCTAGGCAGCGAGGTGCCACTGGGAGTGGAGAAG
GTCCACGAGCTCGCGCTCGGGCTGGAGCTCGCCGGGACGCGCTTCCTCTG
GGCTCTTAGGAAGCCCACTGGCGTCTCCGACGCCGACCTCCTCCCCGCCG
GCTTCGAGGAGCGCACGCGCGGCCGCGGCGTCGTGGCGACGAGATGGGTT
CCTCAGATGAGCATACTGGCGCACGCCGCCGTGGGCGCGTTCCTGACCCA
CTGCGGCTGGAACTCGACCATCGAGGGGCTCATGTTCGGCCACCCGCTTA
TCATGCTGCCGATCTTCGGCGACCAGGGACCGAACGCGCGGCTAATCGAG
GCGAAGAACGCCGGATTGCAGGTGGCAAGAAACGACGGCGATGGATCGTT
CGACCGAGAAGGCGTCGCGGCGGCGATTCGTGCAGTCGCGGTGGAGGAAG
AAAGCAGCAAAGTGTTTCAAGCCAAAGCCAAGAAGCTGCAGGAGATCGTC
GCGGACATGGCCTGCCATGAGAGGTACATCGACGGATTCATTCAGCAATT
GAGATCTTACAAGGATTGA

In certain embodiments, the nucleic acid molecule encodes Os03g0702000 glucosyltransferase and comprises the sequence as set forth in GenBank Accession number XM_015773655 or a variant or fragment thereof.

In certain embodiments, the nucleic acid comprises a sequence encoding UGT91D1 glucosyltransferase. In certain embodiments, the nucleic acid comprises a sequence encoding UGT91D1 glucosyltransferase having the amino acid sequence as set forth in SEQ ID NO:31 and listed below or a variant or fragment thereof.

SEQ ID NO: 31
MYNVTYHQNSKAMATSDSIVDDRKQLHVATFPWLAFGHILPFLQLSKLIA
EKGHKVSFLSTTRNIQRLSSHISPLINVVQLTLPRVQELPEDAEATTDVH
PEDIQYLKKAVDGLQPEVTRFLEQHSPDWIIYDFTHYWLPSIAASLGISR
AYFCVITPWTIAYLAPSSDAMINDSDGRTTVEDLTTPPKWFPFPTKVCWR
KHDLARMEPYEAPGISDGYRMGMVFKGSDCLLFKCYHEFGTQWLPLLETL
HQVPVVPVGLLPPEIPGDEKDETWVSIKKWLDGKQKGSVVYVALGSEALV
SQTEVVELALGLELSGLPFVWAYRKPKGPAKSDSVELPDGFVERTRDRGL
VWTSWAPQLRILSHESVCGFLTHCGSGSIVEGLMFGHPLIMLPIFCDQPL
NARLLEDKQVGIEIPRNEEDGCLTKESVARSLRSVVVENEGEIYKANARA
LSKIYNDTKVEKEYVSQFVDYLEKNARAVAIDHES

In certain embodiments, the nucleic acid molecule encodes UGT91D1 glucosyltransferase and comprises a nucleotide sequence as set forth in SEQ ID NO: 32 and as detailed below or a variant or fragment thereof.

SEQ ID NO: 32
ATGTACAACGTTACTTATCATCAAAATTCAAAAGCAATGGCTACCAGTGA
CTCCATAGTTGACGACCGTAAGCAGCTTCATGTTGCGACGTTCCCATGGC
TTGCTTTCGGTCACATCCTCCCTTTCCTTCAGCTTTCGAAATTGATAGCT
GAAAAGGGTCACAAAGTCTCGTTTCTTTCTACCACCAGAAACATTCAACG
TCTCTCTTCTCATATCTCGCCACTCATAAATGTTGTTCAACTCACACTTC
CACGTGTCCAAGAGCTGCCGGAGGATGCAGAGGCGACCACTGACGTCCAC
CCTGAAGATATTCAATATCTCAAGAAGGCTGTTGATGGTCTTCAACCGGA
GGTCACCCGGTTTCTAGAACAACACTCTCCGGACTGGATTATTTATGATT
TTACTCACTACTGGTTGCCATCCATCGCGGCTAGCCTCGGTATCTCACGA
GCCTACTTCTGCGTCATCACTCCATGGACCATTGCTTATTTGGCACCCTC
ATCTGACGCCATGATAAATGATTCAGATGGTCGAACCACGGTTGAGGATC
TCACGACACCGCCCAAGTGGTTTCCCTTTCCGACCAAAGTATGCTGGCGG
AAGCATGATCTTGCCCGAATGGAGCCTTACGAAGCTCCGGGGATATCTGA
TGGATACCGTATGGGGATGGTTTTTAAGGGATCTGATTGTTTGCTTTTCA
AATGTTACCATGAGTTTGGAACTCAATGGCTACCTCTTTTGGAGACACTA
CACCAAGTACCGGTGGTTCCGGTGGGATTACTGCCGCCGGAAATACCCGG
AGACGAGAAAGATGAAACATGGGTGTCAATCAAGAAATGGCTCGATGGTA
AACAAAAAGGCAGTGTGGTGTACGTTGCATTAGGAAGCGAGGCTTTGGTG
AGCCAAACCGAGGTTGTTGAGTTAGCATTGGGTCTCGAGCTTTCTGGGTT
GCCATTTGTTTGGGCTTATAGAAAACCAAAAGGTCCCGCGAAGTCAGACT
CGGTGGAGTTGCCAGACGGGTTCGTGGAACGAACTCGTGACCGTGGGTTG
GTCTGGACGAGTTGGGCACCTCAGTTACGAATACTGAGCCACGAGTCAGT
TTGTGGTTTCTTGACTCATTGTGGTTCTGGATCAATTGTGGAAGGGCTAA
TGTTTGGTCACCCTCTAATCATGCTACCGATTTTTTGTGACCAACCTCTG
AATGCTCGATTACTGGAGGACAAACAGGTGGGAATCGAGATACCAAGAA
TGAGGAAGATGGTTGCTTGACCAAGGAGTCGGTTGCTAGATCACTGAGGT

CCGTTGTTGTGGAAAACGAAGGGGAGATCTACAAGGCGAACGCGAGGGCG
CTGAGTAAAATCTATAACGACACTAAGGTGGAAAAAGAATATGTAAGCCA
ATTCGTAGACTATTTGGAAAAGAATGCGCGTGCGGTTGCCATCGATCATG
AGAGTTAA

In certain embodiments, the nucleic acid comprises a sequence encoding UGT91D2 glucosyltransferase. In certain embodiments, the nucleic acid comprises a sequence encoding UGT91D2 glucosyltransferase having the amino acid sequence as set forth in SEQ ID NO: 33 and listed below or a variant or fragment thereof.

SEQ ID NO: 33
MATSDSIVDDRKQLHVATFPWLAFGHILPYLQLSKLIAEKGHKVSFLSTT
RNIQRLSSHISPLINVVQLTLPRVQELPEDAEATTDVHPEDIPYLKKASD
GLQPEVTRFLEQHSPDWIIYDYTHYWLPSIAASLGISRAHFSVTTPWAIA
YMGPSADAMINGSDGRTTVEDLTTPPKWFPFPTKVCWRKHDLARLVPYKA
PGISDGYRMGLVLKGSDCLLSKCYHEFGTQWLPLLETLHQVPVVPVGLLP
PEIPGDEKDETWVSIKKWLDGKQKGSVVYVALGSEVLVSQTEVVELALGL
ELSGLPFVWAYRKPKGPAKSDSVELPDGFVERTRDRGLVWTSWAPQLRIL
SHESVCGFLTHCGSGSIVEGLMFGHPLIMLPIFGDQPLNARLLEDKQVGI
EIPRNEEDGCLTKESVARSLRSVVVEKEGEIYKANARELSKIYNDTKVEK
EYVSQFVDYLEKNARAVAIDHES

In certain embodiments, the nucleic acid molecule encodes UGT91D2 glucosyltransferase and comprises a nucleotide sequence as set forth in SEQ ID NO: 34 and as detailed below or a variant or fragment thereof.

SEQ ID NO: 34
ATGGCCACATCTGACTCTATCGTTGATGACAGAAAACAATTGCATGTTGC
TACTTTCCCATGGTTGGCCTTTGGACACATTCTGCCCTACTTGCAATTGT
CAAAGCTGATTGCAGAAAAGGTCATAAGGTGTCCTTTTTGTCTACCACA
AGAAACATCCAGAGACTAAGTTCTCATATTTCTCCATTGATTAATGTGGT
TCAGTTGACCTTGCCTAGAGTCCAAGAACTTCCCGAAGACGCAGAAGCTA
CTACTGATGTTCACCCTGAAGATATCCCATATCTAAAGAAGGCATCTGAT
GGACTTCAACCAGAAGTAACCAGGTTTTTGGAGCAGCACAGTCCTGACTG
GATTATCTATGATTATACTCATTACTGGCTTCCATCCATCGCAGCTAGTC
TAGGCATTTCCAGAGCTCATTTCTCTGTCACTACCCCATGGGCAATTGCA
TATATGGGTCCTTCTGCTGATGCAATGATCAACGGTTCTGATGGTAGGAC
CACTGTTGAAGATTTAACTACACCTCCAAAGTGGTTCCCATTTCCTACTA
AAGTTTGTTGGCGAAAACACGATCTGGCACGTTTGGTCCCATATAAGGCT
CCAGGTATCTCCGATGGATATCGAATGGGTCTGGTGCTAAAGGGTTCTGA
TTGTCTGTTATCTAAGTGTTACCACGAATTTGGAACTCAATGGCTTCCTC
TATTAGAGACTCTGCATCAAGTTCCAGTTGTTCCTGTCGGTCTGCTACCA
CCTGAAATTCCCGGTGACGAAAAGGACGAAACTTGGGTTTCCATAAAAAA
ATGGCTGGATGGTAAGCAGAAGGGTAGTGTTGTATATGTCGCTTTAGGCT

-continued
CCGAGGTTTTGGTATCCCAGACTGAAGTTGTGGAACTTGCCTTAGGATTG

GAGTTGTCCGGTTTGCCATTCGTCTGGGCATATAGAAAGCCAAAGGGACC

AGCTAAGTCAGACTCAGTTGAATTGCCAGATGGTTTCGTAGAAAGGACAA

GAGACAGAGGATTGGTTTGGACATCATGGGCCCCACAATTGAGAATTCTG

AGTCATGAAAGTGTGTGGATTCTTGACTCACTGTGGCTCTGGCAGTAT

TGTTGAAGGACTGATGTTTGGACACCCACTGATAATGTTGCCAATCTTCG

GTGACCAACCTCTGAATGCAAGATTGCTGGAGGATAAACAAGTTGGTATC

GAAATCCCAAGAAACGAGGAAGACGGCTGCCTGACTAAGGAATCAGTTGC

ACGTAGTTTAAGATCTGTAGTTGTTGAAAAAGAAGGTGAAATATATAAGG

CTAACGCTAGAGAACTTTCAAAGATATACAATGATACCAAGGTGGAGAAA

GAATATGTTTCACAGTTTGTGGACTATTTGGAGAAAAACGCTAGAGCCGT

TGCTATCGATCACGAATCATAG

In certain embodiments, the nucleic acid comprises a sequence encoding *Stevia rebaudiana* UDP-glycosyltransferase 74G1. In certain embodiments, the nucleic acid comprises a sequence encoding *Stevia rebaudiana* UDP-glycosyltransferase 74G1 which comprises the amino acid sequence as set forth in SEQ ID NO: 13 and as listed below or a variant or fragment thereof.

SEQ ID NO: 13
MAEQQKIKKSPHVLLIPFPLQGHINPFIQFGKRLISKGVKTTLVTTIHTL

NSTLNHSNTTTTSIEIQAISDGCDEGGFMSAGESYLETFKQVGSKSLADL

IKKLQSEGTTIDAIIYDSMTEWVLDVAIEFGIDGGSFFTQACVVNSLYYH

VHKGLISLPLGETVSVPGFPVLQRWETPLILQNHEQIQSPWSQMLFGQFA

NIDQARWVFTNSFYKLEEEVIEWTRKIWNLKVIGPTLPSMYLDKRLDDDK

DNGFNLYKANHHECMNWLDDKPKESVVYVAFGSLVKHGPEQVEEITRALI

DSDVNFLWVIKHKEEGKLPENLSEVIKTGKGLIVAWCKQLDVLAHESVGC

FVTHCGFNSTLEAISLGVPVVAMPQFSDQTTNAKLLDEILGVGVRVKADE

NGIVRRGNLASCIKMIMEEERGVIIRKNAVKWKDLAKVAVHEGGSSDNDI

VEFVSELIKA

In certain embodiments, the nucleic acid molecule encodes *Stevia rebaudiana* UDP-glycosyltransferase 7401 and comprises a nucleotide sequence as set forth in SEQ ID NO: 14 and as listed below or a variant or fragment thereof.

SEQ ID NO: 14
ATGGCGGAACAACAAAAGATCAAGAAATCACCACACGTTCTACTCATCCC

ATTCCCTTTACAAGGCCATATAAACCCTTTCATCCAGTTTGGCAAACGAT

TAATCTCCAAAGGTGTCAAAACAACACTTGTTACCACCATCCACACCTTA

AACTCAACCCTAAACCACAGTAACACCACCACCACCTCCATCGAAATCCA

AGCAATTTCCGATGGTTGTGATGAAGGCGGTTTTATGAGTGCAGGAGAAT

CATATTTGGAAACATTCAAACAAGTTGGGTCTAAATCACTAGCTGACTTA

ATCAAGAAGCTTCAAAGTGAAGGAACCACAATTGATGCAATCATTTATGA

TTCTATGACTGAATGGGTTTTAGATGTTGCAATTGAGTTTGGAATCGATG

GTGGTTCGTTTTTCACTCAAGCTTGTGTTGTAAACAGCTTATATTATCAT

GTTCATAAGGGTTTGATTTCTTTGCCATTGGGTGAAACTGTTTCGGTTCC

TGGATTTCCAGTGCTTCAACGGTGGGAGACACCGTTAATTTTGCAGAATC

ATGAGCAAATACAGAGCCCTTGGTCTCAGATGTTGTTTGGTCAGTTTGCT

AATATTGATCAAGCACGTTGGGTCTTCACAAATAGTTTTTACAAGCTCGA

GGAAGAGGTAATAGAGTGGACGAGAAAGATATGGAACTTGAAGGTAATCG

GGCCAACACTTCCATCCATGTACCTTGACAAACGACTTGATGATGATAAA

GATAACGGATTTAATCTCTACAAAGCAAACCATCATGAGTGCATGAACTG

GTTAGACGATAAGCCAAAGGAATCAGTTGTTTACGTAGCATTTGGTAGCC

TGGTGAAACATGGACCCGAACAAGTGGAAGAAATCACACGGGCTTTAATA

GATAGTGATGTCAACTTCTTGTGGGTTATCAAACATAAAGAAGAGGGAAA

GCTCCCAGAAAATCTTTCGGAAGTAATAAAAACCGGAAAGGGTTTGATTG

TAGCATGGTGCAAACAATTGGATGTGTTAGCACACGAATCAGTAGGATGC

TTTGTTACACATTGTGGGTTCAACTCAACTCTTGAAGCAATAAGTCTTGG

AGTCCCCGTTGTTGCAATGCCTCAATTTTCGGATCAAACTACAAATGCCA

AGCTTCTAGATGAAATTTTGGGTGTTGGAGTTAGAGTTAAGGCTGATGAG

AATGGGATAGTGAGAAGAGGAAATCTTGCGTCATGTATTAAGATGATTAT

GGAGGAGGAAAGAGGAGTAATAATCCGAAAGAATGCGGTAAAATGGAAGG

ATTTGGCTAAAGTAGCCGTTCATGAAGGTGGTAGCTCAGACAATGATATT

GTCGAATTTGTAAGTGAGCTAATTAAGGCTTAA

In certain embodiments, the nucleic acid molecule encodes *Stevia rebaudiana* UDP-glycosyltransferase 74G1 and comprises the sequence as set forth in Gen Bank Accession number AY345982 or a variant or fragment thereof.

In other embodiments, the invention provides for nucleic acids comprising nucleotide sequences encoding a cyclodextrin glucanotransferase (WO1996033267; U.S. Pat. No. 6,271,010).

Also provided are nucleic acids comprising nucleotide sequences that encode a sucrose synthase. Accordingly, in certain embodiments, the nucleic acid comprises a sequence encoding sucrose synthase which comprises the amino acid sequence as set forth in SEQ ID NO: 15, 17, 19, 21, 23 or 25 and listed below or a variant or fragment thereof.

(*Stevia rebaudiana* SUS1 isoform)
SEQ ID NO: 15
MAERVLTRVHSLRERLDSTLATHRNEILLFLSRIESHGKGILKPHQVMTE

FEAICKEDQSKLSDGAFYEVLKCTQEAIVQPPWVALAIRLRPGVWEYVRV

NVNVLVVEELSVPEYLHFKEELVNGTSNGNFVLELDFEPFTASFPRPTLT

KSIGNGVEFLNRHLSAKMFHDKDSMHPLLDFLRTHHYKGKTMMLNDRIQN

LNALQSVLRKASEYLSTLDAATPYSEFEHKFQEIGLERGWGDKAEVVMEM

IHMLLDLLEAPDACTLEKFLGRIPMVFNVVILSPHGYFAQENVLGYPDTG

GQVVYILDQVPALEREMLKRIKEQGLDIIPRILIVTRLLPDAVGTTCGQR

LEKVFGAEHSHILRVPFRTEKGILRKWISRFEVWPYIETFTEDVAKEVTA

ELQAKPDLIIGNYSEGNLVASLLAHKLGVTQCTIAHALEKTKYPDSDIYW

KNFEEKYHFSSQFTADLIAMNHTDFIITSTFQEIAGSKDTVGQYESHTAF

-continued

TMPGLYRVVHGIDVFDPKFNIVSPGADMGIYYSYTEKEKRLTALHPEIDE
LLFSSVENEEHLCVLKDKSKPILFTMARLDNVKNLTGLVEWYAKNDRLRE
LVNLVVVGGDRRKESKDLEEQAQMQKMHELIETYKLNGQFRWISSQMNRV
RNGELYRVIADTRGAFIQPAFYEAFGLTVVEAMTCGLPTFATLHGGPAEI
IVHGKSGFHIDPYHGDQVTELLVNFFEKTKQDPGHWEAISKGGLQRIQEK
YTWQIYSDRLLTLAGVYGFWKHVSKLDRLEIRRYLEMFYALKYRKLAESV
PLAVDE (Stevia rebaudiana SUS2 isoform)
                                                       SEQ ID NO: 17
MATSKLSRTHSMRERVEETLSAHRNEIVSLLSRYVAQGKAILQPHQILHE
LENIIGDVTSRQKLTDGPFGDALKTAQECIVLPPFVALAVRPRPGVWEYV
RVDAYQLSVEQLTVSEYLTFKEELVGESNSSLMLELDFEPFNASFPRPTR
SSSIGNGVQFLNRHLSSSMFRSKDCLEPLLDFLRTHRHNGHVMMLNDRIT
SMTRLQSSLVKAEEYLSKLPSDTDYSEFQYELQGMGFERGWGNNAERIIE
MMHLLSDILQAPDPSILESFLARIPMVFNVVILSIHGYFGQANVLGLPDT
GGQIVYILDQVRALENEMLLKLKHQGLDIKPRILIVTRLIPDAKGTSCNQ
RLERVSGTEHTHILRVPFRTEKGILRKWISRFDVWPFLEKFTQDAASEIS
AELHGTPDLIIGNYSDGNLVASLLSYKMGVTQCNIAHALEKTKYPDSDLY
WKKFDEKYHFSCQFTADLLAMNNADFIITSTYQEIAGTKNTVGQYESHSS
FTLPGLYRVVHGIDVFDPKFNIVSPGADMSIYFSYTEKEKRLTSLHTTIE
KLLFDPTQTEDYIGNLSDKSKPIIFSMARLDHVKNITGLVEWYAKNEKLR
GLANLVVAGYNNVKRSSDREEIAEIEKMHQLIKKYKLDGQMRWISAQTN
RAQNGELYRYIADGRGIFVQPAIYEAFGLTVVEAMTCGLPTFATCHGGPG
EIIENGVSGFHIDPYHPDTASATMADFFQKCKEDPSYWFKISEAGLKRIY
ERYTWKIYSERLMTLAGVYSFWKYVSKLERRETRRYLEMFYILKFRDLVK
SVPVATDDEA (Stevia rebaudiana SUS3 isoform)
                                                     SEQ ID NO: 19
MATPKLTRTPSMRERLEETLSAHRNDIVSLLSRYVDQGKAILQPHHLLDE
IDNFIGDQNCRQKLADSLFGEILKSAQEGIILPPYVTLAVRPRPGVWDFL
RVNVDELSVEQLTVSEYLSFKEELVDGQSRNPFVLELDLEPFNATFPRMS
RSSSIGNGVQFLNRHLSSIMFRNKDCMDPFLDFLRAHKHKGYAMMLNDRI
QTMSRLESSLAKAEDHLSKLPPETPYSEFEYVLQGMGFERGWGDNCERVL
GMMHLLSDILQAPDPSILEKFLGKMPMIFNVVVLSIHGYFGQANVLGLPD
TGGQVVYILDQVRSLENEMLLKLRHQGLDIKPKILIVTRLIPNAKGTSCN
QRLEKVSGTEYTYILRVPFRTEKGILGKWLSRFDIWPYLEAFTTDAASEI
AAELHGVPDLLIGNYSDGNLVASLLSNKLGVTQCNIAHALEKTKYPDSDL
YWKKFEDKYHFSCQFTADLLAMNNADFIITSTYQEIAGTKNTVGQYENHS
SFTLPGLYRVVHGIDVFDPKFNIVSPGADMAIYFSYADKERRLTSLHPTI
EKLLFDTEQNDVHIGNINDPSKPMIFTMARLDHVKNITGFVECYAKNNKL
REHANLVVIAGYNDAKKSSDREEIAEIEKMHNLIKQYKLDGQMRWISAQT
NRARNGEFYRYIADGRGVFVQPAFYEAFGLTVVEAMTCGLPTFATCHGGP AEIIEDGVSGFHIDPYHPDKMSTTLADFFQKCKEEPSYWGKISDGGLKRI
SERYTWKIYSERLMTLAGVYSFWKYVSKLERRETRRYLEMFYILKFRQLV
KSVPLAVDEEP (Stevia rebaudiana SUS4 isoform)
                                                     SEQ ID NO: 21
MASASSSIMKRSESIVDTMPEALKQSRYHMKKCFLKYVEKGIRMMKRHHL
IQEMETAIEDKDEKAQLLDGLLGYILCTTQEAAVVPPCVAFAIRPNPGFW
EFVKVNSNDLSVDGITATDYLKFKEMIVDETWAKDENALEIDFGSMDFNL
PNMSLSCSIGNGVNFTSKFITCKLYAQSSCQQLLVDYLLSLNHQGENLMI
NDALNSVSKLRAALIVAHASLSSLPNDTPYQSFELRFKEWGFEKGWGDNA
ERARETIRFLLEVLQAPDPINLEALFSRIPNIFNVVLFSIHGYFGQSNVL
GLPDTGGQVVYVLDQVVAMEEELLMRIKQQGLNFKPQILVVTRLLPDAKG
TKCNQVLEPVLNTKHSHILRVPFRTDKGVLRKWVSRFDIYPYLENFTQDA
SAKIIEMMEGKPDLIIGNYTDGNLVASLMANKLGTTLGTIAHALEKTKYE
DSDMNWKQFDPKYHFSCQFTADMIAMNSADFIITSTFQEIAGSKDRPGQY
ESHEAFTLPGLYRVVSGINVFDPKFNIASPGADQTVYFPYTETKKRFTAF
QPAIEELLFSKVENEEHIGYLEDKTKPIIFSMARLDTVKNITGLTEWFGE
NKRLRSLVNLVIVAGFFDPSKSKDREEMAEIKKMHLLIEKYQLKGQIRWI
AAQTDKNRNSELYRFIADSKGAFVQPALYEAFGLTVIEAMNCGLPTFATN
QGGPAEIIVDGVSGFQIDPNFGDQSSNKIADFFQKCKEDPGYWNNISEGG
LKRIYECYTWKIYANKVLNMGNIYSFWKRLNKEQKEAKQRYIELFYNLHY
KNLVRTVPIASDEAQPAPVSRAKLATQPTRRTQSRLQRLFGA (Stevia rebaudiana SUS5 isoform)
                                                     SEQ ID NO: 23
MAASSSPIMKRSESVLDTMPEALRQSRYHMKKCFLKYVGKGKRMVKLHHL
MQEMETVIEDKDEKAQLLEGLLGYILCTTQEAAVVPPYVAFAIRPNPGFW
EFVKVNSNDLSVKGITSTDYLKFKEMIVDETWANDENALEIDFGAMDFNL
PTMSLSSSIGNGVNFTSKFIISKLYAHSGSQLQSLVDYLLSLNHQGEKLM
INDKLNTVSKLQAALIVAHSFLSSLPNDTPYQSFELRFKEWGFEKGWGDY
AERVQETIRFLLEVLQAPDPVNLEAFFSRVPNIFNIVLFSIHGYFGQSNV
LGLPDTGGQVVYVLDQVVAMEEELLLRIKQQGLSFKPHILVVTRLLPDAK
GTECSQVLEPVLNTKHSHILRVPFRTEKGVLRKWVSRFDIYPYLEKFTQD
ASAKITEMMEGKPDLIIGNYTDGNLVASLMANKLGSTLGTIAHALEKTKY
EDSDMKWKHLDTKYHFSCQFTADMIAMNSADFIITSTFQEIAGSKDRPGQ
YESHEAFTLPGLYRVVSGINVFDPKFNIASPGADQTVYFPYTETPKRFTT
FQPAIQELLFSKVENDEHIGYLEDKNKPIIFSMARLDMVKNITGLTEWFG
ENKRLRSLVNLVIVAGFFDPSKSKDREEMEEIKKMHLLIEKYELKGQIRW
IVAQTDKNRNSELYRCIADSKGAFVQPALYEAFGLTVIEAMNCGLPTFAT
NQGGPAEIIVDGVSGFQIDPNYGDESSNKIADFFQKCKQDPGYWNRISDG
GLMRIYECYTWKIYANKVLNMGNIYTFWKQLNKEQKDAKQRYIELFYNQH
YKNLVRTVPIVSDEDDQVTRAKPATQPSTRRTQSALQRLLGA (Stevia rebaudiana SUS6 isoform)
                                                     SEQ ID NO: 25
MDFGIAETLAEALKQNRYHARRCFERFTSRGKRMVKPQELLHMIEKTIDD

KLERTKVLEGSMGQILSSTQEAIVIPPYVILGLRANPGQWAYVKINADDV

TVESLTPSQYLKFKESIYDQEWAKDENALELDFGAFDFDTPRLILPSSIG

NGLGYISKFMTSRIGGDLENAKPLLDHLLALKYHGEKLMINETIDTVSKL

QKALIVADVYLSAHPKDEQYQTLEPKLKEWGFEKGWGDTAERVRETMKML

SEILQAPDPINMQSFFSRLPVVFNIVIFSIHGYFGQSDVLGLPDTGGQVV

YILDQVKALEEEILLRIKMQGLNAKPRILVVSRLIPDAQGTKCNEEMEPI

LNTMHSHILRVPFRTSKGVVPQWVSRFDIYPYLERFSQDAASKILEVMEC

KPDLILGNYTDGNIVASLIAKKFGVTQGTIAHALEKTKYEDSDVNWKNFE

KKYHFSCQFTADLISMNAADFIITSTYQEIVGSKQRPGQYETHGAFSMPG

LCRVVSGINVFDPKFNIASPGAEQSVYFPYTEKEKRLTDFHPAIKELLFN

EQDNDEHMGYLADVTKPIIFSMARLDTVKNITGLTEWFGKNKRLRSLVNL

VVVAGFFDPSKSKDREEMEEIKKMHELIEKYKLKGQMRWIAAQNDRTRNG

ELYRCISDTKGAFVQPALYEAFGLTVIEAMNCGLPTFATNQGGPAEIIVD

GVSGFHIDPVNGDESSNKIADFFTKCKVDGEYWDRVSQAGLQRIYECYTW

KMYANKALNMGSMYGFWRQLNKETKQAKQRYIDILYNLQFKNLAKTIEIP

DFVTPKLQEPVKTEPTKPLQEARPREPVQKLVPEETRLPKLELTKLGQPN

LMSNARKPLIVLVSVLIVAYASKNLYRRYFK

In certain embodiments, the nucleic acid molecule encodes sucrose synthase and comprises a nucleotide sequence as set forth in SEQ ID NO: 16,18, 20, 22, 24 or 26 and listed below or a fragment or variant thereof.

(encodes SUS1 isoform)
SEQ ID NO: 16
ATGGCGGAACGTGTACTCACTCGTGTTCACAGTCTTCGTGAGCGTCTCGA
TTCAACTCTCGCAACTCATCGTAATGAAATCCTCTTGTTTCTTTCAAGGA
TTGAAAGCCATGGAAAAGGAATATTGAAGCCTCATCAAGTTATGACTGAA
TTTGAAGCTATCTGCAAAGAAGATCAGAGCAAACTCTCTGATGGTGCTTT
TTATGAAGTTCTTAAATGCACACAGGAAGCAATAGTGCAACCTCCATGGG
TTGCACTCGCGATCCGTCTTCGACCCGGTGTTTGGGAATATGTTAGAGTC
AATGTTAATGTTTTGGTGGTTGAAGAATTAAGTGTTCCTGAATATCTTCA
CTTCAAAGAAGAATTGGTTAATGGAACATCGAATGGCAACTTCGTGTTGG
AACTGGATTTTGAACCTTTTACCGCATCGTTTCCTCGACCAACTTTAACC
AAGTCTATTGGTAATGGTGTTGAGTTTCTAAACAGACATTTATCTGCTAA
AATGTTTCATGATAAGGATAGCATGCACCCTCTTCTTGATTTCCTACGGA
CTCACCACTATAAGGGAAAGACAATGATGTTGAATGATAGAATCCAAAAC
CTCAATGCTCTACAATCGGTGTTGCGAAAGGCGTCAGAGTACTTATCAAC
ACTCGACGCAGCAACACCGTACTCTGAGTTTGAACATAAGTTTCAAGAAA
TCGGGTTGGAGAGAGGTTGGGGTGATAAAGCGGAGGTCGTAATGGAGATG
ATCCACATGCTTCTAGACCTTCTAGAAGCACCCGACGCATGCACACTCGA
GAAGTTTCTCGGAAGAATCCCAATGGTTTTCAATGTTGTCATTCTTTCGC
CTCACGGCTACTTCGCCCAAGAAAATGTGTTGGGATATCCCGACACTGGC
GGTCAGGTTGTTTACATCTTGGATCAAGTTCCCGCTCTGGAACGCGAGAT GCTCAAAAGGATTAAGGAGCAAGGACTCGATATCATTCCTCGTATATTGA
TTGTTACGAGGCTTCTTCCCGACGCGGTTGGGACCACATGCGGGCAACGT
TTAGAGAAAGTGTTTGGAGCCGAACACTCGCATATTCTTCGGGTCCCGTT
TAGAACCGAAAAGGGTATTCTTCGTAAATGGATCTCTCGTTTTGAGGTGT
GGCCTTACATCGAGACTTTCACCGAGGATGTTGCTAAAGAAGTTACAGCA
GAGTTGCAAGCAAAACCAGATTTGATCATTGGAAACTATAGTGAAGGAAA
TTTGGTTGCATCTTTGCTAGCTCACAAGTTGGGTGTCACTCAGTGTACCA
TTGCTCATGCTTTGGAGAAAACTAAATACCCGGATTCTGATATCTACTGG
AAGAACTTTGAGGAGAAATATCATTTCTCTTCGCAGTTTACCGCTGATCT
TATCGCTATGAACCATACCGACTTCATCATCACCAGTACTTTCCAAGAAA
TTGCTGGAAGTAAGGACACGGTTGGACAGTACGAGAGTCATACCGCGTTC
ACAATGCCGGGATTGTATCGGGTGGTTCACGGGATCGATGTTTTTGACCC
CAAATTCAATATTGTTTCACCCGGGGCCGATATGGGAATTTACTACTCGT
ATACCGAGAAAGAAAAGAGGCTCACTGCGCTTCACCCTGAAATCGATGAA
CTTCTCTTTAGTTCCGTCGAAAACGAAGAACACTTATGTGTGTTGAAGGA
TAAGAGTAAACCAATCTTGTTCACAATGGCGCGATTGGATAATGTGAAGA
ATTTAACCGGACTGGTTGAATGGTACGCTAAAAACGACCGCCTTCGTGAG
CTCGTGAACCTCGTGGTCGTCGGTGGTGACCGAAGGAAAGAGTCGAAAGA
TCTTGAAGAACAAGCTCAGATGCAGAAGATGCATGAACTTATCGAAACCT
ACAAACTCAACGGTCAGTTCAGGTGGATATCCTCACAAATGAACCGCGTG
AGGAACGGTGAGTTGTATCGCGTTATTGCTGACACACGAGGTGCGTTTAT
CCAGCCTGCGTTTTACGAGGCGTTTGGGTTGACGGTTGTGGAGGCCATGA
CTTGTGGCCTGCCGACATTCGCGACACTTCATGGTGGGCCCGCTGAGATT
ATTGTTCACGGGAAATCCGGGTTCCATATTGACCCGTATCACGGTGACCA
GGTCACCGAGTTGCTGGTCAATTTCTTTGAGAAAACTAAACAAGACCCGG
GTCATTGGGAGGCCATTTCCAAGGGTGGTCTGCAACGTATTCAGGAGAAA
TACACGTGGCAGATTTATTCAGATAGGTTGTTGACGCTTGCCGGAGTTTA
TGGATTCTGGAAGCATGTGTCGAAGCTTGACAGGCTCGAGATCCGTCGTT
ATCTTGAAATGTTTTACGCGCTCAAGTATCGCAAACTGGCTGAATCTGTT
CCATTGGCTGTTGATGAGTGA (encodes SUS2 isoform)
SEQ ID NO: 18
ATGGCGACAAGTAAGTTGAGCAGAACGCATAGTATGCGTGAGCGTGTTGA
AGAAACTCTTTCCGCTCATCGCAACGAAATCGTTTCTCTTCTTTCTAGGT
ATGTGGCTCAGGGGAAGGCGATATTGCAGCCGCATCAGATACTCCATGAA
CTTGAGAATATCATCGGTGATGTTACTTCGCGCCAAAAGCTTACAGATGG
TCCGTTTGGAGATGCGTTGAAGACAGCACAGGAATGTATAGTTCTACCTC
CATTTGTAGCTTTAGCAGTTCGTCCAAGACCTGGTGTTTGGGAATACGTG
CGCGTGGATGCATATCAACTAAGTGTGGAACAACTAACTGTTTCAGAGTA
TCTTACCTTCAAAGAAGAACTTGTTGAGAGTCTAATAGTTCTTTAATGC
TCGAGTTGGATTTTGAGCCATTTAATGCTTCGTTTCCTAGACCAACCCGT -continued

```
TCTTCATCCATTGGCAATGGAGTTCAGTTCCTGAATCGCCACCTGTCGTC
AAGCATGTTTCGCAGCAAAGATTGTTTAGAACCGCTTCTGGATTTCCTAC
GCACACACAGACATAATGGACATGTAATGATGTTAAATGACCGCATAACA
AGCATGACTAGACTTCAATCTTCTTTGGTCAAAGCAGAGGAATATCTTTC
TAAACTACCATCTGATACAGACTACTCTGAGTTTCAATATGAATTGCAAG
GAATGGGTTTTGAAAGAGGATGGGGAAACAATGCTGAAAGAATCATTGAG
ATGATGCATCTTCTCTCAGACATTCTACAAGCTCCAGATCCTTCCATTTT
GGAATCTTTTCTTGCTAGAATACCTATGGTGTTTAATGTTGTTATATTAT
CAATACATGGCTACTTTGGGCAAGCAAATGTTTTGGGTTTGCCAGATACT
GGTGGCCAGATTGTATATATATTGGATCAAGTCCGTGCATTGGAAAATGA
GATGCTTCTTAAATTAAAGCACCAAGGACTGGATATCAAACCTAGGATTC
TGATTGTGACTCGGTTAATACCTGATGCAAAAGGTACTTCATGTAACCAA
CGACTGGAAAGAGTCAGTGGAACTGAACACACACATATACTTCGTGTTCC
TTTTAGAACCGAGAAAGGAATTCTTCGTAAATGGATCTCAAGGTTTGATG
TATGGCCTTTTTTGGAGAAATTTACACAGGATGCAGCAAGTGAAATTTCT
GCTGAGTTGCATGGTACTCCAGATCTTATAATTGGAAATTATAGTGATGG
CAATCTTGTTGCCTCTTTATTATCTTACAAAATGGGAGTAACCCAGTGTA
ACATTGCTCATGCTTTAGAGAAAACAAAGTATCCAGATTCTGATTTATAT
TGGAAGAAATTTGATGAGAAATATCACTTTTCTTGTCAATTTACTGCTGA
TCTTTTAGCCATGAACAATGCAGATTTTATCATCACCAGCACATACCAAG
AAATCGCGGGAACGAAAAATACTGTCGGACAATACGAGAGTCATTCGTCT
TTCACTCTCCCGGGGCTCTACAGGGTTGTTCATGGTATTGACGTTTTTGA
CCCTAAGTTCAACATTGTGTCTCCAGGGGCAGATATGTCTATATACTTCT
CATACACCGAGAAGGAAAAAGACTTACATCTCTTCATACTACAATTGAG
AAGTTATTGTTTGACCCTACACAAACTGAAGATTACATTGGAAATCTGAG
TGATAAATCAAAACCGATAATTTTTTCAATGGCAAGACTTGATCATGTGA
AGAACATTACGGGTCTGGTTGAGTGGTACGCTAAGAATGAGAAGCTTAGA
GGACTAGCAAACCTTGTTGTGGTTGCTGGTTATAATAATGTGAAGAGGTC
TAGTGACAGAGAAGAAATTGCAGAAATTGAAAAAATGCATCAACTTATTA
AGAAATACAAATTAGATGGTCAGATGAGATGGATTTCAGCACAAACAAAC
CGCGCACAAAATGGTGAACTTTATCGCTATATTGCTGATGGAAGGGGAAT
CTTTGTACAGCCCGCTATTTATGAAGCTTTTGGGCTGACAGTGGTGGAGG
CCATGACTTGTGGGCTTCCAACATTTGCAACTTGCCATGGTGGGCCAGGA
GAGATAATTGAAAATGGTGTTTCGGGCTTCCATATCGACCCGTATCATCC
GGATACTGCATCAGCCACAATGGCTGATTTTTTCAGAAATGCAAGGAGG
ACCCGAGTTATTGGTTCAAGATATCTGAAGCAGGGCTTAAAAGAATATAT
GAAAGGTACACATGGAAAATTTACTCTGAACGGTTGATGACATTAGCTGG
AGTTTATAGCTTCTGGAAGTATGTCTCGAAACTTGAGAGACGTGAAACAA
GACGATATCTTGAGATGTTTTATATTCTTAAGTTCCGTGATCTGGTAAAA
TCTGTTCCAGTGGCTACTGATGATGAGGCTTAG
```
(encodes SUS3 isoform)

SEQ ID NO: 20
```
ATGGCGACACCTAAGCTTACGCGAACACCAAGCATGCGAGAGCGTCTTGA
AGAAACTTTATCAGCTCATCGCAACGATATCGTCTCTCTTCTTTCCAGGT
ATGTAGATCAAGGTAAGGCCATATTGCAGCCCCACCACCTACTTGACGAA
ATCGATAACTTCATCGGAGATCAAAATTGCCGCCAAAAGCTTGCTGATAG
TCTATTCGGTGAAATCCTCAAGTCCGCACAGGAAGGTATAATTCTTCCTC
CATATGTAACGCTTGCTGTTCGTCCAAGACCTGGTGTTTGGGACTTTTTG
CGTGTGAATGTCGATGAATTGAGTGTCGAGCAACTTACTGTTTCTGAGTA
TTTAAGCTTCAAGGAGGAGCTTGTAGATGGCCAGAGTAGGAACCCGTTTG
TGTTGGAACTGGATCTGGAACCGTTTAATGCAACATTTCCCCGGATGTCA
CGATCTTCATCCATCGGCAATGGAGTTCAGTTTCTCAACCGTCATCTCTC
GTCAATTATGTTTCGCAACAAAGATTGTATGGATCCGTTTCTTGATTTCC
TTCGTGCTCATAAACATAAAGGATACGCGATGATGTTGAATGATCGGATA
CAAACAATGTCTAGACTTGAATCTTCTTTAGCAAAAGCGGAGGATCATCT
CTCTAAACTACCACCCGAAACACCGTACTCCGAATTCGAATACGTATTGC
AAGGAATGGGGTTTGAAAGAGGTTGGGGGGATAATTGTGAAAGAGTTCTT
GGTATGATGCATCTTCTTTCTGACATTCTTCAAGCTCCAGATCCTTCGAT
TCTTGAAAAGTTTCTTGGAAAGATGCCGATGATCTTCAATGTTGTTGTGT
TATCGATTCATGGTTACTTTGGTCAGGCTAATGTTTTGGGTTTGCCGGAT
ACCGGTGGTCAGGTTGTATATATATTGGATCAAGTACGTTCTTTGGAGAA
TGAAATGTTACTTAAATTAAGGCATCAAGGACTTGATATCAAACCCAAGA
TTCTAATTGTAACTCGATTGATACCAAATGCCAAAGGTACTTCATGCAAC
CAACGATTGGAGAAAGTAAGTGGAACCGAATACACGTATATATTACGTGT
CCCTTTTAGGACAGAGAAAGGGATTCTTGGTAAATGGTTATCAAGGTTTG
ATATATGGCCTTATTTGGAGGCGTTTACAACGGATGCAGCAAGTGAAATT
GCTGCTGAGTTACACGGTGTTCCGGATCTTTTAATAGGAAACTACAGTGA
TGGGAATCTCGTTGCCTCCTTGCTATCTAACAAATTGGGCGTAACCCAGT
GCAACATTGCACACGCGTTAGAGAAAACAAAGTATCCAGATTCCGACTTA
TATTGGAAGAAATTTGAGGACAAATATCACTTTTCATGTCAATTTACCGC
CGACCTTCTAGCAATGAACAATGCAGATTTTATCATCACTAGCACATACC
AAGAGATTGCAGGAACGAAAAACACCGTTGGACAATACGAGAATCATTCA
TCGTTCACTCTTCCGGGTCTATACAGGGTTGTTCACGGTATCGATGTCTT
TGACCCGAAGTTCAACATCGTGTCACCAGGGGCAGATATGGCAATTTACT
TCTCATATGCCGATAAAGAGAGCGACTTACATCTCTACATCCCACAATT
GAGAAGCTATTGTTCGACACTGAGCAGAACGATGTACACATTGGAAATAT
AAATGACCCGTCTAAACCCATGATTTTCACAATGGCGAGGCTTGATCATG
TGAAGAATATAACTGGATTCGTCGAGTGTTATGCTAAAAATAATAAGTTG
AGGGAACACGCAAATCTTGTGGTTATTGCTGGTTATAATGACGCGAAGAA
ATCAAGTGATCGAGAAGAAATTGCGGAAATTGAAAAGATGCATAATCTTA
TCAAGCAATACAAACTTGATGGTCAGATGAGATGGATATCAGCCCAAACA
AACCGGGCCCGAAATGGGGAATTTTATCGGTATATCGCTGATGGTAGGGG
```

-continued

CGTTTTCGTCCAGCCCGCTTTCTATGAAGCATTTGGGCTTACGGTTGTGG
AGGCGATGACATGTGGGCTCCCAACATTTGCCACGTGTCATGGTGGGCCT
GCTGAGATCATTGAGGATGGTGTGTCGGGGTTCCATATTGATCCATATCA
TCCTGATAAGATGTCGACTACGTTAGCTGATTTTTTTCAAAAGTGCAAAG
AGGAACCTAGTTACTGGGGTAAAATATCCGATGGCGGGCTGAAAAGAATA
AGTGAAAGGTACACATGGAAGATATATTCGGAACGGTTGATGACGTTGGC
GGGCGTATATAGCTTTTGGAAATATGTGTCAAAACTCGAGAGGCGTGAAA
CCCGTCGATACCTTGAGATGTTCTACATTTTAAAGTTTCGTCAACTGGTG
AAGTCGGTTCCGCTAGCTGTTGATGAGGAGCCGTAA (encodes SUS4 isoform)
SEQ ID NO: 22
ATGGCATCTGCTTCAAGTTCTATCATGAAACGGTCTGAATCAATAGTTGA
CACCATGCCAGAAGCCTTAAAGCAGAGCCGCTATCATATGAAAAAATGTT
TTCTAAAATATGTAGAAAAAGGAATTCGCATGATGAAAAGACATCATTTG
ATACAAGAAATGGAGACCGCAATTGAAGACAAGGATGAAAAGGCTCAGCT
TCTAGATGGCTTACTTGGCTACATCTTGTGCACAACTCAGGAAGCAGCCG
TTGTTCCTCCTTGTGTTGCATTTGCTATAAGACCGAATCCTGGATTCTGG
GAGTTTGTTAAAGTCAACTCTAATGATCTATCGGTTGATGGGATAACTGC
CACAGATTACTTGAAGTTCAAGGAAATGATCGTAGATGAGACATGGGCTA
AAGATGAAAATGCATTGGAGATTGACTTTGGATCGATGGACTTTAACCTA
CCAAACATGAGTTTATCTTGTTCGATTGGAAATGGTGTTAACTTCACATC
AAAATTCATTACTTGTAAACTTTACGCACAATCTAGTTGCCAACAACTGC
TTGTTGATTACTTGCTCTCATTGAATCATCAAGGAGAAAATCTTATGATC
AATGATGCATTAAACTCAGTCTCAAAACTTCGAGCGGCTTTAATTGTAGC
TCATGCGTCGCTATCTTCGTTGCCCAACGATACTCCATATCAAAGCTTCG
AGCTTAGATTCAAAGAATGGGGATTTGAGAAGGGATGGGGAGATAACGCG
GAACGCGCGAGGGAAACAATTCGGTTTCTTTTGGAGGTTCTTCAAGCACC
CGATCCGATAAACCTCGAGGCTTTATTCAGCAGGATTCCAAACATATTCA
ACGTTGTTTTATTCTCGATTCATGGGTATTTTGGTCAATCCAATGTTCTT
GGATTGCCCGATACTGGTGGCCAAGTGGTTTATGTTTTGGATCAAGTGGT
AGCTATGGAAGAAGAACTACTCATGAGGATCAAACAACAAGGACTCAACT
TCAAGCCTCAAATTCTTGTGGTGACCCGACTTCTTCCTGATGCTAAAGGG
ACCAAGTGTAATCAGGTGTTGGAACCAGTTCTGAACACGAAACATTCGCA
TATTCTTAGGGTTCCATTCAGGACTGATAAAGGTGTTCTTCGTAAATGGG
TATCTCGATTTGATATCTATCCATATCTCGAAAACTTCACTCAGGATGCA
AGTGCGAAAATCATTGAAATGATGGAAGGGAAACCGGATCTTATCATCGG
AAACTATACCGATGGAAACCTTGTTGCATCACTCATGGCTAACAAACTCG
GAACGACATTGGGAACAATTGCACATGCTTTGGAGAAAACCAAATACGAA
GATTCAGACATGAATTGGAAGCAATTCGACCCAAAATATCACTTCTCCTG
CCAATTTACAGCCGATATGATTGCAATGAACTCAGCTGATTTCATCATCA
CAAGTACTTTCCAAGAAATCGCTGGAAGTAAAGATAGACCCGGACAATAT
GAAAGCCATGAAGCATTTACACTTCCAGGATTATACAGAGTTGTTTCAGG CATCAACGTGTTCGATCCCAAATTCAATATCGCGTCTCCAGGAGCCGATC
AAACCGTTTATTTCCCGTACACCGAAACAAAGAAACGATTCACTGCATTT
CAACCCGCCATAGAGGAATTACTCTTCAGTAAAGTTGAAAACGAAGAACA
CATTGGATACTTAGAAGACAAAACCAAACCGATCATATTCTCAATGGCGC
GTCTCGACACAGTTAAGAACATAACAGGACTAACCGAATGGTTTGGAGAG
AACAAACGGCTCCGAAGCTTGGTTAATCTTGTAATCGTGGCGGGTTCTT
TGACCCGTCAAAGTCAAAAGACAGAGAAGAAATGGCGGAAATAAAGAAAA
TGCATTTATTGATTGAAAAATATCAGCTTAAAGGTCAAATAAGATGGATT
GCTGCACAAACTGATAAGAACCGAAACAGTGAGCTTTACCGGTTTATTGC
TGACTCAAAAGGCGCGTTTGTGCAGCCCGCTTTGTATGAGGCGTTTGGGC
TCACGGTTATTGAGGCGATGAACTGTGGTTTACCGACTTTTGCAACTAAT
CAAGGTGGTCCAGCTGAGATTATCGTTGATGGTGTTTCTGGGTTCCAGAT
TGATCCTAATTTTGGTGATCAGTCTAGTAATAAGATTGCTGATTTCTTCC
AGAAGTGTAAGGAAGATCCTGGTTATTGGAATAATATTTCAGAAGGCGGT
TTGAAGCGTATATACGAATGTTATACTTGGAAGATTTATGCGAATAAAGT
GTTGAATATGGGGAACATATACTCGTTTTGGAAGCGGTTAAACAAGGAAC
AAAAAGAAGCAAAACAAAGATACATTGAACTATTCTACAATCTACACTAC
AAGAACTTGGTTAGGACTGTACCAATTGCTAGTGATGAAGCTCAACCTGC
ACCAGTGTCAAGGGCAAAACTTGCAACACAACCCACAAGACGTACGCAAT
CCAGGTTGCAAAGGCTGTTTGGAGCTTAA (encodes SUS5 isoform)
SEQ ID NO: 24
ATGGCAGCTTCTTCAAGTCCCATTATGAAACGGTCTGAGTCAGTACTCGA
CACCATGCCAGAAGCTTTGAGGCAAAGTCGGTATCATATGAAAAAATGCT
TTCTAAAATATGTAGGGAAAGGAAAGCGGATGGTGAAACTCCACCATTTG
ATGCAAGAAATGGAGACCGTCATTGAGGACAAGGACGAAAAGGCTCAGCT
CTTGGAAGGCTTACTTGGTTACATCTTGTGCACCACTCAGGAAGCAGCAG
TTGTTCCTCCTTATGTCGCCTTTGCAATAAGGCCAAACCCTGGATTTTGG
GAGTTTGTTAAAGTCAACTCTAATGATCTCTCGGTTAAAGGGATCACTTC
CACCGATTACTTGAAGTTCAAGGAAATGATCGTTGACGAAACATGGGCTA
ATGATGAAAATGCATTGGAGATCGACTTTGGAGCAATGGACTTTAACTTG
CCAACAATGAGCTTATCTTCTTCAATTGGAAATGGAGTTAACTTCACATC
AAAGTTTATTATTTCTAAACTTTATGCTCATTCTGGCAGCCAATTACAAT
CTCTAGTTGATTACTTACTTTCATTAAATCATCAAGGAGAAAAACTTATG
ATAAATGACAAACTAAACACAGTTTCAAAACTTCAAGCCGCTCTAATAGT
AGCTCATTCTTTCCTTTCTTCATTGCCCAACGACACACCGTATCAAAGCT
TTGAACTTAGATTTAAAGAGTGGGGTTTTGAAAAAGGATGGGAGATTAT
GCAGAAAGGGTGCAAGAAACAATTCGGTTTTTGTTGGAGGTTCTTCAAGC
ACCCGACCCCGTAAACCTAGAGGCCTTTTTTAGCAGGGTTCCAAACATAT
TCAATATTGTTTTATTCTCGATTCATGGGTATTTTGGTCAATCCAATGTT
CTTGGCTTGCCCGATACCGGAGGTCAGGTAGTTTATGTTTTGGATCAAGT -continued TGTGGCAATGGAAGAAGAATTGCTACTTAGGATTAAGCAACAAGGACTCA
GCTTCAAGCCTCATATTCTTGTGGTGACTCGACTTCTTCCCGATGCCAAA
GGGACCGAGTGTAGCCAAGTTTTGGAACCAGTTCTCAACACGAAACACTC
ACACATTCTTAGAGTCCCATTTAGGACAGAAAAAGGTGTTCTTCGTAAAT
GGGTGTCTCGATTTGATATCTATCCATACCTCGAAAAGTTTACTCAGGAT
GCAAGTGCAAAATAACTGAAATGATGGAAGGAAAACCTGATCTTATCAT
TGGAAACTACACTGACGGAAACTTGGTTGCATCTCTCATGGCTAACAAAC
TCGGAAGCACATTGGGAACGATTGCACACGCGTTAGAGAAGACTAAATAC
GAAGATTCAGACATGAAATGGAAACATTTGGACACAAAATATCACTTTTC
TTGTCAATTTACAGCTGATATGATAGCAATGAATTCAGCAGATTTCATCA
TCACTAGTACTTTCCAAGAAATTGCTGGAAGTAAAGATAGACCCGGTCAG
TATGAAAGCCATGAAGCATTTACACTCCCGGGTTTATATAGAGTTGTTTC
GGGCATCAACGTGTTTGATCCCAAATTCAACATTGCATCTCCGGGAGCTG
ATCAAACCGTTTATTTCCCTTACACGGAAACACCAAAACGATTCACTACT
TTTCAACCCGCTATACAAGAATTACTCTTTAGTAAAGTTGAAAACGACGA
ACACATTGGATATTTAGAAGATAAGAATAAACCAATCATCTTCTCAATGG
CAAGACTCGACATGGTTAAGAACATAACGGGGCTAACCGAATGGTTTGGG
GAAAACAAGCGGTTAAGAAGTTTGGTTAATCTTGTAATTGTGGCGGGGTT
TTTTGATCCGTCAAAATCAAAAGATAGAGAAGAAATGGAAGAAATAAAGA
AAATGCATTTGTTGATTGAGAAATATGAACTTAAAGGTCAAATAAGATGG
ATAGTAGCACAAACTGATAAAAACAGAAATAGTGAACTTTATCGTTGTAT
CGCTGACTCAAAGGGGCGTTTGTGCAACCGGCTTTATATGAAGCGTTTG
GGTTAACCGTTATTGAGGCTATGAATTGTGGGTTACCAACTTTTGCAACT
AACCAAGGTGGTCCGGCTGAGATTATTGTTGATGGTGTTTCTGGGTTCCA
AATCGATCCTAATTATGGCGACGAGTCTAGCAACAAGATCGCTGATTTTT
TTCAAAAATGCAAACAGGATCCAGGATACTGGAATAGGATTTCAGACGGT
GGTTTGATGCGTATATACGAATGCTACACATGGAAGATTTATGCAAATAA
AGTGTTGAATATGGGAACATTTACACATTTTGGAAGCAGTTAAACAAGG
AACAGAAAGATGCGAAACAAAGATACATTGAGCTATTCTACAATCAACAT
TACAAGAATTTGGTTAGGACTGTGCCGATTGTAAGTGATGAAGATGACCA
AGTTACAAGGGCAAAACCGGCAACACAACCTTCAACAAGGCGCACACAAT
CTGCCTTGCAAAGGCTGCTTGGAGCTTAA (encodes SUS6 isoform)

SEQ ID NO: 26
ATGGATTTCGGTATAGCAGAGACTTTGGCCGAGGCATTGAAGCAAAACCG
GTACCATGCAAGGAGATGCTTTGAGCGTTTTACATCACGTGGAAAAAGGA
TGGTGAAGCCTCAAGAGTTATTACACATGATTGAAAAAACCATTGACGAC
AAGCTTGAAAGAACGAAGGTCTTGGAGGGCTCAATGGGACAAATCTTGAG
TTCCACACAGGAGGCAATCGTTATTCCACCATATGTTATTTTAGGATTGA
GAGCGAATCCAGGACAATGGGCATACGTTAAGATCAATGCTGATGACGTC
ACTGTTGAGTCACTCACACCTTCACAATATCTAAAGTTCAAGAATCCAT
CTACGATCAAGAATGGGCAAAGGACGAAAATGCCCTTGAACTAGATTTCG

-continued

GAGCGTTCGACTTTGATACGCCTCGATTAATCCTCCCGTCATCTATCGGC
AACGGACTCGGTTACATTTCAAAGTTCATGACTTCAAGAATTGGTGGTGA
TCTAGAAAACGCGAAGCCGTTGCTTGACCACTTGCTTGCTCTAAAATATC
ATGGAGAGAAGCTTATGATCAATGAGACAATAGATACAGTTTCAAAGCTC
CAGAAAGCATTAATTGTTGCTGATGTCTACTTATCTGCACACCCGAAAGA
CGAACAATATCAAACCTTAGAGCCCAAGCTTAAAGAATGGGGATTTGAGA
AAGGATGGGAGATACTGCTGAAAGAGTTAGAGAGACAATGAAAATGCTT
TCGGAGATTCTTCAAGCACCCGACCCGATTAACATGCAATCGTTCTTTAG
CAGGCTTCCGGTGGTCTTCAATATTGTCATATTTTCTATTCATGGGTATT
TTGGTCAATCAGATGTTCTTGGATTACCTGATACCGGAGGGCAGGTTGTT
TACATTCTTGATCAAGTTAAAGCATTAGAGGAAGAGATATTGCTAAGAAT
AAAAATGCAAGGATTGAATGCAAAGCCTCGGATTCTTGTGGTGAGTCGAC
TCATTCCCGACGCACAAGGAACAAAGTGTAACGAGGAAATGGAACCGATC
TTGAACACAATGCATTCACACATCCTTCGGGTTCCTTTCAGAACCTCAAA
AGGCGTTGTTCCTCAATGGGTATCGCGGTTTGACATCTACCCGTATCTTG
AAAGATTCTCACAGGACGCTGCCTCTAAAATACTTGAAGTAATGGAATGT
AAACCAGATCTCATACTTGGAAACTACACAGATGGAAACATTGTTGCATC
ACTTATAGCCAAAAGTTTGGAGTAACACAGGGGACGATTGCACACGCGT
TAGAGAAGACAAAGTACGAAGATTCGGATGTTAACTGGAAAAACTTTGAA
AAAAGTATCATTTCTCATGTCAATTTACCGCGGATTTGATCTCAATGAA
CGCTGCAGATTTCATAATCACAAGCACTTATCAAGAAATTGTGGGAAGCA
AACAAAGACCCGGACAGTATGAGACCCACGGGGCGTTTAGTATGCCCGGA
CTTTGTAGAGTCGTGTCGGGCATCAACGTGTTTGATCCTAAGTTCAACAT
TGCTTCACCCGGTGCGGAACAATCGGTTTATTTTCCGTACACCGAGAAGG
AGAAACGGTTAACGGATTTTCATCCCGCAATTAAAGAACTACTTTTCAAC
GAACAAGACAATGACGAGCATATGGGATACCTCGCGGATGTAACCAAACC
GATAATATTCTCAATGGCGAGGCTCGATACGGTGAAGAACATAACAGGGT
TAACCGAGTGGTTCGGTAAGAACAAACGACTTAGAAGTCTTGTAAACTTG
GTTGTTGTCGCGGGGTTCTTCGATCCATCAAAATCTAAAGACCGTGAAGA
GATGGAGGAAATCAAGAAAATGCATGAACTAATAGAGAAATACAAACTCA
AGGGTCAGATGAGATGGATCGCGGCTCAAAACGATAGGACCCGCAATGGT
GAATTGTATCGGTGTATTTCCGATACGAAGGGAGCGTTTGTGCAGCCCGC
GTTGTATGAGGCTTTTGGGCTCACGGTTATCGAGGCAATGAACTGCGGTC
TCCCGACTTTTGCAACCAATCAAGGCGGGCCCGCGGAGATCATAGTTGAC
GGAGTTTCGGGATTTCATATTGATCCCGTTAACGGAGATGAATCAAGCAA
CAAGATTGCTGATTTCTTCACGAAATGCAAAGTCGATGGCGAGTATTGGG
ACCGCGTGTCGCAAGCGGGACTTCAACGTATTTACGAGTGCTACACATGG
AAGATGTATGCTAACAAAGCATTGAACATGGGTTCGATGTATGGTTTTTG
GAGGCAATTAAACAAGAAACTAAGCAAGCGAAGCAACGATACATCGATA
TCTTGTATAACTTACAATTCAAGAATTTGGCAAAAACCATTGAAATCCCT

```
-continued
GATTTTGTGACTCCTAAACTTCAAGAACCGGTCAAAACCGAACCAACAAA

ACCATTACAAGAAGCAAGACCTCGAGAACCGGTGCAAAAACTGGTACCGG

AAGAAACCCGACTGCCAAAACTAGAGTTGACCAAGCTTGGTCAACCGAAT

TTGATGAGCAATGCAAGAAAACCATTGATTGTTCTTGTTTCTGTGTTGAT

AGTTGCATATGCATCCAAGAACTTGTATAGGAGGTATTTCAAATAG
```

In other embodiments, there is provided a nucleic acid comprising a sequence having at least 50%, 55%, 60%, 65%, 70%, 75%, 80%, 85%, 90%, 95%, 96%, 97%, 98%, 99% or 100% identity to any one of the sequences set forth in SEQ ID NOs: 2, 4, 6, 8, 10, 14, 16,18, 20, 22, 24, 26, 28, 30, 32 and 34 and fragments thereof or the complement thereof.

In other embodiments, there is provided a nucleic acid encoding a polypeptide comprising a sequence at least 50%, 55%, 60%, 65%, 70%, 75%, 80%, 85%, 90%, 95%, 96%, 97%, 98%, 99% or 100% percent identity to any one of the sequences set forth in SEQ ID NOs: 1, 3, 5, 7, 9, 13, 15, 17, 19, 21, 23, 25, 27, 29, 30, 31 and 33 and fragments thereof. A worker skilled in the art would readily appreciate that overall sequence identity or similarity may be less than 50% but regions of the enzyme (such as the catalytic site or areas adjacent to the catalytic site) may have conserved amino acids. For example, there are conserved amino acids at the opening adjacent to the UDPG catalytic site. In particular, a leucine at position 379 of UGT76G1 is conserved. In certain embodiments, the nucleic acid encodes an UDP-glucosyl-transferase having the sequence SDFGLDQ at a position corresponding to amino acid residues 375 to 381 of the UGT76G1 set forth in SEQ ID NO:1.

In certain embodiments, fragments are at least 10, at least 20, at least 50 nucleotides in length. The fragments may be used, for example, as primers or probes.

Also provided are nucleic acids that hybridize to the nucleic acids of the present invention or the complement thereof. In certain embodiments, there is provided a nucleic acid that hybridizes to any one of the sequences set forth in SEQ ID NOs: 2, 4, 6, 8, 10, 14, 16, 18, 20, 22, 24,26, 28, 30, 32 and 34 or the complement thereof under conditions of low, moderate or high stringency. A worker skilled in the art readily appreciates that hybridization and the strength of hybridization (i.e., the strength of the association between the nucleic acids) is impacted by such factors as the degree of complementary between the nucleic acids, stringency of the conditions involved, the $T_m$ of the formed hybrid, and the G:C ratio within the nucleic acids. Such a worker could readily determine appropriate stringent (see, for example, Sambrook, et al., Molecular Cloning: A Laboratory Manual, $2^{nd}$ ed., Cold Spring Harbor Laboratory Press, New York (1989) pp. 9.50-51, 11.48-49 and 11.2-11.3).

Typically under high stringency conditions only highly similar sequences will hybridize under these conditions (typically >95% identity). With moderate stringency conditions typically those sequence having greater than 80% identity will hybridize and with low stringency conditions those sequences having greater than 50% identity will hybridize.

A non-limiting example of "high stringency conditions" when used in reference to nucleic acid hybridization comprise conditions equivalent to binding or hybridization at 42° C. in a solution consisting of SXSSPE (43.8 g/l NaCl, 6.9 g/l NaH$_2$PO$_4$H$_2$O and 1.85 g/l EDTA, pH adjusted to 7.4 with NaOH), 0.5% SDS, 5×Denhardt's reagent and 100 μg/ml denatured salmon sperm DNA followed by washing in a solution comprising 0.1×SSPE, 1.0% SDS at 42° C. when a probe of about 500 nucleotides in length is employed. A non-limiting example of "medium stringency conditions" when used in reference to nucleic acid hybridization comprise conditions equivalent to binding or hybridization at 42° C. in a solution consisting of SXSSPE (43.8 g/l NaCl, 6.9 g/l NaH$_2$PO$_4$H$_2$O and 1.85 g/l EDTA, pH adjusted to 7.4 with NaOH), 0.5% SDS, 5×Denhardt's reagent and 100 μg/ml denatured salmon sperm DNA followed by washing in a solution comprising 1.0×SSPE, 1.0% SDS at 42° C. when a probe of about 500 nucleotides in length is employed. A non-limiting example "Low stringency conditions" when used in reference to nucleic acid hybridization comprise conditions equivalent to binding or hybridization at 42.degree. C. in a solution consisting of SXSSPE (43.8 g/l NaCl, 6.9 g/l NaH$_2$PO$_4$H$_2$O and 1.85 g/l EDTA, pH adjusted to 7.4 with NaOH), 0.5% SDS, 5×Denhardt's reagent and 100 μg/ml denatured salmon sperm DNA followed by washing in a solution comprising SXSSPE, 0.1% SDS at 42° C. when a probe of about 500 nucleotides in length is employed.

The polynucleotides include the coding sequence polypeptide, in isolation, in combination with additional coding sequences (e.g., a purification tag, a localization signal, as a fusion-protein, as a pre-protein, or the like), in combination with non-coding sequences (e.g., introns or inteins, regulatory elements such as promoters (including inducible promoters, tissue-specific promoters (such as root-specific or leaf specific promoters), enhancers, terminators, and the like), and/or in a vector or host environment in which the polynucleotide encoding a transcription factor or transcription factor homologue polypeptide is an endogenous or exogenous gene.

Appropriate additional coding sequences (e.g., a purification tag, a localization signal, as a fusion-protein, as a pre-protein, or the like), non-coding sequences (e.g. regulatory elements such as promoters (including inducible promoters, tissue-specific promoters (such as root-specific or leaf specific promoters), enhancers, terminators, and the like), and vectors for use in prokaryotic such as *E. coli* and eukaryotic cells, including but not limited to yeast and plant cells are known in the art.

Polypeptides

The present invention provides for glycosyltransferases. The glycosyltransferases of the present invention are capable of primary, secondary and/or tertiary glycosylations. In certain embodiments, the glycosyltransferases are capable of primary, secondary and tertiary glycosylations. In other embodiments, the glycosyltransferases are capable of secondary and/or tertiary glycosylations. In certain embodiments, the glycosyltransferases is a glucosyltransferase, including but not limited to a UDP-glycotransferase. The glucosyltransferases include but are not limited to a *Stevia rebaudiana* UDP-glucosyltransferase, such as UGT76G1 or UGT74G1 or an *Oryza sativa* glucosyltrasferase, such as Os03g0702000. In other embodiments, the invention provides for a cyclodextrin glucanotransferase. Also provided are sucrose synthases.

In certain embodiments, there is provided an UGT76G1 or UGT76G1-like glucosyltransferase. UGT76G1-like glucosyltransferase include for example, other members of the UGT76G1 clade such as UGT76G2 or UGT76H1. Accordingly, in certain embodiments, there is provided an UGT76G1 comprising the amino acid sequence as set forth in any one of SEQ ID NOs: 1, 3, 5 and 7 or fragments and variants thereof. In certain embodiments, there is provided an UGT76G1 encoded by the nucleic acid molecule comprising the sequence as set forth in any one of SEQ ID NOs: 2, 4, 6 and 8.

In certain embodiments, there is provided an UGT76G2 comprising the amino acid sequence as set forth in SEQ ID NO: 27 or fragments and variants thereof. In certain embodiments, there is provided an UGT76G1 encoded by the nucleic acid molecule comprising the sequence as set forth in SEQ ID NO: 28.

In certain embodiments, there is provided an UGT76H1 comprising the amino acid sequence as set forth in SEQ ID NO: 29 or fragments and variants thereof. In certain embodiments, there is provided an UGT76G1 encoded by the nucleic acid molecule comprising the sequence as set forth in SEQ ID NO: 30.

In certain embodiments, there is provided an Os03g0702000 or Os03g0702000-like glucosyltransferase. Os03g0702000-like glucosyltransferase include for example, other members of the UGT91clade such as UGT91D1 or UGT91D2. Accordingly, in certain embodiments, there is provided an Os03g0702000 comprising an amino acid sequence as set forth in SEQ ID NO: 9 or fragments and variants thereof. In certain embodiments, there is provided an Os03g0702000 encoded by the nucleic acid molecule comprising the sequence as set forth in SEQ ID NO: 10.

In certain embodiments, there is provided an UGT91 D1 comprising the amino acid sequence as set forth in SEQ ID NO: 31 or fragments and variants thereof. In certain embodiments, there is provided an UGT91 D1 encoded by the nucleic acid molecule comprising the sequence as set forth in SEQ ID NO: 32.

In certain embodiments, there is provided an UGT91D2 comprising the amino acid sequence as set forth in SEQ ID NO: 33 or fragments and variants thereof. In certain embodiments, there is provided an UGT76G1 encoded by the nucleic acid molecule comprising the sequence as set forth in SEQ ID NO: 34.

In certain embodiments, there is provided a *Stevia rebaudiana* UGT74G1. Accordingly, in certain embodiments, the UGT74G1 comprises the amino acid sequence as set forth in SEQ ID NO: 13 or fragments and variants thereof. In certain embodiments, the UGT74G1 is encoded by the nucleic acid molecule comprising the sequence as set forth in SEQ ID NO: 14.

In other embodiments, the invention provides for a cyclodextrin glucanotransferase. Cyclodextrin-glucanotransferase is commercially available (CGTase, Toruzyme 3.0L, trademark of Novozymes Inc.).

In certain embodiments, there is provided sucrose synthase. Accordingly, in certain embodiments, the sucrose synthase comprises the amino acid sequence as set forth in SEQ ID NO: 15, 17, 19, 21, 23 or 25 or fragments and variants thereof. In certain embodiments, the polypeptide comprises an amino acid sequence encoded by the nucleic acid molecule comprises comprising the sequence as set forth in SEQ ID NO: 16,18, 20, 22, 24 or 26.

In other embodiments, there is provided a polypeptide comprising a sequence at least 50%, 55%, 60%, 65%, 70%, 75%, 80%, 85%, 90%, 95%, 96%, 97%, 98%, 99% or 100% percent identity to any one of the sequences set forth in SEQ ID NOs: 1, 3, 5, 7, 9, 13, 15, 17, 19, 21, 23, 25, 27, 29, 31 and 33 and fragments thereof. A worker skilled in the art would readily appreciate that overall sequence identity or similarity of related enzymes may be less than 50% but regions of the enzyme (such as the catalytic site or areas adjacent to the catalytic site) may have conserved amino acids and therefore the related enzymes have similar activity. For example, there are conserved amino acids at the opening adjacent to the UDPG catalytic site. In particular, a leucine at position 379 of UGT76G1 is conserved. In certain embodiments, the nucleic acid encodes an UDP-glucosyltransferase having the sequence SDFGLDQ at a position In certain embodiments, fragments are at least 10, at least 20, at least 50 amino acids in length. In certain embodiments, the polypeptide sequences contain heterologous sequences including but not limited to purification tags such as a HIS tag. In a certain embodiments, there is provided a polypeptide comprising a 6×HIS tag at the N-terminus. In other embodiments, there is provided a polypeptide comprising a 6×HIS tag at the C-terminus.

Methods for screening the activity of glycosyltransferases including glucosyltransferases and cyclodextrin glucanotransferases are known in the art. As such, a worker skilled in the art could readily determine if the glycosyltransferases are capable of primary, secondary and/or tertiary glycosylations (see, for example Dewitte et al., *J Biotechnol.* 2016 September 10; 233:49-55. doi: 10.1016/j.jbiotec.2016.06.034; Grubb et al., *Plant J.* (2014) 79, 92-105; Richman et al., *Plant J.* (2005) 41, 56-67; Tanaka et al., *Plant Cell Rep.* (1996) 15, 819-823; Tanaka et al., *J. Nat. Prod* (1993) 56(12), 2068-2072. In addition, methods for screening the activity of sucrose synthase are also known in the art. (Baroja-Fernandez et al., *PNAS.* (2012) 109(1), 321-326. doi: 10.1073/pnas.1117099109; Barratt et al., *Plant Physiol.* (2001) 127, 655-664; Huber and Akazawa, *Plant Physiol.* (1986) 81, 1008-1013.

Cells and Plants

The present invention further provides cells and plants which express one or more of the polypeptides of the present invention. The cells and plants may naturally express one or more of the polypeptides of the present invention or have been modified to express one or more the polypeptides of the present invention. The cells may be prokaryotic or eukaryotic cells and include but are not limited to, *E. coli*, yeast such as *Pichia pastoris, Stevia rebaudiana, Phytolacca Americana, Cannabis* including but not limited to *Cannabis sativa, Cannabis* indica and *Cannabis ruderalis.*

In certain embodiments, there is provided a cell which expresses an UGT76G1 or UGT76G1-like glucosyltransferase (such as UGT76G2 and UGT76H1). Accordingly, in certain embodiments, there is provided a cell which expresses an UGT76G1 glucosyltransferase comprising a sequence encoding the amino acid sequence as set forth in any one of SEQ ID NOs: 1, 3, 5 and 7. In certain embodiments, there is provided a cell which expresses an UGT76G1-like glucosyltransferase comprising a sequence encoding the amino acid sequence as set forth in SEQ ID NO: 27 or 29. The cell may further express further glucosyltransferases, such as Os03g0702000 or Os03g0702000-like glucosyltransferase (such as UGT91 D1 and UGT91 D2) and/or a sucrose synthase, such as the sucrose synthase comprising the sequence as set forth in SEQ ID NO: 15, 17, 19, 21, 23 or 25.

Accordingly, in certain embodiments, there is provided a cell which expresses UGT76G1 glucosyltransferase comprising a sequence encoding the amino acid sequence as set forth in any one of SEQ ID NOs: 1, 3, 5 and 7 and Os03g0702000 glucosyltransferase comprising the sequence as set forth in SEQ ID NO:10. The cell may further express a sucrose synthase comprising the sequence as set forth in SEQ ID NO: 15, 17, 19, 21, 23 or 25.

In certain embodiments, there is provided a cell which expresses an Os03g0702000 or Os03g0702000-like glucosyltransferase. Accordingly, in certain embodiments, there is provided a cell which expresses Os03g0702000 glucosyltransferase comprising a sequence encoding the amino acid sequence as set forth in SEQ ID NO: 10. The cell may further express a sucrose synthase, such as the sucrose synthase comprising the sequence as set forth in SEQ ID NO: 15, 17, 19, 21, 23 or 25.

Transgenic cells and plants (including plant cells, or plant explants, or plant tissues) can be produced by a variety of well established techniques. Following construction of a vector, most typically an expression cassette, including a polynucleotide of the invention, standard techniques can be used to introduce the polynucleotide into cell or a plant. Optionally, the plant cell, explant or tissue can be regenerated to produce a transgenic plant.

In a certain embodiments, there is provided Cannabis plants genetically engineered to express one or more of the proteins of the invention. A worker skilled in the art would readily appreciate appropriate vectors and promoters for genetically engineering Cannabis plats. For example, a tissue specific promoter, such as a secretory trichomes specific promoter may be used such that the proteins of the invention are expressed in the same tissue that cannabinoids are produced in, namely the secretory trichomes of the plant. Suitable promoter elements include the promoter for the cytosolic O-acetylserine(thiol)lyase (OASA1) enzyme from Arabidopsis thaliana (Gutierrez-Alcala 2005).

Transformation and regeneration of plant cells is now routine, and the selection of the most appropriate transformation technique will be determined by the practitioner. Suitable methods can include, but are not limited to: electroporation of plant protoplasts; liposome-mediated transformation; polyethylene glycol (PEG) mediated transformation; transformation using viruses; micro-injection of plant cells; micro-projectile bombardment of plant cells; vacuum infiltration; and Agrobacterium tumeficiens mediated transformation. Transformation means introducing a nucleotide sequence into a plant in a manner to cause stable or transient expression of the sequence.

Successful examples of the modification of plant characteristics by transformation with cloned sequences which serve to illustrate the current knowledge in this field of technology, and which are herein incorporated by reference, include: U.S. Pat. Nos. 5,571,706; 5,677,175; 5,510,471; 5,750,386; 5,597,945; 5,589,615; 5,750,871; 5,268,526; 5,780,708; 5,538,880; 5,773,269; 5,736,369 and 5,610,042.

Following transformation, plants may be selected using a dominant selectable marker incorporated into the transformation vector. Typically, such a marker will confer antibiotic or herbicide resistance on the transformed plants, and selection of transformants can be accomplished by exposing the plants to appropriate concentrations of the antibiotic or herbicide.

Methods

The present invention further provides methods for the production of cannabinoid glycoside prodrugs and the cannabinoid glycosides prodrugs produced by the methods. The methods may be in vitro or in vivo (in a cell system or in planta). In certain embodiments, there is provided a method of producing cannabinoid glycoside prodrugs, said method comprising incubating a cannabinoid aglycone with one or more sugar donors in the presence of one or more glycosyltransferases.

The aglycones include but are not limited to: cannabinoids, including but not limited to cannabidiol, cannabidivarin, cannabigerol, tetrahydrocannabinol, cannabinol and cannabidiolic acid, endocannabinoids including but not limited to arachidonoylethanolamide (anandamide, AEA), 2-arachidonoylethanolamide (2-AG), 1-arachidonoylethanolamide (1-AG), and docosahexaenoyl ethanolamide (DHEA, synaptamide); and vanilloids including but not limited to vanillin, curcumin, and capsaicin.

A worker skilled in the art would readily appreciate that the one or more sugar donors will be dependent on the one or more glycosyltransferases used in the method and/or the desired end products. For example, for UDP-glucosyltransferases, the sugar donors include but are not limited to UDP-glucose, UDP-glucuronic acid, UDP-mannose, UDP-fructose, UDP-xylose, UDP-fluorodeoxyglucose, and UDP-rhamnose. For cyclodextrin glucanotransferase, the sugar donor includes maltodextrin.

In certain embodiments, there is provided a method of producing a cannabinoid glycoside, said method comprising incubating an aglycone with a sugar donor in the presence of a glycosyltransferase. Also provided are the cannabinoid glycosides produced by the above method. In specific embodiments, there is provided a method of producing a cannabinoid glycoside, said method comprising incubating an aglycone with UDP-glucose, in the presence of a UGT76G1 or UGT76G1-like glucosyltransferase under conditions that allow for glycosylation. In other specific embodiments, there is provided a method of producing a glycoside prodrug, said method comprising incubating an aglycone with maltodextrin, in the presence of a cyclodextrin glucanotransferase under conditions that allow for glycosylation.

An exemplary method for producing cannabinoid-glycosides comprises incubating a cannabinoid, with UDP-glucose in the presence of a UGT76G1 or UGT76G1-like glucosyltransferase under conditions which allow for glycosylation. Also provided are cannabinoid-glycosides produced by the above method.

A further exemplary method for producing cannabinoid-glycosides comprises incubating a cannabinoid with maltodextrin in the presence of a cyclodextrin glucanotransferase under conditions which allow for glycosylation. Also provided are cannabinoid-glycosides produced by the above method.

In certain embodiments, there is provided a method of producing a cannabinoid glycoside, said method comprising incubating an aglycone with one or more sugar donors in the presence of a first glycosyltransferase and a second glycosyltransferase under conditions which allow for glycosylation. Also provided are cannabinoid glycosides produced by the above method.

A worker skilled in the art would readily appreciate that the first glycosyltransferase and a second glycosyltransferase may be provided concurrently or added sequentially. In addition, if more than one sugar donor is used, the sugar donors may be provided concurrently or added sequentially. Such a worker would further appreciate that the structure of the resulting cannabinoid glycoside may be dependent on the order the glycosyltransferases are provided. In addition, the ratio of first to second glycosyltransferase may impact the resulting products. A worker skilled in the art would further appreciate that the activity levels of the glycosyltransferases may dictate the ratios and the ratios could be readily determined by a worker skilled in the art. For example, the ratios first to second glycosyltransferase include but are not limited to 1:1, 1:2, 1:10, 1:50 and vice versa.

In specific embodiments, there is provided a method of producing a cannabinoid glycoside, said method comprising incubating an aglycone with UDP-glucose in the presence of a UGT76G1 or UGT76G1-like glucosyltransferase and Os03g0702000 or Os03g0702000-like glucosyltransferase under conditions which allow for glycosylation. In alternative specific embodiments, there is provided a method of producing a cannabinoid glycoside, said method comprising incubating an aglycone with UDP-glucose and maltodextrin in the presence of a UGT76G1 or UGT76G1-like glucosyltransferase and cyclodextrin glucanotransferase under conditions which allow for glycosylation. Also provided are cannabinoid glycosides produced by the above methods.

An exemplary method for producing cannabinoid-glycosides comprises incubating cannabinoid, including but not limited to cannabidiol, cannabidivarin, canabigerol, tetrahydrocannabinol, cannabinol and cannabidiolic acid, with UDP-glucose in the presence of a UGT76G1 or UGT76G1-like glucosyltransferase and Os03g0702000 or Os03g0702000-like glucosyltransferase under conditions which allow for glycosylation. Also provided are cannabinoid-glycosides produced by the above method.

A further exemplary method for producing cannabinoid-glycosides comprises incubating cannabinoids with UDP-glucose and maltodextrin in the presence of a UGT76G1 or UGT76G1-like glucosyltransferase and and cyclodextrin glucanotransferase under conditions which allow for glycosylation. Also provided are cannabinoid-glycosides produced by the above method.

It is within the scope of the present invention that each of the above described glycosylation methods may be applied to a lower order cannabinoid glycoside to form a higher order cannabinoid glycoside. For example, a cannabinoid monoglycoside may be glycosylated using any of the glycosylation methods of the present invention to form a diglycoside, or a cannabinoid diglycoside may be glycosylated to form a triglycoside, etc.

Methods of purifying the cannabinoid glycosides are known in the art and include for example solid phase extraction, such as column purification.

The invention also provides cell culture and in planta methods for the production of cannabinoid glycosides. The methods comprise expressing one or more of the glycosyltransferases in a cell or plant which produces the aglycone and isolating the cannabinoid glycosides. In certain embodiments, one or more sucrose synthases are also expressed. Appropriate vectors and genetic engineering methods are known in the art.

The invention also provides methods for the conversion of UDP to UDPG utilizing the sucrose synthases of the present invention. Accordingly, in certain embodiments of the methods of producing cannabinoid glycosides which utilize UDP-glucose as a sugar donor, the methods further comprise the use of sucrose synthase to recycle UDP. In certain embodiments, there is provided a method of producing a cannabinoid glycoside, said method comprising incubating aglycone with UDP-glucose, in the presence of a UGT76G1 glucosyltransferase and a sucrose synthase under conditions that allow for glycosylation.

The invention will now be described with reference to specific examples. It will be understood that the following examples are intended to describe embodiments of the invention and are not intended to limit the invention in any way.

EXAMPLES

Example 1: Conversion of Cannabinoids to Cannabinoid Glycoside Prodrugs

Glycosylation reactions consisted of 50 mM $KPO_4$ pH 7.2, 3 mM $MgCl_2$, 0.005% CBD, 2.5% UGT76G1 purified enzyme preparation, and 2.5 mM UDP-glucose. Buffers were degassed and tubes were purged with nitrogen, reactions were protected from light and incubated at 28° C. with 180 rpm agitation for 18 hours. Reactions were then extracted 3× with an equal volume of ethyl acetate, evaporated to dryness, and dissolved in a half volume of HPLC grade methanol. 50 microliters was injected on a reverse phase C18 column and eluted with a gradient of acetonitrile starting at 10% and increasing to 99%. UGT76G1 was produced through expression in *Pichia pastoris* and purified through standard molecular biology techniques. The UGT76G1 enzyme was found to glycosylate CBD in a UDP-glucose dependent manner. This activity was also proportional to the amount of UDP-glucose present. Incubation temperature was 28° C., and an acceptable range would be 20° C. to 30° C. as high temperatures can cause significant degradation of CBD. Reactions were carried out in the dark to prevent photo-degradation of the substrates. Gentle agitation from 120 to 200 rpm were used to mix the reactions in an inert atmosphere.

Substrate CBD in the reactions was replaced with Δ9THC and CBDV and performed in an identical fashion with similar results. Enzyme combinations needed to create various products are listed in Table 4 for CBD-glycosides, Table 5 for CBDV-glycosides, and Table 6 for Δ9THC-glycosides.

Other enzymes screened for activity towards CBD were the *Stevia rebaudiana* UGT74G1, UGT85C2, UGPase, *E. coli* Maltodextrin phosphotransferase (MaIP), and *O. sativa* Os03g0702000 (SEQ ID NO. 9). No primary glycosylation activity was seen with any other tested enzyme other than UGT76G1.

Example 2: 2-O glycosylation of of CBD-Monoglycoside

Enzymatic reactions are performed as described in Example 1 but with the inclusion of recombinant Os03g0702000 enzyme at a 1:2 ratio relative to UGT76G1. Samples were extracted and analyzed as in Example 1. Recombinant Os03g0702000 enzyme was codon optimized and expressed in *E. coli* BL21-DE3 cells and purified by immobilized metal ion chromatography.

Example 3: Conversion of CBD to alpha-glycoside Linked CBD Compounds

Recombinant cyclodextrin glucanotransferase (CGTase, Toruzyme 3.0L trade name, Novozymes Inc.) was added to reactions as indicated in Example 1 but without UDPG or UGT76G1. Maltodextrin was used at 0.05% final concentration, and Toruzyme 3.0L was used at 0.1%. Samples were extracted and analyzed as in example 1. Additionally, reactions from Example 1 were carried out to convert cannabinoids to cannabinoid-glycosides, and then CGTase and maltodextrin were added and given adequate time to incubate with the cannabinoid-glycosides. The resulting products contain a β-glycosylation on the cannabinoid backbone, and α-glycosylations emanating from the primary sugar. This additional treatment created a new category of compounds termed β-primed, α-glycosylated cannabinoids.

Example 4: Purification of Cannabinoid Glycosides

Glycoside products were generated through the aforementioned biocatalytic reactions and purified to homogeneity by C18 solid phase extraction. 100 mg Hypersep C18 columns (Thermo) were hydrated in methanol, rinsed with 50% methanol in water, rinsed with water, glycosylation reaction passed through the column, washed with water, washed with 10%, 20%, and 30% methanol, and the glycoside products were eluted with 45 and 60% methanol in water. Eluates were dried and extracted with ethyl acetate, and dried to completion to yield >95% pure cannabinoid-glycosides for further analysis and testing.

Example 5: HPLC Analysis of Cannabinoid Glycoside Prodrugs

The HPLC linetraces of the reaction products of glycosylation reactions of the cannabinoid aglycones CBD, CBDV, Δ9-THC, CBN, 1-AG and 2-AG, DHEA, AEA, capsaicin, and vanillin, are provided in FIGS. 16 to 24, respectively. Enzymatic reactions were performed as described in Example 1. The solid lines indicate the elution profile of the starting aglycone and the dashed lines indicate the elution profile of the glycosylation reaction product mixture.

Figure 16:
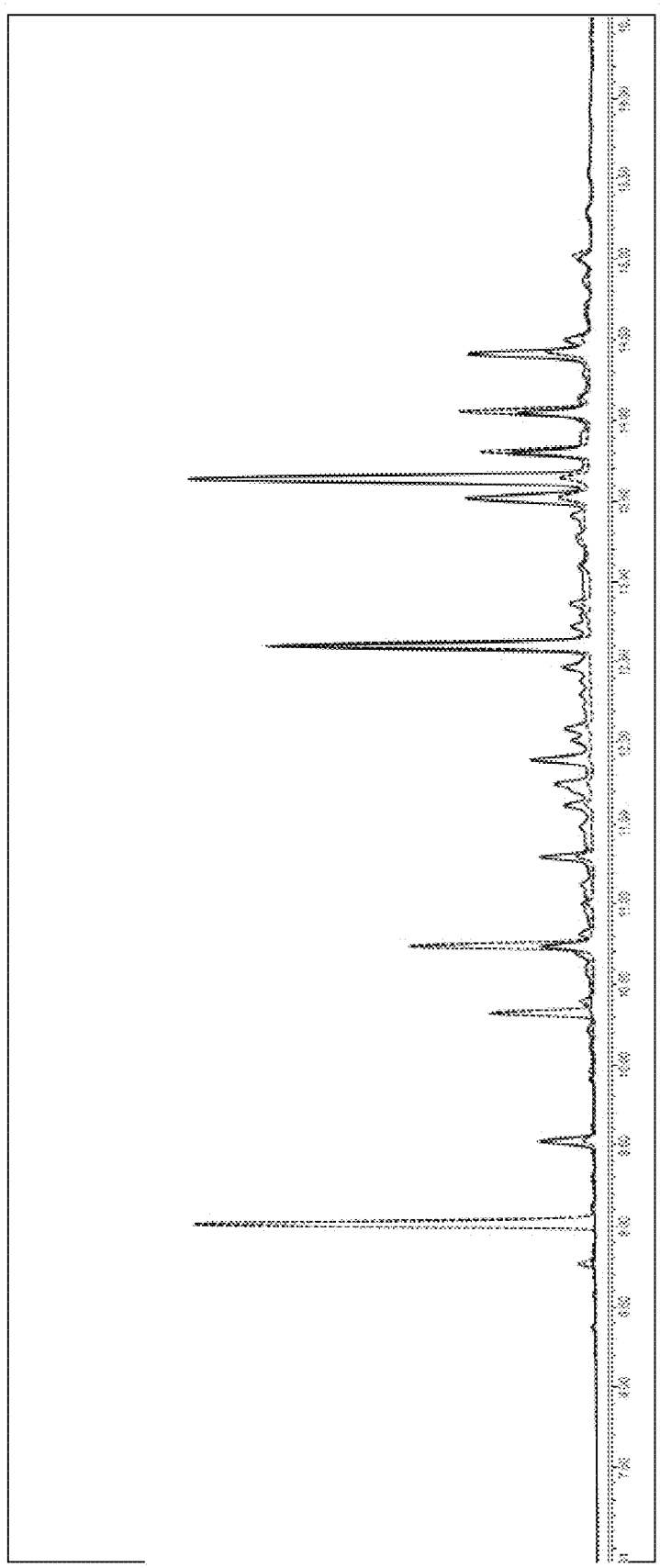
FIG. 16 is an HPLC linetrace of the reaction products of the glycosylation of CBD.

In FIG. 16, the CBD aglycone retention time is 13.65 minutes, and product peaks are observed at 8.87, 9.02, 9.97, 10.33, and 10.37 min.

Figure 17:
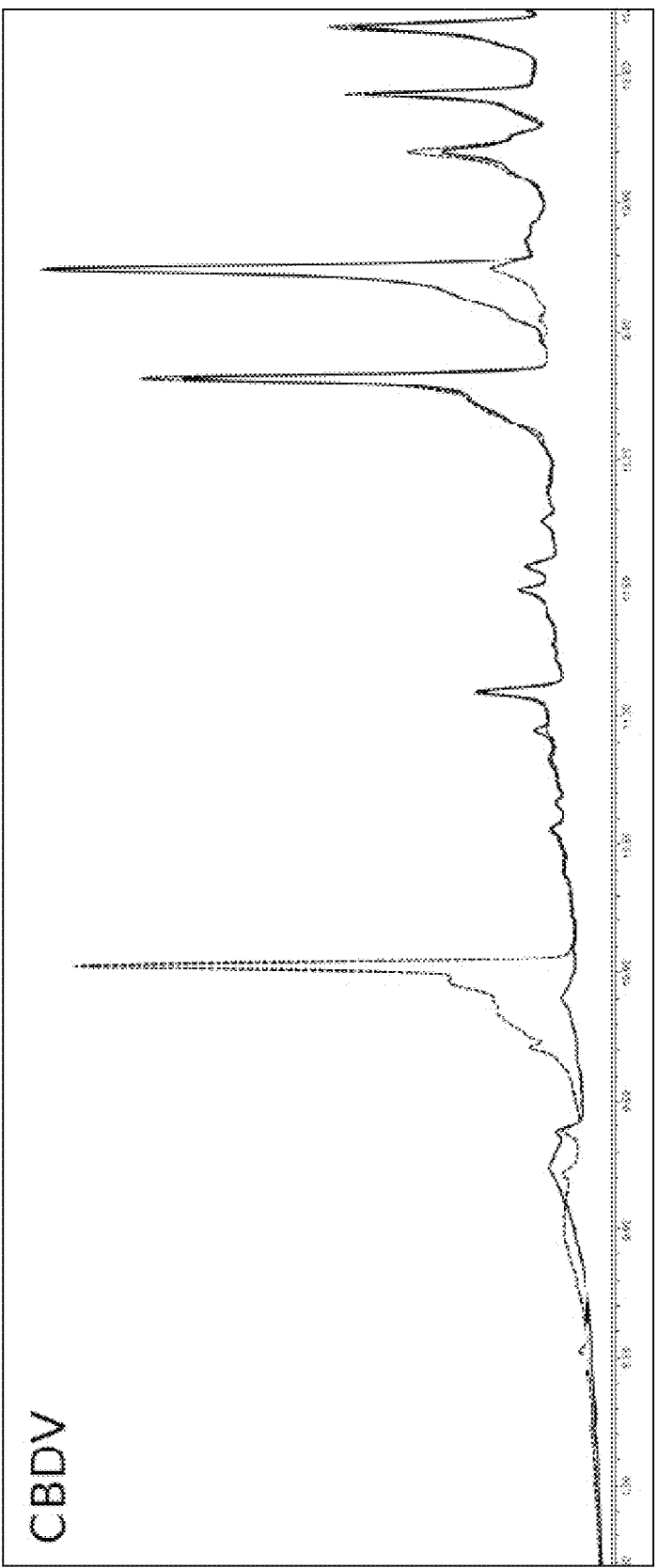
FIG. 17 is an HPLC linetrace of the reaction products of the glycosylation of CBDV.

In FIG. 17, the CBDV aglycone retention time is 12.75 minutes, and product peaks are observed at 8.53, 9.70, and 10.01 min.

Figure 18:
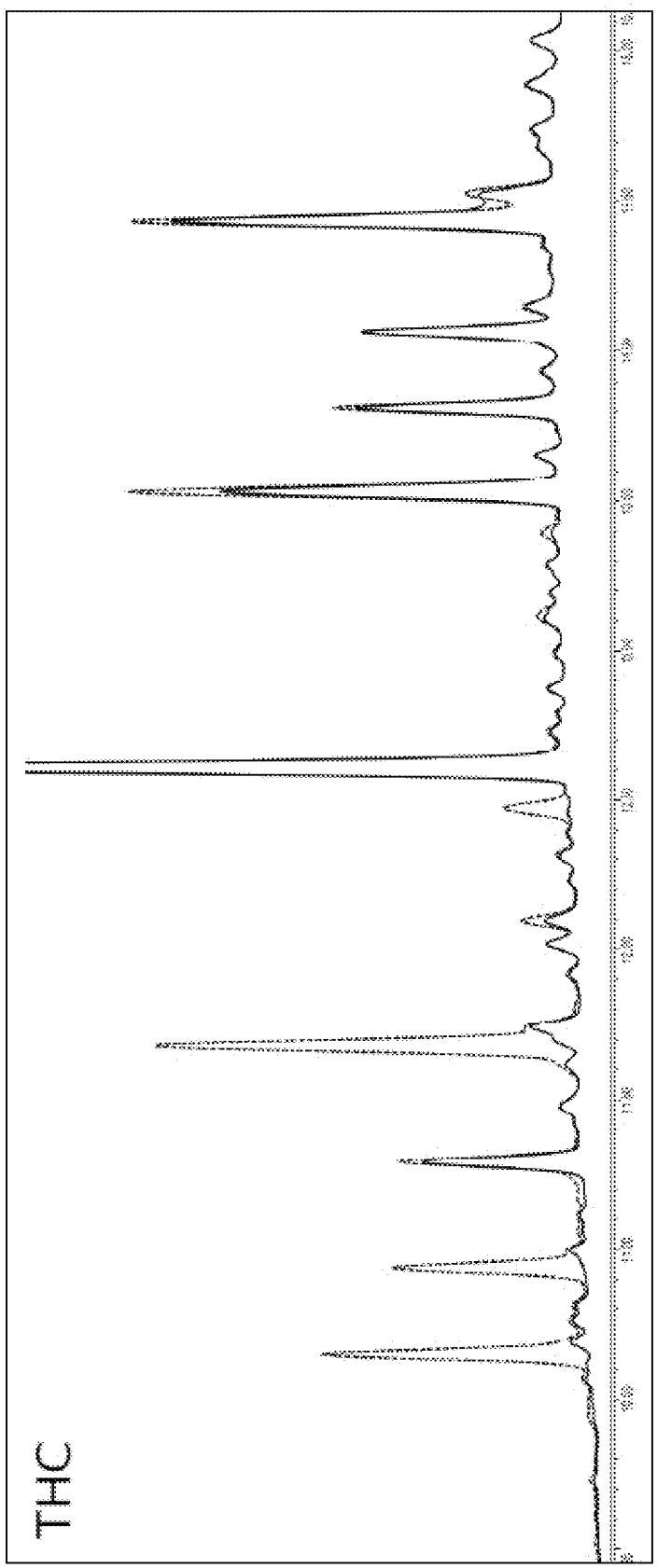
FIG. 18 is an HPLC linetrace of the reaction products of the glycosylation of Δ9-THC.

In FIG. 18, the THC aglycone retention time is 14.45 minutes, and product peaks are observed at 9.46, 10.67, 10.97, 11.28, 11.67, and 12.49 min.

Figure 19:
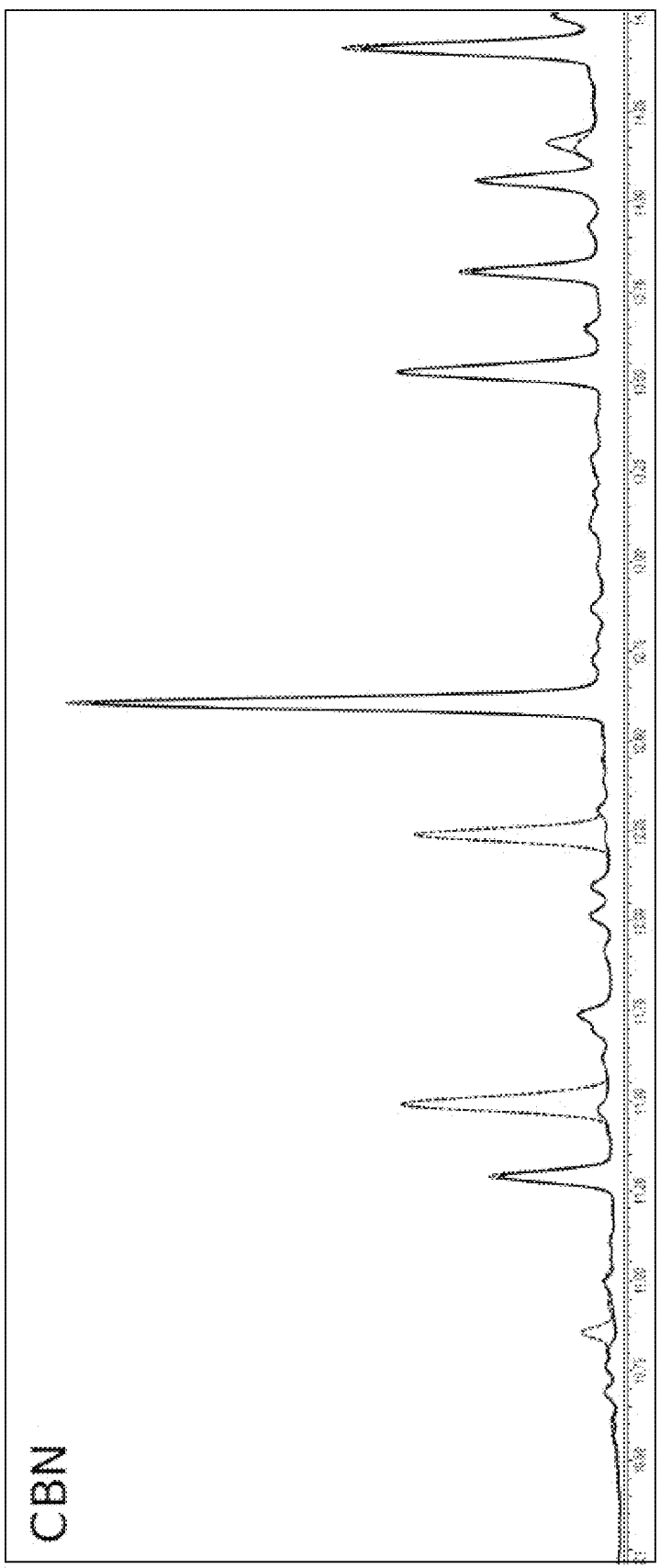
FIG. 19 is an HPLC linetrace of the reaction products of the glycosylation of CBN.

In FIG. 19, the CBN aglycone retention time is 14.32 minutes, and product peaks are observed at 10.87, 11.50, and 12.25 min.

Figure 20:
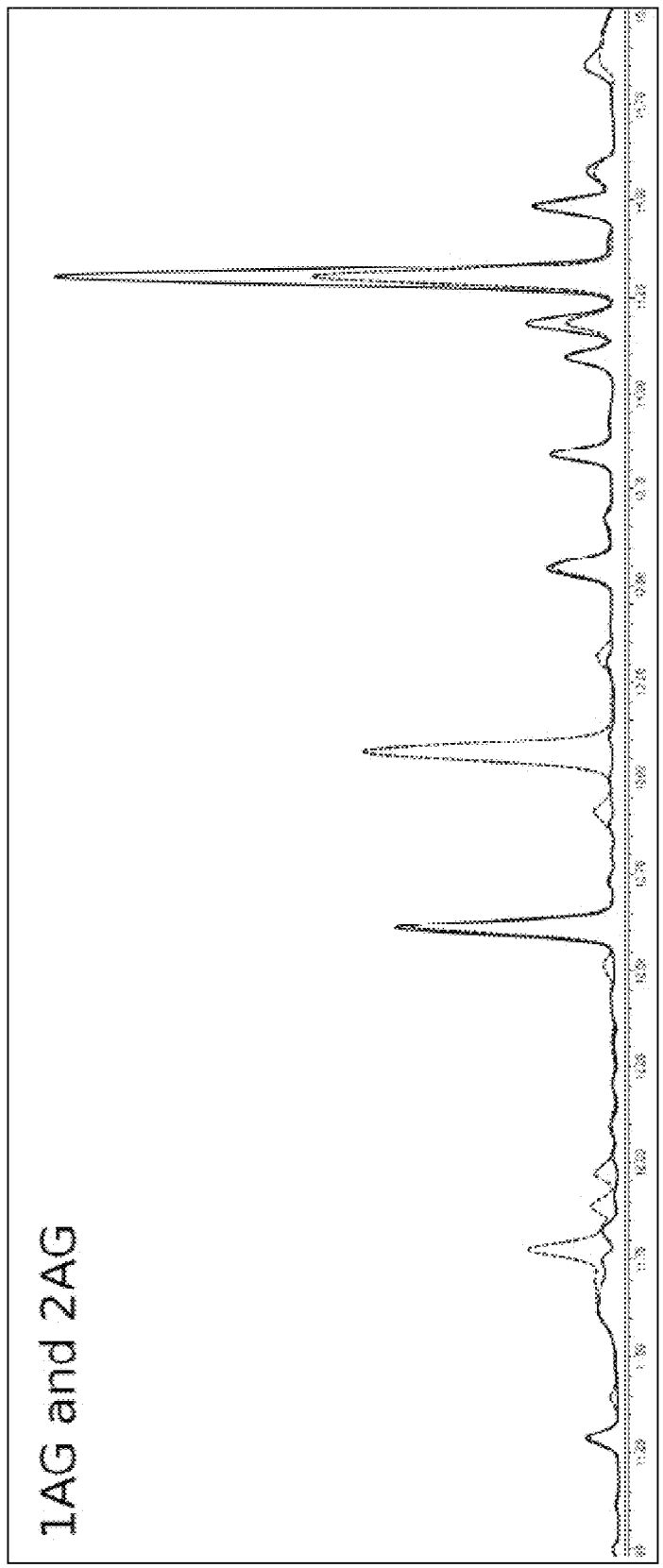
FIG. 20 is an HPLC linetrace of the reaction products of the glycosylation of 1-AG and 2-AG.

In FIG. 20, the 1-AG aglycone retention time is 14.18 minutes and the 2-AG aglycone retention time is 14.32 minutes, and product peaks are observed at 11.40, 11.78, 11.83, 11.97, 12.53, 12.92, 13.07, and 13.35 min.

Figure 21:
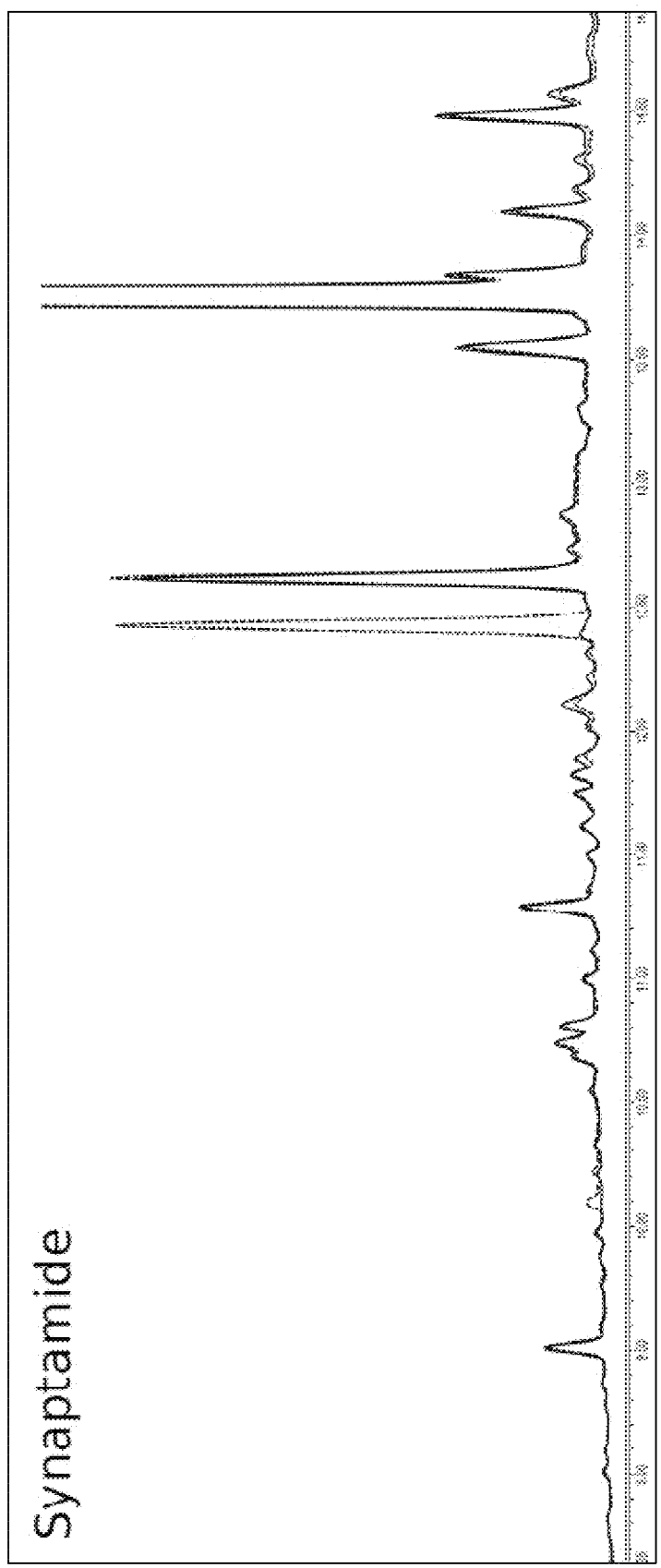
FIG. 21 is an HPLC linetrace of the reaction products of the glycosylation of synaptamide (DHEA).

In FIG. 21, the DHEA aglycone retention time is 13.78 minutes, and product peaks are observed at 10.09 and 12.43 min.

Figure 22:
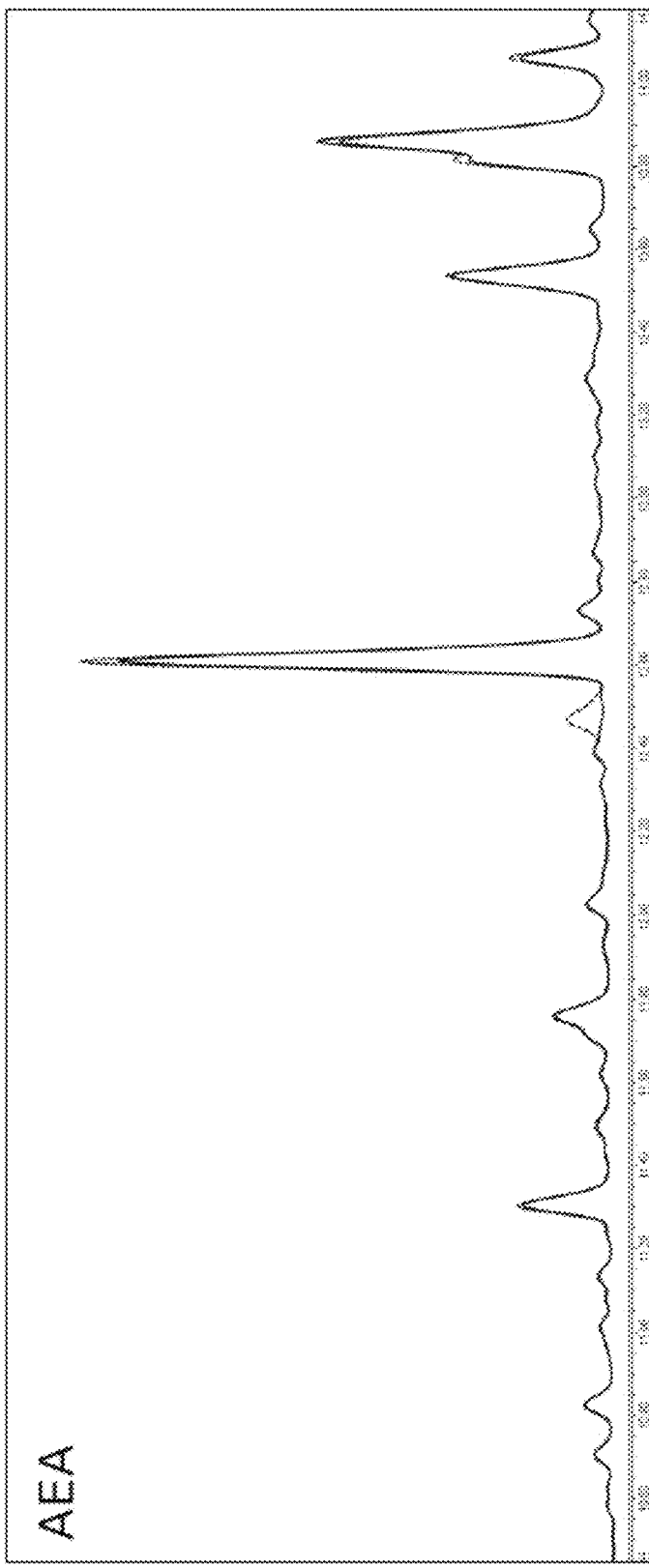
FIG. 22 is an HPLC linetrace of the reaction products of the glycosylation of AEA.

In FIG. 22, the AEA aglycone retention time is 13.87 minutes, and product peaks are observed at 12.47 min.

Figure 23:
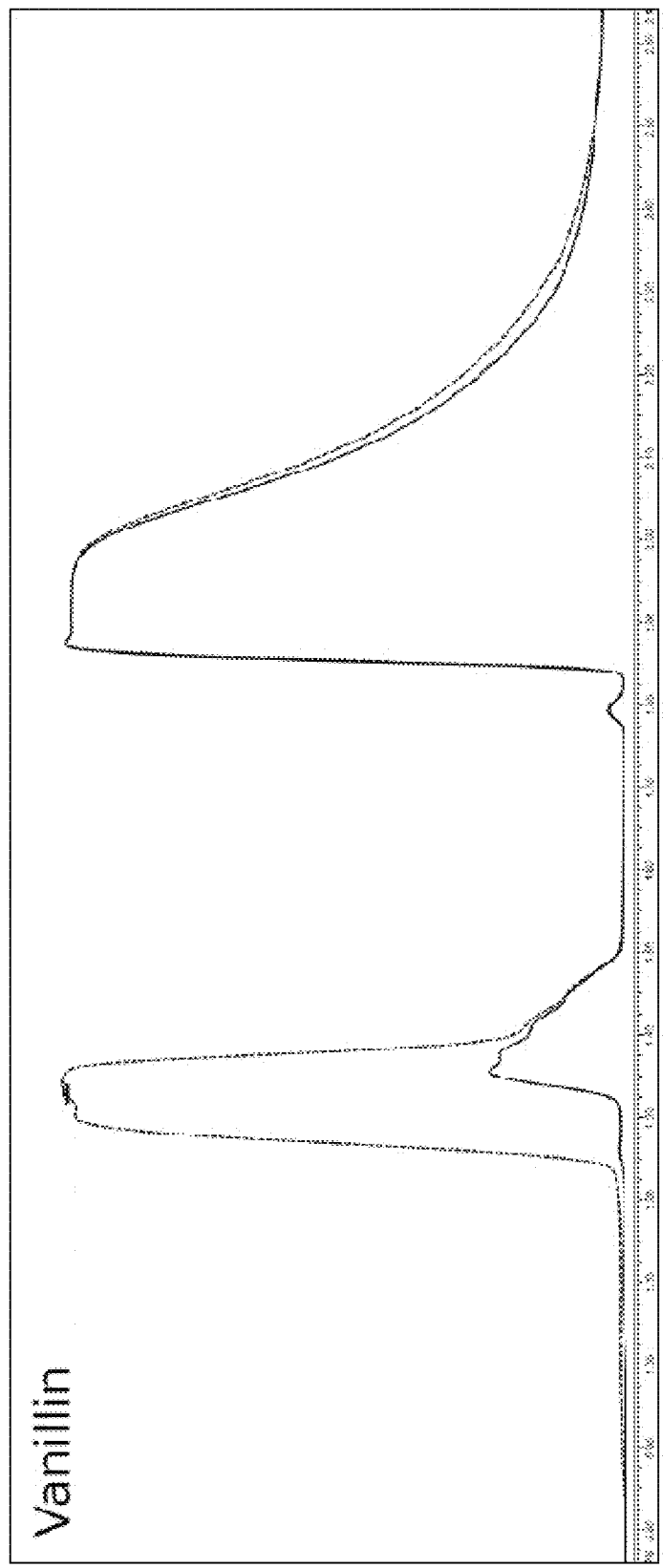
FIG. 23 is an HPLC linetrace of the reaction products of the glycosylation of vanillin.

In FIG. 23, the vanillin aglycone retention time is 1.95 minutes and product peaks are observed from 1.25 to 1.35 min.

Figure 24:
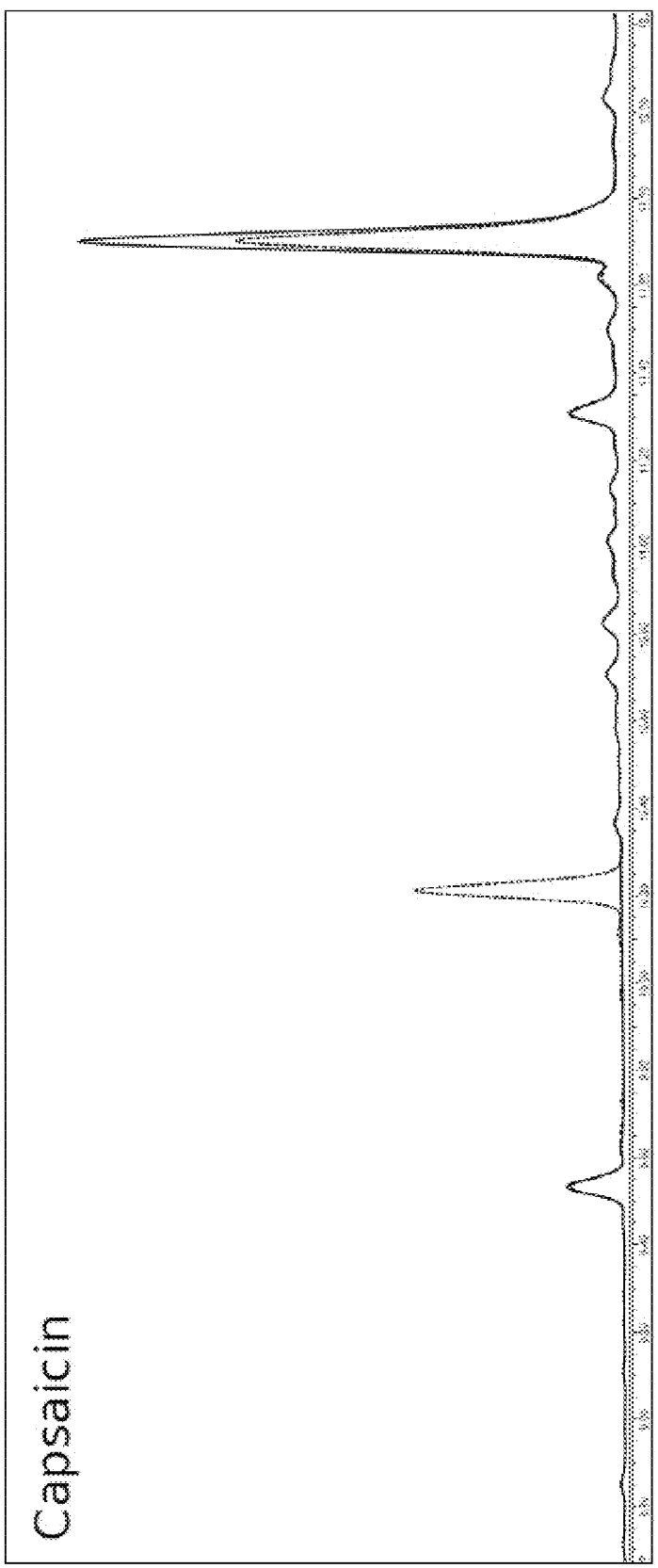
FIG. 24 is an HPLC linetrace of the reaction products of the glycosylation of capsaicin.
Figure 25:
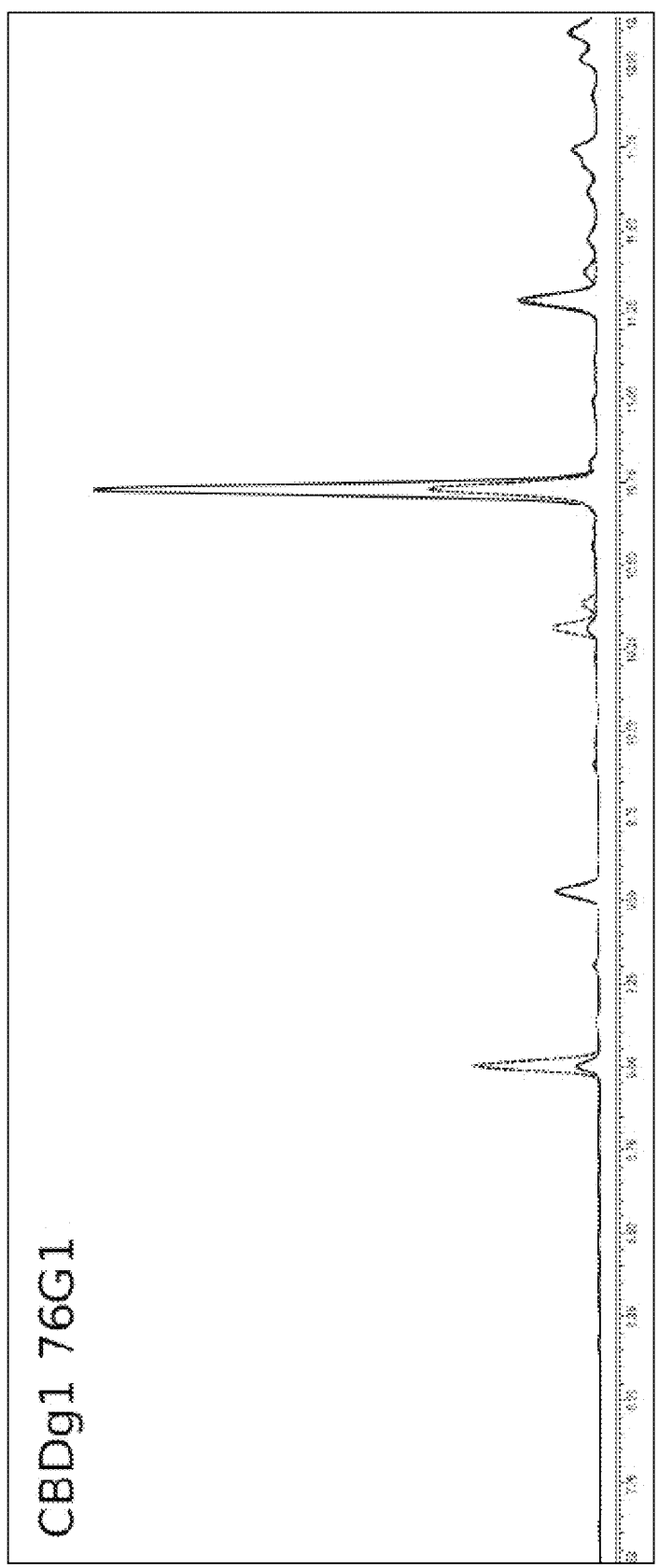
FIG. 25 is an HPLC linetrace of the reaction products of the glycosylation of CBDg1 (VB104) with the glycosyltransferase UGT76G1.
Figure 26:
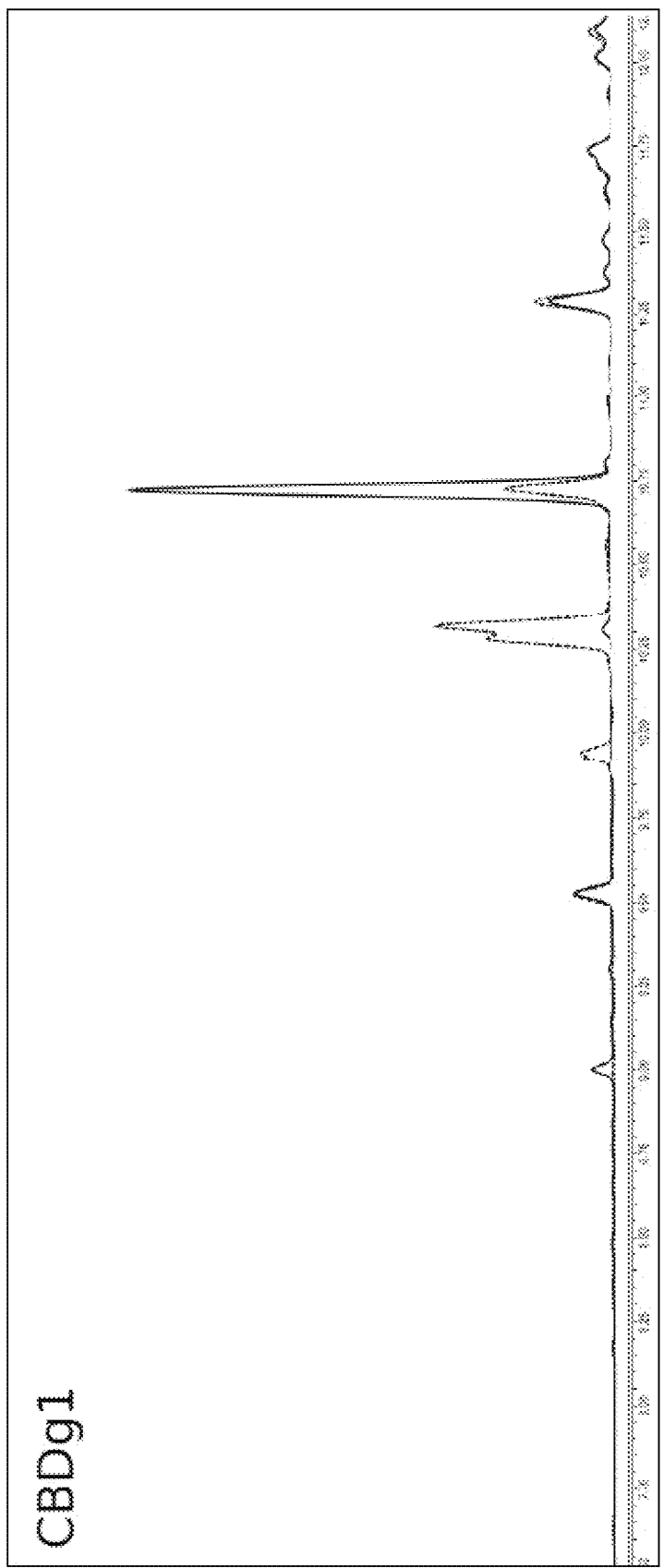
FIG. 26 is an HPLC linetrace of the reaction products of the glycosylation of CBDg1 (VB104) with the glycosyltransferase Os03g0702000

In FIG. 24, the capsaicin aglycone retention time is 11.73 minutes, and product peaks are observed at 10.23 min.

Example 6A: LCMS Analysis of CBD Glycosides

As shown in the HPLC linetrace of FIG. 16, input CBD aglycone (VB101, 13.65') has been depleted to 5% of original quantity after +65 hours of incubation time. The CBD-glycosides elute off the HPLC column at 8.87, 9.02, 9.97, 10.33, and 10.37 min. The glycosylated products were identified by LCMS analysis. The glycosylated product "g1" is a monoglycoside, "g2" is a diglycoside, "g3" is a triglycoside, and "g4" is a tetraglycoside. LC-LRMS was performed on a Shimadzu LC-MS 2010 EV instrument. The LC column used was a Silia Chrom XDB C18 5 um, 150A, 4.6×50 mm. The method was 12 min 5 to 95 $H_2O$:ACN gradient. For LRMS electrospray ionization (ESI) was performed in positive mode.

VB101 (CBD aglycone) MS data: LC/ESI-LRMS. $[M+H]^+$ ($C_{21}H_{31}O_2$) Calcd: m/z=315. Found: m/z=315.

(CBDg1) MS data: LC/ESI-LRMS. $[M+H]^+$ ($C_{27}H_{41}O_7$) Calcd: m/z=477. Found: m/z=477.

VB104 (CBDg2) MS data: LC/ESI-LRMS. $[M+H]^+$ ($C_{33}H_{51}O_{12}$) Calcd: m/z=639. Found: m/z=639.

VB110 (CBDg2) MS data: LC/ESI-LRMS. $[M+H]^+$ ($O_{33}H_{51}O_{12}$) Calcd: m/z=639. Found: m/z=639.

(CBDg3) MS data: LC/ESI-LRMS. $[M+H]^+$($C_{39}H_{61}O_{17}$) Calcd: m/z=801. Found: m/z=801. $[M+K+H]^+$ ($C_{33}H_{61}O_{17}K$) Calcd: m/z=420. Found: m/z=420. $[M+ACN+H_2O+H]^+$ ($C_{41}H_{63}NO_{17}$) Calcd: m/z=860. Found: m/z=860.

(CBDg4) MS data: LC/ESI-LRMS. $[M+H]^+$($C_{45}H_{71}O_{22}$) Calcd: m/z=964. Found: m/z=964. $[M+H_2O+H]^+$ ($C_{45}H_{73}O_{18}$) Calcd: m/z=983. Found: m/z=983.

(CBDg3) MS data: LC/ESI-LRMS. $[M+H]^+$($C_{39}H_{61}O_{17}$) Calcd: m/z=801. Found: m/z=801. $[M+Na]^+$ ($C_{39}H_{60}O_{17}Na$) Calcd: m/z=823. Found: m/z=823. $[M+K+H]^{2+}$ ($C_{33}H_{61}O_{17}K$) Calcd: m/z=420. Found: m/z=420.

Example 6B: LCMS Analysis of Δ9-THC Glycosides

In a manner similar to that carried out in Example 6A, the products of the glycosylation reaction of Δ9-THC (shown in the HPLC linetrace of FIG. 18) were identified by LCMS analysis.

VB301 (THC aglycone) MS data: LC/ESI-LRMS. $[M+H]^+$($C_{21}H_{31}O_2$) Calcd: m/z=315. Found: m/z=315. $[M+3ACN+2H]^{2-}$ ($C_{27}H_{41}N_3O_2$) Calcd: m/z=314. Found: m/z=314.

VB304 (THCg2) MS data: LC/ESI-LRMS. $[M+H]^+$ ($C_{33}H_{51}O_{12}$) Calcd: m/z=639. Found: m/z=639.

VB308 (THCg3) MS data: LC/ESI-LRMS. $[M+H]^+$ ($C_{33}H_{61}O_{17}$) Calcd: m/z=801. Found: m/z=801. $[M+Na]^+$ ($C_{39}H_{60}O_{17}Na$) Calcd: m/z=823. Found: m/z=823. $[M+K+H]^+$ ($C_{33}H_{61}O_{17}K$) Calcd: m/z=420. Found: m/z=420.

Example 7: NMR Analysis of Cannabinoid Glycosides

Figure 27:
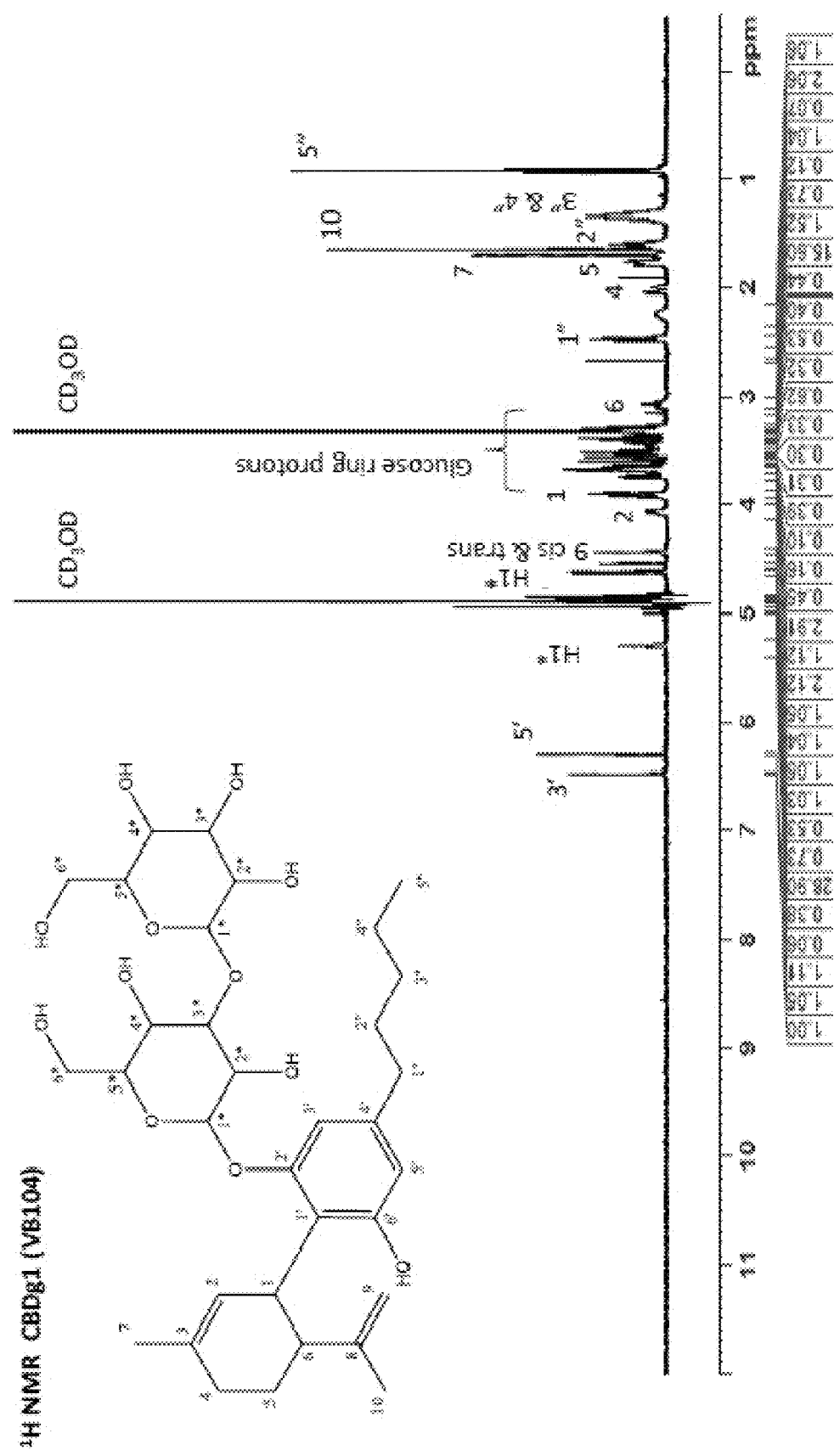
FIG. 27 is a ¹NMR spectrum of an isolated product, VB104, of the glycosylation of CBD.
Figure 28:
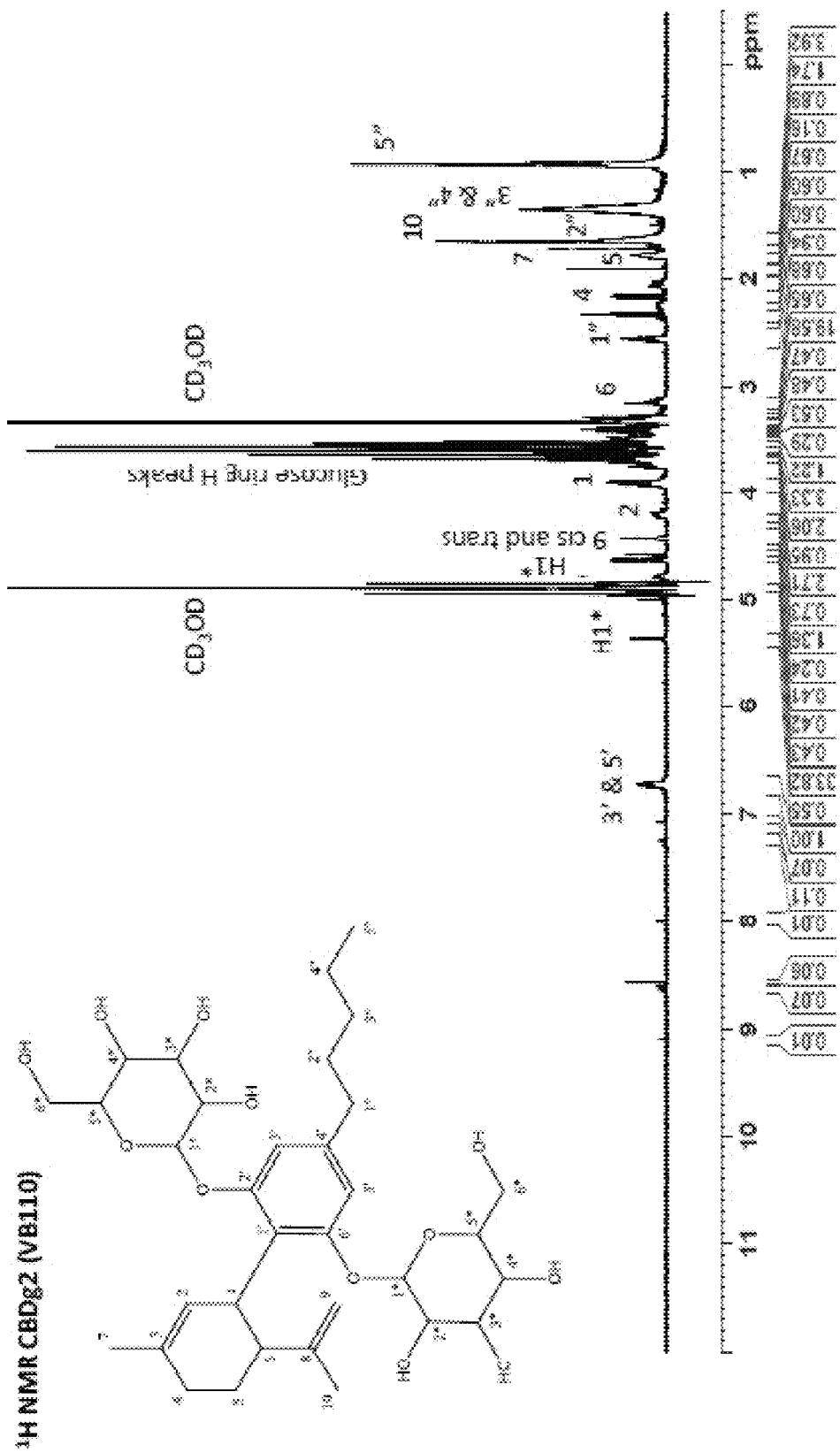
FIG. 28 is a ¹NMR spectrum of an isolated product, VB110 of the glycosylation of CBD.

FIG. 27 depicts the $^1$NMR spectra of isolated VB104 and FIG. 28 depicts the $^1$H MR spectra of isolated VB110. Each of these products was isolated from the reaction mixture produced by the glycosylation reaction of CBD. The $^1$H NMR spectra of 10 mg/ml solutions of each compound prepared in $CD_3OD$ were obtained on a Bruker Avance II 400 MHz instrument using TopSpin acquisition and processing software.

Example 8: Solubility Analysis

Figure 29:
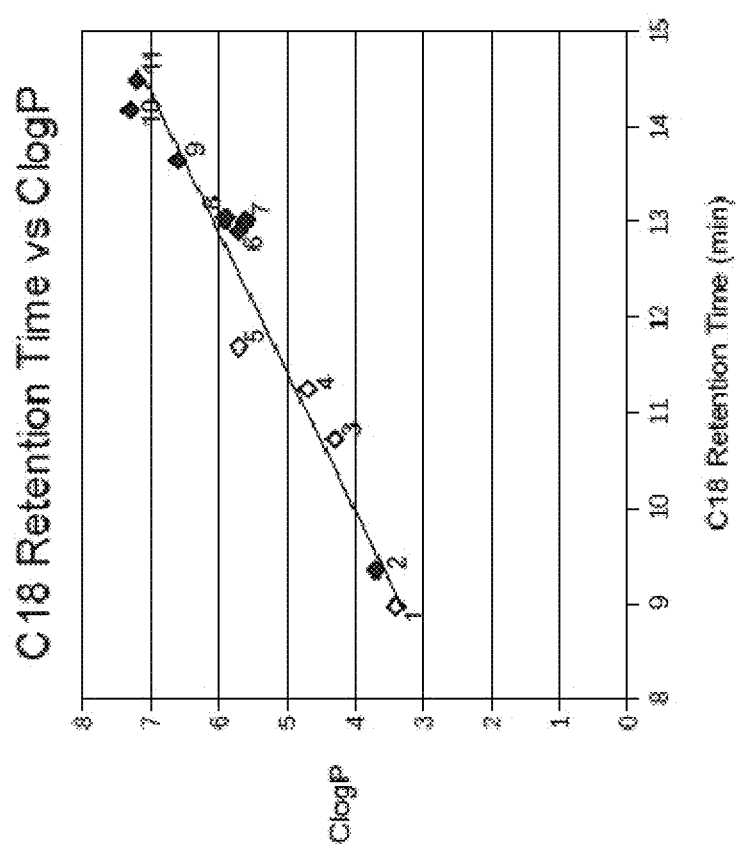
FIG. 29 is a plot of C18 retention times vs cLogP values for selected cannabinoids and cannabinoid glycosides.

C18 retention times were empirically determined on a linear ramp of increasing acetonitrile on a Phenomenex Kinetex 2.6u 100A C18 column, on a Dionex HPLC equipped with Diode Array Detector. CLogP values in Table A were predicted by ChemDraw (CambridgeSoft). Reference cannabinoids were analyzed by HPLC and established log P values (http://pubchem.ncbi.nlm.nih.gov/) and used to create a calibration line as depicted in FIG. 29. The predicted cLogP values correlated with the reference calibration line. C18 reverse phase HPLC retention times were plotted against the cLogP values presented in Table A, as depicted in FIG. 29. Data point numbering correlates with table numbering. Open diamonds indicate novel cannabinoid glycosides, filled diamonds indicate reference cannabinoids and derivatives. Clog P values were predicted by ChemDraw (CambridgeSoft). Linear regression was performed on all data points ($R2=0.9455$).

TABLE A

CLogP values for select cannabinoid glycosides and reference cannabinoids

| # | Compound | Retention Time | ClogP |
|---|---|---|---|
| 1 | VB110 | 8.967 | 3.4 |
| 2 | 11-COOH-Tetrahydrocannabinol Glucuronide | 9.347 | 3.7 |
| 3 | VB104 | 10.720 | 4.3 |
| 4 | VB304 | 11.250 | 4.7 |
| 5 | VB302 | 11.688 | 5.7 |
| 6 | 11-COOH-Tetrahydrocannabinol | 12.910 | 5.7 |
| 7 | Cannabidivarin | 13.017 | 5.6 |
| 8 | 11-OH-Tetrahydrocannabinol | 13.037 | 5.9 |
| 9 | Cannabidiol | 13.647 | 6.6 |
| 10 | Cannabinol | 14.178 | 7.3 |
| 11 | Tetrahydrocannabinol | 14.487 | 7.2 |

Example 9: Bioavailability Assay

Figure 30:
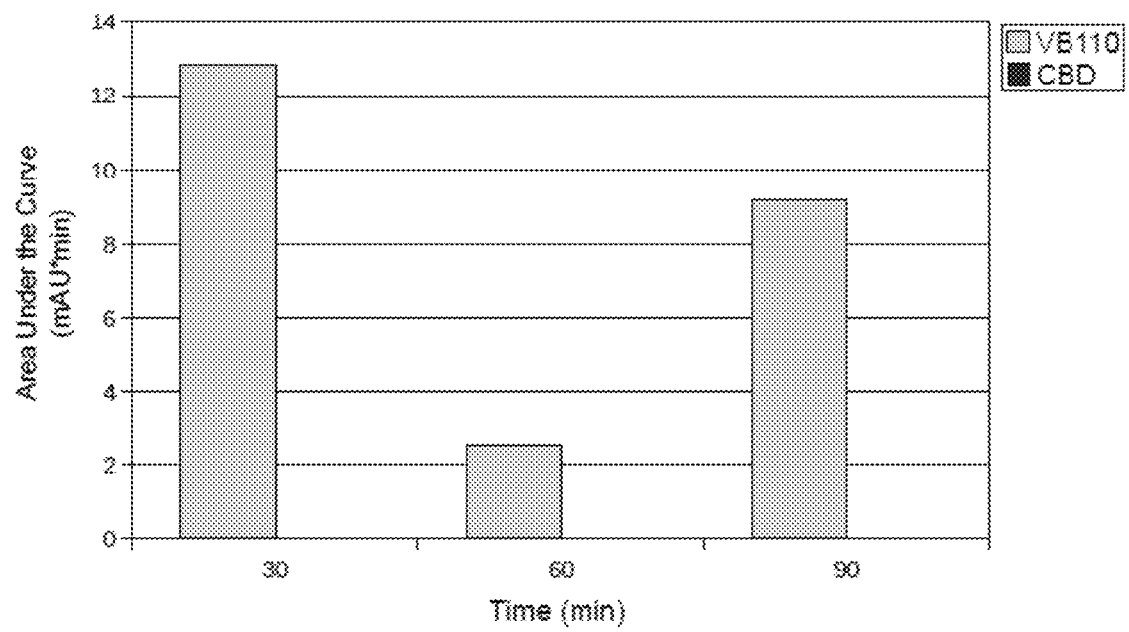
FIG. 30A is a graphical presentation of the results of the analysis of the small intestine extracts of a bioavailability assay.
FIG. 30B is a graphical presentation of the results of the analysis of the large intestine extracts of a bioavailability assay
Figure 30:
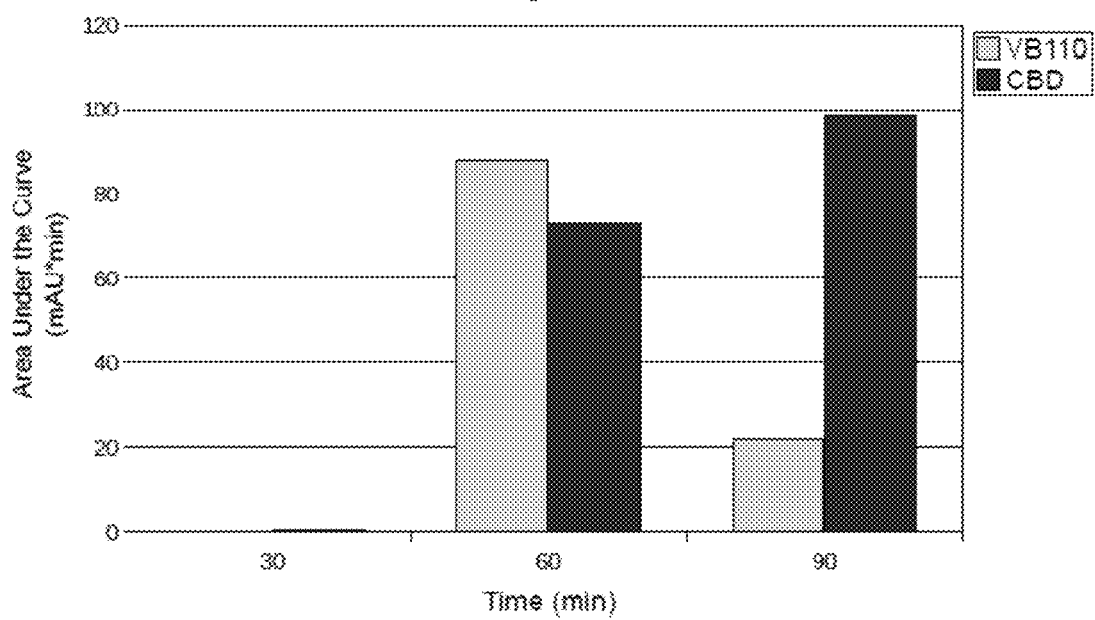

In order to investigate the effectiveness of glycosylation to effect site-specific drug delivery, VB110 was administered to three mice by oral gavage and the animals sacrificed at 30, 60, and 90 minutes. Eight week old male Swiss mice were fasted for 12 hours prior to administration of 120 mg/kg VB110 in 10% Ethanol USP, 10% Propylene Glycol USP, 0.05% Sodium Deoxycholate USP, 79.95% Saline USP. Following termination and tissue harvest, the intestinal contents were then extracted and analyzed by C18 reverse phase HPLC. As shown in FIG. 30A, the small intestinal contents showed intact VB110, but no decoupled CBD. As shown in FIG. 30B, the large intestinal contents contained both VB110 and CBD in the 60 and 90 minute time points. This decoupling of VB110 is consistent with the large intestinal decoupling seen for sennoside beta-glycosides, and is the result of secreted beta-glycosidases from the large intestinal microflora.

Example 10: Analysis of Large Intestine Contents Upon Administration of CBD and CBD Glycosides In order to investigate the metabolism and decoupling of CBD-glycosides in the large intestine, an aqueous solution of a mixture of CBD-glycosides was administered to a mouse by oral gavage. As a control, a solution of CBD in cremophor, ethanol, and saline was administered to a second mouse. The animals were each sacrificed at 2 hours. Following termination and tissue harvest, the intestinal contents were then extracted and analyzed by C18 reverse phase HPLC. The mice employed in this example were eight week old male Swiss mice fasted for 12 hours prior to administration of the solutions.

The resulting extracts were analyzed by LCMS performed using a Shimadzu LC-MS 2010 EV. LC separation was carried out using a Silia Chrom XDB C18 5 um, 150A, 4.6×50 mm. The method was 12 min, 5 to 95 $H_2O$:ACN gradient elution. Low resolution MS was performed in negative mode via electrospray ionization (ESI). Acetic acid and formic acid were used as sample additives during analysis, and the injection volume was 20

Analysis of the large intestinal contents of animals administered a mixture of oral CBD-glycosides indicated that both aglycone and glycosides were present, along with hydroxy metabolites of each:

[CBD–H], [2CBD–H] and [CBD*2OH+Formic acid–H] MS data: LC/ESI-LRMS. [M–H]$^-$ ($C_{21}H_{29}O_2$) Calcd: m/z=313. Found: m/z=313. [2M–H]$^-$ ($O_{42}H_{59}O_4$) Calcd: m/z=627. Found: m/z=627. [M$_{*2OH}$+Formic acid–H]$^-$ ($C_{22}H_{31}O_6^-$) Calcd: m/z=391. Found: m/z=391.

[CBDg1–H], [CBDg1+Cl] and [2CBDg1–H] MS data: LC/ESI-LRMS. [M$_{g1}$–H]$^-$ ($C_{27}H_{39}O_7$) Calcd: m/z=475. Found: m/z=475. [M$_{g1}$+Cl]$^-$ ($C_{27}H_{40}O_7$Cl) Calcd: m/z=511. Found: m/z=511. [2M$_{g1}$–H]$^-$ ($C_{54}H_{79}O_{14}$) Calcd: m/z=951. Found: m/z=951.

[CBDg2–H] and [CBDg2+Acetic acid–H] MS data: LC/ESI-LRMS. [M$_{g2}$–H]$^-$($C_{33}H_{49}O_{12}$) Calcd: m/z=637. Found: m/z=637. [M$_{g2}$+Acetic acid–H]$^-$ ($C_{35}H_{53}O_{14}^-$) Calcd: m/z=697. Found: m/z=697.

[CBDg3–H], [CBDg3*OH–H] and [CBDg3*OH–2H] MS data: LC/ESI-LRMS. [M$_{g3}$–H]$^-$ ($C_{39}H_{59}O_{17}$) Calcd: m/z=799. Found: m/z=799. [M$_{g3*OH}$–H]$^-$ ($C_{39}H_{59}O_{18}$) Calcd: m/z=815. Found: m/z=815. [M$_{g3*OH}$–2H]$^{-2}$ ($C_{39}H_{58}O_{18}$) Calcd: m/z=407. Found: m/z=407.

Analysis of the large intestinal contents of animals administered oral CBD indicated that hydroxy metabolites of CBD were present:

[CBD*2OH+Formic acid–H] and [2CBD*3OH+Acetic acid–H] MS data: LC/ESI-LRMS. [M$_{2*OH}$+Formic acid–H]$^-$ ($C_{22}H_{31}O_6^-$) Calcd: m/z=391. Found: m/z=391. [2M$_{*3OH}$+Acetic acid–H]$^-$ ($C_{44}H_{63}O_{12}^-$) Calcd: m/z=783.9. Found: m/z=784.

The plasma and brains from the same animals were also extracted and analyzed by HPLC for the presence of CBD-glycosides and CBD. CBD was only present in the control animal that received CBD aglycone (data not shown). The contents of the small intestines from the same animals were also extracted and analyzed by HPLC for the presence of CBD-glycosides and CBD, but no CBD aglycone was present in the small intestines (data not shown, consistent with THC decoupling data shown in example 11). The presence of the CBD aglycone in the large intestinal contents indicates the successful delivery of CBD-glycosides, and the subsequent hydrolysis of the glycosides by beta-glycosidase enzymes only present in the large intestine. The presence of decoupled CBD in the large intestine, but not in the small intestine, indicates that glycoside decoupling only occurs upon transit to the large intestine. The presence of CBD detoxification metabolite CBD-2OH is also consistent with delivery of CBD and absorption into the intestinal epithelium where CBD begins to be metabolized. This example illustrates the potential to administer CBD-glycosides, safely transit the CBD-glycosides through the small intestine without absorption, transit to the large intestine where the sugars can be decoupled to release CBD locally, avoiding systemic absorption and delivery of the CBD to other tissues where it can have unwanted effects.

Example 11: Analysis of Large Intestine Contents Upon Administration of THC-Glycosides In order to investigate the metabolism and decoupling of THC-glycosides in the large intestine, an aqueous solution of a mixture of THC-glycosides was administered to two mice by oral gavage. The first animal was sacrificed at 2 hours and the second animal was sacrificed at 4 hours. Following termination and tissue harvest, the intestinal contents were then extracted and analyzed by C18 reverse phase HPLC. The mice employed in this example were eight week old male Swiss mice fasted for 12 hours prior to administration of the solutions.

The resulting extracts were analyzed by LCMS under the same conditions employed in Example 10.

Analysis of the large intestinal contents from mice administered THC glycosides after 2 hours indicated that both THC aglycone and THC glycosides were present, along with hydroxy metabolites of each:

[THC–H], [THC*OH–H], [2THC*3OH+Acetic acid–H] and [THC*2OH+Formic acid–H] MS data: LC/ESI-LRMS. [M–H]$^-$ ($C_{21}H_{29}O_2$) Calcd: m/z=313. Found: m/z=313. [M$_{*OH}$–H]$^-$ ($C_{21}H_{29}O_3$) Calcd: m/z=329. Found: m/z=329. [2M$_{*3OH}$+Acetic acid–H]$^-$ ($C_{44}H_{63}O_{12}^-$) Calcd: m/z=783.9. Found: m/z=783. [M$_{*2OH}$+Formic acid–H]$^-$ ($C_{22}H_{31}O_6^-$) Calcd: m/z=391. Found: m/z=391.

[THCg1+Cl], [THCg1+Acetic acid–H], [2THCg1–H], and [2THCg1+Acetic acid–H] MS data: LC/ESI-LRMS. [M$_{g1}$+Cl]$^-$ ($C_{27}H_{40}O_7Cl^-$) Calcd: m/z=511. Found: m/z=511. [M$_{g1}$+Acetic acid–H]$^-$ ($C_{29}H_{43}O_9^-$) Calcd: m/z=535. Found: m/z=535. [2M$_{g1}$–H]$^-$ ($C_{54}H_{79}O_{14}$) Calcd: m/z=951. Found: m/z=951. [2M$_{g1}$+Acetic acid–H]$^-$ ($C_{56}H_{83}O_{16}^-$) Calcd: m/z=1011. Found: m/z=1011.

[THCg2–H], [THCg2+Acetic acid–H] and [THCg2*OH+Formic acid–H] MS data: LC/ESI-LRMS. [M$_{g2}$–H]$^-$ ($C_{33}H_{49}O_{12}$) Calcd: m/z=637. Found: m/z=637. [M$_{g2}$+Acetic acid–H]$^-$ ($C_{35}H_{53}O_{14}$) Calcd: m/z=697. Found: m/z=697. [M$_{g2*OH}$+Acetic acid–H]$^-$ ($C_{34}H_{51}O_{15}^-$) Calcd: m/z=699. Found: m/z=699.

[THCg3–H], [THCg3+Acetic acid–H], [CBDg3*OH–H] and [CBDg3*OH–2H] MS data: LC/ESI-LRMS. [M$_{g3}$–H]$^-$ ($C_{39}H_{59}O_{17}$) Calcd: m/z=799. Found: m/z=799. [M$_{g3}$+Acetic acid–H]$^-$ ($C_{41}H_{63}O_{19}^-$) Calcd: m/z=859. Found: m/z=859. [M$_{g3*OH}$–H]$^-$ ($C_{39}H_{59}O_{18}^-$) Calcd: m/z=815. Found: m/z=815. [M$_{g3*OH}$–2H]$^{-2}$ ($C_{39}H_{58}O_{18}^{2-}$) Calcd: m/z=407. Found: m/z=407.

Analysis of the THC glycosides mixture extract after 4 hours indicated that both THC aglycone and THC glycosides were confirmed, along with hydroxy metabolites of each:

[THC–H], [THC*OH+Acetic acid–H], [2THC*3OH+Acetic acid–H] and [THC*2OH+Formic acid–H] MS data: LC/ESI-LRMS. [M–H]$^-$ ($C_{21}H_{29}O_2$) Calcd: m/z=313. Found: m/z=313. [M$_{*OH}$+Acetic acid–H]$^-$ ($C_{23}H_{33}O_5^-$) Calcd: m/z=389. Found: m/z=389. [2M$_{*3OH}$+Acetic acid–H]$^-$ ($C_{44}H_{63}O_{12}^-$) Calcd: m/z=783.9. Found: m/z=784. [M$_{*2OH}$+Formic acid–H]$^-$ ($C_{22}H_{31}O_6^-$) Calcd: m/z=391. Found: m/z=391.

[THCg1+Cl], [THCg1+Acetic acid–H], [2THCg1–H], and [2THCg1+Acetic acid–H] MS data: LC/ESI-LRMS. [M$_{g1}$+Cl]$^-$ ($C_{27}H_{40}O_7Cl^-$) Calcd: m/z=511. Found: m/z=511. [M$_{g1}$+Acetic acid–H]$^-$ ($C_{29}H_{43}O_9^-$) Calcd: m/z=535. Found: m/z=535. [2M$_{g1}$–H]$^-$ ($C_{54}H_{79}O_{14}$) Calcd: m/z=951. Found: m/z=951. [2M$_{g1}$+Acetic acid–H]$^-$ ($C_{56}H_{83}O_{16}^-$) Calcd: m/z=1011. Found: m/z=1011.

[THCg2–H] and [THCg2+Acetic acid–H] MS data: LC/ESI-LRMS. [M$_{g2}$–H]$^-$ ($C_{33}H_{43}O_{12}$) Calcd: m/z=637. Found: m/z=637. [M$_{g2}$+Acetic acid–H]$^-$ ($C_{35}H_{53}O_{14}^-$) Calcd: m/z=697. Found: m/z=697.

[THCg3–H], [THCg3+Acetic acid–H], [CBDg3*OH–H], [CBDg3*OH–2H] and [CBDg3*OH+Acetic acid–2H] MS data: LC/ESI-LRMS. [M$_{g3}$–H]$^-$ ($C_{33}H_{59}O_{17}$) Calcd: m/z=799. Found: m/z=799. [M$_{g3}$+Acetic acid–H]$^-$ ($C_{41}H_{63}O_{19}^-$) Calcd: m/z=859. Found: m/z=859. [M$_{g3*OH}$–H]$^-$ ($C_{33}H_{59}O_{18}^-$) Calcd: m/z=815. Found: m/z=815. [M$_{g3*OH}$–2H]$^{-2}$ ($C_{39}H_{58}O_{18}^{2-}$) Calcd: m/z=407. Found: m/z=407. [M$_{g3*OH}$+Acetic acid–2H]$^{-2}$ ($C_{41}H_{62}O_{20}^{2-}$) Calcd: m/z=467. Found: m/z=467.

The plasma and brains from the same animals were also extracted and analyzed by HPLC for the presence of THC-glycosides and THC, but neither compound was seen in these tissues (data not shown). The contents of the small intestines from the same animals were also extracted and analyzed by HPLC for the presence of THC-glycosides and THC, but no THC aglycone was observed (data not shown, consistent with CBD decoupling data shown in Example 10). The presence of the THC aglycone in the large intestinal contents at 2 and 4 hours indicates the successful delivery of THC-glycosides, and their subsequent hydrolysis of the glycosides by beta-glycosidases in the large intestine. The presence of decoupled THC in the large intestine, but not in the small intestine, indicates that glycoside decoupling only occurs upon transit to the large intestine. The presence of THC detoxification metabolites in the large intestine is further proof that the THC aglycone is present and being absorbed by the intestinal epithelium where it begins to be metabolized. This example illustrates the potential to administer THC-glycosides orally, transit the THC-glycosides through the small intestine without absorption, transit to the large intestine where the sugars can be decoupled to release THC locally, avoiding systemic absorption and delivery of the THC to the central nervous system where it can have unwanted psychoactivity.

Example 12: Discovery of Novel Sucrose Synthase Isoforms from *Stevia rebaudiana*

A number of research groups have utilized simple UDP to UDPG recycling systems to decrease the amount of UDPG needed for product formation (Hardin 2004, Bungarang 2013). These studies have characterized the primary sucrose synthase isoforms found in leaf tissue, which presumably carry out the synthesis of sucrose by reacting fructose with UDPG, producing sucrose and spent UDP.

As plants are known to contain numerous isoforms of the sucrose synthase enzyme, identification of alternative SUS enzymes from the *Stevia rebaudiana* plant with enhanced activity for the back reaction of UDP+sucrose→UDPG+fructose was carried out. As steviol glycosides occur at a high level in *Stevia* leaves, it was postulated that a sucrose synthase from the leaves of *Stevia* would have improved ability to catalyze the back reaction that recycles UDP to UDPG. Six sucrose synthase isoforms were identified within the *stevia* transcriptome, all having similar homology to the 6 isoforms found in *Arabidopsis thaliana* and named in conjunction with their homologues. These transcripts were cloned as described in materials and methods with the corresponding sequence ID information listed herein.

Enzymatic activities were tested and assayed for their ability to enhance UGT reactions with decreased UDPG input. The best isoform, SrSUS4, was capable of recycling UDP to UDPG with sucrose, in concert with the steviol 19-O-glucosyltransferase SrUGT74G1 mediated glycosylation of steviol bioside to stevioside.

Targeted mutagenesis was performed to mutate a serine residue at the N-terminus that is commonly phosphorylated in planta to prevent dimerization (Hardin 2004). SrSUS1-S13D mutants were created by mutating serine at position 13 to an aspartic acid residue (S13D), thus forming a phosphomimetic protein. Additionally, the creation of SrSus1-S13R, L141 was created to replace the serine with an arginine, a large charged residue, also to prevent dimerization and inactivation of the enzyme. Sucrose synthase mutants showed improved UDPG production activity compared to their native counterparts. SrSUS5 (SEQ ID NOs. 19 and 20) was identified in the *Stevia* transcriptome and primers designed (SEQ ID NOs. 67 and 68), but was not able to be amplified from cDNA. SrSus4 showed an impressive UDPG recycling activity with a 20% improvement over the activity seen in SrSus1. It is proposed that SrSus4 is the ideal isoform for carrying out the back reaction of converting of UDP to UDPG in the presence of sucrose. For midi-scale purification of cannabinoid glycosides the use of C18 flash chromatography columns were employed. Biotage flash C18 columns with 33 g of resin were washed, loaded, washed, and eluted using peristaltic pumps to achieve the similar separation and purification as the gravity fed Hypersep columns listed previously.

Relative activity for UDPG production with SUS isoforms is as follows:

SrSus4>SrSus1-Untagged>SrSus6>SrSus2>SrSus1>6xHis-SrSus1>SrSus3

Example 13: Improved In Vitro Catalysis of Cannabinoid-Glycosides

As the formation of cannabinoid glycosides via UGT enzyme requires the nucleotide sugar donor UDPG in stoichiometric amounts, it is advantageous to recycle or recapture the spent UDP following a glycosylation reaction. Utilizing the SUS4 isoform from *Stevia rebaudiana*, cannabinoid glycosides were successfully produced using only UMP as the input nucleotide.

A two step reaction took place, first to produce UDP from UMP, and second to produce UDPG from the UDP in tandem with the UGT reaction. First, a 5L reaction containing 50 mM $KPO_4$ pH7.2, 200 mM UMP disodium salt, 200 mM ATP disodium salt, 1M $MgCl_2$, 10% UMPK recombinant enzyme in 50% glycerol was prepared. The reaction was incubated at 28 C with stirring for >24 hours. The 5L reaction 1 was filtered at 0.45 microns to remove precipitate then applied to a 50L reaction containing 50 mM $KPO_4$ pH7.2, 50 mM $MgCl_2$, 300 mM Sucrose, 200 mg of CBD in 200 ml DMSO, 5L UGT76G1 in 50% glycerol, 2.5L SrSUS4 in 50% glycerol. The main 50L reaction was then mixed and allowed to react. An additional 200 mg of CBD in 200 ml DMSO was added after the reaction went to completion, and allowed to continue incubating at the same conditions. After the remaining CBD was consumed by the reaction, the mixture was filtered by tangential flow filtration with a ultrafiltration membrane at 5 kDa to remove enzymes and particulate, and then concentrated using nanofiltration membrane at 500 Da. The nanofiltration retentate containing the cannabosides was then applied to hydrated C18 flash columns, washed with 10-30% methanol, and eluted with 40-65% methanol. The eluate was then concentrated by rotary evaporation to remove all solvent, shell-frozen in a vacuum beaker and lyophilized to dryness. The powdered cannabosides produced were then collected and stored at −20 C in sealed vials. Sucrose should be sterile filtered to avoid carmelization or sugar breakdown, as autoclaving sucrose stock solutions greatly decreases reaction activity.

TABLE 1

Figure 1B:
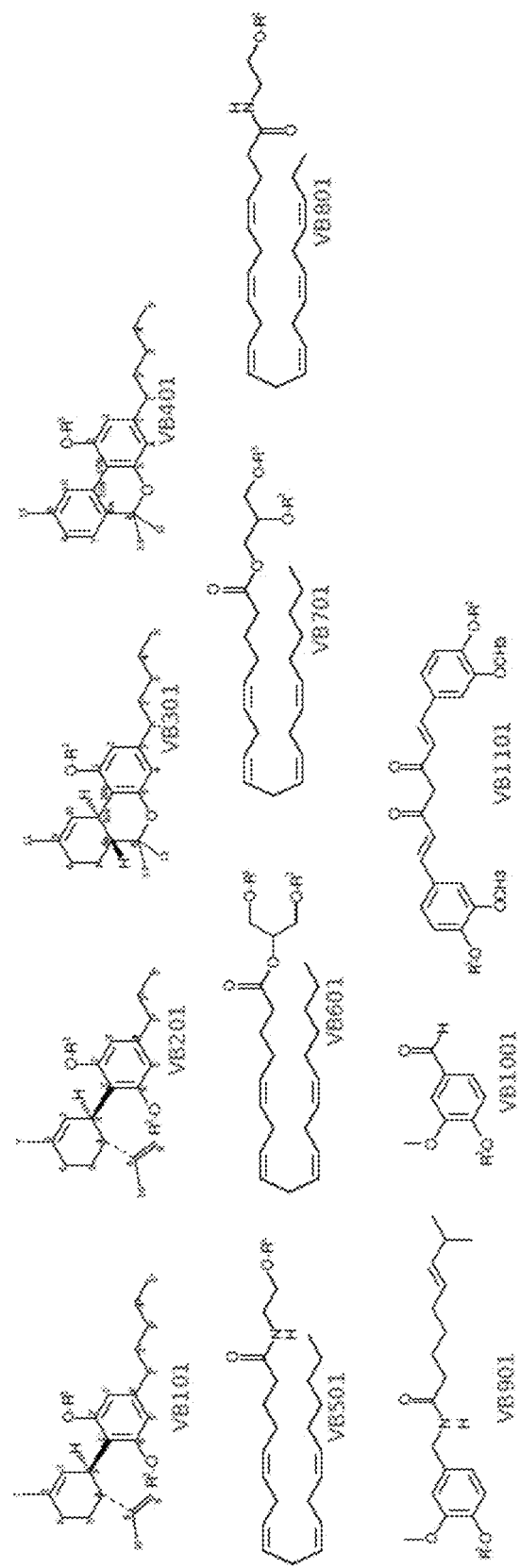
FIG. 1B illustrates the possible points of glycosylation on the aglycones.

Cannabidiol-glycoside compositions by R-group
R-group location is as depicted in FIG. 1B

| VB # | | 1° 1-O Position | 2° 2-O- | 2° 3-O- | 3° 3-O- | | | 1° Position | 2° 2-O- | 2° 3-O- |
|---|---|---|---|---|---|---|---|---|---|---|
| VB101 | R1 = | H | | | | R2 | = | H | | |
| VB102 | R1 = | β-D-glucose | H | | | R2 | = | H | | |
| VB103 | R1 = | β-D-glucose | β-D-glucose | | | R2 | = | H | | |
| VB104 | R1 = | β-D-glucose | H | β-D-glucose | | R2 | = | H | | |
| VB105 | R1 = | β-D-glucose | β-D-glucose | β-D-glucose | | R2 | = | H | | |
| VB106 | R1 = | H | | | | R2 | = | β-D-glucose | | |
| VB107 | R1 = | H | | | | R2 | = | β-D-glucose | β-D-glucose | |
| VB108 | R1 = | H | | | | R2 | = | β-D-glucose | H | β-D-glucose |
| VB109 | R1 = | H | | | | R2 | = | β-D-glucose | β-D-glucose | β-D-glucose |
| VB110 | R1 = | β-D-glucose | | | | R2 | = | β-D-glucose | | |
| VB111 | R1 = | β-D-glucose | β-D-glucose | | | R2 | = | β-D-glucose | | |
| VB112 | R1 = | β-D-glucose | H | β-D-glucose | | R2 | = | β-D-glucose | | |
| VB113 | R1 = | β-D-glucose | β-D-glucose | β-D-glucose | | R2 | = | β-D-glucose | | |
| VB114 | R1 = | β-D-glucose | | | | R2 | = | β-D-glucose | β-D-glucose | |
| VB115 | R1 = | β-D-glucose | β-D-glucose | | | R2 | = | β-D-glucose | β-D-glucose | |
| VB116 | R1 = | β-D-glucose | H | β-D-glucose | | R2 | = | β-D-glucose | β-D-glucose | |
| VB117 | R1 = | β-D-glucose | β-D-glucose | β-D-glucose | | R2 | = | β-D-glucose | β-D-glucose | |
| VB118 | R1 = | β-D-glucose | | | | R2 | = | β-D-glucose | H | β-D-glucose |
| VB119 | R1 = | β-D-glucose | H | β-D-glucose | | R2 | = | β-D-glucose | H | β-D-glucose |
| VB120 | R1 = | β-D-glucose | β-D-glucose | | | R2 | = | β-D-glucose | H | β-D-glucose |
| VB121 | R1 = | β-D-glucose | β-D-glucose | β-D-glucose | | R2 | = | β-D-glucose | H | β-D-glucose |
| VB122 | R1 = | β-D-glucose | | | | R2 | = | β-D-glucose | β-D-glucose | β-D-glucose |
| VB123 | R1 = | β-D-glucose | β-D-glucose | | | R2 | = | β-D-glucose | β-D-glucose | β-D-glucose |
| VB124 | R1 = | β-D-glucose | H | β-D-glucose | | R2 | = | β-D-glucose | β-D-glucose | β-D-glucose |
| VB125 | R1 = | β-D-glucose | β-D-glucose | β-D-glucose | | R2 | = | β-D-glucose | β-D-glucose | β-D-glucose |
| VB126 | R1 = | α-D-glucose | | | | R2 | = | H | | |
| VB127 | R1 = | H | | | | R2 | = | α-D-glucose | | |
| VB128 | R1 = | α-D-glucose | | | | R2 | = | α-D-glucose | | |
| VB129 | R1 = | β-D-glucose | α-D-glucose | | | R2 | = | H | | |
| VB130 | R1 = | H | | | | R2 | = | β-D-glucose | α-D-glucose | |
| VB131 | R1 = | β-D-glucose | α-D-glucose | | | R2 | = | β-D-glucose | α-D-glucose | |
| VB132 | R1 = | β-D-glucose | | β-D-glucose | β-D-glucose | R2 | = | H | | |
| VB133 | R1 = | H | | | | R2 | = | β-D-glucose | H | β-D-glucose |
| VB134 | R1 = | β-D-glucose | H | β-D-glucose | β-D-glucose | R2 | = | β-D-glucose | H | β-D-glucose |

| VB # | 3° 3-O- | Name | | 1° Enzyme | 2° Enzyme |
|---|---|---|---|---|---|
| VB101 | | Cannabidiol (CBD) | | | |
| VB102 | | CBD-1-O-glucopyranoside | | UGT76G1 | |
| VB103 | | CBD-1-O-(2-1)-diglucopyranoside | | UGT76G1 | Os03g0702000 |

TABLE 1-continued

Cannabidiol-glycoside compositions by R-group
R-group location is as depicted in FIG. 1B

| | | |
|---|---|---|
| VB104 | CBD-1-O-(3-1)-diglucopyranoside | UGT76G1 |
| VB105 | CBD-1-O-(2-1,3-1)-triglucopyranoside | UGT76G1 Os03g0702000 |
| VB106 | CBD-2-O-glucopyranoside | UGT76G1 Os03g0702000 |
| VB107 | CBD-2-O-(2-1)-diglucopyranoside | UGT76G1 Os03g0702000 |
| VB108 | CBD-2-O-(3-1)-diglucopyranoside | UGT76G1 |
| VB109 | CBD-1-O-(2-1,3-1)-triglucopyranoside | UGT76G1 Os03g0702000 |
| VB110 | CBD-1,2-O-diglucopyranoside | UGT76G1 |
| VB111 | CBD-1-O-(2-1),2-O-triglucopyranoside | UGT76G1 Os03g0702000 |
| VB112 | CBD-1-O-(3-1),2-O-triglucopyranoside | UGT76G1 |
| VB113 | CBD-1-O-(2-1,3-1),2-O-tetraglucopyranoside | UGT76G1 Os03g0702000 |
| VB114 | CBD-1-O,2-O-(2-1)-triglucopyranoside | UGT76G1 Os03g0702000 |
| VB115 | CBD-1-O-(2-1),2-O-(2-1)-tetraglucopyranoside | UGT76G1 Os03g0702000 |
| VB116 | CBD-1-O-(3-1),2-O-(2-1)-tetraglucopyranoside | UGT76G1 Os03g0702000 |
| VB117 | CBD-1-O-(2-1,3-1),2-O-(2-1)-pentaglucopyranoside | UGT76G1 Os03g0702000 |
| VB118 | CBD-1-O,2-O-(3-1)-triglucopyranoside | UGT76G1 |
| VB119 | CBD-1-O-(3-1),2-O-(3-1)-tetraglucopyranoside | UGT76G1 |
| VB120 | CBD-1-O-(2-1),2-O-(3-1)-tetraglucopyranoside | UGT76G1 Os03g0702000 |
| VB121 | CBD-1-O-(2-1,3-1), 2-O-(3-1)-pentaglucopyranoside | UGT76G1 Os03g0702000 |
| VB122 | CBD-1-O,2-O-(2-1,3-1)-tetraglucopyranoside | UGT76G1 Os03g0702000 |
| VB123 | CBD-1-O-(2-1),2-O-(2-1,3-1)-pentaglucopyranoside | UGT76G1 Os03g0702000 |
| VB124 | CBD-1-O-(3-1),2-O-(2-1,3-1)-pentaglucopyranoside | UGT76G1 Os03g0702000 |
| VB125 | CBD-1-O-(2-1,3-1),2-O-(2-1,3-1)-hexaglucopyranoside | UGT76G1 Os03g0702000 |
| VB126 | CBD-1-O-α-glucopyranoside | CGTase |
| VB127 | CBD-2-O-α-glucopyranoside | CGTase |
| VB128 | CBD-1,2-O-α-glucopyranoside | CGTase |
| VB129 | CBD-1-O-β-primed-α-diglucopyranoside | UGT76G1 CGTase |
| VB130 | CBD-2-O-β-primed-α-diglucopyranoside | UGT76G1 CGTase |
| VB131 | CBD-1,2-O-β-primed-α-diglucopyranoside | UGT76G1 CGTase |
| VB132 | CBD-1-O-(3-1,3-1)-triglucopyranoside | UGT76G1 |
| VB133 β-D-glucose | CBD-2-O-(3-1,3-1)-triglucopyranoside | UGT76G1 |
| VB134 β-D-glucose | CBD-1,2-O-(3-1,3-1)-hexaglucopyranoside | UGT76G1 |

TABLE 2

Cannabidivarin-glycoside compositions by R-group
R-group location is as depicted in FIG. 1B

| VB # | | 1° 1-O Position | 2° 2-O- | 2° 3-O- | 3° 3-O- | | | 1° Position | 2° 2-O- | 2° 3-O- |
|---|---|---|---|---|---|---|---|---|---|---|
| VB201 | R1 = | H | | | | R2 | = | H | | |
| VB202 | R1 = | β-D-glucose | | | | R2 | = | H | | |
| VB203 | R1 = | β-D-glucose | β-D-glucose | | | R2 | = | H | | |
| VB204 | R1 = | β-D-glucose | H | β-D-glucose | | R2 | = | H | | |
| VB205 | R1 = | β-D-glucose | β-D-glucose | β-D-glucose | | R2 | = | H | | |
| VB206 | R1 = | H | | | | R2 | = | β-D-glucose | | |
| VB207 | R1 = | H | | | | R2 | = | β-D-glucose | β-D-glucose | |
| VB208 | R1 = | H | | | | R2 | = | β-D-glucose | H | β-D-glucose |
| VB209 | R1 = | H | | | | R2 | = | β-D-glucose | β-D-glucose | β-D-glucose |
| VB210 | R1 = | β-D-glucose | | | | R2 | = | β-D-glucose | | |
| VB211 | R1 = | β-D-glucose | β-D-glucose | | | R2 | = | β-D-glucose | | |
| VB212 | R1 = | β-D-glucose | H | β-D-glucose | | R2 | = | β-D-glucose | | |
| VB213 | R1 = | β-D-glucose | β-D-glucose | β-D-glucose | | R2 | = | β-D-glucose | | |
| VB214 | R1 = | β-D-glucose | | | | R2 | = | β-D-glucose | β-D-glucose | |
| VB215 | R1 = | β-D-glucose | β-D-glucose | | | R2 | = | β-D-glucose | β-D-glucose | |
| VB216 | R1 = | β-D-glucose | H | β-D-glucose | | R2 | = | β-D-glucose | β-D-glucose | |
| VB217 | R1 = | β-D-glucose | β-D-glucose | β-D-glucose | | R2 | = | β-D-glucose | β-D-glucose | |
| VB218 | R1 = | β-D-glucose | | | | R2 | = | β-D-glucose | H | β-D-glucose |
| VB219 | R1 = | β-D-glucose | H | β-D-glucose | | R2 | = | β-D-glucose | H | β-D-glucose |
| VB220 | R1 = | β-D-glucose | β-D-glucose | | | R2 | = | β-D-glucose | H | β-D-glucose |
| VB221 | R1 = | β-D-glucose | β-D-glucose | β-D-glucose | | R2 | = | β-D-glucose | H | β-D-glucose |
| VB222 | R1 = | β-D-glucose | | | | R2 | = | β-D-glucose | β-D-glucose | β-D-glucose |
| VB223 | R1 = | β-D-glucose | β-D-glucose | | | R2 | = | β-D-glucose | β-D-glucose | β-D-glucose |
| VB224 | R1 = | β-D-glucose | H | β-D-glucose | | R2 | = | β-D-glucose | β-D-glucose | β-D-glucose |
| VB225 | R1 = | β-D-glucose | β-D-glucose | β-D-glucose | | R2 | = | β-D-glucose | β-D-glucose | β-D-glucose |
| VB226 | R1 = | α-D-glucose | | | | R2 | = | H | | |
| VB227 | R1 = | H | | | | R2 | = | α-D-glucose | | |
| VB228 | R1 = | α-D-glucose | | | | R2 | = | α-D-glucose | | |
| VB229 | R1 = | β-D-glucose | α-D-glucose | | | R2 | = | H | | |
| VB230 | R1 = | H | | | | R2 | = | β-D-glucose | α-D-glucose | |
| VB231 | R1 = | β-D-glucose | α-D-glucose | | | R2 | = | β-D-glucose | α-D-glucose | |
| VB232 | R1 = | β-D-glucose | H | β-D-glucose | β-D-glucose | R2 | = | H | | |
| VB233 | R1 = | H | | | | R2 | = | β-D-glucose | H | β-D-glucose |
| VB234 | R1 = | β-D-glucose | H | β-D-glucose | β-D-glucose | R2 | = | β-D-glucose | H | β-D-glucose |

TABLE 2-continued

Cannabidivarin-glycoside compositions by R-group
R-group location is as depicted in FIG. 1B

| VB # | 3° 3-O- | Name | 1° Enzyme | 2° Enzyme |
|---|---|---|---|---|
| VB201 | | Cannabidiol (CBDV) | | |
| VB202 | | CBDV-1-O-glucopyranoside | UGT76G1 | |
| VB203 | | CBDV-1-O-(2-1)-diglucopyranoside | UGT76G1 | Os03g0702000 |
| VB204 | | CBDV-1-O-(3-1)-diglucopyranoside | UGT76G1 | |
| VB205 | | CBDV-1-O-(2-1,3-1)-triglucopyranoside | UGT76G1 | Os03g0702000 |
| VB206 | | CBDV-2-O-glucopyranoside | UGT76G1 | |
| VB207 | | CBDV-2-O-(2-1)-diglucopyranoside | UGT76G1 | Os03g0702000 |
| VB208 | | CBDV-2-O-(3-1)-diglucopyranoside | UGT76G1 | |
| VB209 | | CBDV-1-O-(2-1,3-1)-triglucopyranoside | UGT76G1 | Os03g0702000 |
| VB210 | | CBDV-1,2-O-diglucopyranoside | UGT76G1 | |
| VB211 | | CBDV-1-O-(2-1),2-O-triglucopyranoside | UGT76G1 | Os03g0702000 |
| VB212 | | CBDV-1-O-(3-1),2-O-triglucopyranoside | UGT76G1 | |
| VB213 | | CBDV-1-O-(2-1,3-1),2-O-tetraglucopyranoside | UGT76G1 | Os03g0702000 |
| VB214 | | CBDV-1-O,2-O-(2-1)-triglucopyranoside | UGT76G1 | Os03g0702000 |
| VB215 | | CBDV-1-O-(2-1),2-O-(2-1)-tetraglucopyranoside | UGT76G1 | Os03g0702000 |
| VB216 | | CBDV-1-O-(3-1),2-O-(2-1)-tetraglucopyranoside | UGT76G1 | Os03g0702000 |
| VB217 | | CBDV-1-O-(2-1,3-1),2-O-(2-1)-pentaglucopyranoside | UGT76G1 | Os03g0702000 |
| VB218 | | CBDV-1-O,2-O-(3-1)-triglucopyranoside | UGT76G1 | |
| VB219 | | CBDV-1-O-(3-1),2-O-(3-1)-tetraglucopyranoside | UGT76G1 | |
| VB220 | | CBDV-1-O-(2-1),2-O-(3-1)-tetraglucopyranoside | UGT76G1 | Os03g0702000 |
| VB221 | | CBDV-1-O-(2-1,3-1), 2-O-(3-1)-pentaglucopyranoside | UGT76G1 | Os03g0702000 |
| VB222 | | CBDV-1-O,2-O-(2-1,3-1)-tetraglucopyranoside | UGT76G1 | Os03g0702000 |
| VB223 | | CBDV-1-O-(2-1),2-O-(2-1,3-1)-pentaglucopyranoside | UGT76G1 | Os03g0702000 |
| VB224 | | CBDV-1-O-(3-1),2-O-(2-1,3-1)-pentaglucopyranoside | UGT76G1 | Os03g0702000 |
| VB225 | | CBDV-1-O-(2-1,3-1),2-O-(2-1,3-1)-hexaglucopyranoside | UGT76G1 | Os03g0702000 |
| VB226 | | CBDV-1-O-α-glucopyranoside | CGTase | |
| VB227 | | CBDV-2-O-α-glucopyranoside | CGTase | |
| VB228 | | CBDV-1,2-O-α-glucopyranoside | CGTase | |
| VB229 | | CBDV-1-O-β-primed-α-diglucopyranoside | UGT76G1 | CGTase |
| VB230 | | CBDV-2-O-β-primed-α-diglucopyranoside | UGT76G1 | CGTase |
| VB231 | | CBDV-1,2-O-β-primed-α-diglucopyranoside | UGT76G1 | CGTase |
| VB232 | | CBDV-1-O-(3-1,3-1)-triglucopyranoside | UGT76G1 | |
| VB233 | β-D-glucose | CBDV-2-O-(3-1,3-1)-triglucopyranoside | UGT76G1 | |
| VB234 | β-D-glucose | CBDV-1,2-O-(3-1,3-1)-hexaglucopyranoside | UGT76G1 | |

TABLE 3

Δ9-Tetrahydrocannabinol-glycoside compositions by R-group
R-group location is as depicted in FIG. 1B

| VB# | | 1° 1-O Position | 2° 2-O- | 2° 3-O- | 3° 3-O- | Name | 1° Enzyme | 2° Enzyme |
|---|---|---|---|---|---|---|---|---|
| VB301 | R1 = | H | | | | Δ9-Tetrahydrocannabinol | | |
| VB302 | R1 = | β-D-glucose | | | | Δ9THC-1-O-glucopyranoside | UGT76G1 | |
| VB303 | R1 = | β-D-glucose | β-D-glucose | | | Δ9THC-1-O-(2-1)-diglucopyranoside | UGT76G1 | Os03g0702000 |
| VB304 | R1 = | β-D-glucose | H | β-D-glucose | | Δ9THC-1-O-(3-1)-diglucopyranoside | UGT76G1 | |
| VB305 | R1 = | β-D-glucose | β-D-glucose | β-D-glucose | | Δ9THC-1-O-(2-1,3-1)-triglucopyranoside | UGT76G1 | Os03g0702000 |
| VB306 | R1 = | α-D-glucose | | | | Δ9THC-1-O-α-glucopyranoside | CGTase | |
| VB307 | R1 = | β-D-glucose | α-D-glucose | | | Δ9THC-1-O-β-primed-α-diglucopyranoside | UGT76G1 | CGTase |
| VB308 | R1 = | β-D-glucose | H | β-D-glucose | β-D-glucose | Δ9THC-1-O-(3-1,3-1)-triglucopyranoside | UGT76G1 | |

TABLE 4

Cannabinol-glycoside compositions by R-group
R-group location is as depicted in FIG. 1B

| VB# | | 1° 1-O Position | 2° 2-O- | 2° 3-O- | 3° 3-O- | Name | 1° Enzyme | 2° Enzyme |
|---|---|---|---|---|---|---|---|---|
| VB401 | R1 = | H | | | | Cannabinol | | |
| VB402 | R1 = | β-D-glucose | | | | CBN-1-O-glucopyranoside | UGT76G1 | |
| VB403 | R1 = | β-D-glucose | β-D-glucose | | | CBN-1-O-(2-1)-diglucopyranoside | UGT76G1 | Os03g0702000 |
| VB404 | R1 = | β-D-glucose | H | β-D-glucose | | CBN-1-O-(3-1)-diglucopyranoside | UGT76G1 | |

TABLE 4-continued

Cannabinol-glycoside compositions by R-group
R-group location is as depicted in FIG. 1B

| VB# | | 1° 1-O Position | 2° 2-O- | 2° 3-O- | 3° 3-O- | Name | 1° Enzyme | 2° Enzyme |
|---|---|---|---|---|---|---|---|---|
| VB405 | R1 = | β-D-glucose | β-D-glucose | β-D-glucose | | CBN-1-O-(2-1,3-1)-triglucopyranoside | UGT76G1 | Os03g0702000 |
| VB406 | R1 = | α-D-glucose | | | | CBN-1-O-α-glucopyranoside | CGTase | |
| VB407 | R1 = | β-D-glucose | α-D-glucose | | | CBN-1-O-β-primed-α-diglucopyranoside | UGT76G1 | CGTase |
| VB408 | R1 = | β-D-glucose | H | β-D-glucose | β-D-glucose | CBN-1-O-(3-1,3-1)-triglucopyranoside | UGT76G1 | |

TABLE 5

Anandamide (AEA) glycoside Compositions by R-group
R-group location is as depicted in FIG. 1B

| VB# | | 1° 1-O Position | 2° 2-O- | 2° 3-O- | 3° 3-O- | Name | 1° Enzyme | 2° Enzyme |
|---|---|---|---|---|---|---|---|---|
| VB501 | R1 = | H | | | | Anandamide (AEA) | | |
| VB502 | R1 = | β-D-glucose | | | | AEA-1-O-glucopyranoside | UGT76G1 | |
| VB503 | R1 = | β-D-glucose | H | β-D-glucose | | AEA-1-O-(3-1)-diglucopyranoside | UGT76G1 | |
| VB504 | R1 = | β-D-glucose | β-D-glucose | | | AEA-1-O-(2-1)-diglucopyranoside | UGT76G1 | Os03g0702000 |
| VB505 | R1 = | β-D-glucose | H | β-D-glucose | β-D-glucose | AEA-1-O-(3-1,3-1)-triglucopyranoside | UGT76G1 | |
| VB506 | R1 = | β-D-glucose | β-D-glucose | β-D-glucose | | AEA-1-O-(3-1,2-1)-triglucopyranoside | UGT76G1 | Os03g0702000 |
| VB507 | R1 = | α-D-glucose | | | | AEA-1-O-α-glucopyranoside | CGTase | |
| VB508 | R1 = | β-D-glucose | α-D-glucose | | | AEA-1-O-β-primed-α-diglucopyranoside | UGT76G1 | CGTase |

TABLE 6

2-Arachidonoylglycerol (2-AG)-glycoside compositions by R-group
R-group location is as depicted in FIG. 1B

| VB# | | 1° 1-O Position | 2° 2-O- | 2° 3-O- | 3° 3-O- | | 2° Position | 2° 2-O- | 2° 3-O- |
|---|---|---|---|---|---|---|---|---|---|
| VB601 | R1 = | H | | | | R2 = | H | | |
| VB602 | R1 = | β-D-glucose | | | | R2 = | H | | |
| VB603 | R1 = | H | | | | R2 = | β-D-glucose | | |
| VB604 | R1 = | β-D-glucose | β-D-glucose | | | R2 = | H | | |
| VB605 | R1 = | β-D-glucose | H | B-D-glucose | | R2 = | H | | |
| VB606 | R1 = | H | | | | R2 = | β-D-glucose | β-D-glucose | |
| VB607 | R1 = | H | | | | R2 = | β-D-glucose | H | B-D-glucose |
| VB608 | R1 = | β-D-glucose | | | | R2 = | β-D-glucose | | |
| VB609 | R1 = | β-D-glucose | | | | R2 = | β-D-glucose | H | β-D-glucose |
| VB610 | R1 = | β-D-glucose | H | β-D-glucose | | R2 = | β-D-glucose | | |
| VB611 | R1 = | β-D-glucose | | | | R2 = | β-D-glucose | β-D-glucose | |
| VB612 | R1 = | β-D-glucose | H | β-D-glucose | β-D-glucose | R2 = | β-D-glucose | | |
| VB613 | R1 = | H | | | | R2 = | β-D-glucose | H | β-D-glucose |
| VB614 | R1 = | β-D-glucose | β-D-glucose | | | R2 = | β-D-glucose | | |
| VB615 | R1 = | β-D-glucose | H | β-D-glucose | | R2 = | β-D-glucose | H | β-D-glucose |
| VB616 | R1 = | β-D-glucose | β-D-glucose | | | R2 = | β-D-glucose | H | β-D-glucose |
| VB617 | R1 = | β-D-glucose | H | β-D-glucose | | R2 = | β-D-glucose | β-D-glucose | |
| VB618 | R1 = | β-D-glucose | β-D-glucose | | | R2 = | β-D-glucose | β-D-glucose | |
| VB619 | R1 = | α-D-glucose | | | | R2 = | H | | |
| VB620 | R1 = | β-D-glucose | α-D-glucose | | | R2 = | H | | |
| VB621 | R1 = | H | | | | R2 = | α-D-glucose | | |
| VB622 | R1 = | H | | | | R2 = | β-D-glucose | α-D-glucose | |
| VB623 | R1 = | α-D-glucose | | | | R2 = | α-D-glucose | | |

| VB# | 3° 3-O- | Name | 1° Enzyme | 2° Enzyme |
|---|---|---|---|---|
| VB601 | | 2-Arachidonoylglycerol (2-AG) | | |
| VB602 | | 2-AG-1-O-glucopyranoside | UGT76G1 | |
| VB603 | | 2-AG-2-O-glucopyranoside | UGT76G1 | |
| VB604 | | 2-AG-1-O-(3-1)-diglucopyranoside | UGT76G1 | |
| VB605 | | 2-AG-1-O-(2-1)-diglucopyranoside | UGT76G1 | Os03g0702000 |
| VB606 | | 2-AG-2-O-(3-1)-diglucopyranoside | UGT76G1 | |
| VB607 | | 2-AG-2-O-(2-1)-diglucopyranoside | UGT76G1 | Os03g0702000 |
| VB608 | | 2-AG-1-O,2-O-diglucopyranoside | UGT76G1 | |
| VB609 | | 2-AG-1-O, 2-O-(3-1)-triglucopyranoside | UGT76G1 | |
| VB610 | | 2-AG-1-O-(3-1), 2-O-triglucopyranoside | UGT76G1 | |

TABLE 6-continued

2-Arachidonoylglycerol (2-AG)-glycoside compositions by R-group
R-group location is as depicted in FIG. 1B

| VB# | | Name | 1° Enzyme | 2° Enzyme |
|---|---|---|---|---|
| VB611 | | 2-AG-1-O,2-O-(2-1)-triglucopyranoside | UGT76G1 | |
| VB612 | | 2-AG-1-O-(3-1, 3-1)-triglucopyranoside | UGT76G1 | |
| VB613 | β-D-glucose | 2-AG-2-O-(3-1, 3-1)-triglucopyranoside | UGT76G1 | |
| VB614 | | 2-AG-1-O-(2-1), 2-O-triglucopyranoside | UGT76G1 | Os03g0702000 |
| VB615 | | 2-AG-1-O-(3-1), 2-O-(3-1)-tetraglucopyranoside | UGT76G1 | |
| VB616 | | 2-AG-1-O-(2-1), 2-O-(3-1)-tetraglucopyranoside | UGT76G1 | Os03g0702000 |
| VB617 | | 2-AG-1-O-(3-1), 2-O-(2-1)-tetraglucopyranoside | UGT76G1 | Os03g0702000 |
| VB618 | | 2-AG-1-O-(2-1), 2-O-(2-1)-tetraglucopyranoside | UGT76G1 | Os03g0702000 |
| VB619 | | 2-AG-1-O-α-glucopyranoside | CGTase | |
| VB620 | | 2-AG-1-O-β-primed-α-diglucopyranoside | UGT76G1 | CGTase |
| VB621 | | 2-AG-2-O-α-glucopyranoside | CGTase | |
| VB622 | | 2-AG-2-O-β-primed-α-diglucopyranoside | UGT76G1 | CGTase |
| VB623 | | 2-AG-1,2-O-α-diglucopyranoside | CGTase | |

TABLE 7

1-Arachidonoylglycerol (1-AG)-glycoside compositions by R-group
R-group location is as depicted in FIG. 1B

| VB# | | 1° 1-O Position | 2° 2-O- | 2° 3-O- | 3° 3-O- | | | 2° Position | 2° 2-O- | 2° 3-O- |
|---|---|---|---|---|---|---|---|---|---|---|
| VB701 | R1 = | H | | | | R2 | = | H | | |
| VB702 | R1 = | β-D-glucose | | | | R2 | = | H | | |
| VB703 | R1 = | H | | | | R2 | = | β-D-glucose | | |
| VB704 | R1 = | β-D-glucose | β-D-glucose | | | R2 | = | H | | |
| VB705 | R1 = | β-D-glucose | H | B-D-glucose | | R2 | = | H | | |
| VB706 | R1 = | H | | | | R2 | = | β-D-glucose | β-D-glucose | |
| VB707 | R1 = | H | | | | R2 | = | β-D-glucose | H | B-D-glucose |
| VB708 | R1 = | β-D-glucose | | | | R2 | = | β-D-glucose | | |
| VB709 | R1 = | β-D-glucose | | | | R2 | = | β-D-glucose | H | β-D-glucose |
| VB710 | R1 = | β-D-glucose | H | β-D-glucose | | R2 | = | β-D-glucose | | |
| VB711 | R1 = | β-D-glucose | | | | R2 | = | β-D-glucose | β-D-glucose | |
| VB712 | R1 = | β-D-glucose | β-D-glucose | | | R2 | = | β-D-glucose | | |
| VB713 | R1 = | β-D-glucose | H | β-D-glucose | β-D-glucose | R2 | = | H | | |
| VB714 | R1 = | H | | | | R2 | = | β-D-glucose | H | β-D-glucose |
| VB715 | R1 = | β-D-glucose | | β-D-glucose | | R2 | = | β-D-glucose | H | β-D-glucose |
| VB716 | R1 = | β-D-glucose | β-D-glucose | | | R2 | = | β-D-glucose | H | β-D-glucose |
| VB717 | R1 = | β-D-glucose | H | β-D-glucose | | R2 | = | β-D-glucose | β-D-glucose | |
| VB718 | R1 = | β-D-glucose | β-D-glucose | | | R2 | = | β-D-glucose | β-D-glucose | |
| VB719 | R1 = | α-D-glucose | | | | R2 | = | H | | |
| VB720 | R1 = | β-D-glucose | α-D-glucose | | | R2 | = | H | | |
| VB721 | R1 = | H | | | | R2 | = | α-D-glucose | | |
| VB722 | R1 = | H | | | | R2 | = | β-D-glucose | α-D-glucose | |
| VB723 | R1 = | α-D-glucose | | | | R2 | = | α-D-glucose | | |

| VB# | 3° 3-O- | Name | 1° Enzyme | 2° Enzyme |
|---|---|---|---|---|
| VB701 | | 1-Arachidonoylglycerol (1-AG) | | |
| VB702 | | 1-AG-1-O-glucopyranoside | UGT76G1 | |
| VB703 | | 1-AG-2-O-glucopyranoside | UGT76G1 | |
| VB704 | | 1-AG-1-O-(2-1)-diglucopyranoside | UGT76G1 | |
| VB705 | | 1-AG-1-O-(3-1)-diglucopyranoside | UGT76G1 | Os03g0702000 |
| VB706 | | 1-AG-2-O-(2-1)-diglucopyranoside | UGT76G1 | |
| VB707 | | 1-AG-2-O-(3-1)-diglucopyranoside | UGT76G1 | Os03g0702000 |
| VB708 | | 1-AG-1-O,2-O-diglucopyranoside | UGT76G1 | |
| VB709 | | 1-AG-1-O, 2-O-(3-1)-triglucopyranoside | UGT76G1 | |
| VB710 | | 1-AG-1-O-(3-1), 2-O-triglucopyranoside | UGT76G1 | |
| VB711 | | 1-AG-1-O, 2O-(2-1)-triglucopyranoside | UGT76G1 | Os03g0702000 |
| VB712 | | 1-AG-1-O-(2-1), 2-O-triglucopyranoside | UGT76G1 | Os03g0702000 |
| VB713 | | 1-AG-1-O-(3-1, 3-1)-triglucopyranoside | UGT76G1 | |
| VB714 | β-D-glucose | 1-AG-2-O-(3-1, 3-1)-triglucopyranoside | UGT76G1 | |
| VB715 | | 1-AG-1-O-(3-1), 2-O-(3-1)-tetraglucopyranoside | UGT76G1 | |
| VB716 | | 1-AG-1-O-(2-1), 2-O-(3-1)-tetraglucopyranoside | UGT76G1 | Os03g0702000 |
| VB717 | | 1-AG-1-O-(3-1), 2-O-(2-1)-tetraglucopyranoside | UGT76G1 | Os03g0702000 |
| VB718 | | 1-AG-1-O-(2-1), 2-O-(2-1)-tetraglucopyranoside | UGT76G1 | Os03g0702000 |
| VB719 | | 1-AG-1-O-α-glucopyranoside | CGTase | |
| VB720 | | 1-AG-1-O-β-primed-α-diglucopyranoside | UGT76G1 | CGTase |
| VB721 | | 1-AG-2-O-α-glucopyranoside | CGTase | |
| VB722 | | 1-AG-2-O-β-primed-α-diglucopyranoside | UGT76G1 | CGTase |
| VB723 | | 1-AG-1,2-O-α-diglucopyranoside | CGTase | |

TABLE 8

Docosahaenoyl ethanoloamide (DHEA) glycoside compositions by R-group
R-group location is as depicted in FIG. 1B

| VB# | | 1° 1-O Position | 2° 2-O- | 2° 3-O- | 3° 3-O- | Name | 1° Enzyme | 2° Enzyme |
|---|---|---|---|---|---|---|---|---|
| VB801 | R1 = | H | | | | Docosahexaenoyl ethanoloamide (DHEA) | | |
| VB802 | R1 = | β-D-glucose | | | | DHEA-1-O-glucopyranoside | UGT76G1 | |
| VB803 | R1 = | β-D-glucose | H | β-D-glucose | | DHEA-1-O-(3-1)-diglucopyranoside | UGT76G1 | |
| VB804 | R1 = | β-D-glucose | β-D-glucose | | | DHEA-1-O-(2-1)-diglucopyranoside | UGT76G1 | Os03g0702000 |
| VB805 | R1 = | β-D-glucose | H | β-D-glucose | β-D-glucose | DHEA-1-O-(3-1,3-1)-triglucopyranoside | UGT76G1 | |
| VB806 | R1 = | α-D-glucose | β-D-glucose | β-D-glucose | | DHEA-1-O-(3-1,2-1)-triglucopyranoside | UGT76G1 | Os03g0702000 |
| VB807 | R1 = | α-D-glucose | | | | DHEA-1-O-α-glucopyranoside | CGTase | |
| VB808 | R1 = | β-D-glucose | α-D-glucose | | | DHEA-1-O-β-primed-α-diglucopyranoside | UGT76G1 | CGTase |

TABLE 9

Capsiacin glycoside compositions by R-group
R-group location is as depicted in FIG. 1B

| VB# | | 1° 1-O Position | 2° 2-O- | 2° 3-O- | 3° 3-O- | Name | 1° Enzyme | 2° Enzyme |
|---|---|---|---|---|---|---|---|---|
| VB901 | R1 = | H | | | | Capsaicin | | |
| VB902 | R1 = | β-D-glucose | | | | Capsaicin-1-O-glucopyranoside | UGT76G1 | |
| VB903 | R1 = | β-D-glucose | H | β-D-glucose | | Capsaicin-1-O-(3-1)-diglucopyranoside | UGT76G1 | |
| VB904 | R1 = | β-D-glucose | β-D-glucose | | | Capsaicin-1-O-(2-1)-diglucopyranoside | UGT76G1 | Os03g0702000 |
| VB905 | R1 = | β-D-glucose | H | β-D-glucose | β-D-glucose | Capsaicin-1-O-(3-1, 3-1)-triglucopyranoside | UGT76G1 | |
| VB906 | R1 = | β-D-glucose | β-D-glucose | β-D-glucose | | Capsaicin-1-O-(2-1,3-1)-triglucopyranoside | UGT76G1 | Os03g0702000 |
| VB907 | R1 = | α-D-glucose | | | | Capsiacin-1-O-α-glucopyranoside | CGTase | |
| VB908 | R1 = | β-D-glucose | α-D-glucose | | | Capsiacin-1-O-β-primed-α-diglucopyranoside | UGT76G1 | CGTase |

TABLE 10

Vanillin glycoside compositions by R-group
R-group location is as depicted in FIG. 1B

| VB# | | 1° 1-O Position | 2° 2-O- | 2° 3-O- | 3° 3-O- | Name | 1° Enzyme | 2° Enzyme |
|---|---|---|---|---|---|---|---|---|
| VB1001 | R1 = | H | | | | Vanillin | | |
| VB1002 | R1 = | β-D-glucose | | | | Vanillin-1-O-glucopyranoside | UGT76G1 | |
| VB1003 | R1 = | β-D-glucose | H | β-D-glucose | | Vanillin-1-O-(3-1)-diglucopyranoside | UGT76G1 | |
| VB1004 | R1 = | β-D-glucose | β-D-glucose | | | Vanillin-1-O-(2-1)-diglucopyranoside | UGT76G1 | Os03g0702000 |
| VB1005 | R1 = | β-D-glucose | β-D-glucose | β-D-glucose | | Vanillin-1-O-(2-1,3-1)-triglucopyranoside | UGT76G1 | Os03g0702000 |
| VB1006 | R1 = | β-D-glucose | H | β-D-glucose | β-D-glucose | Vanillin-1-O-(3-1,3-1)-triglucopyranoside | UGT76G1 | |
| VB1007 | R1 = | α-D-glucose | | | | Vanillin-1-O-α-glucopyranoside | CGTase | |
| VB1008 | R1 = | β-D-glucose | α-D-glucose | | | Vanillin-1-O-β-primed-α-diglucopyranoside | UGT76G1 | CGTase |

TABLE 11

Curcumin glycoside compositions by R-group
R-group location is as depicted in FIG. 1B

| VB# | | 1° 1-O Position | 2° 2-O- | 2° 3-O- | 3° 3-O- | | | 2° Position | 2° 2-O- | 2° 3-O- |
|---|---|---|---|---|---|---|---|---|---|---|
| VB1101 | R1 = | H | | | | R2 | = | H | | |
| VB1102 | R1 = | β-D-glucose | | | | R2 | = | H | | |
| VB1103 | R1 = | H | | | | R2 | = | β-D-glucose | | |
| VB1104 | R1 = | β-D-glucose | H | β-D-glucose | | R2 | = | H | | |
| VB1105 | R1 = | β-D-glucose | B-D-glucose | | | R2 | = | H | | |
| VB1106 | R1 = | H | | | | R2 | = | β-D-glucose | H | β-D-glucose |
| VB1107 | R1 = | H | | | | R2 | = | β-D-glucose | β-D-glucose | |
| VB1108 | R1 = | β-D-glucose | | | | R2 | = | β-D-glucose | | |

TABLE 11-continued

Curcumin glycoside compositions by R-group
R-group location is as depicted in FIG. 1B

| | | | | | | | | | | |
|---|---|---|---|---|---|---|---|---|---|---|
| VB1109 | R1 | = | β-D-glucose | | | R2 | = | β-D-glucose | H | β-D-glucose |
| VB1110 | R1 | = | β-D-glucose | H | β-D-glucose | R2 | = | β-D-glucose | H | |
| VB1111 | R1 | = | β-D-glucose | H | | R2 | = | β-D-glucose | β-D-glucose | |
| VB1112 | R1 | = | β-D-glucose | β-D-glucose | | R2 | = | β-D-glucose | | |
| VB1113 | R1 | = | β-D-glucose | β-D-glucose | β-D-glucose | R2 | = | H | | |
| VB1114 | R1 | = | H | | | R2 | = | β-D-glucose | β-D-glucose | β-D-glucose |
| VB1115 | R1 | = | H | | | R2 | = | β-D-glucose | H | β-D-glucose |
| VB1116 | R1 | = | β-D-glucose | H | β-D-glucose | R2 | = | H | | |
| VB1117 | R1 | = | β-D-glucose | H | | R2 | = | β-D-glucose | H | β-D-glucose |
| VB1118 | R1 | = | β-D-glucose | β-D-glucose | | R2 | = | β-D-glucose | H | β-D-glucose |
| VB1119 | R1 | = | β-D-glucose | H | β-D-glucose | R2 | = | β-D-glucose | β-D-glucose | |
| VB1120 | R1 | = | β-D-glucose | β-D-glucose | | R2 | = | β-D-glucose | β-D-glucose | |
| VB1121 | R1 | = | β-D-glucose | H | β-D-glucose | β-D-glucose | R2 | = | β-D-glucose | |
| VB1122 | R1 | = | β-D-glucose | β-D-glucose | β-D-glucose | R2 | = | β-D-glucose | | |
| VB1123 | R1 | = | β-D-glucose | | | R2 | = | β-D-glucose | H | β-D-glucose |
| VB1124 | R1 | = | β-D-glucose | | | R2 | = | β-D-glucose | β-D-glucose | β-D-glucose |
| VB1125 | R1 | = | β-D-glucose | H | β-D-glucose | R2 | = | β-D-glucose | H | β-D-glucose |
| VB1126 | R1 | = | β-D-glucose | H | β-D-glucose | R2 | = | β-D-glucose | β-D-glucose | H |
| VB1127 | R1 | = | β-D-glucose | H | β-D-glucose | β-D-glucose | R2 | = | β-D-glucose | H | β-D-glucose |
| VB1128 | R1 | = | β-D-glucose | β-D-glucose | H | β-D-glucose | R2 | = | β-D-glucose | H | β-D-glucose |
| VB1129 | R1 | = | β-D-glucose | H | β-D-glucose | β-D-glucose | R2 | = | β-D-glucose | H | β-D-glucose |
| VB1130 | R1 | = | β-D-glucose | β-D-glucose | H | β-D-glucose | R2 | = | β-D-glucose | H | β-D-glucose |
| VB1131 | R1 | = | β-D-glucose | H | β-D-glucose | β-D-glucose | R2 | = | β-D-glucose | β-D-glucose | H |
| VB1132 | R1 | = | α-D-glucose | | | R2 | = | H | | |
| VB1133 | R1 | = | β-D-glucose | α-D-glucose | | R2 | = | H | | |
| VB1134 | R1 | = | H | | | R2 | = | α-D-glucose | | |
| VB1135 | R1 | = | H | | | R2 | = | β-D-glucose | α-D-glucose | |
| VB1136 | R1 | = | α-D-glucose | | | R2 | = | α-D-glucose | | |

| VB# | 3° 3-O- | Name | 1° Enzyme | 2° Enzyme |
|---|---|---|---|---|
| VB1101 | | Curcumin | | |
| VB1102 | | Curcumin-1-O-glucopyranoside | UGT76G1 | |
| VB1103 | | Curcumin-2-O-glucopyranoside | UGT76G1 | |
| VB1104 | | Curcumin-1-O-(3-1)-diglucopyranoside | UGT76G1 | |
| VB1105 | | Curcumin-1-O-(2-1)-diglucopyranoside | UGT76G1 | Os03g0702000 |
| VB1106 | | Curcumin-2-O-(3-1)-diglucopyranoside | UGT76G1 | |
| VB1107 | | Curcumin-2-O-(2-1)-diglucopyranoside | UGT76G1 | Os03g0702000 |
| VB1108 | | Curcumin-1-O,2-O-diglucopyranoside | UGT76G1 | |
| VB1109 | | Curcumin-1-O,2-O-(3-1)-triglucopyranoside | UGT76G1 | |
| VB1110 | | Curcumin-1-O-(3-1), 2-O-triglucopyranoside | UGT76G1 | |
| VB1111 | | Curcumin-1-O,2-O-(2-1)-triglucopyranoside | UGT76G1 | Os03g0702000 |
| VB1112 | | Curcumin-1-O-(2-1), 2-O-triglucopyranoside | UGT76G1 | Os03g0702000 |
| VB1113 | | Curcumin-1-O-(2-1,3-1)-triglucopyranoside | UGT76G1 | Os03g0702000 |
| VB1114 | | Curcumin-2-O-(2-1,3-1)-triglucopyranoside | UGT76G1 | Os03g0702000 |
| VB1115 | β-D-glucose | Curcumin-2-O-(3-1,3-1)-triglucopyranoside | UGT76G1 | |
| VB1116 | | Curcumin-1-O-(3-1,3-1)-triglucopyranoside | UGT76G1 | |
| VB1117 | | Curcumin-1-O-(3-1), 2-O-(3-1)-tetraglucopyranoside | UGT76G1 | |
| VB1118 | | Curcumin-1-O-(2-1), 2-O-(3-1)-tetraglucopyranoside | UGT76G1 | Os03g0702000 |
| VB1119 | | Curcumin-1-O-(3-1), 2-O-(2-1)-tetraglucopyranoside | UGT76G1 | Os03g0702000 |
| VB1120 | | Curcumin-1-O-(2-1), 2-O-(2-1)-tetraglucopyranoside | UGT76G1 | Os03g0702000 |
| VB1121 | | Curcumin-1-O-(3-1,3-1), 2-O-tetraglucopyranoside | UGT76G1 | |
| VB1122 | | Curcumin-1-O-(2-1,3-1), 2-O-tetraglucopyranoside | UGT76G1 | Os03g0702000 |
| VB1123 | β-D-glucose | Curcumin-1-O,2O-(3-1,3-1)-tetraglucopyranoside | UGT76G1 | |
| VB1124 | | Curcumin-1-O,2-O-(2-1, 3-1)-tetraglucopyranoside | UGT76G1 | Os03g0702000 |
| VB1125 | β-D-glucose | Curcumin-1-O-(3-1), 2-O-(3-1, 3-1)-pentaglucopyranoside | UGT76G1 | |
| VB1126 | β-D-glucose | Curcumin-1-O-(3-1), 2-O-(2-1, 3-1)-pentaglucopyranoside | UGT76G1 | Os03g0702000 |
| VB1127 | | Curcumin-1-O-(3-1, 3-1), 2-O-(3-1)-pentaglucopyranoside | UGT76G1 | |
| VB1128 | | Curcumin-1-O-(2-1,3-1), 2-O-(3-1)-pentaglucopyranoside | UGT76G1 | Os03g0702000 |
| VB1129 | β-D-glucose | Curcumin-1-O-(3-1, 3-1), 2-O-(3-1, 3-1)-hexaglucopyranoside | UGT76G1 | |
| VB1130 | β-D-glucose | Curcumin-1-O-(2-1, 3-1), 2-O-(3-1, 3-1)-hexaglucopyranoside | UGT76G1 | Os03g0702000 |
| VB1131 | β-D-glucose | Curcumin-1-O-(3-1, 3-1), 2-O-(2-1, 3-1)-hexaglucopyranoside | UGT76G1 | Os03g0702000 |
| VB1132 | | Curcumin-1-O-α-glucopyranoside | CGTase | |
| VB1133 | | Curcumin-1-O-β-primed-α-diglucopyranoside | UGT76G1 | CGTase |
| VB1134 | | Curcumin-2-O-α-glucopyranoside | CGTase | |
| VB1135 | | Curcumin-2-O-β-primed-α-diglucopyranoside | UGT76G1 | CGTase |
| VB1136 | | Curcumin-1,2-O-α-glucopyranoside | CGTase | |

It is obvious that the foregoing embodiments of the invention are examples and can be varied in many ways. Such present or future variations are not to be regarded as a departure from the spirit and scope of the invention, and all such modifications as would be obvious to one skilled in the art are intended to be included within the scope of the following claims.

REFERENCES

Bartzokis G. (2004). Age-related myelin breakdown: a developmental model of cognitive decline and Alzheimer's disease. Neurobiology of Aging. 25:5-18.

Bisogno T, et al. (2001) Molecular targets for cannabidiol and its synthetic analogues: effect on vanilloid VR1 receptors and on the cellular uptake and enzymatic hydrolysis of anandamide. British Journal of Pharmacology. 134, 845-852.

Chen Q, et al. (2009). Synthesis, in vitro and in vivo characterization of glycosyl derivatives of ibuprofen as novel prodrugs for brain drug delivery. J Drug Targeting. 17(4):318-328.

Conchie J., Findlay J., Levvy G A. (1958). Mammalian Glycosidases, Distribution in the body. Biochem J. 71(2): 318-325.

De Petrocellis L, et al. (2011) Effects of cannabinoids and cannabinoid-enriched *Cannabis* extracts on TRP channels and endocannabinoid metabolic enzymes. British Journal of Pharmacology. 163, 1479-1494.

Dewitte G, et al. (2016) Screening of Recombinant Glycosyltransferases Reveals the Broad acceptor Specificity of *Stevia* UGT-76G1. Journal of Biotechnology. Accepted Manuscript, DOI: http://dx.doi.org/doi:10.1016/j.jbiotec.2016.06.034.

Friend D R., Chang G W. (1984). A Colon-Specific Drug-Delivery System Based on Drug Glycosides and the Glycosidases of the Colonic Bacteria. J Med Chem. 27:261-266.

Friend D R., Chang G W. (1985). Drug Glycosides: Potential Prodrugs for Colon-Specific Drug Delivery. J Med Chem. 28:51-57.

Gomez O., Arevalo-Martin A., Garcia-Ovejero D., Ortega-Gutierrez S., Cisneros J A., Almazan G, Sanchez-Rodriguez M A., Molina-Holgado F., Molina-Holgado E. (2010). The Constitutive Production of the Endocannabinoid 2-Arachidonoylglycerol Participates in Oligodendrocyte Differentiation. Glia. 58:1913-1927.

Iuvone T., Esposito G., De Filippis D., Scuderi C., Steardo L. (2009). Cannabidiol: a promising drug for neurodegenerative disorders? CNS Neurosci Ther. 15(1):65-75.

Jarh, P., Pate D W., Brenneisen R., Jarvinen T. (1998). Hydroxypropyl-beta-cyclodextrin and its combination with hydroxypropyl-methylcellulose increases aqueous solubility of delta9-tetrahydrocannabinol. Life Sci. 63(26):PL381-384.

Jiang R, et al. (2011) Identification of cytochrome P450 enzymes responsible for metabolism of cannabidiol by human liver microsomes. Life Sciences. 89, 165-170.

Kren V (2008) Glycoside vs. Aglycon: The Role of Glycosidic Residue in Biologic Activity. Glycoscience. pp 2589-2644.

Kren V, Rezanka T (2008) Sweet antibiotics—the role of glycosidic residues in antibiotic and antitumor activity and their randomization. FEMS Microbiol Rev. 32, 858-889.

Li S., Li W., Xiao Q., Xia Y. (2012). Transglycosylation of stevioside to improve the edulcorant quality by lower substitution using cornstarch hydrolyzate and CGTase. J Food Chem. 138(2013):2064-2069.

Mazur A., et al. (2009). Characterization of Human Hepatic and Extrahepatic UDP-Glucuronosyltransferase Enzymes Involved in the Metabolism of Classic Cannabinoids. Drug Metabolism and Disposition. 37(7):1496-1504.

Mecha M., Torrao A S., Mestre L., Carrillo-Salinas F J., Mechoulam R., Guaza C. (2012). Cannabidiol protects oligodendrocyte progenitor cells from inflammation-induced apoptosis by attenuating endoplasmic reticulum stress. Cell Death and Disease. 3(e331).

Mechoulam R., Parker L A., Gallily R. (2002). Cannabidiol: An Overview of Some Pharmacological Aspects. 42(S1): 11S-19S.

Mighdoll M I., Tao R., Kleinman J E., Hyde T M. (2015). Myelin, myelin-related disorders, and psychosis. Schizophr Res. 161(1):85-93.

Molina-Holgado E., Vela J M., Arevalo-Martin A., Almazan G., Molina-Holgado F., Borrell J., Guaza C. (2002). Cannabinoids Promote Oligodendrocyte Progenitor Survival: Involvement of Cannavinoid Receptors and Phosphatidylinositol-3-Kinase/Akt Signaling. J. Neurosci. 22(22):9742-9753.

Noguchi A, et al. (2009). Identification of an inducible glucosyltransferase from *Phytolacca americana* L. cells that are capable of glucosylating capsiacin. Plant Biotechnology. 26, 285-292.

Pacher P, et al. (2006) The endocannabinoid system as an emerging target of pharmacotherapy. Pharmacology Review. 58(3), 389-462.

Richman A., Swanso, A., Humphrey T., Chapman R., McGarvey B., Pocs R., Brandle J. (2005). Functional genomics uncovers three glucosyltransferases involved in the synthesis of the major sweet glucosides of *Stevia rebaudiana*. Plant J. 41(1):56-67.

Russo E., Guy, G W. (2006) A tale of two cannabinoids: the therapeutic rationale for combining tetrahydrocannabinol and cannabidiol. Medical Hypotheses. 66(2):234-46.

Tanaka H., et al. (1993). *Cannabis*, 21.[1] Biotransformation of cannabinol to its glycosides by in vitro plant tissue. Journal of Natural Products. 56(12):2068-2072.

Tanaka H., et al. (1996). *Cannabis* 25, biotransformation of cannabidiol and cannabidiolic acid by *Pinellia ternata* tissue segments. Plant Cell Reports. 15:819-823.

Terao J., Murota K., Kawai Y. (2011). Conjugated quercetin glucuronides as bioactive metabolites and precursors of aglycone in vivo. Food Function. 2:11-17.

Thomas A., et al. (2007) Cannabidiol displays unexpectedly high potency as an antagonist of $CB_1$ and $CB_2$ receptor agonists in vitro. British Journal of Pharmacology. 150, 613-623.

U.S. Pat. No. 8,410,064 B2. 2013. Classical cannabinoid metabolites and methods of use thereof.

U.S. Pat. No. 8,227,627 B2. 2012. Prodrugs of tetrahydrocannabinol, compositions comprising prodrugs of tetrahyrocannabinol and methods of using the same.

Watanabe K, et al. (1998) Distribution and characterization of anandamide amidohydrolase in mouse brain and liver. Life Sciences. 62(14), 1223-1229.

WO2009018389 A4. 2009. Prodrugs of cannabidiol, compositions comprising prodrugs of cannabidiol and methods of using the same.

WO2012011112 A1. 2011. Non psychoactive cannabinoids and uses thereof.

WO 2014108899 A1. 2014. Fluorinated CBD compounds, compositions and uses thereof.

Yamaori S, et al. (2011) Potent inhibition of human cytochrome P450 3A isoforms by cannabidiol: Role of phenolic hydroxyl groups in the resorcinol moiety. Life Sciences, 88, 730-736.

Zuardi A W, et al. (2012). A Critical Review of the Antipyschotic Effects of Cannabidiol: 30 Years of a Translational Investigation. Current Pharmaceutical Design, 18, 5131-5140.

We claim:

1. A method for the site-specific delivery of a cannabinoid drug to a subject in need thereof, comprising the step of administering a cannabinoid glycoside prodrug compound to a subject in need thereof, wherein the cannabinoid glycoside prodrug compound has the formula (I):

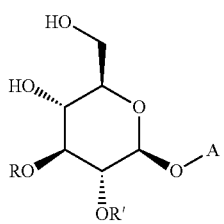
(I)

wherein:
R is H, β-D-glucopyranosyl, or 3-O-β-D-glucopyranosyl-β-D-glucopyranosyl, wherein if R' is H, then R is not H;
R' is H or β-D-glucopyranosyl, or 3-O-β-D-glucopyranosyl-β-D-glucopyranosyl, wherein if R is H, then R' is not H; and
A is A' and A' is:

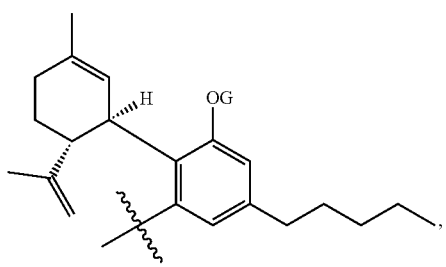

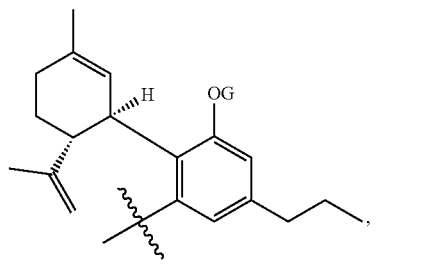

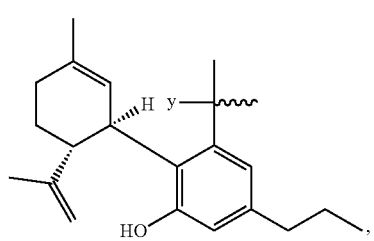

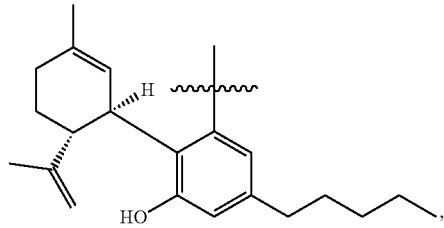

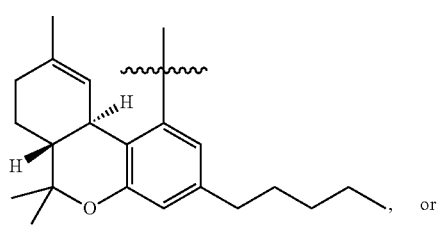, or

-continued

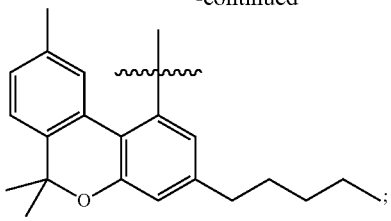

and wherein G is H, β-D-glucopyranosyl, 3-O-β-D-glucopyranosyl-β-D-glucopyranosyl, or β-D-glucopyranosyl-(1-3)-β-D-glucopyranosyl-(1-3)-D-glucopyranosyl, or a pharmaceutically compatible salt or derivative thereof, wherein upon reaching the specific site of delivery, the cannabinoid glycoside prodrug or pharmaceutically compatible salt or derivative thereof, is converted to the active cannabinoid drug.

2. The method of claim 1, wherein the cannabinoid glycoside prodrug compound is formulated for oral administration.

3. The method of claim 1, wherein the cannabinoid glycoside prodrug compound is formulated for parenteral administration.

4. The method of claim 1, wherein the cannabinoid glycoside prodrug compound is formulated for transdermal administration.

5. The method of claim 1, wherein A' is:

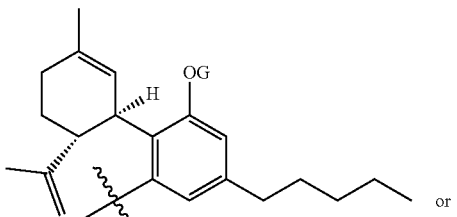

or

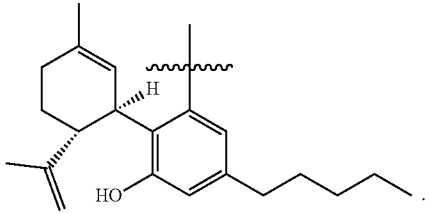

.

6. The method of claim 1, wherein A' is:

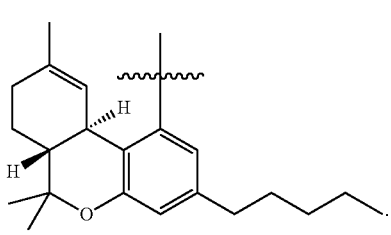 [SMILES: *c1cc(CCCCC)cc2c1[C@@H]1C=C(C)CC[C@H]1C(C)(C)O2]

.

7. The method according to claim 5, wherein the cannabinoid glycoside prodrug compound is selected from:

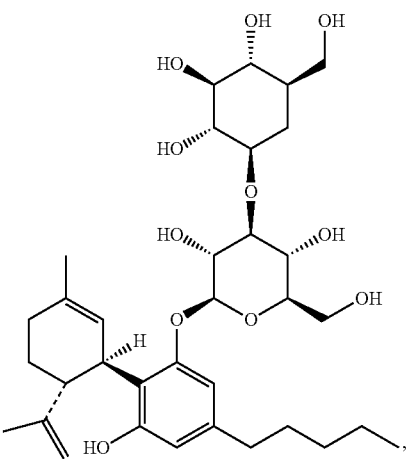
VB104

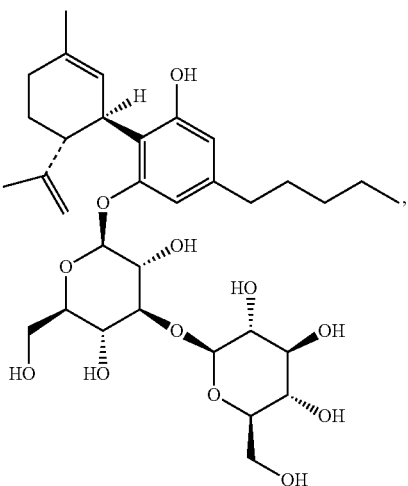
VB108

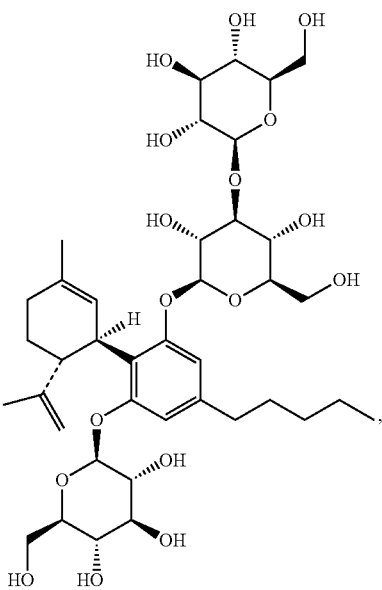
VB112

VB118
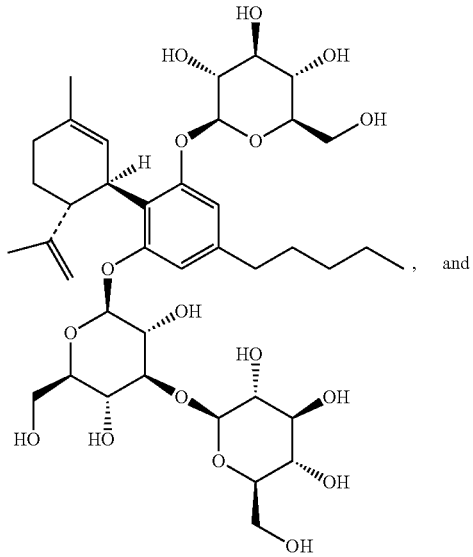
, and
VB119
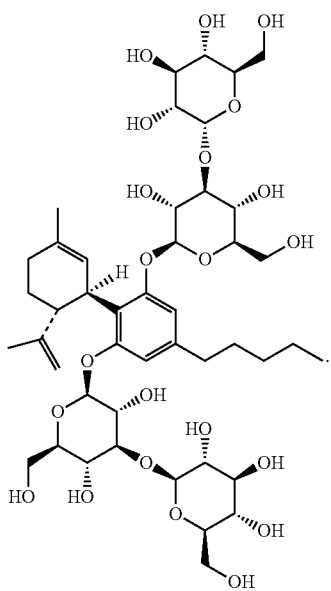
VB303
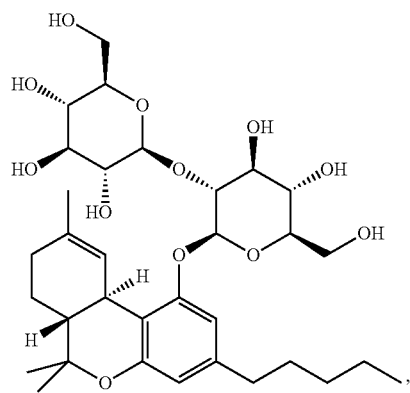
,
VB304
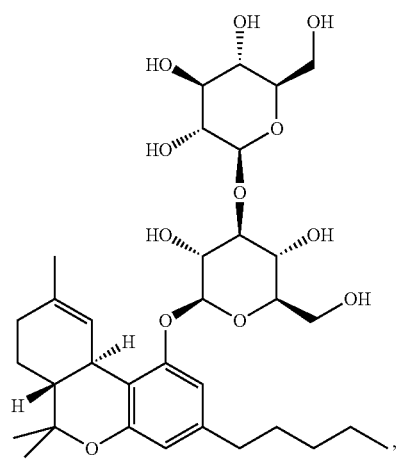
,
VB305
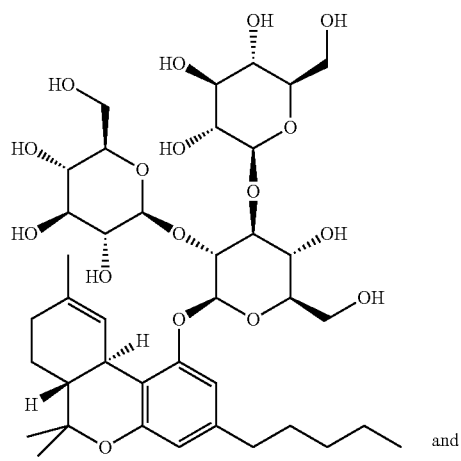
and
8. The method of claim 6, wherein the cannabinoid glycoside prodrug compound is selected from:

-continued
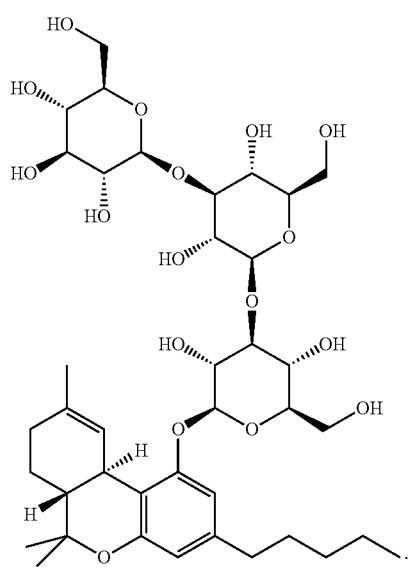
VB308
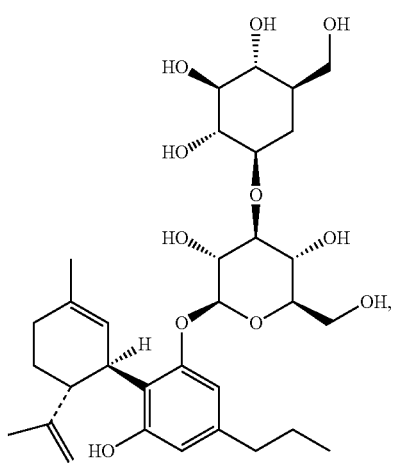
VB204
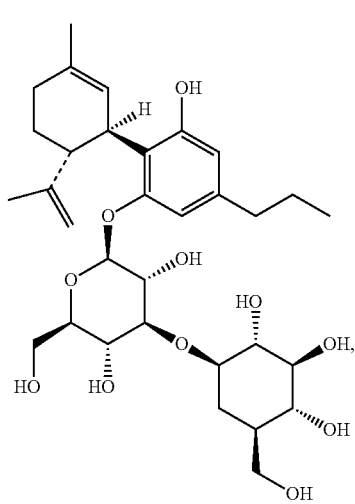
VB208
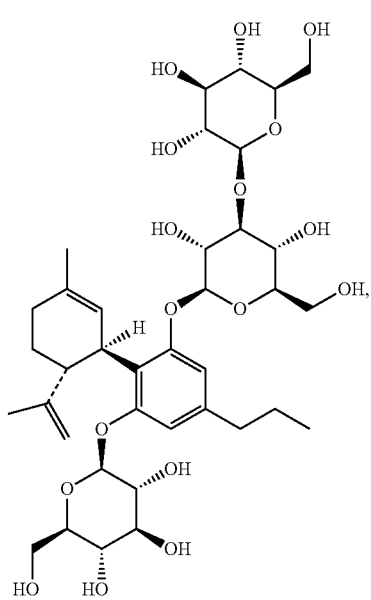
VB212
9. The method according to claim 1, wherein A' is:
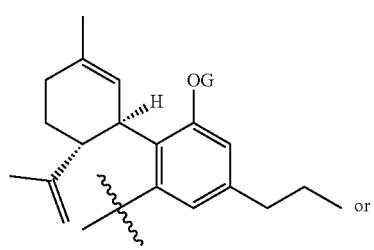
or
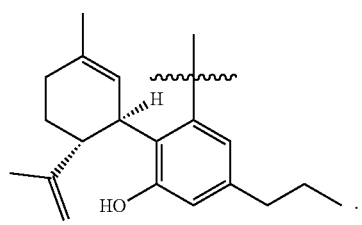
10. The method according to claim 9, wherein the cannabinoid glycoside prodrug compound is selected from:

-continued
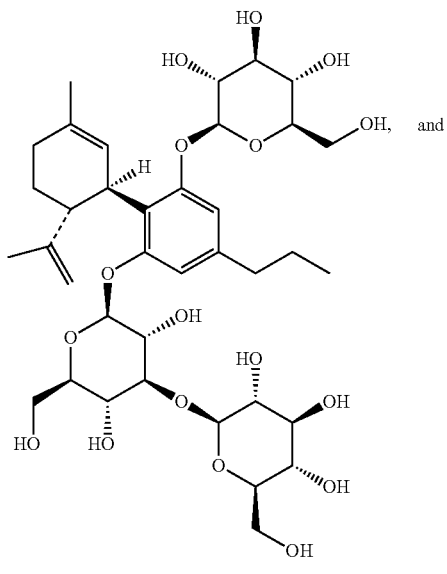
VB218
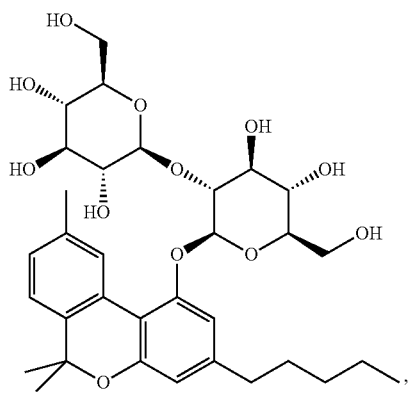
VB403
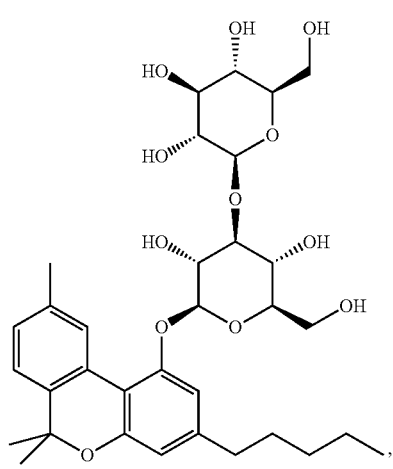
VB404
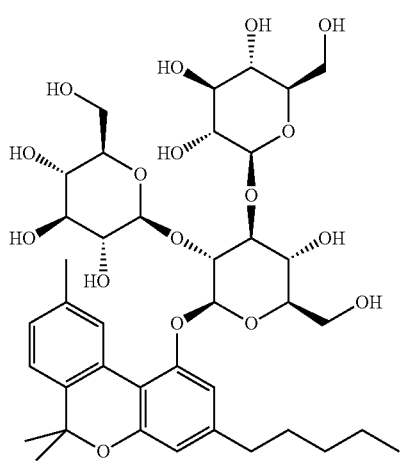
VB219
11. The method according to claim 1, wherein A' is:
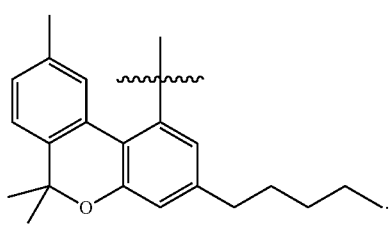 [SMILES: *c1cc(CCCCC)cc2c1-c1cc(C)ccc1C(C)(C)O2]
12. The method according to claim 11, wherein the cannabinoid glycoside prodrug compound is selected from:
VB405

-continued

VB408

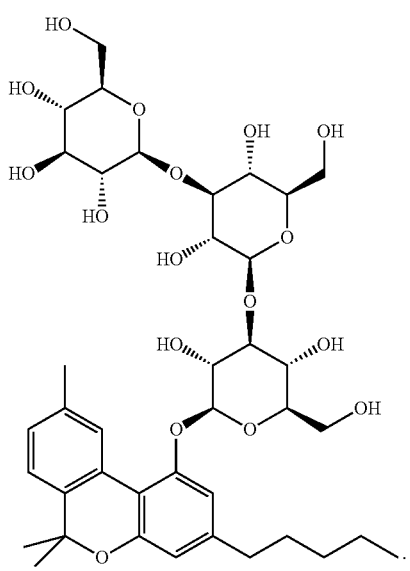

13. The method according to claim 1, wherein the specific site of delivery is the large intestine, the rectum, the liver, or the skin.

14. The method according to claim 13, wherein the specific site of delivery is the large intestine.

15. The method according to claim 13, wherein the specific site of delivery is the skin.

16. The method according to claim 1, wherein the cannabinoid glycoside prodrug compound is administered in combination with at least one substance that has glycosidase activity.

17. The method according to claim 1, wherein the method further comprises the step of administering at least one substance that has glycosidase activity.

* * * * *